United States Patent [19]
Grote et al.

[11] Patent Number: 5,985,919
[45] Date of Patent: Nov. 16, 1999

[54] (HET)ARYLOXY-, -THIO-, AMINOCROTONATES, METHODS OF PREPARING THEM AND THEIR USE AS INSECTICIDES AND FUNGICIDES

[75] Inventors: Thomas Grote, Göttingen; Reinhard Kirstgen, Neustadt; Bernd Müller, Frankenthal; Hubert Sauter, Mannheim; Albrecht Harreus, Ludwigshafen; Hartmann König, Heidelberg; Eberhard Ammermann, Heppenheim; Gisela Lorenz, Hambach; Siegfried Strathmann, Limburgerhof; Franz Röhl, Schifferstadt, all of Germany

[73] Assignee: BASF Aktiengesellschaft, Ludwigshafen, Germany

[21] Appl. No.: 08/945,912

[22] PCT Filed: Apr. 26, 1996

[86] PCT No.: PCT/EP96/01754

§ 371 Date: Oct. 30, 1997

§ 102(e) Date: Oct. 30, 1997

[87] PCT Pub. No.: WO96/35669

PCT Pub. Date: Nov. 14, 1996

[30] Foreign Application Priority Data

May 9, 1995 [DE] Germany ............ 195 16 844

[51] Int. Cl.[6] .......... A01N 43/40; A01N 37/10; A01N 43/54; A01N 43/84; C07D 213/55; C07D 239/26; C07D 239/34; C07C 69/618

[52] U.S. Cl. .......... 514/520; 514/256; 514/277; 514/374; 514/378; 514/438; 514/452; 514/461; 514/475; 514/524; 514/532; 544/335; 546/342; 548/236; 548/247; 549/79; 549/362; 549/501; 549/549; 558/252; 558/253; 558/256; 558/257; 558/260; 560/9; 560/20; 560/21; 560/23; 560/24; 560/27; 560/29; 560/31; 560/32; 560/45; 560/47; 560/48; 560/49

[58] Field of Search .......... 558/252, 253, 558/256, 257, 260; 560/9, 20, 21, 23, 24, 27, 29, 31, 32, 45, 47, 48, 49; 514/520, 524, 532, 378, 452, 461, 475, 438, 374, 277, 256; 544/335; 546/342; 548/247, 236; 549/362, 549, 501, 79

[56] References Cited

U.S. PATENT DOCUMENTS

| | | | |
|---|---|---|---|
| 4,813,721 | 3/1989 | Mora | 296/65.1 |
| 4,968,709 | 11/1990 | Kleefeld et al. | 514/370 |
| 5,008,275 | 4/1991 | Klausener et al. | 514/334 |
| 5,036,085 | 7/1991 | Heinemann et al. | 514/361 |
| 5,041,618 | 8/1991 | Brand et al. | 560/104 |
| 5,114,959 | 5/1992 | Klausener et al. | 514/369 |
| 5,120,755 | 6/1992 | Kleefeld et al. | 514/370 |
| 5,189,175 | 2/1993 | Heinemann et al. | 548/128 |

(List continued on next page.)

FOREIGN PATENT DOCUMENTS

| | | |
|---|---|---|
| 0 049 508 | 4/1982 | European Pat. Off. . |
| 212 859 | 3/1987 | European Pat. Off. . |
| 331 966 | 9/1989 | European Pat. Off. . |
| 348 766 | 1/1990 | European Pat. Off. . |
| 383 117 | 8/1990 | European Pat. Off. . |
| 384 211 | 8/1990 | European Pat. Off. . |
| 389 901 | 10/1990 | European Pat. Off. . |
| 409 369 | 1/1991 | European Pat. Off. . |
| 464 381 | 1/1992 | European Pat. Off. . |
| 471 261 | 2/1992 | European Pat. Off. . |
| 503 436 | 9/1992 | European Pat. Off. . |
| 546 387 | 6/1993 | European Pat. Off. . |
| 548 650 | 6/1993 | European Pat. Off. . |
| 579 908 | 1/1994 | European Pat. Off. . |
| 584 625 | 3/1994 | European Pat. Off. . |
| 2 321 291 | 3/1977 | France . |
| 23 41 307 | 2/1975 | Germany . |
| 24 43 401 | 3/1975 | Germany . |
| 56-59732 | 5/1981 | Japan . |
| 2 238 308 | 5/1991 | United Kingdom . |

OTHER PUBLICATIONS

Suzuki et al., Photocyclization Reactions. Part 2[1]. Synthesis of Dihydrobenzofuranols Using Photocyclization of Ethyl 2–Formylphenoxyacetates and Ethyl 2–Acetylphenoxyacetates, Journal of Heterocyclic Chemistry, vol. 28, No. 5, pp. 1273–1280, Aug. 1991.

Rosnati et al., Ring Opening and Ring–Chain Tautomerism in 2–Carbalkoxy– and 2–Acyl–2,3–Dihydro–1,4–Benzodiozins, Tetrahedron, vol. 42, No. 16, pp. 4541–4548, 1986.

Zecchi, New Features of the Reaction Between Catechol and Ethyl 2,3–Dibromobutanoate, Gazzetta Chimica Italiana, vol. 105, No. 3–4, pp. 439–442, Mar. 1975.

*Primary Examiner*—Mukund J. Shah
*Assistant Examiner*—Brenda Coleman
*Attorney, Agent, or Firm*—Keil & Weinkauf

[57] ABSTRACT

(Het)aryloxy-, -thio- and -aminocrotonates of the formula I

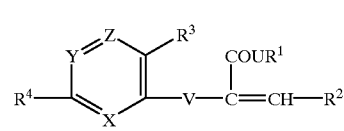

where the substituents have the following meanings:

U is oxygen, sulfur or amino;

V is oxygen, sulfur, amino or alkylamino;

X, Y and Z independently of one another are =N— or =CR$^3$—;

R$^1$ and R$^2$ independently of one another are alkyl;

R$^3$ is hydrogen, cyano, nitro, halogen, alkyl, haloalkyl, alkoxy, haloalkoxy, alkylthio and haloalkylthio; and R$^4$ is an organic radical which is bonded to the skeleton directly or via an oxy, mercapto, amino, carboxyl or carbonylamino group, process for their preparation, and their use.

16 Claims, No Drawings

U.S. PATENT DOCUMENTS

| | | | |
|---|---|---|---|
| 5,231,097 | 7/1993 | Klausener et al. | 514/256 |
| 5,238,934 | 8/1993 | Knueppel et al. | 514/241 |
| 5,254,693 | 10/1993 | Klausener et al. | 548/187 |
| 5,270,289 | 12/1993 | Harde et al. | 504/243 |
| 5,284,946 | 2/1994 | Knueppel et al. | 544/219 |
| 5,312,960 | 5/1994 | Kraemer et al. | 560/35 |
| 5,322,949 | 6/1994 | Heinemann et al. | 548/128 |
| 5,371,095 | 12/1994 | Knueppel et al. | 514/332 |
| 5,380,914 | 1/1995 | Kraemer et al. | 560/35 |
| 5,412,100 | 5/1995 | Klausener et al. | 548/187 |
| 5,434,267 | 7/1995 | Kraus et al. | 546/301 |
| 5,464,809 | 11/1995 | Kraemer et al. | 504/227 |
| 5,580,868 | 12/1996 | Lunkenheimer et al. | 514/222.5 |

(HET)ARYLOXY-, -THIO-, AMINOCROTONATES, METHODS OF PREPARING THEM AND THEIR USE AS INSECTICIDES AND FUNGICIDES

This application is a National Stage filing of PCT/EP96/01754 filed Apr. 26, 1996.

The present invention relates to (het)aryloxy-, -thio- and -aminocrotonates of the formula I

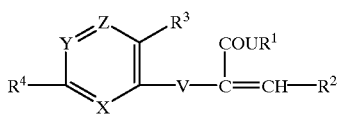

where the substituents have the following meanings:

U is oxygen (—O—), sulfur (—S—) or amino (—NH—);

V is oxygen (—O—), sulfur (—S—), amino (—NH—) or alkylamino [—N(alkyl)-];

X, Y and Z independently of one another are =N— or =CR$^3$—;

R$^1$ and R$^2$ independently of one another are C$_1$–C$_4$-alkyl;

R$^3$ is hydrogen, cyano, nitro, halogen, C$_1$–C$_4$-alkyl, C$_1$–C$_4$-haloalkyl, C$_1$–C$_4$-alkoxy, C$_1$–C$_4$-haloalkoxy, C$_1$–C$_4$-alkylthio and C$_1$–C$_4$-haloalkylthio;

R$^4$ is an organic radical which is bonded to the skeleton directly or via an oxy, mercapto, amino, carboxyl or carbonylamino group.

The invention furthermore relates to processes for the preparation of these compounds, to compositions comprising them, and to their use for controlling animal pests and fungal pests.

The literature discloses (het)aryloxy-, -thio- and -amino-β-alkoxyacrylates which are fungicidally active (EP-A 212 859; EP-A 383 117; EP-A 471 261; EP-A 503 436; EP-A 584 625). EP-A 409 369 furthermore describes herbicidally, growth-regulatory and fungicidally active hetaryloxy- and -thiocrotonates in which the hetaryl ring is either a pyrimidin-2-yl ring or a 1,3,5-triazin-2-yl ring.

It was an object of the present invention to provide compounds having improved properties.

We have found that this object is achieved by the compounds I which are defined at the outset. We have also found processes for the preparation of these compounds, compositions comprising them, and their use for controlling animal pests and fungal pests.

The compounds I can generally be prepared by the processes described in the literature cited.

The compounds I where V is oxygen or sulfur are preferably obtained by reacting a corresponding alcohol or a corresponding thiol of the formula IIa with a crotonate of the formula III in a manner known per se (J. Chem. Soc. 1963, 4210) in the presence of a base.

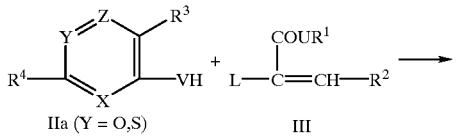

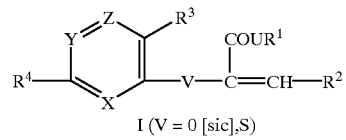

In formula III, L is a nucleophilically replaceable leaving group such as halogen (eg. chlorine, bromine and iodine) or a sulfonate (eg. trifluoromethylsulfonate, phenylsulfonate and p-methylphenylsulfonate).

This reaction is conventionally carried out at from 0° C. to 200° C., preferably 0° C. to 150° C., in particular 10° C. to 100° C., in an inert solvent or diluent.

Suitable solvents or diluents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitrites such as acetonitrile and propionitrile, ketones such as acetone, methyl ethyl ketone, diethyl ketone and tert-butyl methyl ketone, alcohols such as methanol, ethanol, n-propanol, isopropanol, n-butanol and tert-butanol, and also dimethyl sulfoxide and dimethylformamide, particularly preferably acetonitrile, dimethylformamide, dimethyl sulfoxide and 1,3-dimethyltetrahydro-2(1H)-pyrimidinone (DMPU). Mixtures of these can also be used.

Bases which are generally suitable are inorganic compounds such as alkali metal hydroxides and alkaline earth metal hydroxides, such as lithium hydroxide, sodium hydroxide, potassium hydroxide and calcium hydroxide, alkali metal and alkaline earth metal oxides such as lithium oxide, sodium oxide, calcium oxide and magnesium oxide, alkali metal hydrides and alkaline earth metal hydrides such as lithium hydride, sodium hydride, potassium hydride and calcium hydride, alkali metal amides such as lithium amide, sodium amide and potassium amide, alkali metal carbonates and alkaline earth metal carbonates such as lithium carbonate and calcium carbonate, and also alkali metal hydrogen carbonates such as sodium hydrogen carbonate, organometal compounds, in particular alkali metal alkyls such as methyllithium, butyllithium and phenyllithium, alkylmagnesium halides such as methylmagnesium chloride and also alkali metal alcoholates and alkaline earth metal alcoholates such as sodium methanolate, sodium ethanolate, potassium ethanolate, potassium tert-butanolate and dimethoxymagnesium, furthermore organic bases, eg. tertiary amines such as trimethylamine, triethylamine, triisopropylethylamine and N-methylpiperidine, pyridine, substituted pyridines such as collidine, lutidine and 4-dimethylaminopyridine, and also bicyclic amines.

Potassium carbonate, potassium hydroxide and sodium hydrogen carbonate are particularly preferred.

The bases are generally used in equimolar amounts, in an excess or, if desired, as the solvent.

The educts are generally reacted with each other in equimolar amounts. It may be advantageous for the yield to employ II in an excess or a substoichiometric amount, based on III.

The starting materials of the formula IIa which are required for the preparation of the compounds I are already known from the literature or can be synthesized by methods known from the literature cited in connection with the description of the preparation of the individual groups R$^4$.

The starting materials of the formula III which are also required for the preparation are likewise already known from the literature [J. Org. Chem. 44, 2608 (1979); J. Chem. Soc. PTI 21, 2651 (1993)] or can be obtained by the methods described therein.

Compounds I where V is amino or alkylamino are preferably obtained by reacting a corresponding amine of the formula IIb with an α-ketocarbonyl compound of the formula IV in a manner known per se (Synthesis 1975, 512) in the presence of protic acids.

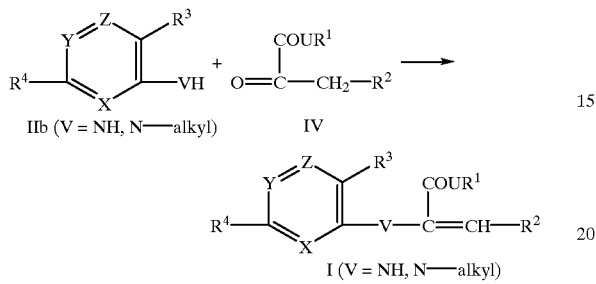

IIb (V = NH, N—alkyl)   IV

I (V = NH, N—alkyl)

This reaction is conventionally carried out at from 0° C. to 200° C., preferably 0° C. to 150° C., in particular 10° C. to 150° C., in an inert solvent or diluent.

Suitable solvents or diluents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitrites such as acetonitrile and propionitrile, ketones such as acetone, methyl ethyl ketone, diethyl ketone and tert-butyl methyl ketone, alcohols such as methanol, ethanol, n-propanol, isopropanol, n-butanol and tert-butanol, and also dimethyl sulfoxide and dimethylformamide, particularly preferably toluene.

Mixtures of these can also be used.

Protic acids which are used are inorganic acids such as hydrofluoric acid, hydrochloric acid, hydrobromic acid, sulfuric acid and perchloric acid, and also organic acids such as formic acid, acetic acid, propionic acid, oxalic acid, citric acid and trifluoroacetic acid.

The acids are generally employed in catalytic amounts, but they can also be used in equimolar amounts, in an excess or, if desired, as the solvent.

The educts are generally reacted with each other in equimolar amounts. It may be advantageous for the yield to employ II in an excess or a substoichiometric amount, based on IV.

The starting materials of the formula IIb which are required for the preparation of the compounds I are already known from the literature or can be synthesized by methods known from the literature cited in connection with the description of the preparation of the individual groups $R^4$.

The starting materials of the formula IV which are also required for the preparation are likewise already known from the literature [Helv. Chim. Acta 30, 1372 (1947); J. Org. Chem. 43, 4245 (1978); Biochemistry 10, 2669 (1971)] or can be obtained by the methods described therein.

The reaction mixtures are worked up in the customary manner, for example by mixing with water, separating the phases and, if desired, purifying the crude products by chromatography. Some of the intermediates and end products are obtained in the form of colorless or pale brown viscous oils which are freed from volatile components or purified under reduced pressure and under moderately elevated temperature. If the intermediates and end products are obtained in the form of solids, they can also be purified by recrystallization or digestion.

The group $R^4$ can be synthesized independently of the above-described couplings and depends on the nature of the group $R^4$. For reasons of clarity, —V—C(COUR$^1$)=CH—$R^2$ or its precursor is abbreviated to R# in the equations which follow.

Conventionally, the synthesis of compounds I where $R^4$ is bonded via a carbon atom starts from the corresponding methyl or alkyl compound (I.1), and this compound I.1 is first halogenated to give the corresponding benzyl halide I.2 [cf. Angew. Chem 71, 349 (1959)].

I.1

I.2

This halogenation is conventionally carried out at from 0° C. to 100° C., preferably 20° C. to 80° C., in an inert solvent, either in the presence of a free-radical initiator (for example dibenzoyl peroxide or azobisisobutyronitrile, or under UV irradiation, for example using a mercury vapor lamp.

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, and also ethers such as diethyl ether, diisopropyl ether, tert-butyl methyl ether, dioxane, anisole and tetrahydrofuran, particularly preferably cyclohexane, methylene chloride and carbon tetrachloride. Mixtures of these can also be used.

Substances which are used as halogenating agents are, for example, elemental halogens (eg., $Cl_2$, $Br_2$, $I_2$), N-bromosuccinimide, N-chlorosuccinimide or dibromodimethylhydrantoin [sic]. The halogenating agents are generally used in equimolar amounts, in an excess or, if desired, as the solvent.

The compounds I.2 where Hal is iodine can additionally be prepared in a known manner [J. Chem. Soc. PTI, 416 (1976)] from the chlorides or bromides by reacting them with iodides (for example sodium iodide) in acetone.

The benzyl halide acts as the central intermediate for preparing a large number of compounds I by the equations which follow.

B.1 $R^4$=unsubstituted or substituted alkyl.

By reacting the benzyl halides I.2 with nucleophiles, preferably N-, O- or S-nucleophiles, eg. with alcohols, carboxylic acids, thiols or amines, the corresponding ethers, esters, thioethers or amines I.4 are obtained.

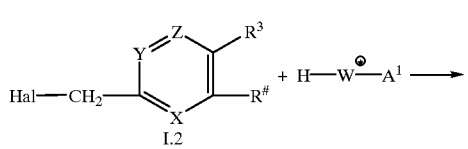

I.2

-continued

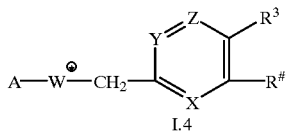

I.4

In the formulae, W* is oxygen, sulfur, amino or alkylamino; A1 is unsubstituted or substituted alkyl, acyl or an unsubstituted or substituted saturated or partially unsaturated cyclic radical which can contain, as ring members, hetero atoms from the group consisting of oxygen, sulfur and nitrogen, as well as carbon atoms, or an unsubstituted or substituted aromatic ring system which can contain hetero atoms from the group consisting of oxygen, sulfur and nitrogen, as well as carbon ring members.

This reaction is conventionally carried out at from 0° C. to 80° C., preferably 20° C. to 60° C., by standard methods [cf. Organikum, 17th Edition, p. 172 et seq. (1988)] in an inert solvent in the presence of a base.

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, and also dimethyl sulfoxide and dimethylformamide, particularly preferably methylene chloride, toluene, acetone, acetonitrile and dimethylformamide. Mixtures of these can also be used.

Bases which are generally suitable are inorganic compounds such as alkali metal hydroxides and alkaline earth metal hydroxides (eg. lithium hydroxide, sodium hydroxide, potassium hydroxide and calcium hydroxide), alkali metal oxides and alkaline earth metal oxides (eg. lithium oxide, sodium oxide, calcium oxide and magnesium oxide), silver oxide, alkali metal hydrides and alkaline earth metal hydrides (eg. lithium hydride, sodium hydride, potassium hydride and calcium hydride), alkali metal amides (eg. lithium amide, sodium amide and potassium amide), alkali metal carbonates and alkaline earth metal carbonates (eg. lithium carbonate and calcium carbonate), and also alkali metal hydrogen carbonates (eg. sodium hydrogen carbonate), organometal compounds, in particular alkali metal alkyls (eg. methyllithium, butyllithium and phenyllithium), alkylmagnesium halides (eg. methylmagnesium chloride) and alkali metal alcoholates and alkaline earth metal alcoholates (eg. sodium methanolate, sodium ethanolate, potassium ethanolate, potassium tert-butanolate and dimethoxymagnesium), furthermore organic bases, eg. tertiary amines such as trimethylamine, triethylamine, triisopropylethylamine and N-methylpiperidine, pyridine, substituted pyridines such as collidine, lutidine and 4-dimethylaminopyridine, and also bicyclic amines. Substances which are particularly preferred are sodium hydroxide, potassium carbonate and potassium tert-butanolate. The bases are generally used in equimolar amounts, in an excess or, if desired, as the solvent.

It may be advantageous for the reaction to add a catalytic amount of a crown ether (eg. 18-crown-6 or 15-crown-5) or 0.01 to 10% by weight of potassium iodide to act as a catalyst.

The reaction can also be carried out in two-phase systems composed of a solution of alkali metal hydroxides, alkali metal carbonates, alkaline earth metal hydroxides or alkaline earth metal carbonates in water and an organic phase (eg. aromatic and/or halogenated hydrocarbons). Suitable phase transfer catalysts are, for example, ammonium halides and ammonium tetrafluoroborates (eg. benzyltriethylammonium chloride, benzyltributylammonium bromide, tetrabutylammonium chloride, hexadecyltrimethylammonium bromide or terabutylammonium-tetrafluoroborate [sic]) and also phosphonium halides (eg. tetrabutylphosphonium chloride and tetraphenylphosphonium bromide).

It may be advantageous for the reaction first to react H—Y*—A¹ with the base to give the corresponding anion, which is then reacted with the benzyl derivative.

B.2 R=unsubstituted or substituted alkenyl.

The corresponding ethenylene derivatives I.6 are obtained by phosphorylating [sic] the benzyl halides I.2 and subsequently subjecting the phosphorus compounds I.5 with aldehydes to a Wittig or Wittig-Horner reaction.

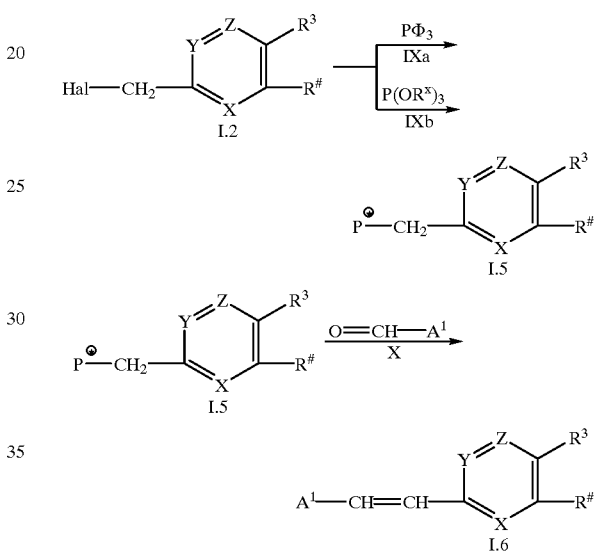

φ in formula IXa is aryl, in particular phenyl; $R^x$ in formula IXb is alkyl or aryl, in particular $C_1$–$C_4$-alkyl or phenyl.

In formulae X and I.5, $A^1$ is unsubstituted or substituted alkyl, alkenyl or alkynyl, or an unsubstituted or substituted saturated or partially unsaturated cyclic radical which can contain, as ring members, hetero atoms from the group consisting of oxygen, sulfur and nitrogen, as well as carbon atoms, or is an unsubstituted or substituted aromatic ring system which can contain hetero atoms from the group consisting of oxygen, sulfur and nitrogen, as well as carbon ring members.

The halides I.2 are reacted with the phosphines IXa or the phosphites IXb in a manner known per se [cf. Houben-Weyl, 4th Ed., Vol. XII/1, p. 79 et seq. and p. 433 et seq. (1963)].

The educts I.2 and IXa or IXb are generally reacted with each other in equimolar amounts. It may be advantageous for the yield to employ IXa or IXb in an excess based on I.2.

The resulting phosphorus derivatives I.5 are subsequently subjected to a Wittig or Wittig-Horner reaction with an aldehyde of the formula X at from −30° C. to 60° C., preferably 0° C. to 40° C., in an inert solvent in the presence of a base.

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitrites such as acetonitrile and propionitrile, ketones such as acetone, methyl ethyl ketone, diethyl ketone and tert-butyl methyl ketone, alcohols such as methanol, ethanol, n-propanol, isopropanol, n-butanol and tert-butanol and also dimethyl sulfoxide and dimethylformamide, particularly preferably diethyl ester, tetrahydrofuran, dimethyl sulfoxide and dimethylformamide. Mixtures of these can also be used.

Bases which are generally suitable are inorganic compounds such as alkali metal hydroxides and alkaline earth metal hydroxides such as lithium hydroxide, sodium hydroxide, potassium hydroxide and calcium hydroxide, alkali metal and alkaline earth metal oxides such as lithium oxide, sodium oxide, calcium oxide and [lacuna] sodium hydride, potassium hydride and calcium hydride, alkali metal amides such as lithium amide, sodium amide and potassium amide, alkali metal carbonates and alkaline earth metal carbonates such as lithium carbonate and calcium carbonate, and also alkali metal hydrogen carbonates such as sodium hydrogen carbonate, organometal compounds, in particular alkali metal alkyls such as methyllithium, butyllithium and phenyllithium, alkylmagnesium halides such as methylmagnesium chloride and also alkali metal alcoholates and alkaline earth metal alcoholates, such as sodium methanolate, sodium ethanolate, potassium ethanolate, potassium tert-butanolate and dimethoxymagnesium, furthermore organic bases, eg. tertiary amines such as trimethylamine, triethylamine, diisopropylethylamine and N-methylpiperidine, pyridine, substituted pyridines such as collidine, lutidine and 4-dimethylaminopyridine, and also bicyclic amines. Substances which are particularly preferably employed are sodium methanolate, potassium t-butylate, sodium hydride, potassium carbonate and n-butyllithium. The bases are generally employed in equimolar amounts, but they can also be used in an excess or, if desired, as the solvent.

The educts I.5 and X are generally reacted with each other in equimolar amounts. It may be advantageous for the yield to employ X in an excess based on I.5.

In a modification of the above process, the compounds I.6 are also obtained by first oxidizing the benzyl halide I.2 to give the corresponding benzaldehyde I.7 and subsequently reacting I.7 with a phosphorus compound Xa or Xb analogously to a Wittig or Wittig-Horner reaction.

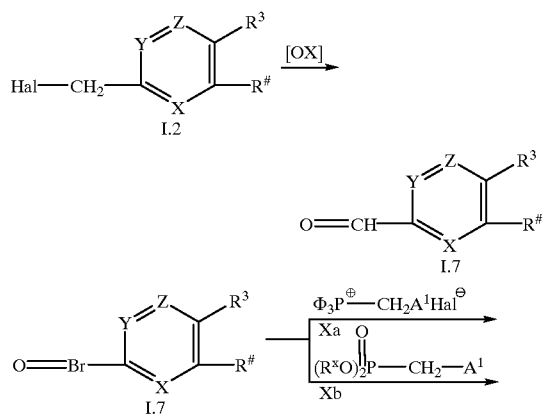

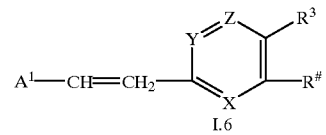

Suitable oxidants [OX] are, for example, methylmorpholine N-oxide monohydrate (cf. EP-A 393 428) or dimethyl sulfoxide [cf. J. Chem. Soc. 1964, p. 520; J. Org. Chem. 24, 1792 (1959)].

The subsequent Wittig or Wittig-Horner reaction is carried out under the above-described conditions.

B.3 R=organic radical bonded via oxy, mercapto or amino.

Compounds I where R is an organic radical which is bonded via an oxy, mercapto or amino group are obtained from the corresponding derivatives I.8 in accordance with the following equation:

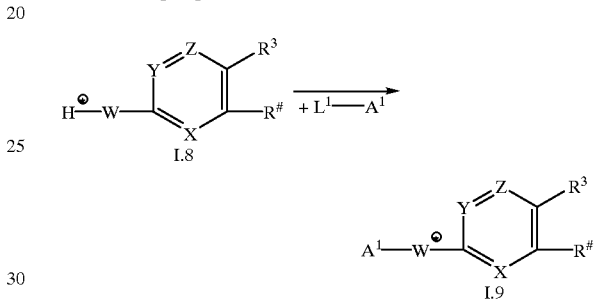

In formulae I.8 and I.9, W* is oxygen, sulfur, amino or alkylamino; $A^1$ has the abovementioned meanings.

$L^1$ in formula XI is a nucleophilically replaceable leaving group such as halogen (eg. chlorine, bromine and iodine) or alkyl- or arylsulfonate (eg. methylsulfonate, trifluoromethylsulfonate, phenylsulfonate and 4-methylphenylsulfonate).

This reaction is generally carried out in an inert solvent in the presence of a base and in the presence or absence of a transition metal catalyst following the principles of an Ullmann reaction [cf. Russ. Chem. Rev. 43, 679 (1974); J. Org. Chem. 29, 977 (1964)] or the principles of a nucleophilic substitution reaction [cf. J. Chem. Soc. 1942, 381, J. Heterocycl. Chem. 15, 1513 (1978)].

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, and also dimethyl sulfoxide and dimethylformamide, particularly preferably acetone and dimethylformamide. Mixtures of these can also be used.

The educts are generally reacted with each other in equimolar amounts. It may be advantageous for the yield to employ $L^1$—$A^1$ in an excess or a substoichiometric amount based on I.8.

B.4 $R^4$=—$CR^a$=N—$W^a$—$A^2$.

Compounds I where R is a group —$CR^a$—N—$W^a$—$A^2$ are obtained, for example, from the corresponding ketones I.10 by reacting them with an O-substituted hydroxylamine or hydroxylammonium salt or a hydrazine or hydrazonium salt in accordance with the methods described in EP-A 499 823 by the following equation.

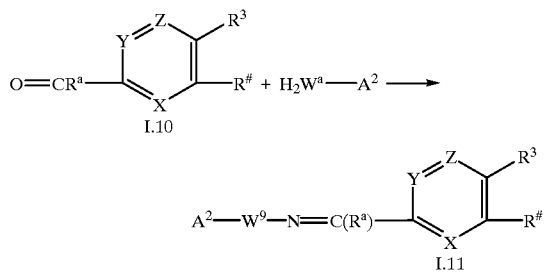

The radicals $R^a$, $W^a$ and $A^2$ in formulae I.10 and I.11 have the following meanings:
$R^a$ is hydrogen, alkyl, haloalkyl or unsubstituted or substituted aryl;
$W^a$ is oxygen, amino or alkylamino;
$A^2$ is hydrogen, unsubstituted or substituted alkyl, alkenyl or alkynyl, or
an unsubstituted or substituted saturated or partially unsaturated cyclic radical which can contain, as ring members, hetero atoms from the group consisting of oxygen, sulfur and nitrogen, as well as carbon atoms;
an unsubstituted or substituted aromatic ring system which can contain hetero atoms from the group consisting of oxygen, sulfur and nitrogen, as well as carbon ring members.

The reaction conditions, in general and in particular, correspond to the conditions described in the literature cited.

The ketones I.10 ($R^a \neq H$) are obtained from the aldehydes I.7 by oxidizing them to the carboxylic acids [cf. Organikum, 15th Edition, 447 (1977)], reacting the carboxylic acids to give the corresponding carboxylic acid halides [cf. Organikum, 15th Edition, 526 (1977)] and subsequently reacting the products with organotin compounds [cf. Org. React. (8), 28 (1954)].

B.5 $R^4$=—$CHR^c$—O—N=$CR^b$—$A^3$.

Compounds I where $R^4$ is a group —$CHR^c$—O—N=$CR^b$—$A^3$ are obtained, for example, from the benzyl halides I.2 by reacting them with a hydroxylimine XII following the methods described in EP-A 354 571, EP-A 370 629, EP-A 414 153, EP-A 426 460, EP-A 460 575, EP-A 472 300, EP-A 585 751, WO-A 90/07,493, WO-A 92/13,830, WO-A 92/18,487, WO-A 92/18,494, WO-A 93/16,986 and JP-A 05/201,946 in accordance with the following equation.

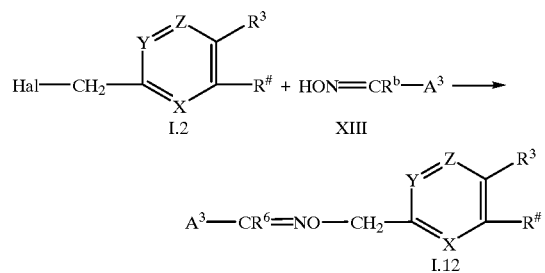

The radicals $R^b$, $R^c$ and $A^3$ in formulae I.2, XII and I.12 have the following meanings:
$R^b$ is hydrogen, cyano, nitro, halogen, alkyl, haloalkyl, cycloalkyl, alkoxy, haloalkoxy or unsubstituted or substituted aryl;
$R^c$ is hydrogen, alkyl or cycloalkyl;

$A^3$ is unsubstituted or substituted alkyl, alkenyl or alkynyl, or
an unsubstituted or substituted saturated or partially unsaturated cyclic radical which can contain, as ring members, hetero atoms from the group consisting of oxygen, sulfur and nitrogen, as well as carbon atoms;
an unsubstituted or substituted aromatic ring system which can contain hetero atoms from the group consisting of oxygen, sulfur and nitrogen, as well as carbon ring members.

The reaction conditions, in general and in particular, correspond to the conditions described in the literature cited.

B.6 $R^4$=—$CHR^f$—ON=$CR^e$—$CR^d$=NO—$A^4$.

Compounds I in which $R^4$ is a group —$CHR^f$—ON=$CR^e$—$CR^d$—NO—$A^4$ are obtained, for example, from the benzyl halides I.2 by reacting them with a dioxime XIV following the methods described in German Application Nos. P 44 21 180.5, P 44 21 181.3 and P 44 21 182.1 by the following equation.

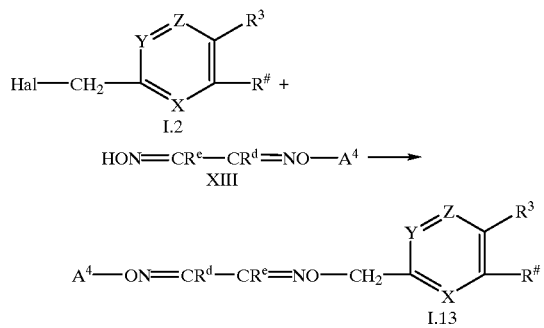

The radicals $R^f$, $R^e$, $R^d$ and $A^4$ in formulae I.2, XIV and I.13 have the following meanings:
$R^d$ and $R^e$ are hydrogen, cyano, nitro, halogen, alkyl, haloalkyl, cycloalkyl, alkoxy, haloalkoxy or unsubstituted or substituted aryl;
$R^f$ is hydrogen, alkyl or cycloalkyl;
$A^4$ is unsubstituted or substituted alkyl, alkenyl or alkynyl, or
an unsubstituted or substituted saturated or partially unsaturated cyclic radical which can contain, as ring members, hetero atoms from the group consisting of oxygen, sulfur and nitrogen, as well as carbon atoms;
an unsubstituted or substituted aromatic ring system which can contain hetero atoms from the group consisting of oxygen, sulfur and nitrogen, as well as carbon ring members.

The reaction is carried out in a manner known per se in an inert organic solvent in the presence of a base (eg. sodium hydride, sodium hydroxide, potassium carbonate and triethylamine) in accordance with the methods described in Houben-Weyl, Vol. E14b, p. 370 et seq. and Houben-Weyl, Vol. 10/1, p. 1189 et seq.

The dioxime XIV which is required is obtained by the following equation:

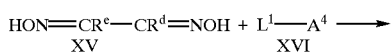
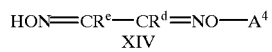

$L^2$ in formula XVI is a nucleophilically replaceable leaving group, eg. halogen or sulfonate groups, preferably chlorine, bromine, iodine, methylsulfonate, trifluoromethylsulfonate, phenylsulfonate or 4-methylphenylsulfonate.

The reaction is carried out in a manner known per se in an inert organic solvent in the presence of a base (eg. potassium carbonate, potassium hydroxide, sodium hydride, pyridine and triethylamine) in accordance with the methods described in Houben-Weyl Vol. E14b, p. 307 et seq., p. 370 et seq. and p. 385 et seq., Houben-Weyl Vol. 10/4, p. 55 et seq., p. 180 et seq. and p. 217 et seq. and Houben-weyl, Vol. E5, p. 780 et seq.

Similarly, the dioxime XIV is obtained by reacting the corresponding ketoxime XVII with an O-substituted hydroxylamine or a salt thereof (XVIII) by the following equation.

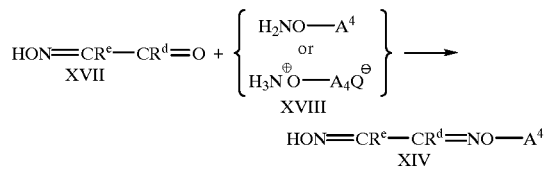

$Q^{\ominus}$ in formula XVIII is the anion of an acid, in particular an inorganic acid (eg. halide such as chloride or bromide).

The reaction is carried out in a manner known per se in an inert organic solvent following the methods described in EP-A 513 580, Houben-Weyl Vol. 10/4, p. 73 et seq. or Houben-Weyl Vol. E14b, page 369 et seq. and p. 385 et seq.

Alternatively, the compounds I.13 are also obtained by first reacting the benzyl halide I.2 with the dioxime XV to give the corresponding benzyloxime I.14 and subsequently converting I.14 with a compound XVI into I.13.

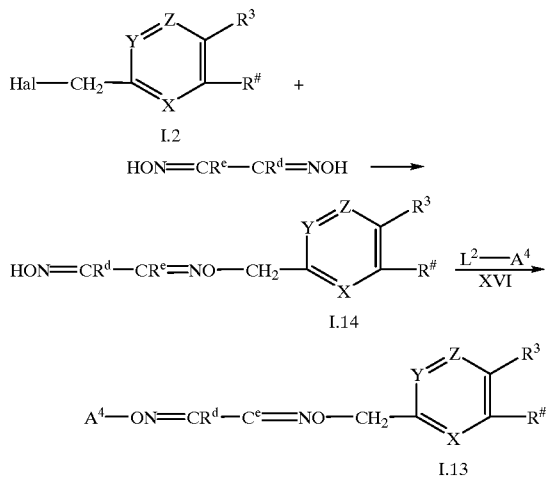

The reaction is carried out in a manner known per se in an inert organic solvent in the presence of a base (eg. potassium carbonate, potassium hydroxide, sodium hydride, pyridine and triethylamine in accordance with the methods described in Houben-Weyl Vol. 10/1, p. 1189 et seq., Houben-Weyl Vol. E14b, p. 307 et seq., p. 370 et seq. and p. 385 et seq., Houben-Weyl Vol. 10/4, p. 55 et seq. p. 180 et seq. and p. 214 et seq. and Houben-Weyl Vol. E5, p. 780 et seq.

A further possibility of preparing the compounds I.13 consists in first reacting the benzyl halide of the formula I.2 with N-hydroxyphthalimide, converting the resulting product into the corresponding benzylhydroxylamine (I.15) by means of hydrazinolysis and subsequently reacting I.13 with a ketoxime of the formula XVIIa to give I.13.

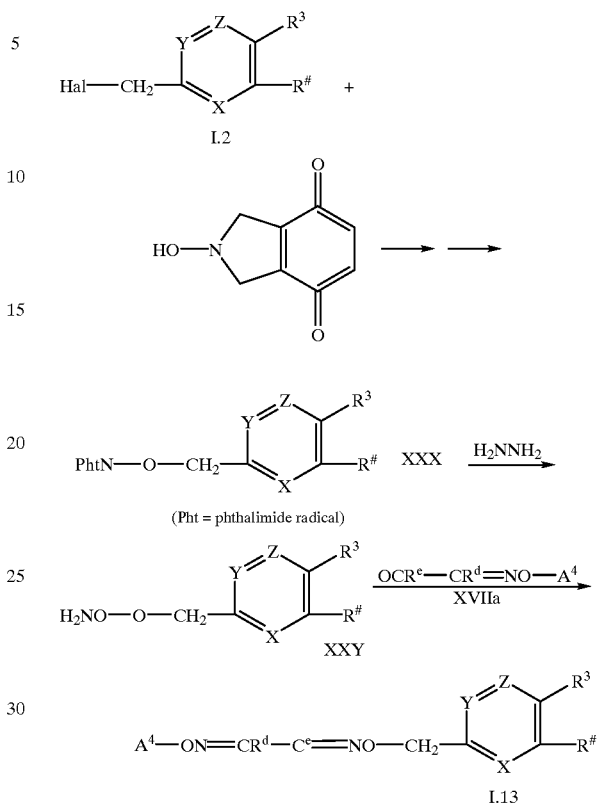

The benzyl halide I.2 is reacted to the benzylhydroxylamine I.15 in a manner known per se in an inert organic solvent following the methods described in EP-A 463 488 and EP-A 585 751.

Compounds I where $R^4$ is unsubstituted or substituted alkynyl are obtained from the compounds I.15 (R=halogen, in particular bromine and iodine) by reacting them with an acetylene derivative following the principles of a Heck reaction [cf. J. Organomet. Chem. 93, 259 (1975)] in the presence of a transition metal catalyst [TM], eg. a palladium or nickel compound such as diacetylpalladium, palladium dichloride, palladium terta(triphenylphosphine) [sic] or nickel dichloride, in an inert solvent (eg. dimethylformamide, acetonitrile, tetrahydrofuran or toluene) and in the presence of a base (eg. potassium carbonate, sodium hydride, diethylamine, triethylamine or pyridine).

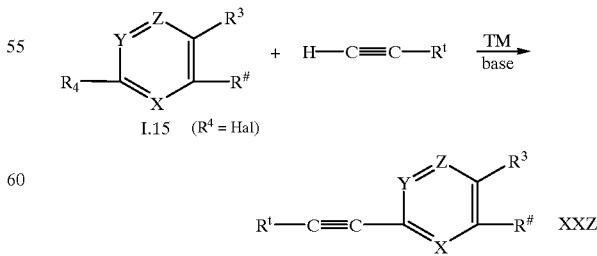

$R^t$ is hydrogen, unsubstituted or substituted alkyl, an unsubstituted or substituted saturated or partially unsaturated is cyclic radical which can contain, as ring members, hetero atoms from the group consisting of oxygen, sulfur and nitrogen, as well as carbon atoms, or an unsubstituted or substituted aromatic ring which can contain hetero atoms from the group consisting of oxygen, sulfur and nitrogen, as well as carbon ring members.

Particularly preferred compounds are alkyl phenylacetates of the formula I where $R^4$ is a group $A^1$—$Y^1$— in which $A^1$ and $Y^1$ have the following meanings:

$Y^1$ is a direct bond, oxygen, sulfur, amino or alkylamino;

$A^1$ is unsubstituted or substituted alkyl, alkenyl or alkynyl, or an optionally substituted saturated or partially unsaturated cyclic radical which can contain, as ring members, hetero atoms from the group consisting of oxygen, sulfur and nitrogen, as well as carbon atoms;

an unsubstituted or substituted aromatic ring system which can contain hetero atoms from the group consisting of oxygen, sulfur and nitrogen, as well as carbon ring members.

Other preferred alkyl phenylacetates of the formula I are those where $R^4$ is $CH_2OA^1$ in which $A^1$ is, in particular, an unsubstituted or substituted saturated or partially unsaturated cyclic radical which can contain, as ring members, hetero atoms from the group consisting of oxygen, sulfur and nitrogen, as well as carbon atoms, or in which $A^1$ is, in particular, an unsubstituted or substituted aromatic ring which can contain hetero atoms from the group consisting of oxygen, sulfur and nitrogen, as well as carbon ring members.

Equally, preferred alkyl phenylacetates of the formula I are those where $R^4$ is a group $A^2$—$W^a$N=$CR^a$— in which $A^2$, $Z^a$ and $R^a$ have the following meanings:

$R^a$ is hydrogen, alkyl, haloalkyl or unsubstituted or substituted aryl;

$W^a$ is oxygen, amino or alkylamino;

$A^2$ is hydrogen, unsubstituted or substituted alkyl, alkenyl or alkynyl, or an unsubstituted or substituted saturated or partially unsaturated cyclic radical which can contain, as ring members, hetero atoms from the group consisting of oxygen, sulfur and nitrogen, as well as carbon atoms, or an unsubstituted or substituted aromatic ring system which can contain hetero atoms from the group consisting of oxygen, sulfur and nitrogen, as well as carbon ring members.

In addition, preferred alkyl phenylacetates of the formula I are those where R is a group $A^3$—$CR^b$=NOCH$R^c$— in which $A^3$, $R^b$ and $R^c$ have the following meanings:

$R^b$ is hydrogen, cyano, nitro, halogen, alkyl, haloalkyl, cycloalkyl, alkoxy, haloalkoxy or unsubstituted or substituted aryl;

$R^c$ is hydrogen, alkyl or cycloalkyl;

$A^3$ is unsubstituted or substituted alkyl, alkenyl or alkynyl, or an optionally substituted saturated or partially unsaturated cyclic radical which can contain, as ring members, hetero atoms from the group consisting of oxygen, sulfur and nitrogen, as well as carbon atoms, or an unsubstituted or substituted aromatic ring system which can contain hetero atoms from the group consisting of oxygen, sulfur and nitrogen, as well as carbon ring members.

Moreover, preferred alkyl phenylacetates of the formula I are those where $R^4$ is a group $A^4$—ON=$CR^d$—$CR^e$=NO—CH$R^f$— in which $A^4$, $R^d$, $R^e$ and $R^f$ have the following meanings:

$R^d$ and $R^e$ are hydrogen, cyano, nitro, halogen, alkyl, haloalkyl, cycloalkyl, alkoxy, haloalkoxy or unsubstituted or substituted aryl;

$R^f$ is hydrogen, alkyl or cycloalkyl;

$A^4$ is unsubstituted or substituted alkyl, alkenyl or alkynyl, or an optionally substituted saturated or partially unsaturated cyclic radical which can contain, as ring members, hetero atoms from the group consisting of oxygen, sulfur and nitrogen, as well as carbon atoms, or an unsubstituted or substituted aromatic ring system which can contain hetero atoms from the group consisting of oxygen, sulfur and nitrogen, as well as carbon ring members.

Other particularly preferred alkyl phenylacetates of the formula I are those where $R^4$ and one of the radicals $R^3$ together with the phenyl ring to which they are bonded form an unsubstituted or substituted bicyclic ring from amongst the following group: benzofuran, benzothiophene, indole, isoindole or naphthalene.

In the definitions of the symbols given in the above formulae, collective terms were used which generally represent the following substituents:

halogen: fluorine, chlorine, bromine and iodine;

alkyl: saturated, straight-chain or branched hydrocarbon radicals having 1 to 10 carbon atoms, eg. $C_1$–$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-di-methylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

haloalkyl: straight-chain or branched alkyl groups having 1 to 10 carbon atoms (as mentioned above), it being possible for all or some of the hydrogen atoms in these groups to be replaced by halogen atoms as mentioned above, eg. $C_1$–$C_2$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

alkoxy: straight-chain or branched alkyl groups having 1 to 10 carbon atoms (as mentioned above) which are bonded to the skeleton via an oxygen atom (—O—);

haloalkoxy: straight-chain or branched haloalkyl groups having 1 to 10 carbon atoms (as mentioned above) which are bonded to the skeleton via an oxygen atom (—O—);

alkylthio: straight-chain or branched alkyl groups having 1 to 10 or 1 to 4 carbon atoms (as mentioned above) which are bonded to the skeleton via a sulfur atom (—S—);

alkylamino: a straight-chain or branched alkyl group having 1 to 10 carbon atoms (as mentioned above) which bonded to the skeleton via an amino group (—NH—);

alkenyl: unsaturated, straight-chain or branched hydrocarbon radicals having 2 to 10 carbon atoms and a double bond in any desired position, eg. $C_2$–$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl [sic], 1,1-dimethyl-2-propenyl, 1,2-dimethyl-1-propenyl, 1,2-dimethyl-2-propenyl, 1-ethyl-1-propenyl [sic], 1-ethyl-2-propenyl, 1-hexenyl, 2-hexenyl, 3-hexenyl, 4-hexenyl, 5-hexenyl, 1-methyl-1-pentenyl [sic], 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl [sic], 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1 -butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl [sic] and 1-ethyl-2-methyl-2-propenyl;

alkynyl: straight-chain or branched hydrocarbon groups having 2 to 10 carbon atoms and a triple bond in any desired position, eg. $C_2$–$C_6$-alkynyl such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

cycloalkyl: monocyclic alkyl groups having 3 to 12 carbon ring members, eg. $C_3$–$C_8$-cycloalkyl such as cyclopropyl, cyclobutyl, cyclopentyl, cyclohexyl, cycloheptyl and cyclooctyl;

saturated or partially unsaturated cyclic radical which can contain, as ring members, hetero atoms from the group consisting of oxygen, sulfur or nitrogen, as well as carbon atoms: cycloalkyl having 3 to 12 carbon ring members as mentioned above or 5- or 6-membered heterocycles (heterocyclyl) containing one to three nitrogen atoms and/or one oxygen or sulfur atom or one or two oxygen and/or sulfur atoms, as well as carbon ring members, eg. 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2,3-pyrrolin-2-yl, 2,3-pyrrolin-3-yl, 2,4-pyrrolin-2-yl, 2,4-pyrrolin-3-yl, 2,3-isoxazolin-3-yl, 3,4-isoxazolin-3-yl, 4,5-isoxazolin-3-yl, 2,3-isoxazolin-4-yl, 3,4-isoxazolin-4-yl, 4,5-isoxazolin-4-yl, 2,3-isoxazolin-5-yl, 3,4-isoxazolin-5-yl, 4,5-isoxazolin-5-yl, 2,3-isothiazolin-3-yl, 3,4-isothiazolin-3-yl, 4,5-isothiazolin-3-yl, 2,3-isothiazolin-4-yl, 3,4-isothiazolin-4-yl, 4,5-isothiazolin-4-yl, 2,3-isothiazolin-5-yl, 3,4-isothiazolin-5-yl, 4,5-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydro-triazin-2-yl and 1,2,4-tetrahydrotriazin-3-yl;

aryl: a mono- to trinuclear aromatic ring system containing 6 to 14 carbon ring members, eg. phenyl, naphthyl and anthracenyl;

aromatic ring system which can contain hetero atoms from the group consisting of oxygen, sulfur and nitrogen, as well as carbon ring members: aryl as mentioned above or mono- or dinuclear heteroaryl, eg.

5-membered heteroaryl containing one to four nitrogen atoms or one to three nitrogen atoms and one sulfur or oxygen atom: 5-membered heteroaryl groups which can contain, as ring members, one to four nitrogen atoms or one to three nitrogen atoms and one sulfur or oxygen atom, as well as carbon atoms, eg. 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl;

benzo-fused 5-membered heteroaryl containing one to three nitrogen atoms or one nitrogen atom and one oxygen or sulfur atom: 5-membered heteroaryl groups which can contain, as ring members, one to four nitrogen atoms or one to three nitrogen atoms and one sulfur or oxygen atom, as well as carbon atoms, and in which two adjacent carbon ring members or one nitrogen ring member and one adjacent carbon ring member can be bridged by a buta-1,3-diene-1,4-diyl group;

5-membered heteroaryl containing one to four nitrogen atoms which is bonded via nitrogen, or benzo-fused 5-membered heteroaryl containing one to three nitrogen atoms which is bonded via nitrogen: 5-membered heteroaryl groups which can contain, as ring members, one to four nitrogen atoms, or one to three nitrogen atoms, as well as carbon atoms, and in which two adjacent carbon ring members or one nitrogen ring member and one adjacent carbon ring member can be bridged by a buta-1,3-diene-1,4-diyl group, these rings being bonded to the skeleton via one of the nitrogen ring members;

6-membered heteroaryl containing one to three, or one to four, nitrogen atoms: 6-membered heteroaryl groups which can contain, as ring members, one to three, or one to four, nitrogen atoms as well as carbon atoms, eg. 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl;

alkylene: divalent unbranched chains composed of 3 to 5 $CH_2$ groups, eg. $-CH_2-$, $-CH_2CH_2-$, $-CH_2CH_2CH_2-$, $-CH_2CH_2CH_2CH_2-$ and $-CH_2CH_2CH_2CH_2CH_2-$;

oxyalkylene: divalent unbranched chains composed of 2 to 4 $CH_2$ groups, one valency being bonded to the skeleton via an oxygen atom, eg. $-OCH_2CH_2-$, $-OCH_2CH_2CH_2-$ and $-OCH_2CH_2CH_2CH_2-$;

oxyalkylenoxy: divalent unbranched chains composed of 1 to 3 $CH_2$ groups, both valencies being bonded to the skeleton via an oxygen atom, eg. $-OCH_2O-$, $-OCH_2CH_2O-$ and $-OCH_2CH_2CH_2O-$;

alkenylene: divalent unbranched chains composed of 1 to 3 $CH_2$ groups and one $CH=CH$ group in any desired position, eg. $-CH=CHCH_2-$, $-CH_2CH=CHCH_2-$, $-CH=CHCH_2CH_2-$, $-CH_2CH=CHCH_2CH_2-$ and $-CH=CHCH_2CH_2CH_2-$;

oxyalkenylene: divalent unbranched chains composed of 0 to 2 $CH_2$ groups and one $CH=CH$ group in any desired position, one valency being bonded to the skeleton via an oxygen atom, eg. $-OCH=CH-$, $-OCH=CHCH_2-$, $-OCH_2CH=CH-$, $-OCH_2CH=CHCH_2-$, $-OCH=CHCH_2CH_2-$ and $-OCH_2CH_2-CH=CH-$;

oxyalkenylenoxy: divalent unbranched chains composed of 0 to 2 $CH_2$ groups and one $CH=CH$ group in any desired position, both valencies being bonded to the skeleton via an oxygen atom, eg. $-OCH=CHO-$, $-OCH=CHCH_2O-$, $-OCH_2CH=CHCH_2O-$ and $-OCH=CHCH_2CH_2O-$;

organic radical: unsubstituted or substituted alkyl, alkenyl, alkynyl, cycloalkyl, heterocyclyl, aryl or hetaryl.

The added term "unsubstituted or substituted", when referring to alkyl, alkenyl and alkynyl groups, is intended to express the fact that these groups can be partially or fully halogenated (eg. some or all of the hydrogen atoms of these groups can can [sic] be replaced by identical or different halogen atoms as mentioned above (preferably fluorine, chlorine or bromine) and/or can have attached to them one to three (preferably one) of the following radicals:

cyano, nitro, hydroxyl, amino, formyl, carboxyl, aminocarbonyl, alkoxy, haloalkoxy, alkylthio, haloalkylthio, alkylamino, dialkylamino, alkylcarbonyl, alkoxycarbonyl, alkylcarbonyloxy, alkylaminocarbonyl, dialkylaminocarbonyl, alkylcarbonylamino, alkoxycarbonylamino, alkylcarbonyl-N-alkylamino and alkylcarbonyl-N-alkylamino, the alkyl groups in these radicals preferably containing 1 to 6 carbon atoms, in particular 1 to 4 carbon atoms;

cycloalkyl, cycloalkoxy, cycloalkylthio, cycloalkylamino, cycloalkyl-n-alkylamino, heterocyclyl, heterocyclyloxy, heterocyclylthio, heterocyclylamino or heterocyclyl-N-alkylamino, each of which is unsubstituted or substituted by customary groups, the cyclic systems containing 3 to 12 ring members, preferably 2 to 8 ring members, in particular 3 to 6 ring members, and the alkyl groups in these radicals preferably containing 1 to 6 carbon atoms, in particular 1 to 4 carbon atoms;

aryl, aryloxy, arylthio, arylamino, aryl-n-alkylamino, arylalkoxy, arylalkylthio, arylalkylamino, arylalkyl-N-alkylamino, hetaryl, hetaryloxy, hetarylthio, hetarylamino, hetaryl-N-alkylamino, hetarylalkoxy, hetarylalkylthio, hetarylalkylamino and hetarylalkyl-N-alkylamino, each of which is unsubstituted or substituted by customary groups, the aryl radicals preferably containing 6 to 10 ring members, in particular 6 ring members (phenyl), the hetaryl radicals containing in particular 5 or 6 ring members and the alkyl groups in these radicals preferably containing 1 to 6 carbon atoms, in particular 1 to 4 carbon atoms.

The added term "unsubstituted or substituted" when referring to the cyclic (saturated, unsaturated or aromatic) groups is intended to express the fact that these groups can be partially or fully halogenated (eg. some or all of the hydrogen atoms of these groups can can [sic] be replaced by identical or different halogen atoms as mentioned above (preferably fluorine, chlorine or bromine, in particular fluorine or chlorine) and/or can have attached to them one to four (in particular one to three) of the following radicals cyano, nitro, hydroxyl, amino, carboxyl, aminocarbonyl, alkyl, haloalkyl, alkenyl, haloalkenyl, alkenyloxy, haloalkenyloxy, alkynyl, haloalkynyl, alkynyloxy, haloalkynyloxy, alkoxy, haloalkoxy, alkylthio, haloalkylthio, alkylamino, dialkylamino, alkylcarbonyl, alkoxycarbonyl, alkylcarbonyloxy, alkylaminocarbonyl, dialkylaminocarbonyl, alkylcarbonylamino, alkoxycarbonylamino, alkylcarbonyl-N-alkylamino and alkylcarbonyl-N-alkylamino, the alkyl groups in these radicals preferably containing 1 to 6 carbon atoms, in particular 1 to 4 carbon atoms, and the alkenyl or alkynyl groups which have been mentioned in these radicals containing 2 to 8, preferably 2 to 6, in particular 2 to 4, carbon atoms;

and/or one to three (in particular one) of the following radicals cycloalkyl, cycloalkoxy, cycloalkylthio, cycloalkylamino, cycloalkyl-N-alkylamino, heterocyclyl, heterocyclyloxy, heterocyclylthio, heterocyclylamino or heterocyclyl-N-alkylamino, each of which is unsubstituted or substituted by customary groups, the cyclic systems containing 3 to 12 ring members, preferably 2 to 8 ring members, in particular 3 to 6 ring members, and the alkyl groups in these radicals preferably containing 1 to 6 carbon atoms, in particular 1 to 4 carbon atoms;

aryl, aryloxy, arylthio, arylamino, aryl-n-alkylamino, arylalkoxy, arylalkylthio, arylalkylamino, arylalkyl-N-alkylamino, hetaryl, hetaryloxy, hetarylthio, hetarylamino, hetaryl-N-alkylamino, hetarylalkoxy, hetarylalkylthio, hetarylalkylamino and hetarylalkyl-N-alkylamino, each of which is unsubstituted or substituted by customary groups, the aryl radicals preferably containing 6 to 10 ring members, in particular 6 ring members (phenyl), the hetaryl radicals containing in particular 5 or 6 ring members and the alkyl groups in these radicals preferably containing 1 to 6 carbon atoms, in particular 1 to 4 carbon atoms and/or one or two (in particular one) of the following radicals formyl or $CR^{iii}=NOR^{iv}$ where $R^{iii}$ is hydrogen or alkyl and $R^{iv}$ is alkyl or arylalkyl and where the alkyl groups mentioned preferably contain 1 to 6 carbon atoms, in particular 1 to 4 carbon atoms, and aryl is, in particular, phenyl which is unsubstituted or can carry [sic], can be substituted by customary groups, or where two adjacent C atoms of the cyclic systems can have attached to them a $C_3$–$C_5$-alkylene, $C_3$–$C_5$-alkenylene, oxy-$C_2$–$C_4$-alkylene, oxy-$C_1$–$C_3$-alkylenoxy, oxy-$C_2$–$C_4$-alkenylene, oxy-$C_2$–$C_4$-alkenylenoxy or butadienediyl group, it being possible for these bridges, in turn, to be partially or fully halogenated and/or to have attached to them one to three, in particular one or two of the following radicals: $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio.

Customary groups are to be understood as meaning, in particular, the following substituents: halogen, cyano, nitro, $C_1$–$C_4$-alkyl, $C_1$–$C_4$-haloalkyl, $C_1$–$C_4$-alkyoxy, $C_1$–$C_4$-haloalkoxy, $C_1$–$C_4$-alkylamino, di-$C_1$–$C_4$-alkylamino and $C_1$–$C_4$-alkylthio.

With regard to their biological activity, particularly preferred compounds of the formula I.A

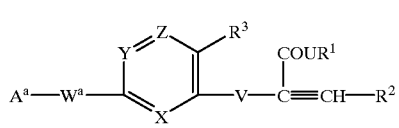

I.A are those where the substituents have the following meanings:

$W^a$ is oxymethylene, methylenoxy, ethylene or ethenylene, $A^a$ is aryl or heteroaryl, each of which can be substituted by customary groups and/or can have attached to it one or two (in particular one) of the following radicals: formyl or $CR^{iii}$=$NOR^{iv}$.

Particularly preferred compounds I.A are those where $W^a$ is methylenoxy.

Other particularly preferred compounds I.A are those where $W^a$ is oxymethylene.

Also particularly preferred compounds I.A are those where $W^a$ is ethenylene.

Other particularly preferred compounds I.A are those where $W^a$ is ethylene.

Other compounds I.A which are particularly preferred are those where $A^a$ is unsubstituted or substituted aryl.

Other particularly preferred compounds I.A are those where $A^a$ is an unsubstituted or substituted 6-membered heteroaryl ring.

Also particularly preferred compounds I.A are those where $A^a$ is an unsubstituted or substituted 5-membered heteroaryl ring.

Other particularly preferred compounds I.A are those where $A^a$ is unsubstituted or substituted aryl which has attached to it a group $CR^{iii}$=$NOR^{iv}$.

Furthermore, compounds I.A which are particularly preferred are those where $A^a$ is unsubstituted or substituted phenyl which has attached to it a group $CR^{ii}$=O.

Other particularly preferred compounds I.A are those where $A^a$ is unsubstituted or substituted phenyl which has attached to it a group $CR^{iii}$=$NOR^{iv}$.

Also particularly preferred compounds I.A are those where $A^a$ is unsubstituted or substituted pyridyl or pyrimidyl.

Other preferred compounds of the formula I.B

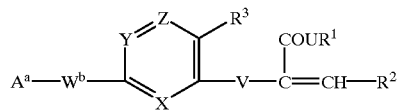

I.B are those where the substituents have the following meanings:

$W^b$ is a direct bond, oxygen, sulfur, amino or alkylamino, and $A^b$ is aryl or heteroaryl, each of which can be substituted by customary groups and/or can have attached to it one or two (in particular one) of the following radicals: formyl, $CR^{iii}$=$NOR^{iv}$ or aryl which is unsubstituted or substituted by customary groups (in particular phenyl) or heteroaryl (in particular pyridyl, pyrimidyl or triazinyl).

Particularly preferred compounds I.B are those where $W^b$ is oxygen.

Also preferred compounds I.B are those where $W^b$ is a direct bond.

Other particularly preferred compounds I.B are those where $W^b$ is sulfur.

Particularly preferred compounds I.B are also those where $W^b$ is unsubstituted or substituted aryl.

Other particularly preferred compounds I.B are those where $W^b$ is an unsubstituted or substituted 6-membered heteroaryl ring.

Also particularly preferred compounds I.B are those where $A^b$ is an unsubstituted or substituted aryl or hetaryl ring from the group consisting of phenyl, pyridyl, pyrimidyl, pyrazinyl and 1,3,5-triazinyl.

Other particularly preferred compounds I.B are those where $A^b$ is unsubstituted or substituted 4-pyridinyl which has an unsubstituted or substituted phenoxy radical attached to it in the 6-position.

Furthermore, compounds I.B which are particularly preferred are those where $A^b$ is unsubstituted or substituted pyrimidyl which has attached to it an unsubstituted or substituted pyridinyloxy radical.

Also particularly preferred compounds I.B are those where $A^b$ is unsubstituted or substituted 1,3,5-triazinyl which has an unsubstituted or substituted phenoxy radical attached to it in the 4-position.

Other preferred compounds of the formula I.C

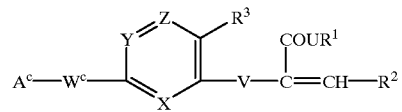

I.C are those where the substituents have the following meanings:

$R^1$ and $R^2$ are $C_1$–$C_4$-alkyl, $W^c$ is $CR^{\gamma}R^{\delta}$—C(=O)—$T_c$—*

--- is a single or double bond where, in the case of a single bond, the C atoms in question in each case also have a hydrogen atom attached to them, $R^\gamma$ is hydrogen or alkyl, $R^a$ is hydrogen, cyano, nitro, halogen or alkyl, T is oxygen, sulfur, amino or alkylamino, c is 0 or 1,
—* is a bond to $A^c$,
$A^c$ is alkyl, alkenyl, alkynyl, cycloalkyl or is aryl, arylalkyl, arylalkenyl, heteroaryl, heteroarylalkyl or heteroarylalkenyl, each of which is unsubstituted or substituted by customary groups.

Particularly preferred compounds I.C are those where $W^c$ is CH=C(halo)-C(=O)—O—*.

Other particularly preferred compounds I.C are those where $W^c$ is CH=C(halo)-C(=O)—NH—*.

Also particularly preferred compounds I.C are those where $W^c$ is CH=C(halo)-C(=O)—NH—*.

Other particularly preferred compounds I.C are those where $W^c$ is CH=C(halo)-C(=O)—*.

Particularly preferred compounds I.C are also those where $A^c$ is alkyl.

Other particularly preferred compounds I.C are those where $A^c$ is alkenyl.

Also particularly preferred compounds I.C are those where $A^c$ is alkynyl.

Furthermore, compounds of the formula I.D which are preferred $$A^d-CO-O-CH_2 \underset{X}{\overset{Y\overset{Z}{=}}{\bigcirc}} \overset{R^3}{-}V-\underset{|}{C}=CH-R^2 \quad \text{I.D}$$
$$\phantom{A^d-CO-O-CH_2 \underset{X}{\overset{Y\overset{Z}{=}}{\bigcirc}} \overset{R^3}{-}V-}\overset{COUR^1}{\phantom{C}}$$

are those where $A^d$ has the following meaning:
$A^d$ is cycloalkyl which can have attached to it one to four of the following substituents: cyano, halogen, alkyl, haloalkyl, alkoxycarbonyl, or aryl, arylalkyl or arylalkenyl, each of which is unsubstituted or substituted by customary groups.

Particularly preferred compounds I.D are those where $A^d$ is unsubstituted or substituted cyclopropyl.

Compounds of the formula I.E $$A^e-W^e \underset{X}{\overset{Y\overset{Z}{=}}{\bigcirc}} \overset{R^3}{-}V-\underset{|}{C}=CH-R^2 \quad \text{I.E}$$
$$\phantom{A^e-W^e \underset{X}{\overset{Y\overset{Z}{=}}{\bigcirc}} \overset{R^3}{-}V-}\overset{COUR^1}{\phantom{C}}$$

which are furthermore preferred are those where the substituents have the following meanings:
$W^e$ is $CR^a$=N—$T^a$-#,
$R^a$ is hydrogen, alkyl, haloalkyl, or is aryl which is unsubstituted or substituted by customary groups,
$T^a$ is oxygen, amino or alkylamino,
-# is a bond to $A^e$,
$A^e$ is hydrogen,
unsubstituted or substituted alkyl, alkylcarbonyl, alkoxycarbonyl, alkenyl, alkenylcarbonyl, alkenyloxycarbonyl, alkynyl, alkynylcarbonyl and alkynyloxycarbonyl, or
unsubstituted or substituted cycloalkyl, heterocyclyl, aryl, arylalkyl, aryloxyalkyl, arylalkenyl, aryloxyalkenyl, arylcarbonyl, aryloxycarbonyl, hetaryl, hetarylalkyl, hetaryloxyalkyl, hetarylalkenyl, hetaryloxyalkenyl, hetarylcarbonyl and hetaryloxycarbonyl.

Particularly preferred compounds I.E are those where $W^e$ is $CH(CH_3)$=N—O-#.

Other particularly preferred compounds I.E are those where $W^e$ is $CH(CH_3)$=N—NH-#.

Also particularly preferred compounds I.E are those where $W^e$ is CH=N—N(CH_3)-#.

Particularly preferred compounds I.E are also those where $A^e$ is alkyl.

Other particularly preferred compounds I.E are those where $A^e$ is unsubstituted or substituted arylalkyl.

Also particularly preferred compounds I.E are those where $A^e$ is unsubstituted or substituted hetarylalkyl.

Compounds of the formula I.F $$A^f-OCH_2 \underset{X}{\overset{Y\overset{Z}{=}}{\bigcirc}} \overset{R^3}{-}V-\underset{|}{C}=CH-R^2 \quad \text{I.F}$$
$$\phantom{A^f-OCH_2 \underset{X}{\overset{Y\overset{Z}{=}}{\bigcirc}} \overset{R^3}{-}V-}\overset{COUR^1}{\phantom{C}}$$

which are equally preferred are those where the substituents have the following meanings:
$A^f$ is a phthalimide group which is unsubstituted or substituted by customary groups, or is a radical —N=$CR^gR^h$,
$R^g$ is hydrogen, halogen, cyano, nitro,
unsubstituted or substituted alkyl, alkenyl or alkynyl,
unsubstituted or substituted cycloalkyl, heterocyclyl, aryl or heteroaryl,
$R^h$ is hydrogen, unsubstituted or substituted alkyl, alkoxy, alkylcarbonyl, alkoxycarbonyl, alkenyl, alkenyloxy, alkenylcarbonyl, alkenyloxycarbonyl, alkynyl, alkynyloxy, alkynylcarbonyl and alkynyloxycarbonyl,
unsubstituted or substituted cycloalkyl, cycloalkyloxy, heterocyclyl, heterocyclyloxy, aryl, aryloxy, arylalkyl, arylalkoxy, aryloxyalkyl, aryloxyalkoxy, arylalkenyl, arylalkenyloxy, aryloxyalkenyl, aryloxyalkenyloxy, arylcarbonyl, arylcarbonyloxy, aryloxycarbonyl, aryloxycarbonyloxy, hetaryl, hetaryloxy, hetarylalkyl, hetarylalkyloxy, hetaryloxyalkyl, hetaryloxyalkyloxy, hetarylalkenyl, hetarylalkenyloxy, hetaryloxyalkenyl, hetaryloxyalkenyloxy, hetarylcarbonyl, hetarylcarbonyloxy, hetaryloxycarbonyl and hetaryloxycarbonyloxy, or
$R^g$ and $R^h$ together with the C atom to which they are bonded are cycloalkyl, cycloalkenyl or saturated or partially unsaturated heterocyclyl, each of which is unsubstituted or substituted by customary groups.

Particularly preferred compounds I.F are also those where $R^g$ is alkyl.

Also particularly preferred compounds I.F are those where $R^g$ is cycloalkyl.

Other particularly preferred compounds I.F are those where $R^g$ is haloalkyl.

Moreover, compounds I.F which are particularly preferred are those where $R^g$ is cyano.

Other particularly preferred compounds I.F are those where $R^g$ is alkylthio.

Other particularly preferred compounds I.F are those where $R^g$ is methyl, ethyl, n-propyl, cyclopropyl, trifluoromethyl, cyano or methylthio.

Particularly preferred compounds I.F are also those where $R^h$ is unsubstituted or substituted aryl.

Other particularly preferred compounds I.F are those where $R^h$ is unsubstituted or substituted heteroaryl.

Also particularly preferred compounds I.F are those where $R^h$ is alkyl.

Other particularly preferred compounds I.F are those where $R^h$ is cycloalkyl.

Moreover, compounds I.F which are particularly preferred are those where $R^h$ is unsubstituted or substituted phenyl or pyridyl.

Moreover, preferred compounds of the formula I.G

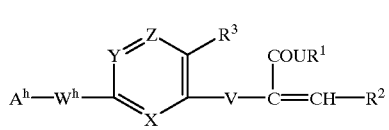

I.G are those where the substituents have the following meanings:

$W^h$ is $CHR^f$—ON=$CR^e$—$CR^d$=NO-#, $R^d$ and $R^e$ are hydrogen, cyano, nitro, halogen, alkyl, haloalkyl, cycloalkyl, alkoxy, haloalkoxy or unsubstituted or substituted aryl;

$R^f$ is hydrogen, alkyl or cycloalkyl;

-# is a bond to $A^k$, $A^h$ is hydrogen, $C_1$–$C_{10}$-alkyl, $C_3$–$C_6$-cycloalkyl, $C_2$-$C_{10}$-alkenyl, $C_3$–$C_{10}$-alkynyl, $C_1$–$C_{10}$-alkylcarbonyl, $C_2$-$C_{10}$-alkenylcarbonyl, $C_3$–$C_{10}$-alkynylcarbonyl or $C_1$–$C_{10}$-alkylsulfonyl, it being possible for these groups to be partially or fully halogenated or to have attached to them one to 3 of the following groups: cyano, nitro, hydroxyl, merkapto [sic], amino, carboxyl, aminocarbonyl, aminothiocarbonyl, halogen, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, arylthio, hetaryl, hetaryloxy and hetarylthio, it being possible for the aromatic and heteroaromatic radicals, in turn, to be partially or fully halogenated and/or to have attached to them one to three of the following groups: cyano, nitro, hydroxyl, mercapto, amino, carboxyl, aminocarbonyl, halogen, aminothiocarbonyl, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkyloxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, arylthio, hetaryl, hetaryloxy, hetarylthio or $C(=NOR^1)$—$X_o$—$R^2$;

aryl, hetaryl, arylcarbonyl, hetarylcarbonyl, arylsulfonyl or hetarylsulfonyl, it being possible for these groups to be partially or fully halogenated or to have attached to them one to 3 of the following groups: cyano, nitro, hydroxyl, merkapto [sic], amino, carboxyl, aminocarbonyl, aminothiocarbonyl, halogen, $C_1$–$C_6$-alkyl, $C_1$–$C_6$-haloalkyl, $C_1$–$C_6$-alkylcarbonyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, hetaryl, hetaryloxy or $C(=NOR^1)$—$X_o$—$R^2$;

where

T is oxygen, sulfur or nitrogen and where the nitrogen has hydrogen or $C_1$–$C_6$-alkyl attached to it;

o is 0 or 1;

$R^1$ is hydrogen or $C_1$–$C_6$-alkyl and $R^2$ is hydrogen or $C_1$–$C_6$-alkyl.

Particularly preferred compounds I.H are those where $W^h$ is $CH_2$—ON=$C(CH_3)$—$C(alkyl)$=N—O-#.

Other particularly preferred compounds I.H are those where $W^h$ is $CH_2$—ON=$C(CH_3)$—$C(aryl)$=NO-#.

Also particularly preferred compounds I.K are those where $Y^k$ is $CH_2$—ON=$C(CH_3)$—$C(cycloalkyl)$=NO-#.

In addition, particularly preferred compounds I.H are those where $W^h$ is $CH_2$—ON=$C(CH_3)$—$C(hetaryl)$=NO-#.

Particularly preferred compounds I.H are also those where $W^h$ is $CH_2$—ON=$C(CH_3)$—$C(CH_3)$=NO-#.

Other particularly preferred compounds I.H are those where $W^h$ is $CH_2$—ON=$C(CH_3)$—$C(C_6H_5)$=NO-#.

Also particularly preferred compounds I.H are those where $A^h$ is hydrogen or $C_1$–$C_6$-alkyl.

In addition, particularly preferred compounds I.H are those where $A^h$ is unsubstituted or substituted arylalkyl, hetarylalkyl, aryloxyalkyl or hetaryloxyalkyl.

Moreover, particularly preferred compounds I.H are those where $A^h$ is unsubstituted or substituted aryl or heteroaryl.

Other particularly preferred compounds I.H are those where $A^h$ is methyl or ethyl.

Also particularly preferred compounds I.H are those where $A^h$ is unsubstituted or substituted arylalkyl or heteroarylalkyl.

Particularly preferred compounds I (or I.A to I.H) are those where U is oxygen and V is oxygen or amino.

Moreover, compounds I (or I.A to I.H) which are particularly preferred are those where U is amino and V is oxygen.

Moreover, compounds I (or I.A to I.H) which are particularly preferred are those where U is aminooxy and V is oxygen.

Particularly preferred compounds I (or I.A to I.H) are those where $R^1$ is methyl or ethyl, in particular methyl.

Other particularly preferred compounds I (or I.A to I.H) are those where $R^2$ is methyl or ethyl, in particular methyl.

With a view to their biological activity, the isomer mixtures and also the pure isomers can be employed, it being possible for the pure isomers to be more active than the isomer mixtures.

With a view to their use, the compounds I, which have been compiled in the tables which follow, are particularly preferred. Moreover, the groups mentioned in the tables for a substituent are, themselves (independently of the combination in which they are mentioned), a particularly preferred embodiment of the substituent in question.

Table 1

Compounds of the formula I.A where $R^1$ and $R^2$ are methyl, $R^3$ is hydrogen, U and V are oxygen, $W^a$ is a direct bond, X, Y and Z are =CH— and $A^a$ for a compound in each case corresponds to one group of Table A.

Table 2

Compounds of the formula I.A where $R^1$ and $R^2$ are methyl, $R^3$ is hydrogen, U and V are oxygen, $W^a$ is —CH=CH—, X, Y and Z are =CH— and $A^a$ for a compound in each case corresponds to one group of Table A.

Table 3
Compounds of the formula I.A where $R^1$ and $R^2$ are methyl, $R^3$ is hydrogen, U and V are oxygen, $W^a$ is —C≡C—, X, Y and Z are =CH— and $A^a$ for a compound in each case corresponds to one group of Table A.

Table 4
Compounds of the formula I.A where $R^1$ and $R^2$ are methyl, $R^3$ is hydrogen, U and V are oxygen, $W^a$ is oxygen (—O—), X, Y and Z are =CH— and $A^a$ for a compound in each case corresponds to one group of Table A.

Table 5
Compounds of the formula I.A where $R^1$ and $R^2$ are methyl, $R^3$ is hydrogen, U and V are oxygen, $W^a$ is —CH$_2$O—* (*=bond to $A^a$), X, Y and Z are =CH— and $A^a$ for a compound in each case corresponds to one group of Table A.

Table 6
Compounds of the formula I.A where $R^1$ and $R^2$ are methyl, $R^3$ is hydrogen, U and V are oxygen, $W^a$ is —OCH$_2$—* (*=bond to $A^a$), X, Y and Z are =CH— and $A^a$ for a compound in each case corresponds to one group of Table A.

Table 7
Compounds of the formula I.A where $R^1$ and $R^2$ are methyl, $R^3$ is hydrogen, U and V are oxygen, $W^a$ is —CO—O—* (*=bond to $A^a$), X, Y and Z are =CH— and $A^a$ for a compound in each case corresponds to one group of Table A.

Table 8
Compounds of the formula I.A where $R^1$ and $R^2$ are methyl, $R^3$ is hydrogen, U and V are oxygen, $W^a$ is —O—CO—* (*=bond to $A^a$), X, Y and Z are =CH— and $A^a$ for a compound in each case corresponds to one group of Table A.

Table 9
Compounds of the formula I.A where $R^1$ and $R^2$ are methyl, $R^3$ is hydrogen, U and V are oxygen, $W^a$ is —CO—NH—* (*=bond to $A^a$), X, Y and Z are =CH— and $A^a$ for a compound in each case corresponds to one group of Table A.

Table 10
Compounds of the formula I.A where $R^1$ and $R^2$ are methyl, $R^3$ is hydrogen, U and V are oxygen, $W^a$ is —NH—CO—* (*=bond to $A^a$), X, Y and Z are =CH— and $A^a$ for a compound in each case corresponds to one group of Table A.

Table 11
Compounds of the formula I.A where $R^1$ and $R^2$ are methyl, $R^3$ is hydrogen, U and V are oxygen, $W^a$ is —C(CH$_3$)=NO—* (*=bond to $A^a$), X, Y and Z are =CH— and $A^a$ for a compound in each case corresponds to one group of Table A.

Table 12
Compounds of the formula I.A where $R^1$ and $R^2$ are methyl, $R^3$ is hydrogen, U and V are oxygen, $W^a$ is —CH$_2$O—N=C(CH$_3$)—* (*=bond to $A^a$), X, Y and Z are =CH— and $A^a$ for a compound in each case corresponds to one group of Table A.

Table 13
Compounds of the formula I.A where $R^1$ and $R^2$ are methyl, $R^3$ is hydrogen, U and V are oxygen, $W^a$ is —CH$_2$O—N=C(CH$_3$)—C(C$_6$H$_5$)=NO—* (*=bond to $A^a$), X, Y and Z are =CH— and $A^a$ for a compound in each case corresponds to one group of Table A.

Table 14
Compounds of the formula I.A where $R^1$ and $R^2$ are methyl, $R^3$ is hydrogen, U and V are oxygen, $W^a$ is —CH$_2$O—N=C(CH$_3$)—C(2-Cl—C$_6$H$_4$)=NO—* (*=bond to $A^a$), X, Y and Z are =CH— and $A^a$ for a compound in each case corresponds to one group of Table A.

Table 15
Compounds of the formula I.A where $R^1$ and $R^2$ are methyl, $R^3$ is hydrogen, U and V are oxygen, $W^a$ is —CH$_2$O—N=C(CH$_3$)—C(4-Cl—C$_6$H$_4$)=NO—* (*=bond to $A^a$), X, Y and Z are =CH— and $A^a$ for a compound in each case corresponds to one group of Table A.

Table 16
Compounds of the formula I.A where $R^1$ and $R^2$ are methyl, $R^3$ is hydrogen, U and V are oxygen, $W^a$ is a direct bond, X is =N—, Y and Z are =CH— and $A^a$ for a compound in each case corresponds to one group of Table A.

Table 17
Compounds of the formula I.A where $R^1$ and $R^2$ are methyl, $R^3$ is hydrogen, U and V are oxygen, $W^a$ is —CH=CH—, X is =N—, Y and Z are =CH— and $A^a$ for a compound in each case corresponds to one group of Table A.

Table 18
Compounds of the formula I.A where $R^1$ and $R^2$ are methyl, $R^3$ is hydrogen, U and V are oxygen, $W^a$ is —C≡C—, X is =N—, Y and Z are =CH— and $A^a$ for a compound in each case corresponds to one group of Table A.

Table 19
Compounds of the formula I.A where $R^1$ and $R^2$ are methyl, $R^3$ is hydrogen, U and V are oxygen, $W^a$ is oxygen (—O—), X is =N—, Y and Z are =CH— and $A^a$ for a compound in each case corresponds to one group of Table A.

Table 20
Compounds of the formula I.A where $R^1$ and $R^2$ are methyl, $R^3$ is hydrogen, U and V are oxygen, $W^a$ is —CH$_2$O—* (*=bond to $A^a$), X is =N—, Y and Z are =CH— and $A^a$ for a compound in each case corresponds to one group of Table A.

Table 21
Compounds of the formula I.A where $R^1$ and $R^2$ are methyl, $R^3$ is hydrogen, U and V are oxygen, $W^a$ is —OCH$_2$—* (*=bond to $A^a$), X is =N—, Y and Z are =CH— and $A^a$ for a compound in each case corresponds to one group of Table A.

Table 22
Compounds of the formula I.A where $R^1$ and $R^2$ are methyl, $R^3$ is hydrogen, U and V are oxygen, $W^a$ is —CO—O—* (*=bond to $A^a$), X is =N—, Y and Z are =CH— and $A^a$ for a compound in each case corresponds to one group of Table A.

Table 23
Compounds of the formula I.A where $R^1$ and $R^2$ are methyl, $R^3$ is hydrogen, U and V are oxygen, $W^a$ is —O—CO—* (*=bond to $A^a$), X is =N—, Y and Z are =CH— and $A^a$ for a compound in each case corresponds to one group of Table A.

Table 24
Compounds of the formula I.A where $R^1$ and $R^2$ are methyl, $R^3$ is hydrogen, U and V are oxygen, $W^a$ is —CO—NH—* (*=bond to $A^a$), X is =N—, Y and Z are =CH— and $A^a$ for a compound in each case corresponds to one group of Table A.

Table 25
Compounds of the formula I.A where $R^1$ and $R^2$ are methyl, $R^3$ is hydrogen, U and V are oxygen, $W^a$ is —NH—CO—* (*=bond to $A^a$), X is =N—, Y and Z are Table 26
Compounds of the formula I.A where $R^1$ and $R^2$ are methyl, $R^3$ is hydrogen, U and V are oxygen, $W^a$ is —C(CH$_3$)=NO—* (*=bond to $A^a$), X is =N—, Y and Z are =CH— and $A^a$ for a compound in each case corresponds to one group of Table A.

Table 27
Compounds of the formula I.A where $R^1$ and $R^2$ are methyl, $R^3$ is hydrogen, U and V are oxygen, $W^a$ is —CH$_2$O—N=C(CH$_3$)—* (*=bond to $A^a$), X is =N—, Y and Z are =CH— and $A^a$ for a compound in each case corresponds to one group of Table A.

Table 28
Compounds of the formula I.A where $R^1$ and $R^2$ are methyl, $R^3$ is hydrogen, U and V are oxygen, $W^a$ is —CH$_2$O—N=C(CH$_3$)—C(C$_6$H$_5$)=NO—* (*=bond to $A^a$), X is =N—, Y and Z are =CH— and $A^a$ for a compound in each case corresponds to one group of Table A.

Table 29
Compounds of the formula I.A where $R^1$ and $R^2$ are methyl, $R^3$ is hydrogen, U and V are oxygen, $W^a$ is —CH$_2$O—N=C(CH$_3$)—C(2-Cl—C$_6$H$_4$)=NO—* (*=bond to $A^a$), X is =N—, Y and Z are =CH— and $A^a$ for a compound in each case corresponds to one group of Table A.

Table 30
Compounds of the formula I.A where $R^1$ and $R^2$ are methyl, $R^3$ is hydrogen, U and V are oxygen, $W^a$ is —CH$_2$O—N=C(CH$_3$)—C(4-Cl—C$_6$H$_4$)=NO—* (*=bond to $A^a$), X is =N—, Y and Z are =CH— and $A^a$ for a compound in each case corresponds to one group of Table A.

Table 31
Compounds of the formula I.A where $R^1$ and $R^2$ are methyl, $R^3$ is hydrogen, U and V are oxygen, $W^a$ is a direct bond, X and Y are =N—, Z is =CH— and $A^a$ for a compound in each case corresponds to one group of Table A.

Table 32
Compounds of the formula I.A where $R^1$ and $R^2$ are methyl, $R^3$ is hydrogen, U and V are oxygen, $W^a$ is —CH=CH—, X and Y are =N—, Z is =CH— and $A^a$ for a compound in each case corresponds to one group of Table A.

Table 33
Compounds of the formula I.A where $R^1$ and $R^2$ are methyl, $R^3$ is hydrogen, U and V are oxygen, $W^a$ is —C≡C—, X and Y are =N—, Z is =CH— and $A^a$ for a compound in each case corresponds to one group of Table A.

Table 34
Compounds of the formula I.A where $R^1$ and $R^2$ are methyl, $R^3$ is hydrogen, U and V are oxygen, $W^a$ is oxygen (—O—), X and Y are =N—, Z is =CH— and $A^a$ for a compound in each case corresponds to one group of Table A.

Table 35
Compounds of the formula I.A where $R^1$ and $R^2$ are methyl, $R^3$ is hydrogen, U and V are oxygen, $W^a$ is —CH$_2$O—* (*=bond to $A^a$), X and Y are =N—, Z is =CH— and $A^a$ for a compound in each case corresponds to one group of Table A.

Table 36
Compounds of the formula I.A where $R^1$ and $R^2$ are methyl, $R^3$ is hydrogen, U and V are oxygen, $W^a$ is —OCH$_2$—* (*=bond to $A^a$), X and Y are =N—, Z is =CH— and $A^a$ for a compound in each case corresponds to one group of Table A.

Table 37
Compounds of the formula I.A where $R^1$ and $R^2$ are methyl, $R^3$ is hydrogen, U and V are oxygen, $W^a$ is —CO—O—* (*=bond to $A^a$), X and Y are =N—, Z is =CH— and $A^a$ for a compound in each case corresponds to one group of Table A.

Table 38
Compounds of the formula I.A where $R^1$ and $R^2$ are methyl, $R^3$ is hydrogen, U and V are oxygen, $W^a$ is —O—CO—* (*=bond to $A^a$), X and Y are =N—, Z is =CH— and $A^a$ for a compound in each case corresponds to one group of Table A.

Table 39
Compounds of the formula I.A where $R^1$ and $R^2$ are methyl, $R^3$ is hydrogen, U and V are oxygen, $W^a$ is —CO—NH—* (*=bond to $A^a$), X and Y are =N—, Z is =CH— and $A^a$ for a compound in each case corresponds to one group of Table A.

Table 40
Compounds of the formula I.A where $R^1$ and $R^2$ are methyl, $R^3$ is hydrogen, U and V are oxygen, $W^a$ is —NH—CO—* (*=bond to $A^a$), X and Y are =N—, Z is =CH— and $A^a$ for a compound in each case corresponds to one group of Table A.

Table 41
Compounds of the formula I.A where $R^1$ and $R^2$ are methyl, $R^3$ is hydrogen, U and V are oxygen, $W^a$ is —C(CH$_3$)=NO—* (*=bond to $A^a$), X and Y are =N—, Z is =CH— and $A^a$ for a compound in each case corresponds to one group of Table A.

Table 42
Compounds of the formula I.A where $R^1$ and $R^2$ are methyl, $R^3$ is hydrogen, U and V are oxygen, $W^a$ is —CH$_2$O—N=C(CH$_3$)—* (*=bond to $A^a$), X and Y are =N—, Z is =CH— and $A^a$ for a compound in each case corresponds to one group of Table A.

Table 43
Compounds of the formula I.A where $R^1$ and $R^2$ are methyl, $R^3$ is hydrogen, U and V are oxygen, $W^a$ is —CH$_2$O—N=C(CH$_3$)—C(C$_6$H$_5$)=NO—* (*=bond to $A^a$), X and Y are =N—, Z is =CH— and $A^a$ for a compound in each case corresponds to one group of Table A.

Table 44
Compounds of the formula I.A where $R^1$ and $R^2$ are methyl, $R^3$ is hydrogen, U and V are oxygen, $W^a$ is —CH$_2$O—N=C(CH$_3$)—C(2-Cl—C$_6$H$_4$)=NO—* (*=bond to $A^a$), X and Y are =N—, Z is =CH— and $A^a$ for a compound in each case corresponds to one group of Table A.

Table 45
Compounds of the formula I.A where $R^1$ and $R^2$ are methyl, $R^3$ is hydrogen, U and V are oxygen, $W^a$ is —CH$_2$O—N=C(CH$_3$)—C(4-Cl—C$_6$H$_4$)=NO—* (*=bond to $A^a$), X and Y are =N—, Z is =CH— and $A^a$ for a compound in each case corresponds to one group of Table A.

Table 46
Compounds of the formula I.A where $R^1$ and $R^2$ are methyl, $R^3$ is hydrogen, U and V are oxygen, $W^a$ is a direct bond, X and Z are =N—, Y is =CH— and $A^a$ for a compound in each case corresponds to one group of Table A.

Table 47
Compounds of the formula I.A where $R^1$ and $R^2$ are methyl, $R^3$ is hydrogen, U and V are oxygen, $W^a$ is —CH=CH—, X and Z are =N—, Y is =CH— and $A^a$ for a compound in each case corresponds to one group of Table A.

Table 48
Compounds of the formula I.A where $R^1$ and $R^2$ are methyl, $R^3$ is hydrogen, U and V are oxygen, $W^a$ is —C≡C—, X and Z are =N—, Y is =CH— and $A^a$ for a compound in each case corresponds to one group of Table A.

Table 49
Compounds of the formula I.A where $R^1$ and $R^2$ are methyl, $R^3$ is hydrogen, U and V are oxygen, $W^a$ is oxygen (—O—), X and Z are =N—, Y is =CH— and $A^a$ for a compound in each case corresponds to one group of Table A.

Table 50
Compounds of the formula I.A where $R^1$ and $R^2$ are methyl, $R^3$ is hydrogen, U and V are oxygen, $W^a$ is —CH$_2$O—* (*=bond to $A^a$), X and Z are =N—, Y is =CH— and $A^a$ for a compound in each case corresponds to one group of Table A.

Table 51
Compounds of the formula I.A where $R^1$ and $R^2$ are methyl, $R^3$ is hydrogen, U and V are oxygen, $W^a$ is —OCH$_2$—* (*=bond to $A^a$), X and Z are =N—, Y is =CH— and $A^a$ for a compound in each case corresponds to one group of Table A.

Table 52
Compounds of the formula I.A where $R^1$ and $R^2$ are methyl, $R^3$ is hydrogen, U and V are oxygen, $W^a$ is —CO—O—* (*=bond to $A^a$), X and Z are =N—, Y is =CH— and $A^a$ for a compound in each case corresponds to one group of Table A.

Table 53
Compounds of the formula I.A where $R^1$ and $R^2$ are methyl, $R^3$ is hydrogen, U and V are oxygen, $W^a$ is —O—CO—* (*=bond to $A^a$), X and Z are =N—, Y is =CH— and $A^a$ for a compound in each case corresponds to one group of Table A.

Table 54
Compounds of the formula I.A where $R^1$ and $R^2$ are methyl, $R^3$ is hydrogen, U and V are oxygen, $W^a$ is —CO—NH—* (*=bond to $A^a$), X and Z are =N—, Y is =CH— and $A^a$ for a compound in each case corresponds to one group of Table A.

Table 55
Compounds of the formula I.A where $R^1$ and $R^2$ are methyl, $R^3$ is hydrogen, U and V are oxygen, $W^a$ is —NH—CO—* (*=bond to $A^a$), X and Z are =N—, Y is =CH— and $A^a$ for a compound in each case corresponds to one group of Table A.

Table 56
Compounds of the formula I.A where $R^1$ and $R^2$ are methyl, $R^3$ is hydrogen, U and V are oxygen, $W^a$ is —C(CH$_3$)=NO—* (*=bond to $A^a$), X and Z are =N—, Y is =CH— and $A^a$ for a compound in each case corresponds to one group of Table A.

Table 57
Compounds of the formula I.A where $R^1$ and $R^2$ are methyl, $R^3$ is hydrogen, U and V are oxygen, $W^a$ is —CH$_2$O—N=C(CH$_3$)—* (*=bond to $A^a$), X and Z are =N—, Y is =CH— and $A^a$ for a compound in each case corresponds to one group of Table A.

Table 58
Compounds of the formula I.A where $R^1$ and $R^2$ are methyl, $R^3$ is hydrogen, U and V are oxygen, $W^a$ is —CH$_2$O—N=C(CH$_3$)—C(C$_6$H$_5$)=NO—* (*=bond to $A^a$), X and Z are =N—, Y is =CH— and $A^a$ for a compound in each case corresponds to one group of Table A.

Table 59
Compounds of the formula I.A where $R^1$ and $R^2$ are methyl, $R^3$ is hydrogen, U and V are oxygen, $W^a$ is —CH$_2$O—N=C(CH$_3$)—C(2-Cl—C$_6$H$_4$)=NO—* (*=bond to $A^a$), X and Z are =N—, Y is =CH— and $A^a$ for a compound in each case corresponds to one group of Table A.

Table 60
Compounds of the formula I.A where $R^1$ and $R^2$ are methyl, $R^3$ is hydrogen, U and V are oxygen, $W^a$ is —CH$_2$O—N=C(CH$_3$)—C(4-Cl—C$_6$H$_4$)=NO—* (*=bond to $A^a$), X and Z are =N—, Y is =CH— and $A^a$ for a compound in each case corresponds to one group of Table A.

Table 61
Compounds of the formula I.A where $R^1$ and $R^2$ are methyl, $R^3$ is hydrogen, U is amino (—NH—) and V is oxygen, $W^a$ is a direct bond, X, Y and Z are =CH— and $A^a$ for a compound in each case corresponds to one group of Table A.

Table 62
Compounds of the formula I.A where $R^1$ and $R^2$ are methyl, $R^3$ is hydrogen, U is amino (—NH—) and V is oxygen, $W^a$ is —CH=CH—, X, Y and Z are =CH— and $A^a$ for a compound in each case corresponds to one group of Table A.

Table 63
Compounds of the formula I.A where $R^1$ and $R^2$ are methyl, $R^3$ is hydrogen, U is amino (—NH—) and V is oxygen, $W^a$ is —C≡C—, X, Y and Z are =CH— and $A^a$ for a compound in each case corresponds to one group of Table A.

Table 64
Compounds of the formula I.A where $R^1$ and $R^2$ are methyl, $R^3$ is hydrogen, U is amino (—NH—) and V is oxygen, $W^a$ is oxygen (—O—), X, Y and Z are =CH— and $A^a$ for a compound in each case corresponds to one group of Table A.

Table 65
Compounds of the formula I.A where $R^1$ and $R^2$ are methyl, $R^3$ is hydrogen, U is amino (—NH—) and V is oxygen, $W^a$ is —CH$_2$O—* (*=bond to $A^a$), X, Y and Z are =CH— and $A^a$ for a compound in each case corresponds to one group of Table A.

Table 66
Compounds of the formula I.A where $R^1$ and $R^2$ are methyl, $R^3$ is hydrogen, U is amino (—NH—) and V is oxygen, $W^a$ is —OCH$_2$—* (*=bond to $A^a$), X, Y and Z are =CH— and $A^a$ for a compound in each case corresponds to one group of Table A.

Table 67
Compounds of the formula I.A where $R^1$ and $R^2$ are methyl, $R^3$ is hydrogen, U is amino (—NH—) and V is oxygen, $W^a$ is —CO—O—* (*=bond to $A^a$), X, Y and Z are =CH— and $A^a$ for a compound in each case corresponds to one group of Table A.

Table 68
Compounds of the formula I.A where $R^1$ and $R^2$ are methyl, $R^3$ is hydrogen, U is amino (—NH—) and V is oxygen, $W^a$ is —O—CO—* (*=bond to $A^a$), X, Y and Z are =CH— and $A^a$ for a compound in each case corresponds to one group of Table A.

Table 69
Compounds of the formula I.A where $R^1$ and $R^2$ are methyl, $R^3$ is hydrogen, U is amino (—NH—) and V is oxygen, $W^a$ is —CO—NH—* (*=bond to $A^a$), X, Y and Z are =CH— and $A^a$ for a compound in each case corresponds to one group of Table A.

Table 70
Compounds of the formula I.A where $R^1$ and $R^2$ are methyl, $R^3$ is hydrogen, U is amino (—NH—) and V is Table 71
Compounds of the formula I.A where $R^1$ and $R^2$ are methyl, $R^3$ is hydrogen, U is amino (—NH—) and V is oxygen, $W^a$ is —NH—CO—* (*=bond to $A^a$), X, Y and Z are =CH— and $A^a$ for a compound in each case corresponds to one group of Table A.

Table 72
Compounds of the formula I.A where $R^1$ and $R^2$ are methyl, $R^3$ is hydrogen, U is amino (—NH—) and V is oxygen, $W^a$ is —C(CH$_3$)=NO—* (*=bond to $A^a$), X, Y and Z are =CH— and $A^a$ for a compound in each case corresponds to one group of Table A.

Table 73
Compounds of the formula I.A where $R^1$ and $R^2$ are methyl, $R^3$ is hydrogen, U is amino (—NH—) and V is oxygen, $W^a$ is —CH$_2$O—N=C(CH$_3$)—* (*=bond to $A^a$), X, Y and Z are =CH— and $A^a$ for a compound in each case corresponds to one group of Table A.

Table 74
Compounds of the formula I.A where $R^1$ and $R^2$ are methyl, $R^3$ is hydrogen, U is amino (—NH—) and V is oxygen, $W^a$ is —CH$_2$O—N=C(CH$_3$)—C(C$_6$H$_5$)=NO—* (*=bond to $A^a$), X, Y and Z are =CH— and $A^a$ for a compound in each case corresponds to one group of Table A.

Table 75
Compounds of the formula I.A where $R^1$ and $R^2$ are methyl, $R^3$ is hydrogen, U is amino (—NH—) and V is oxygen, $W^a$ is —CH$_2$O—N=C(CH$_3$)—C(2-Cl—C$_6$H$_4$)=NO—* (*=bond to $A^a$), X, Y and Z are =CH— and $A^a$ for a compound in each case corresponds to one group of Table A.

Table 76
Compounds of the formula I.A where $R^1$ and $R^2$ are methyl, $R^3$ is hydrogen, U is amino (—NH—) and V is oxygen, $W^a$ is —CH$_2$O—N=C(CH$_3$)—C(4-Cl—C$_6$H$_4$)=NO—* (*=bond to $A^a$), X, Y and Z are =CH— and $A^a$ for a compound in each case corresponds to one group of Table A.

Table 77
Compounds of the formula I.A where $R^1$ and $R^2$ are methyl, $R^3$ is hydrogen, U is amino (—NH—) and V is oxygen, $W^a$ is a direct bond, X is =N—, Y and Z are =CH— and $A^a$ for a compound in each case corresponds to one group of Table A.

Table 78
Compounds of the formula I.A where $R^1$ and $R^2$ are methyl, $R^3$ is hydrogen, U is amino (—NH—) and V is oxygen, $W^a$ is —CH=CH—, X is =N—, Y and Z are =CH— and $A^a$ for a compound in each case corresponds to one group of Table A.

Table 79
Compounds of the formula I.A where $R^1$ and $R^2$ are methyl, $R^3$ is hydrogen, U is amino (—NH—) and V is oxygen, $W^a$ is —C≡C—, X is =N—, Y and Z are =CH— and $A^a$ for a compound in each case corresponds to one group of Table A.

Table 80
Compounds of the formula I.A where $R^1$ and $R^2$ are methyl, $R^3$ is hydrogen, U is amino (—NH—) and V is oxygen, $W^a$ is oxygen (—O—), X is =N—, Y and Z are =CH— and $A^a$ for a compound in each case corresponds to one group of Table A.

Table 81
Compounds of the formula I.A where $R^1$ and $R^2$ are methyl, $R^3$ is hydrogen, U is amino (—NH—) and V is oxygen, $W^a$ is —CH$_2$O—* (*=bond to $A^a$), X is =N—, Y and Z are =CH— and $A^a$ for a compound in each case corresponds to one group of Table A.

Table 82
Compounds of the formula I.A where $R^1$ and $R^2$ are methyl, $R^3$ is hydrogen, U is amino (—NH—) and V is oxygen, $W^a$ is —OCH$_2$—* (*=bond to $A^a$), X is =N—, Y and Z are =CH— and $A^a$ for a compound in each case corresponds to one group of Table A.

Table 83
Compounds of the formula I.A where $R^1$ and $R^2$ are methyl, $R^3$ is hydrogen, U is amino (—NH—) and V is oxygen, $W^a$ is —CO—O—* (*=bond to $A^a$), X is =N—, Y and Z are =CH— and $A^a$ for a compound in each case corresponds to one group of Table A.

Table 84
Compounds of the formula I.A where $R^1$ and $R^2$ are methyl, $R^3$ is hydrogen, U is amino (—NH—) and V is oxygen, $W^a$ is —O—CO—* (*=bond to $A^a$), X is =N—, Y and Z are =CH— and $A^a$ for a compound in each case corresponds to one group of Table A.

Table 85
Compounds of the formula I.A where $R^1$ and $R^2$ are methyl, $R^3$ is hydrogen, U is amino (—NH—) and V is oxygen, $W^a$ is —CO—NH—* (*=bond to $A^a$), X is =N—, Y and Z are =CH— and $A^a$ for a compound in each case corresponds to one group of Table A.

Table 86
Compounds of the formula I.A where $R^1$ and $R^2$ are methyl, $R^3$ is hydrogen, U is amino (—NH—) and V is oxygen, $W^a$ is —NH—CO—* (*=bond to $A^a$), X is =N—, Y and Z are =CH— and $A^a$ for a compound in each case corresponds to one group of Table A.

Table 87
Compounds of the formula I.A where $R^1$ and $R^2$ are methyl, $R^3$ is hydrogen, U is amino (—NH—) and V is oxygen, $W^a$ is —C(CH$_3$)=NO—* (*=bond to $A^a$), X is =N—, Y and Z are =CH— and $A^a$ for a compound in each case corresponds to one group of Table A.

Table 88
Compounds of the formula I.A where $R^1$ and $R^2$ are methyl, $R^3$ is hydrogen, U is amino (—NH—) and V is oxygen, $W^a$ is —CH$_2$O—N=C(CH$_3$)—* (*=bond to $A^a$), X is =N—, Y and Z are =CH— and $A^a$ for a compound in each case corresponds to one group of Table A.

Table 89
Compounds of the formula I.A where $R^1$ and $R^2$ are methyl, $R^3$ is hydrogen, U is amino (—NH—) and V is oxygen, $W^a$ is —CH$_2$O—N=C(CH$_3$)—C(C$_6$H$_5$)=NO—* (*=bond to $A^a$), X is =N—, Y and Z are =CH— and $A^a$ for a compound in each case corresponds to one group of Table A.

Table 90
Compounds of the formula I.A where $R^1$ and $R^2$ are methyl, $R^3$ is hydrogen, U is amino (—NH—) and V is oxygen, $W^a$ is —CH$_2$O—N=C(CH$_3$)—C(2-Cl—C$_6$H$_4$)=NO—* (*=bond to $A^a$), X is =N—, Y and Z are =CH— and $A^a$ for a compound in each case corresponds to one group of Table A.

Table 91
Compounds of the formula I.A where $R^1$ and $R^2$ are methyl, $R^3$ is hydrogen, U is amino (—NH—) and V is oxygen, $W^a$ is —CH$_2$O—N=C(CH$_3$)—C(4-Cl—C$_6$H$_4$)=NO—* (*=bond to $A^a$), X is =N—, Y and Z are =CH— and $A^a$ for a compound in each case corresponds to one group of Table A.

Table 91
Compounds of the formula I.A where $R^1$ and $R^2$ are methyl, $R^3$ is hydrogen, U is amino (—NH—) and V is oxygen, $W^a$ is a direct bond, X and Y are =N—, Z is =CH— and $A^a$ for a compound in each case corresponds to one group of Table A.

Table 92
Compounds of the formula I.A where $R^1$ and $R^2$ are methyl, $R^3$ is hydrogen, U is amino (—NH—) and V is oxygen, $W^a$ is —CH=CH—, X and Y are =N—, Z is =CH— and $A^a$ for a compound in each case corresponds to one group of Table A.

Table 93
Compounds of the formula I.A where $R^1$ and $R^2$ are methyl, $R^3$ is hydrogen, U is amino (—NH—) and V is oxygen, $W^a$ is —C≡C—, X and Y are =N—, Z is =CH— and $A^a$ for a compound in each case corresponds to one group of Table A.

Table 94
Compounds of the formula I.A where $R^1$ and $R^2$ are methyl, $R^3$ is hydrogen, U is amino (—NH—) and V is oxygen, $W^a$ is oxygen (—O—), X and Y are =N—, Z is =CH— and $A^a$ for a compound in each case corresponds to one group of Table A.

Table 95
Compounds of the formula I.A where $R^1$ and $R^2$ are methyl, $R^3$ is hydrogen, U is amino (—NH—) and V is oxygen, $W^a$ is —CH$_2$O—* (*=bond to $A^a$), X and Y are =N—, Z is =CH— and $A^a$ for a compound in each case corresponds to one group of Table A.

Table 96
Compounds of the formula I.A where $R^1$ and $R^2$ are methyl, $R^3$ is hydrogen, U is amino (—NH—) and V is oxygen, $W^a$ is —OCH$_2$—* (*=bond to $A^a$), X and Y are =N—, Z is =CH— and $A^a$ for a compound in each case corresponds to one group of Table A.

Table 97
Compounds of the formula I.A where $R^1$ and $R^2$ are methyl, $R^3$ is hydrogen, U is amino (—NH—) and V is oxygen, $W^a$ is —CO—O—* (*=bond to $A^a$), X and Y are =N—, Z is =CH— and $A^a$ for a compound in each case corresponds to one group of Table A.

Table 98
Compounds of the formula I.A where $R^1$ and $R^2$ are methyl, $R^3$ is hydrogen, U is amino (—NH—) and V is oxygen, $W^a$ is —O—CO—* (*=bond to $A^a$), X and Y are =N—, Z is =CH— and $A^a$ for a compound in each case corresponds to one group of Table A.

Table 99
Compounds of the formula I.A where $R^1$ and $R^2$ are methyl, $R^3$ is hydrogen, U is amino (—NH—) and V is oxygen, $W^a$ is —CO—NH—* (*=bond to $A^a$), X and Y are =N—, Z is =CH— and $A^a$ for a compound in each case corresponds to one group of Table A.

Table 100
Compounds of the formula I.A where $R^1$ and $R^2$ are methyl, $R^3$ is hydrogen, U is amino (—NH—) and V is oxygen, $W^a$ is —NH—CO—* (*=bond to $A^a$), X and Y are =N—, Z is =CH— and $A^a$ for a compound in each case corresponds to one group of Table A.

Table 101
Compounds of the formula I.A where $R^1$ and $R^2$ are methyl, $R^3$ is hydrogen, U is amino (—NH—) and V is oxygen, $W^a$ is —C(CH$_3$)=NO—* (*=bond to $A^a$), X and Y are =N—, Z is =CH— and $A^a$ for a compound in each case corresponds to one group of Table A.

Table 102
Compounds of the formula I.A where $R^1$ and $R^2$ are methyl, $R^3$ is hydrogen, U is amino (—NH—) and V is oxygen, $W^a$ is —CH$_2$O—N=C(CH$_3$)—* (*=bond to $A^a$), X and Y are =N—, Z is =CH— and $A^a$ for a compound in each case corresponds to one group of Table A.

Table 103
Compounds of the formula I.A where $R^1$ and $R^2$ are methyl, $R^3$ is hydrogen, U is amino (—NH—) and V is oxygen, $W^a$ is —CH$_2$O—N=C(CH$_3$)—C(C$_6$H$_5$)=NO—* (*=bond to $A^a$), X and Y are =N—, Z is =CH— and $A^a$ for a compound in each case corresponds to one group of Table A.

Table 104
Compounds of the formula I.A where $R^1$ and $R^2$ are methyl, $R^3$ is hydrogen, U is amino (—NH—) and V is oxygen, $W^a$ is —CH$_2$O—N=C(CH$_3$)—C(2-Cl—C$_6$H$_4$)=N—* (*=bond to $A^a$), X and Y are =N—, Z is =CH— and $A^a$ for a compound in each case corresponds to one group of Table A.

Table 105
Compounds of the formula I.A where $R^1$ and $R^2$ are methyl, $R^3$ is hydrogen, U is amino (—NH—) and V is oxygen, $W^a$ is —CH$_2$O—N=C(CH$_3$)—C(4-Cl—C$_6$H$_4$)=NO—* (*=bond to $A^a$), X and Y are =N—, Z is =CH— and $A^a$ for a compound in each case corresponds to one group of Table A.

Table 106
Compounds of the formula I.A where $R^1$ and $R^2$ are methyl, $R^3$ is hydrogen, U is amino (—NH—) and V is oxygen, $W^a$ is a direct bond, X and Z are =N—, Y is =CH— and $A^a$ for a compound in each case corresponds to one group of Table A.

Table 107
Compounds of the formula I.A where $R^1$ and $R^2$ are methyl, $R^3$ is hydrogen, U is amino (—NH—) and V is oxygen, $W^a$ is —CH=CH—, X and Z are =N—, Y is =CH— and $A^a$ for a compound in each case corresponds to one group of Table A.

Table 108
Compounds of the formula I.A where $R^1$ and $R^2$ are methyl, $R^3$ is hydrogen, U is amino (—NH—) and V is oxygen, $W^a$ is —C≡C—, X and Z are =N—, Y is =CH— and $A^a$ for a compound in each case corresponds to one group of Table A.

Table 109
Compounds of the formula I.A where $R^1$ and $R^2$ are methyl, $R^3$ is hydrogen, U is amino (—NH—) and V is oxygen, $W^a$ is oxygen (—O—), X and Z are =N—, Y is =CH— and $A^a$ for a compound in each case corresponds to one group of Table A.

Table 110
Compounds of the formula I.A where $R^1$ and $R^2$ are methyl, $R^3$ is hydrogen, U is amino (—NH—) and V is oxygen, $W^a$ is —CH$_2$O—* (*=bond to $A^a$), X and Z are =N—, Y is =CH— and $A^a$ for a compound in each case corresponds to one group of Table A.

Table 111
Compounds of the formula I.A where $R^1$ and $R^2$ are methyl, $R^3$ is hydrogen, U is amino (—NH—) and V is oxygen, $W^a$ is —OCH$_2$—* (*=bond to $A^a$), X and Z are =N—, Y is =CH— and $A^a$ for a compound in each case corresponds to one group of Table A.

Table 112
Compounds of the formula I.A where $R^1$ and $R^2$ are methyl, $R^3$ is hydrogen, U is amino (—NH—) and V is oxygen, $W^a$ is —CO—O—* (*=bond to $A^a$), X and Z are =N—, Y is =CH— and $A^a$ for a compound in each case corresponds to one group of Table A.

Table 113
Compounds of the formula I.A where $R^1$ and $R^2$ are methyl, $R^3$ is hydrogen, U is amino (—NH—) and V is oxygen, $W^a$ is —O—CO—* (*=bond to $A^a$), X and Z are =N—, Y is =CH— and $A^a$ for a compound in each case corresponds to one group of Table A.

Table 114
Compounds of the formula I.A where $R^1$ and $R^2$ are methyl, $R^3$ is hydrogen, U is amino (—NH—) and V is oxygen, $W^a$ is —CO—NH—* (*=bond to $A^a$), X and Z are =N—, Y is =CH— and $A^a$ for a compound in each case corresponds to one group of Table A.

Table 115
Compounds of the formula I.A where $R^1$ and $R^2$ are methyl, $R^3$ is hydrogen, U is amino (—NH—) and V is oxygen, $W^a$ is —NH—CO—* (*=bond to $A^a$), X and Z are =N—, Y is =CH— and $A^a$ for a compound in each case corresponds to one group of Table A.

Table 116
Compounds of the formula I.A where $R^1$ and $R^2$ are methyl, $R^3$ is hydrogen, U is amino (—NH—) and V is oxygen, $W^a$ is —C(CH$_3$)=NO—* (*=bond to $A^a$), X and Z are =N—, Y is =CH— and $A^a$ for a compound in each case corresponds to one group of Table A.

Table 117
Compounds of the formula I.A where $R^1$ and $R^2$ are methyl, $R^3$ is hydrogen, U is amino (—NH—) and V is oxygen, $W^a$ is —CH$_2$O—N=C(CH$_3$)—* (*=bond to $A^a$), X and Z are =N—, Y is =CH— and $A^a$ for a compound in each case corresponds to one group of Table A.

Table 118
Compounds of the formula I.A where $R^1$ and $R^2$ are methyl, $R^3$ is hydrogen, U is amino (—NH—) and V is oxygen, $W^a$ is —CH$_2$O—N=C(CH$_3$)—C(C$_6$H$_5$)=NO—* (*=bond to $A^a$), X and Z are =N—, Y is =CH— and $A^a$ for a compound in each case corresponds to one group of Table A.

Table 119
Compounds of the formula I.A where $R^1$ and $R^2$ are methyl, $R^3$ is hydrogen, U is amino (—NH—) and V is oxygen, $W^a$ is —CH$_2$O—N=C(CH$_3$)—C(2-Cl—C$_6$H$_4$)=NO—* (*=bond to $A^a$), X and Z are =N—, Y is =CH— and $A^a$ for a compound in each case corresponds to one group of Table A.

Table 120
Compounds of the formula I.A where $R^1$ and $R^2$ are methyl, $R^3$ is hydrogen, U is amino (—NH—) and V is oxygen, $W^a$ is —CH$_2$O—N=C(CH$_3$)—C(4-Cl—C$_6$H$_4$)=NO—* (*=bond to $A^a$), X and Z are =N—, Y is =CH— and $A^a$ for a compound in each case corresponds to one group of Table A.

Table 121
Compounds of the formula I.A where $R^1$ and $R^2$ are methyl, $R^3$ is hydrogen, U is oxygen and V is sulfur, $W^a$ is a direct bond, X, Y and Z are =CH— and $A^a$ for a compound in each case corresponds to one group of Table A.

Table 122
Compounds of the formula I.A where $R^1$ and $R^2$ are methyl, $R^3$ is hydrogen, U is oxygen and V is sulfur, $W^a$ is —CH=CH—, X, Y and Z are =CH— and $A^a$ for a compound in each case corresponds to one group of Table A.

Table 123
Compounds of the formula I.A where $R^1$ and $R^2$ are methyl, $R^3$ is hydrogen, U is oxygen and V is sulfur, $W^a$ is —C≡C—, X, Y and Z are =CH— and $A^a$ for a compound in each case corresponds to one group of Table A.

Table 124
Compounds of the formula I.A where $R^1$ and $R^2$ are methyl, $R^3$ is hydrogen, U is oxygen and V is sulfur, $W^a$ is oxygen (—O—), X, Y and Z are =CH— and $A^a$ for a compound in each case corresponds to one group of Table A.

Table 125
Compounds of the formula I.A where $R^1$ and $R^2$ are methyl, $R^3$ is hydrogen, U is oxygen and V is sulfur, $W^a$ is —CH$_2$O—* (*=bond to $A^a$), X, Y and Z are =CH— and $A^a$ for a compound in each case corresponds to one group of Table A.

Table 126
Compounds of the formula I.A where $R^1$ and $R^2$ are methyl, $R^3$ is hydrogen, U is oxygen and V is sulfur, $W^a$ is —OCH$_2$—* (*=bond to $A^a$), X, Y and Z are =CH— and $A^a$ for a compound in each case corresponds to one group of Table A.

Table 127
Compounds of the formula I.A where $R^1$ and $R^2$ are methyl, $R^3$ is hydrogen, U is oxygen and V is sulfur, $W^a$ is —CO—O—* (*=bond to $A^a$), X, Y and Z are =CH— and $A^a$ for a compound in each case corresponds to one group of Table A.

Table 128
Compounds of the formula I.A where $R^1$ and $R^2$ are methyl, $R^3$ is hydrogen, U is oxygen and V is sulfur, $W^a$ is —O—CO—* (*=bond to $A^a$), X, Y and Z are =CH— and $A^a$ for a compound in each case corresponds to one group of Table A.

Table 129
Compounds of the formula I.A where $R^1$ and $R^2$ are methyl, $R^3$ is hydrogen, U is oxygen and V is sulfur, $W^a$ is —CO—NH—* (*=bond to $A^a$), X, Y and Z are =CH— and $A^a$ for a compound in each case corresponds to one group of Table A.

Table 130
Compounds of the formula I.A where $R^1$ and $R^2$ are methyl, $R^3$ is hydrogen, U is oxygen and V is sulfur, $W^a$ is —NH—CO—* (*=bond to $A^a$), X, Y and Z are =CH— and $A^a$ for a compound in each case corresponds to one group of Table A.

Table 131
Compounds of the formula I.A where $R^1$ and $R^2$ are methyl, $R^3$ is hydrogen, U is oxygen and V is sulfur, $W^a$ is —C(CH$_3$)=NO—* (*=bond to $A^a$), X, Y and Z are =CH— and $A^a$ for a compound in each case corresponds to one group of Table A.

Table 132
Compounds of the formula I.A where $R^1$ and $R^2$ are methyl, $R^3$ is hydrogen, U is oxygen and V is sulfur, $W^a$ is —CH$_2$O—N=C(CH$_3$)—* (*=bond to $A^a$), X, Y and Z are =CH— and $A^a$ for a compound in each case corresponds to one group of Table A.

Table 133
Compounds of the formula I.A where $R^1$ and $R^2$ are methyl, $R^3$ is hydrogen, U is oxygen and V is sulfur, $W^a$ is —CH$_2$O—N=C(CH$_3$)—C(C$_6$H$_5$)=NO—* (*=bond to $A^a$), X, Y and Z are =CH— and $A^a$ for a compound in each case corresponds to one group of Table A.

Table 134
Compounds of the formula I.A where $R^1$ and $R^2$ are methyl, $R^3$ is hydrogen, U is oxygen and V is sulfur, $W^a$ is —CH$_2$O—N=C(CH$_3$)—C(2-Cl—C$_6$H$_4$)=NO—* (*=bond to $A^a$), X, Y and Z are =CH— and $A^a$ for a compound in each case corresponds to one group of Table A.

Table 135
Compounds of the formula I.A where $R^1$ and $R^2$ are methyl, $R^3$ is hydrogen, U is oxygen and V is sulfur, $W^a$ is —CH$_2$O—N=C(CH$_3$)—C(4-Cl—C$_6$H$_4$)=NO—* (*=bond to $A^a$), X, Y and Z are =CH— and $A^a$ for a compound in each case corresponds to one group of Table A.

Table 136
Compounds of the formula I.A where $R^1$ and $R^2$ are methyl, $R^3$ is hydrogen, U is oxygen and V is sulfur, $W^a$ is a direct bond, X is =N—, Y and Z are =CH— and $A^a$ for a compound in each case corresponds to one group of Table A.

Table 137
Compounds of the formula I.A where $R^1$ and $R^2$ are methyl, $R^3$ is hydrogen, U is oxygen and V is sulfur, $W^a$ is —CH=CH—, X is =N—, Y and Z are =CH— and $A^a$ for a compound in each case corresponds to one group of Table A.

Table 138
Compounds of the formula I.A where $R^1$ and $R^2$ are methyl, $R^3$ is hydrogen, U is oxygen and V is sulfur, $W^a$ is —C≡C—, X is =N—, Y and Z are =CH— and $A^a$ for a compound in each case corresponds to one group of Table A.

Table 139
Compounds of the formula I.A where $R^1$ and $R^2$ are methyl, $R^3$ is hydrogen, U is oxygen and V is sulfur, $W^a$ is oxygen (—O—), X is =N—, Y and Z are =CH— and $A^a$ for a compound in each case corresponds to one group of Table A.

Table 140
Compounds of the formula I.A where $R^1$ and $R^2$ are methyl, $R^3$ is hydrogen, U is oxygen and V is sulfur, $W^a$ is —CH$_2$O—* (*=bond to $A^a$), X is =N—, Y and Z are =CH— and $A^a$ for a compound in each case corresponds to one group of Table A.

Table 141
Compounds of the formula I.A where $R^1$ and $R^2$ are methyl, $R^3$ is hydrogen, U is oxygen and V is sulfur, $W^a$ is —OCH$_2$—* (*=bond to $A^a$), X is =N—, Y and Z are =CH— and $A^a$ for a compound in each case corresponds to one group of Table A.

Table 142
Compounds of the formula I.A where $R^1$ and $R^2$ are methyl, $R^3$ is hydrogen, U is oxygen and V is sulfur, $W^a$ is —CO—O—* (*=bond to $A^a$), X is =N—, Y and Z are =CH— and $A^a$ for a compound in each case corresponds to one group of Table A.

Table 143
Compounds of the formula I.A where $R^1$ and $R^2$ are methyl, $R^3$ is hydrogen, U is oxygen and V is sulfur, $W^a$ is —O—CO—* (*=bond to $A^a$), X is =N—, Y and Z are =CH— and $A^a$ for a compound in each case corresponds to one group of Table A.

Table 144
Compounds of the formula I.A where $R^1$ and $R^2$ are methyl, $R^3$ is hydrogen, U is oxygen and V is sulfur, $W^a$ is —CO—NH—* (*=bond to $A^a$), X is =N—, Y and Z are =CH— and $A^a$ for a compound in each case corresponds to one group of Table A.

Table 145
Compounds of the formula I.A where $R^1$ and $R^2$ are methyl, $R^3$ is hydrogen, U is oxygen and V is sulfur, $W^a$ is —NH—CO—* (*=bond to $A^a$), X is =N—, Y and Z are =CH— and $A^a$ for a compound in each case corresponds to one group of Table A.

Table 146
Compounds of the formula I.A where $R^1$ and $R^2$ are methyl, $R^3$ is hydrogen, U is oxygen and V is sulfur, $W^a$ is —C(CH$_3$)=NO—* (*=bond to $A^a$), X is =N—, Y and Z are =CH— and $A^a$ for a compound in each case corresponds to one group of Table A.

Table 147
Compounds of the formula I.A where $R^1$ and $R^2$ are methyl, $R^3$ is hydrogen, U is oxygen and V is sulfur, $W^a$ is —CH$_2$O—N=C(CH$_3$)—* (*=bond to $A^a$), X is =N—, Y and Z are =CH— and $A^a$ for a compound in each case corresponds to one group of Table A.

Table 148
Compounds of the formula I.A where $R^1$ and $R^2$ are methyl, $R^3$ is hydrogen, U is oxygen and V is sulfur, $W^a$ is —CH$_2$O—N=C(CH$_3$)—C(C$_6$H$_5$)=NO—* (*=bond to $A^a$), X is =N—, Y and Z are =CH— and $A^a$ for a compound in each case corresponds to one group of Table A.

Table 149
Compounds of the formula I.A where $R^1$ and $R^2$ are methyl, $R^3$ is hydrogen, U is oxygen and V is sulfur, $W^a$ is —CH$_2$O—N=C(CH$_3$)—C(2-Cl—C$_6$H$_4$)=NO—* (*=bond to $A^a$), X is =N—, Y and Z are =CH— and $A^a$ for a compound in each case corresponds to one group of Table A.

Table 150
Compounds of the formula I.A where $R^1$ and $R^2$ are methyl, $R^3$ is hydrogen, U is oxygen and V is sulfur, $W^a$ is —CH$_2$O—N=C(CH$_3$)—C(4-Cl—C$_6$H$_4$)=NO—* (*=bond to $A^a$), X is =N—, Y and Z are =CH— and $A^a$ for a compound in each case corresponds to one group of Table A.

Table 151
Compounds of the formula I.A where $R^1$ and $R^2$ are methyl, $R^3$ is hydrogen, U is oxygen and V is sulfur, $W^a$ is a direct bond, X and Y are =N—, Z is =CH— and $A^a$ for a compound in each case corresponds to one group of Table A.

Table 152
Compounds of the formula I.A where $R^1$ and $R^2$ are methyl, $R^3$ is hydrogen, U is oxygen and V is sulfur, $W^a$ is —CH=CH—, X and Y are =N—, Z is =CH— and $A^a$ for a compound in each case corresponds to one group of Table A.

Table 153
Compounds of the formula I.A where $R^1$ and $R^2$ are methyl, $R^3$ is hydrogen, U is oxygen and V is sulfur, $W^a$ is —C≡C—, X and Y are =N—, Z is =CH— and $A^a$ for a compound in each case corresponds to one group of Table A.

Table 154
Compounds of the formula I.A where $R^1$ and $R^2$ are methyl, $R^3$ is hydrogen, U is oxygen and V is sulfur, $W^a$ is oxygen (—O—), X and Y are =N—, Z is =CH— and $A^a$ for a compound in each case corresponds to one group of Table A.

Table 155
Compounds of the formula I.A where $R^1$ and $R^2$ are methyl, $R^3$ is hydrogen, U is oxygen and V is sulfur, $W^a$ is —CH$_2$O—* (*=bond to $A^a$), X and Y are =N—, Z is =CH— and $A^a$ for a compound in each case corresponds to one group of Table A.

Table 156
Compounds of the formula I.A where $R^1$ and $R^2$ are methyl, $R^3$ is hydrogen, U is oxygen and V is sulfur, $W^a$ is —OCH$_2$—* (*=bond to $A^a$), X and Y are =N—, Z is =CH— and $A^a$ for a compound in each case corresponds to one group of Table A.

Table 157
Compounds of the formula I.A where $R^1$ and $R^2$ are methyl, $R^3$ is hydrogen, U is oxygen and V is sulfur, $W^a$ is —CO—O—* (*=bond to $A^a$), X and Y are =N—, Z is =CH— and $A^a$ for a compound in each case corresponds to one group of Table A.

Table 158
Compounds of the formula I.A where $R^1$ and $R^2$ are methyl, $R^3$ is hydrogen, U is oxygen and V is sulfur, $W^a$ is —O—CO—* (*=bond to $A^a$), X and Y are =N—, Z is =CH— and $A^a$ for a compound in each case corresponds to one group of Table A.

Table 159
Compounds of the formula I.A where $R^1$ and $R^2$ are methyl, $R^3$ is hydrogen, U is oxygen and V is sulfur, $W^a$ is —CO—NH—* (*=bond to $A^a$), X and Y are =N—, Z is =CH— and $A^a$ for a compound in each case corresponds to one group of Table A.

Table 160
Compounds of the formula I.A where $R^1$ and $R^2$ are methyl, $R^3$ is hydrogen, U is oxygen and V is sulfur, $W^a$ is —NH—CO—* (*=bond to $A^a$), X and Y are =N—, Z is =CH— and $A^a$ for a compound in each case corresponds to one group of Table A.

Table 161
Compounds of the formula I.A where $R^1$ and $R^2$ are methyl, $R^3$ is hydrogen, U is oxygen and V is sulfur, $W^a$ is —C($CH_3$)=NO—* (*=bond to $A^a$), X and Y are =N—, Z is =CH— and $A^a$ for a compound in each case corresponds to one group of Table A.

Table 162
Compounds of the formula I.A where $R^1$ and $R^2$ are methyl, $R^3$ is hydrogen, U is oxygen and V is sulfur, $W^a$ is —$CH_2$O—N=C($CH_3$)—* (*=bond to $A^a$), X and Y are =N—, Z is =CH— and $A^a$ for a compound in each case corresponds to one group of Table A.

Table 163
Compounds of the formula I.A where $R^1$ and $R^2$ are methyl, $R^3$ is hydrogen, U is oxygen and V is sulfur, $W^a$ is —$CH_2$O—N=C($CH_3$)—C($C_6H_5$)=NO—* (*=bond to $A^a$), X and Y are =N—, Z is =CH— and $A^a$ for a compound in each case corresponds to one group of Table A.

Table 164
Compounds of the formula I.A where $R^1$ and $R^2$ are methyl, $R^3$ is hydrogen, U is oxygen and V is sulfur, $W^a$ is —$CH_2$O—N=C($CH_3$)—C(2-Cl—$C_6H_4$)=NO—* (*=bond to $A^a$), X and Y are =N—, Z is =CH— and $A^a$ for a compound in each case corresponds to one group of Table A.

Table 165
Compounds of the formula I.A where $R^1$ and $R^2$ are methyl, $R^3$ is hydrogen, U is oxygen and V is sulfur, $W^a$ is —$CH_2$O—N=C($CH_3$)—C(4-Cl—$C_6H_4$)=NO—* (*=bond to $A^a$), X and Y are =N—, Z is =CH— and $A^a$ for a compound in each case corresponds to one group of Table A.

Table 166
Compounds of the formula I.A where $R^1$ and $R^2$ are methyl, $R^3$ is hydrogen, U is oxygen and V is sulfur, $W^a$ is a direct bond, X and Z are =N—, Y is =CH— and $A^a$ for a compound in each case corresponds to one group of Table A.

Table 167
Compounds of the formula I.A where $R^1$ and $R^2$ are methyl, $R^3$ is hydrogen, U is oxygen and V is sulfur, $W^a$ is —CH=CH—, X and Z are =N—, Y is =CH— and $A^a$ for a compound in each case corresponds to one group of Table A.

Table 168
Compounds of the formula I.A where $R^1$ and $R^2$ are methyl, $R^3$ is hydrogen, U is oxygen and V is sulfur, $W^a$ is —C≡C—, X and Z are =N—, Y is =CH— and $A^a$ for a compound in each case corresponds to one group of Table A.

Table 169
Compounds of the formula I.A where $R^1$ and $R^2$ are methyl, $R^3$ is hydrogen, U is oxygen and V is sulfur, $W^a$ is oxygen (—O—), X and Z are =N—, Y is =CH— and $A^a$ for a compound in each case corresponds to one group of Table A.

Table 170
Compounds of the formula I.A where $R^1$ and $R^2$ are methyl, $R^3$ is hydrogen, U is oxygen and V is sulfur, $W^a$ is —$CH_2$O—* (*=bond to $A^a$), X and Z are =N—, Y is =CH— and $A^a$ for a compound in each case corresponds to one group of Table A.

Table 171
Compounds of the formula I.A where $R^1$ and $R^2$ are methyl, $R^3$ is hydrogen, U is oxygen and V is sulfur, $W^a$ is —O$CH_2$—* (*=bond to $A^a$), X and Z are =N—, Y is =CH— and $A^a$ for a compound in each case corresponds to one group of Table A.

Table 172
Compounds of the formula I.A where $R^1$ and $R^2$ are methyl, $R^3$ is hydrogen, U is oxygen and V is sulfur, $W^a$ is —CO—O—* (*=bond to $A^a$), X and Z are =N—, Y is =CH— and $A^a$ for a compound in each case corresponds to one group of Table A.

Table 173
Compounds of the formula I.A where $R^1$ and $R^2$ are methyl, $R^3$ is hydrogen, U is oxygen and V is sulfur, $W^a$ is —O—CO—* (*=bond to $A^a$), X and Z are =N—, Y is =CH— and $A^a$ for a compound in each case corresponds to one group of Table A.

Table 174
Compounds of the formula I.A where $R^1$ and $R^2$ are methyl, $R^3$ is hydrogen, U is oxygen and V is sulfur, $W^a$ is —CO—NH—* (*=bond to $A^a$), X and Z are =N—, Y is =CH— and $A^a$ for a compound in each case corresponds to one group of Table A.

Table 175
Compounds of the formula I.A where $R^1$ and $R^2$ are methyl, $R^3$ is hydrogen, U is oxygen and V is sulfur, $W^a$ is —NH—CO—* (*=bond to $A^a$), X and Z are =N—, Y is =CH— and $A^a$ for a compound in each case corresponds to one group of Table A.

Table 176
Compounds of the formula I.A where $R^1$ and $R^2$ are methyl, $R^3$ is hydrogen, U is oxygen and V is sulfur, $W^a$ is —C($CH_3$)=NO—* (*=bond to $A^a$), X and Z are =N—, Y is =CH— and $A^a$ for a compound in each case corresponds to one group of Table A.

Table 177
Compounds of the formula I.A where $R^1$ and $R^2$ are methyl, $R^3$ is hydrogen, U is oxygen and V is sulfur, $W^a$ is —$CH_2$O—N=C($CH_3$)—* (*=bond to $A^a$), X and Z are =N—, Y is =CH— and $A^a$ for a compound in each case corresponds to one group of Table A.

Table 178
Compounds of the formula I.A where $R^1$ and $R^2$ are methyl, $R^3$ is hydrogen, U is oxygen and V is sulfur, $W^a$ is —$CH_2$O—N=C($CH_3$)—C($C_6H_5$)=NO—* (*=bond to $A^a$), X and Z are =N—, Y is =CH— and $A^a$ for a compound in each case corresponds to one group of Table A.

Table 179
Compounds of the formula I.A where $R^1$ and $R^2$ are methyl, $R^3$ is hydrogen, U is oxygen and V is sulfur, $W^a$ is —$CH_2$O—N=C($CH_3$)—C(2-Cl—$C_6H_4$)=NO—* (*=bond to $A^a$), X and Z are =N—, Y is =CH— and $A^a$ for a compound in each case corresponds to one group of Table A.

Table 180
Compounds of the formula I.A where $R^1$ and $R^2$ are methyl, $R^3$ is hydrogen, U is oxygen and V is sulfur, $W^a$ is —CH$_2$O—N=C(CH$_3$)—C(4-Cl—C$_6$H$_4$)=NO—* (*=bond to A$^a$), X and Z are =N—, Y is =CH— and A$^a$ for a compound in each case corresponds to one group of Table A.

Table 181
Compounds of the formula I.A where R$^1$ and R$^2$ are methyl, R$^3$ is hydrogen, U is amino (—NH—) and V is sulfur, W$^a$ is a direct bond, X, Y and Z are =CH— and A$^a$ for a compound in each case corresponds to one group of Table A.

Table 182
Compounds of the formula I.A where R$^1$ and R$^2$ are methyl, R$^3$ is hydrogen, U is amino (—NH—) and V is sulfur, W$^a$ is —CH=CH—, X, Y and Z are =CH— and A$^a$ for a compound in each case corresponds to one group of Table A.

Table 183
Compounds of the formula I.A where R$^1$ and R$^2$ are methyl, R$^3$ is hydrogen, U is amino (—NH—) and V is sulfur, W$^a$ is —C≡C—, X, Y and Z are =CH— and A$^a$ for a compound in each case corresponds to one group of Table A.

Table 184
Compounds of the formula I.A where R$^1$ and R$^2$ are methyl, R$^3$ is hydrogen, U is amino (—NH—) and V is sulfur, W$^a$ is oxygen (—O—), X, Y and Z are =CH— and A$^a$ for a compound in each case corresponds to one group of Table A.

Table 185
Compounds of the formula I.A where R$^1$ and R$^2$ are methyl, R$^3$ is hydrogen, U is amino (—NH—) and V is sulfur, W$^a$ is —CH$_2$O—* (*=bond to A$^a$), X, Y and Z are =CH— and A$^a$ for a compound in each case corresponds to one group of Table A.

Table 186
Compounds of the formula I.A where R$^1$ and R$^2$ are methyl, R$^3$ is hydrogen, U is amino (—NH—) and V is sulfur, W$^a$ is —OCH$_2$—* (*=bond to A$^a$), X, Y and Z are =CH— and A$^a$ for a compound in each case corresponds to one group of Table A.

Table 187
Compounds of the formula I.A where R$^1$ and R$^2$ are methyl, R$^3$ is hydrogen, U is amino (—NH—) and V is sulfur, W$^a$ is —CO—O—* (*=bond to A$^a$), X, Y and Z are =CH— and A$^a$ for a compound in each case corresponds to one group of Table A.

Table 188
Compounds of the formula I.A where R$^1$ and R$^2$ are methyl, R$^3$ is hydrogen, U is amino (—NH—) and V is sulfur, W$^a$ is —O—CO—* (*=bond to A$^a$), X, Y and Z are =CH— and A$^a$ for a compound in each case corresponds to one group of Table A.

Table 189
Compounds of the formula I.A where R$^1$ and R$^2$ are methyl, R$^3$ is hydrogen, U is amino (—NH—) and V is sulfur, W$^a$ is —CO—NH—* (*=bond to A$^a$), X, Y and Z are =CH— and A$^a$ for a compound in each case corresponds to one group of Table A.

Table 190
Compounds of the formula I.A where R$^1$ and R$^2$ are methyl, R$^3$ is hydrogen, U is amino (—NH—) and V is sulfur, W$^a$ is —NH—CO—* (*=bond to A$^a$), X, Y and Z are =CH— and A$^a$ for a compound in each case corresponds to one group of Table A.

Table 191
Compounds of the formula I.A where R$^1$ and R$^2$ are methyl, R$^3$ is hydrogen, U is amino (—NH—) and V is sulfur, W$^a$ is —C(CH$_3$)=NO—* (*=bond to A$^a$), X, Y and Z are =CH— and A$^a$ for a compound in each case corresponds to one group of Table A.

Table 192
Compounds of the formula I.A where R$^1$ and R$^2$ are methyl, R$^3$ is hydrogen, U is amino (—NH—) and V is sulfur, W$^a$ is —CH$_2$O—N=C(CH$_3$)—* (*=bond to A$^a$), X, Y and Z are =CH— and A$^a$ for a compound in each case corresponds to one group of Table A.

Table 193
Compounds of the formula I.A where R$^1$ and R$^2$ are methyl, R$^3$ is hydrogen, U is amino (—NH—) and V is sulfur, W$^a$ is —CH$_2$O—N=C(CH$_3$)—C(C$_6$H$_5$)=NO—* (*=bond to A$^a$), X, Y and Z are =CH— and A$^a$ for a compound in each case corresponds to one group of Table A.

Table 194
Compounds of the formula I.A where R$^1$ and R$^2$ are methyl, R$^3$ is hydrogen, U is amino (—NH—) and V is sulfur, W$^a$ is —CH$_2$O—N=C(CH$_3$)—C(2-Cl—C$_6$H$_4$)=NO—* (*=bond to A$^a$), X, Y and Z are =CH— and A$^a$ for a compound in each case corresponds to one group of Table A.

Table 195
Compounds of the formula I.A where R$^1$ and R$^2$ are methyl, R$^3$ is hydrogen, U is amino (—NH—) and V is sulfur, W$^a$ is —CH$_2$O—N=C(CH$_3$)—C(4-Cl—C$_6$H$_4$)=NO—* (*=bond to A$^a$), X, Y and Z are =CH— and A$^a$ for a compound in each case corresponds to one group of Table A.

Table 196
Compounds of the formula I.A where R$^1$ and R$^2$ are methyl, R$^3$ is hydrogen, U is amino (—NH—) and V is sulfur, W$^a$ is a direct bond, X is =N—, Y and Z are =CH— and A$^a$ for a compound in each case corresponds to one group of Table A.

Table 197
Compounds of the formula I.A where R$^1$ and R$^2$ are methyl, R$^3$ is hydrogen, U is amino (—NH—) and V is sulfur, W$^a$ is —CH=CH—, X is =N—, Y and Z are =CH— and A$^a$ for a compound in each case corresponds to one group of Table A.

Table 198
Compounds of the formula I.A where R$^1$ and R$^2$ are methyl, R$^3$ is hydrogen, U is amino (—NH—) and V is sulfur, W$^a$ is —C≡C—, X is =N—, Y and Z are =CH— and A$^a$ for a compound in each case corresponds to one group of Table A.

Table 199
Compounds of the formula I.A where R$^1$ and R$^2$ are methyl, R$^3$ is hydrogen, U is amino (—NH—) and V is sulfur, W$^a$ is oxygen (—O—), X is =N—, Y and Z are =CH— and A$^a$ for a compound in each case corresponds to one group of Table A.

Table 200
Compounds of the formula I.A where R$^1$ and R$^2$ are methyl, R$^3$ is hydrogen, U is amino (—NH—) and V is sulfur, W$^a$ is —CH$_2$O—* (*=bond to A$^a$), X is =N—, Y and Z are =CH— and A$^a$ for a compound in each case corresponds to one group of Table A.

Table 201
Compounds of the formula I.A where R$^1$ and R$^2$ are methyl, R$^3$ is hydrogen, U is amino (—NH—) and V is sulfur, W$^a$ is —OCH$_2$—* (*=bond to A$^a$), X is =N—, Y and Z are =CH— and A$^a$ for a compound in each case corresponds to one group of Table A.

Table 202
Compounds of the formula I.A where R$^1$ and R$^2$ are methyl, R$^3$ is hydrogen, U is amino (—NH—) and V is sulfur, $W^a$ is —CO—O—* (*=bond to $A^a$), X is =N—, Y and Z are =CH— and $A^a$ for a compound in each case corresponds to one group of Table A.

Table 203
Compounds of the formula I.A where $R^1$ and $R^2$ are methyl, $R^3$ is hydrogen, U is amino (—NH—) and V is sulfur, $W^a$ is —O—CO—* (*=bond to $A^a$), X is =N—, Y and Z are =CH— and $A^a$ for a compound in each case corresponds to one group of Table A.

Table 204
Compounds of the formula I.A where $R^1$ and $R^2$ are methyl, $R^3$ is hydrogen, U is amino (—NH—) and V is sulfur, $W^a$ is —CO—NH—* (*=bond to $A^a$), X is =N—, Y and Z are =CH— and $A^a$ for a compound in each case corresponds to one group of Table A.

Table 205
Compounds of the formula I.A where $R^1$ and $R^2$ are methyl, $R^3$ is hydrogen, U is amino (—NH—) and V is sulfur, $W^a$ is —NH—CO—* (*=bond to $A^a$), X is =N—, Y and Z are =CH— and $A^a$ for a compound in each case corresponds to one group of Table A.

Table 206
Compounds of the formula I.A where $R^1$ and $R^2$ are methyl, $R^3$ is hydrogen, U is amino (—NH—) and V is sulfur, $W^a$ is —C(CH$_3$)=NO—* (*=bond to $A^a$), X is =N—, Y and Z are =CH— and $A^a$ for a compound in each case corresponds to one group of Table A.

Table 207
Compounds of the formula I.A where $R^1$ and $R^2$ are methyl, $R^3$ is hydrogen, U is amino (—NH—) and V is sulfur, $W^a$ is —CH$_2$O—N=C(CH$_3$)—* (*=bond to $A^a$), X is =N—, Y and Z are =CH— and $A^a$ for a compound in each case corresponds to one group of Table A.

Table 208
Compounds of the formula I.A where $R^1$ and $R^2$ are methyl, $R^3$ is hydrogen, U is amino (—NH—) and V is sulfur, $W^a$ is —CH$_2$O—N=C(CH$_3$)—C(C$_6$H$_5$)=NO—* (*=bond to $A^a$), X is =N—, Y and Z are =CH— and $A^a$ for a compound in each case corresponds to one group of Table A.

Table 209
Compounds of the formula I.A where $R^1$ and $R^2$ are methyl, $R^3$ is hydrogen, U is amino (—NH—) and V is sulfur, $W^a$ is —CH$_2$O—N=C(CH$_3$)—C(2-Cl—C$_6$H$_4$)=NO—* (*=bond to $A^a$), X is =N—, Y and Z are =CH— and $A^a$ for a compound in each case corresponds to one group of Table A.

Table 210
Compounds of the formula I.A where $R^1$ and $R^2$ are methyl, $R^3$ is hydrogen, U is amino (—NH—) and V is sulfur, $W^a$ is —CH$_2$O—N=C(CH$_3$)—C(4-Cl—C$_6$H$_4$)=NO—* (*=bond to $A^a$), X is =N—, Y and Z are =CH— and $A^a$ for a compound in each case corresponds to one group of Table A.

Table 211
Compounds of the formula I.A where $R^1$ and $R^2$ are methyl, $R^3$ is hydrogen, U is amino (—NH—) and V is sulfur, $W^a$ is a direct bond, X and Y are =N—, Z is =CH— and $A^a$ for a compound in each case corresponds to one group of Table A.

Table 212
Compounds of the formula I.A where $R^1$ and $R^2$ are methyl, $R^3$ is hydrogen, U is amino (—NH—) and V is sulfur, $W^a$ is —CH=CH—, X and Y are =N—, Z is =CH— and $A^a$ for a compound in each case corresponds to one group of Table A.

Table 213
Compounds of the formula I.A where $R^1$ and $R^2$ are methyl, $R^3$ is hydrogen, U is amino (—NH—) and V is sulfur, $W^a$ is —C≡C—, X and Y are =N—, Z is =CH— and $A^a$ for a compound in each case corresponds to one group of Table A.

Table 214
Compounds of the formula I.A where $R^1$ and $R^2$ are methyl, $R^3$ is hydrogen, U is amino (—NH—) and V is sulfur, $W^a$ is oxygen (—O—), X and Y are =N—, Z is =CH— and $A^a$ for a compound in each case corresponds to one group of Table A.

Table 215
Compounds of the formula I.A where $R^1$ and $R^2$ are methyl, $R^3$ is hydrogen, U is amino (—NH—) and V is sulfur, $W^a$ is —CH$_2$O—* (*=bond to $A^a$), X and Y are =N—, Z is =CH— and $A^a$ for a compound in each case corresponds to one group of Table A.

Table 216
Compounds of the formula I.A where $R^1$ and $R^2$ are methyl, $R^3$ is hydrogen, U is amino (—NH—) and V is sulfur, $W^a$ is —OCH$_2$—* (*=bond to $A^a$), X and Y are =N—, Z is =CH— and $A^a$ for a compound in each case corresponds to one group of Table A.

Table 217
Compounds of the formula I.A where $R^1$ and $R^2$ are methyl, $R^3$ is hydrogen, U is amino (—NH—) and V is sulfur, $W^a$ is —CO—O—* (*=bond to $A^a$), X and Y are =N—, Z is =CH— and $A^a$ for a compound in each case corresponds to one group of Table A.

Table 218
Compounds of the formula I.A where $R^1$ and $R^2$ are methyl, $R^3$ is hydrogen, U is amino (—NH—) and V is sulfur, $W^a$ is —O—CO—* (*=bond to $A^a$), X and Y are =N—, Z is =CH— and $A^a$ for a compound in each case corresponds to one group of Table A.

Table 219
Compounds of the formula I.A where $R^1$ and $R^2$ are methyl, $R^3$ is hydrogen, U is amino (—NH—) and V is sulfur, $W^a$ is —CO—NH—* (*=bond to $A^a$), X and Y are =N—, Z is =CH— and $A^a$ for a compound in each case corresponds to one group of Table A.

Table 220
Compounds of the formula I.A where $R^1$ and $R^2$ are methyl, $R^3$ is hydrogen, U is amino (—NH—) and V is sulfur, $W^a$ is —NH—CO—* (*=bond to $A^a$), X and Y are =N—, Z is =CH— and $A^a$ for a compound in each case corresponds to one group of Table A.

Table 221
Compounds of the formula I.A where $R^1$ and $R^2$ are methyl, $R^3$ is hydrogen, U is amino (—NH—) and V is sulfur, $W^a$ is —C(CH$_3$)=NO—* (*=bond to $A^a$), X and Y are =N—, Z is =CH— and $A^a$ for a compound in each case corresponds to one group of Table A.

Table 222
Compounds of the formula I.A where $R^1$ and $R^2$ are methyl, $R^3$ is hydrogen, U is amino (—NH—) and V is sulfur, $W^a$ is —CH$_2$O—N=C(CH$_3$)—* (*=bond to $A^a$), X and Y are =N—, Z is =CH— and $A^a$ for a compound in each case corresponds to one group of Table A.

Table 223
Compounds of the formula I.A where $R^1$ and $R^2$ are methyl, $R^3$ is hydrogen, U is amino (—NH—) and V is sulfur, $W^a$ is —CH$_2$O—N=C(CH$_3$)—C(C$_6$H$_5$)=NO—* (*=bond to $A^a$), X and Y are =N—, Z is =CH— and $A^a$ for a compound in each case corresponds to one group of Table A.

Table 224

Compounds of the formula I.A where $R^1$ and $R^2$ are methyl, $R^3$ is hydrogen, U is amino (—NH—) and V is sulfur, $W^a$ is —CH$_2$O—N=C(CH$_3$)—C(2-Cl—C$_6$H$_4$)=NO—* (*=bond to $A^a$), X and Y are =N—, Z is =CH— and $A^a$ for a compound in each case corresponds to one group of Table A.

Table 225

Compounds of the formula I.A where $R^1$ and $R^2$ are methyl, $R^3$ is hydrogen, U is amino (—NH—) and V is sulfur, $W^a$ is —CH$_2$O—N=C(CH$_3$)—C(4-Cl—C$_6$H$_4$)=NO—* (*=bond to $A^a$), X and Y are =N—, Z is =CH— and $A^a$ for a compound in each case corresponds to one group of Table A.

Table 226

Compounds of the formula I.A where $R^1$ and $R^2$ are methyl, $R^3$ is hydrogen, U is amino (—NH—) and V is sulfur, $W^a$ is a direct bond, X and Z are =N—, Y is =CH— and $A^a$ for a compound in each case corresponds to one group of Table A.

Table 227

Compounds of the formula I.A where $R^1$ and $R^2$ are methyl, $R^3$ is hydrogen, U is amino (—NH—) and V is sulfur, $W^a$ is —CH=CH—, X and Z are =N—, Y is =CH— and $A^a$ for a compound in each case corresponds to one group of Table A.

Table 228

Compounds of the formula I.A where $R^1$ and $R^2$ are methyl, $R^3$ is hydrogen, U is amino (—NH—) and V is sulfur, $W^a$ is —C≡C—, X and Z are =N—, Y is =CH— and $A^a$ for a compound in each case corresponds to one group of Table A.

Table 229

Compounds of the formula I.A where $R^1$ and $R^2$ are methyl, $R^3$ is hydrogen, U is amino (—NH—) and V is sulfur, $W^a$ is oxygen (—O—), X and Z are =N—, Y is =CH— and $A^a$ for a compound in each case corresponds to one group of Table A.

Table 230

Compounds of the formula I.A where $R^1$ and $R^2$ are methyl, $R^3$ is hydrogen, U is amino (—NH—) and V is sulfur, $W^a$ is —CH$_2$O—* (*=bond to $A^a$), X and Z are =N—, Y is =CH— and $A^a$ for a compound in each case corresponds to one group of Table A.

Table 231

Compounds of the formula I.A where $R^1$ and $R^2$ are methyl, $R^3$ is hydrogen, U is amino (—NH—) and V is sulfur, $W^a$ is —OCH$_2$—* (*=bond to $A^a$), X and Z are =N—, Y is =CH— and $A^a$ for a compound in each case corresponds to one group of Table A.

Table 232

Compounds of the formula I.A where $R^1$ and $R^2$ are methyl, $R^3$ is hydrogen, U is amino (—NH—) and V is sulfur, $W^a$ is —CO—O—* (*=bond to $A^a$), X and Z are =N—, Y is =CH— and $A^a$ for a compound in each case corresponds to one group of Table A.

Table 233

Compounds of the formula I.A where $R^1$ and $R^2$ are methyl, $R^3$ is hydrogen, U is amino (—NH—) and V is sulfur, $W^a$ is —O—CO—* (*=bond to $A^a$), X and Z are =N—, Y is =CH— and $A^a$ for a compound in each case corresponds to one group of Table A.

Table 234

Compounds of the formula I.A where $R^1$ and $R^2$ are methyl, $R^3$ is hydrogen, U is amino (—NH—) and V is sulfur, $W^a$ is —CO—NH—* (*=bond to $A^a$), X and Z are =N—, Y is =CH— and $A^a$ for a compound in each case corresponds to one group of Table A.

Table 235

Compounds of the formula I.A where $R^1$ and $R^2$ are methyl, $R^3$ is hydrogen, U is amino (—NH—) and V is sulfur, $W^a$ is —NH—CO—* (*=bond to $A^a$), X and Z are =N—, Y is =CH— and $A^a$ for a compound in each case corresponds to one group of Table A.

Table 236

Compounds of the formula I.A where $R^1$ and $R^2$ are methyl, $R^3$ is hydrogen, U is amino (—NH—) and V is sulfur, $W^a$ is —C(CH$_3$)=NO—* (*=bond to $A^a$), X and Z are =N—, Y is =CH— and $A^a$ for a compound in each case corresponds to one group of Table A.

Table 237

Compounds of the formula I.A where $R^1$ and $R^2$ are methyl, $R^3$ is hydrogen, U is amino (—NH—) and V is sulfur, $W^a$ is —CH$_2$O—N=C(CH$_3$)—* (*=bond to $A^a$), X and Z are =N—, Y is =CH— and $A^a$ for a compound in each case corresponds to one group of Table A.

Table 238

Compounds of the formula I.A where $R^1$ and $R^2$ are methyl, $R^3$ is hydrogen, U is amino (—NH—) and V is sulfur, $W^a$ is —CH$_2$O—N=C(CH$_3$)—C(C$_6$H$_5$)=NO—* (*=bond to $A^a$), X and Z are =N—, Y is =CH— and $A^a$ for a compound in each case corresponds to one group of Table A.

Table 239

Compounds of the formula I.A where $R^1$ and $R^2$ are methyl, $R^3$ is hydrogen, U is amino (—NH—) and V is sulfur, $W^a$ is —CH$_2$O—N=C(CH$_3$)—C(2-Cl—C$_6$H$_4$)=NO—* (*=bond to $A^a$), X and Z are =N—, Y is =CH— and $A^a$ for a compound in each case corresponds to one group of Table A.

Table 240

Compounds of the formula I.A where $R^1$ and $R^2$ are methyl, $R^3$ is hydrogen, U is amino (—NH—) and V is sulfur, $W^a$ is —CH$_2$O—N=C(CH$_3$)—C(4-Cl—C$_6$H$_4$)=NO—* (*=bond to $A^a$), X and Z are =N—, Y is =CH— and $A^a$ for a compound in each case corresponds to one group of Table A.

Table 241

Compounds of the formula I.A where $R^1$ and $R^2$ are methyl, $R^3$ is hydrogen, U is oxygen and V is amino (—NH—), $W^a$ is a direct bond, X, Y and Z are =CH— and $A^a$ for a compound in each case corresponds to one group of Table A.

Table 242

Compounds of the formula I.A where $R^1$ and $R^2$ are methyl, $R^3$ is hydrogen, U is oxygen and V is amino (—NH—), $W^a$ is —CH=CH—, X, Y and Z are =CH— and $A^a$ for a compound in each case corresponds to one group of Table A.

Table 243

Compounds of the formula I.A where $R^1$ and $R^2$ are methyl, $R^3$ is hydrogen, U is oxygen and V is amino (—NH—), $W^a$ is —C≡C—, X, Y and Z are =CH— and $A^a$ for a compound in each case corresponds to one group of Table A.

Table 244

Compounds of the formula I.A where $R^1$ and $R^2$ are methyl, $R^3$ is hydrogen, U is oxygen and V is amino (—NH—), $W^a$ is oxygen (—O—), X, Y and Z are =CH— and $A^a$ for a compound in each case corresponds to one group of Table A.

Table 245

Compounds of the formula I.A where $R^1$ and $R^2$ are methyl, $R^3$ is hydrogen, U is oxygen and V is amino (—NH—), $W^a$ is —CH$_2$O—* (*=bond to $A^a$), X, Y and Z Table 246
Compounds of the formula I.A where $R^1$ and $R^2$ are methyl, $R^3$ is hydrogen, U is oxygen and V is amino (—NH—), $W^a$ is —OCH$_2$—* (*=bond to $A^a$), X, Y and Z are =CH— and $A^a$ for a compound in each case corresponds to one group of Table A.

Table 247
Compounds of the formula I.A where $R^1$ and $R^2$ are methyl, $R^3$ is hydrogen, U is oxygen and V is amino (—NH—), $W^a$ is —CO—O—* (*=bond to $A^a$), X, Y and Z are =CH— and $A^a$ for a compound in each case corresponds to one group of Table A.

Table 248
Compounds of the formula I.A where $R^1$ and $R^2$ are methyl, $R^3$ is hydrogen, U is oxygen and V is amino (—NH—), $W^a$ is —O—CO—* (*=bond to $A^a$), X, Y and Z are =CH— and $A^a$ for a compound in each case corresponds to one group of Table A.

Table 249
Compounds of the formula I.A where $R^1$ and $R^2$ are methyl, $R^3$ is hydrogen, U is oxygen and V is amino (—NH—), $W^a$ is —CO—NH—* (*=bond to $A^a$), X, Y and Z are =CH— and $A^a$ for a compound in each case corresponds to one group of Table A.

Table 250
Compounds of the formula I.A where $R^1$ and $R^2$ are methyl, $R^3$ is hydrogen, U is oxygen and V is amino (—NH—), $W^a$ is —NH—CO—* (*=bond to $A^a$), X, Y and Z are =CH— and $A^a$ for a compound in each case corresponds to one group of Table A.

Table 251
Compounds of the formula I.A where $R^1$ and $R^2$ are methyl, $R^3$ is hydrogen, U is oxygen and V is amino (—NH—), $W^a$ is —C(CH$_3$)=NO—* (*=bond to $A^a$), X, Y and Z are =CH— and $A^a$ for a compound in each case corresponds to one group of Table A.

Table 252
Compounds of the formula I.A where $R^1$ and $R^2$ are methyl, $R^3$ is hydrogen, U is oxygen and V is amino (—NH—), $W^a$ is —CH$_2$O—N=C(CH$_3$)—* (*=bond to $A^a$), X, Y and Z are =CH— and $A^a$ for a compound in each case corresponds to one group of Table A.

Table 253
Compounds of the formula I.A where $R^1$ and $R^2$ are methyl, $R^3$ is hydrogen, U is oxygen and V is amino (—NH—), $W^a$ is —CH$_2$O—N=C(CH$_3$)—C(C$_6$H$_5$)=NO—* (*=bond to $A^a$), X, Y and Z are =CH— and $A^a$ for a compound in each case corresponds to one group of Table A.

Table 254
Compounds of the formula I.A where $R^1$ and $R^2$ are methyl, $R^3$ is hydrogen, U is oxygen and V is amino (—NH—), $W^a$ is —CH$_2$O—N=C(CH$_3$)—C(2-Cl—C$_6$H$_4$)=NO—* (*=bond to $A^a$), X, Y and Z are =CH— and $A^a$ for a compound in each case corresponds to one group of Table A.

Table 255
Compounds of the formula I.A where $R^1$ and $R^2$ are methyl, $R^3$ is hydrogen, U is oxygen and V is amino (—NH—), $W^a$ is —CH$_2$O—N=C(CH$_3$)—C(4-Cl—C$_6$H$_4$)=NO—* (*=bond to $A^a$), X, Y and Z are =CH— and $A^a$ for a compound in each case corresponds to one group of Table A.

Table 256
Compounds of the formula I.A where $R^1$ and $R^2$ are methyl, $R^3$ is hydrogen, U is oxygen and V is amino (—NH—), $W^a$ is a direct bond, X is =N—, Y and Z are =CH— and $A^a$ for a compound in each case corresponds to one group of Table A.

Table 257
Compounds of the formula I.A where $R^1$ and $R^2$ are methyl, $R^3$ is hydrogen, U is oxygen and V is amino (—NH—), $W^a$ is —CH=CH—, X is =N—, Y and Z are =CH— and $A^a$ for a compound in each case corresponds to one group of Table A.

Table 258
Compounds of the formula I.A where $R^1$ and $R^2$ are methyl, $R^3$ is hydrogen, U is oxygen and V is amino (—NH—), $W^a$ is —C≡C—, X is =N—, Y and Z are =CH— and $A^a$ for a compound in each case corresponds to one group of Table A.

Table 259
Compounds of the formula I.A where $R^1$ and $R^2$ are methyl, $R^3$ is hydrogen, U is oxygen and V is amino (—NH—), $W^a$ is oxygen (—O—), X is =N—, Y and Z are =CH— and $A^a$ for a compound in each case corresponds to one group of Table A.

Table 260
Compounds of the formula I.A where $R^1$ and $R^2$ are methyl, $R^3$ is hydrogen, U is oxygen and V is amino (—NH—), $W^a$ is —CH$_2$O—* (*=bond to $A^a$), X is =N—, Y and Z are =CH— and $A^a$ for a compound in each case corresponds to one group of Table A.

Table 261
Compounds of the formula I.A where $R^1$ and $R^2$ are methyl, $R^3$ is hydrogen, U is oxygen and V is amino (—NH—), $W^a$ is —OCH$_2$—* (*=bond to $A^a$), X is =N—, Y and Z are =CH— and $A^a$ for a compound in each case corresponds to one group of Table A.

Table 262
Compounds of the formula I.A where $R^1$ and $R^2$ are methyl, $R^3$ is hydrogen, U is oxygen and V is amino (—NH—), $W^a$ is —CO—O—* (*=bond to $A^a$), X is =N—, Y and Z are =CH— and $A^a$ for a compound in each case corresponds to one group of Table A.

Table 263
Compounds of the formula I.A where $R^1$ and $R^2$ are methyl, $R^3$ is hydrogen, U is oxygen and V is amino (—NH—), $W^a$ is —O—CO—* (*=bond to $A^a$), X is =N—, Y and Z are =CH— and $A^a$ for a compound in each case corresponds to one group of Table A.

Table 264
Compounds of the formula I.A where $R^1$ and $R^2$ are methyl, $R^3$ is hydrogen, U is oxygen and V is amino (—NH—), $W^a$ is —CO—NH—* (*=bond to $A^a$), X is =N—, Y and Z are =CH— and $A^a$ for a compound in each case corresponds to one group of Table A.

Table 265
Compounds of the formula I.A where $R^1$ and $R^2$ are methyl, $R^3$ is hydrogen, U is oxygen and V is amino (—NH—), $W^a$ is —NH—CO—* (*=bond to $A^a$), X is =N—, Y and Z are =CH— and $A^a$ for a compound in each case corresponds to one group of Table A.

Table 266
Compounds of the formula I.A where $R^1$ and $R^2$ are methyl, $R^3$ is hydrogen, U is oxygen and V is amino (—NH—), $W^a$ is —C(CH$_3$)=NO—* (*=bond to $A^a$), X is =N—, Y and Z are =CH— and $A^a$ for a compound in each case corresponds to one group of Table A.

Table 267
Compounds of the formula I.A where $R^1$ and $R^2$ are methyl, $R^3$ is hydrogen, U is oxygen and V is amino (—NH—), $W^a$ is —CH$_2$O—N=C(CH$_3$)—* (*=bond to $A^a$), X is =N—, Y and Z are =CH— and $A^a$ for a compound in each case corresponds to one group of Table A.

Table 268

Compounds of the formula I.A where $R^1$ and $R^2$ are methyl, $R^3$ is hydrogen, U is oxygen and V is amino (—NH—), $W^a$ is —CH$_2$O—N=C(CH$_3$)—C(C$_6$H$_5$)=NO—* (*=bond to $A^a$), X is =N—, Y and Z are =CH— and $A^a$ for a compound in each case corresponds to one group of Table A.

Table 269

Compounds of the formula I.A where $R^1$ and $R^2$ are methyl, $R^3$ is hydrogen, U is oxygen and V is amino (—NH—), $W^a$ is —CH$_2$O—N=C(CH$_3$)—C(2-Cl—C$_6$H$_4$)=NO—* (*=bond to $A^a$), X is =N—, Y and Z are =CH— and $A^a$ for a compound in each case corresponds to one group of Table A.

Table 270

Compounds of the formula I.A where $R^1$ and $R^2$ are methyl, $R^3$ is hydrogen, U is oxygen and V is amino (—NH—), $W^a$ is —CH$_2$O—N=C(CH$_3$)—C(4-Cl—C$_6$H$_4$)=NO—* (*=bond to $A^a$), X is =N—, Y and Z are =CH— and $A^a$ for a compound in each case corresponds to one group of Table A.

Table 271

Compounds of the formula I.A where $R^1$ and $R^2$ are methyl, $R^3$ is hydrogen, U is oxygen and V is amino (—NH—), $W^a$ is a direct bond, X and Y are =N—, Z is =CH— and $A^a$ for a compound in each case corresponds to one group of Table A.

Table 272

Compounds of the formula I.A where $R^1$ and $R^2$ are methyl, $R^3$ is hydrogen, U is oxygen and V is amino (—NH—), $W^a$ is —CH=CH—, X and Y are =N—, Z is =CH— and $A^a$ for a compound in each case corresponds to one group of Table A.

Table 273

Compounds of the formula I.A where $R^1$ and $R^2$ are methyl, $R^3$ is hydrogen, U is oxygen and V is amino (—NH—), $W^a$ is —C≡C—, X and Y are =N—, Z is =CH— and $A^a$ for a compound in each case corresponds to one group of Table A.

Table 274

Compounds of the formula I.A where $R^1$ and $R^2$ are methyl, $R^3$ is hydrogen, U is oxygen and V is amino (—NH—), $W^a$ is oxygen (—O—), X and Y are =N—, Z is =CH— and $A^a$ for a compound in each case corresponds to one group of Table A.

Table 275

Compounds of the formula I.A where $R^1$ and $R^2$ are methyl, $R^3$ is hydrogen, U is oxygen and V is amino (—NH—), $W^a$ is —CH$_2$O—* (*=bond to $A^a$), X and Y are =N—, Z is =CH— and $A^a$ for a compound in each case corresponds to one group of Table A.

Table 276

Compounds of the formula I.A where $R^1$ and $R^2$ are methyl, $R^3$ is hydrogen, U is oxygen and V is amino (—NH—), $W^a$ is —OCH$_2$—* (*=bond to $A^a$), X and Y are =N—, Z is =CH— and $A^a$ for a compound in each case corresponds to one group of Table A.

Table 277

Compounds of the formula I.A where $R^1$ and $R^2$ are methyl, $R^3$ is hydrogen, U is oxygen and V is amino (—NH—), $W^a$ is —CO—O—* (*=bond to $A^a$), X and Y are =N—, Z is =CH— and $A^a$ for a compound in each case corresponds to one group of Table A.

Table 278

Compounds of the formula I.A where $R^1$ and $R^2$ are methyl, $R^3$ is hydrogen, U is oxygen and V is amino (—NH—), $W^a$ is —O—CO—* (*=bond to $A^a$), X and Y are =N—, Z is =CH— and $A^a$ for a compound in each case corresponds to one group of Table A.

Table 279

Compounds of the formula I.A where $R^1$ and $R^2$ are methyl, $R^3$ is hydrogen, U is oxygen and V is amino (—NH—), $W^a$ is —CO—NH—* (*=bond to $A^a$), X and Y are =N—, Z is =CH— and $A^a$ for a compound in each case corresponds to one group of Table A.

Table 280

Compounds of the formula I.A where $R^1$ and $R^2$ are methyl, $R^3$ is hydrogen, U is oxygen and V is amino (—NH—), $W^a$ is —NH—CO—* (*=bond to $A^a$), X and Y are =N—, Z is =CH— and $A^a$ for a compound in each case corresponds to one group of Table A.

Table 281

Compounds of the formula I.A where $R^1$ and $R^2$ are methyl, $R^3$ is hydrogen, U is oxygen and V is amino (—NH—), $W^a$ is —C(CH$_3$)=NO—* (*=bond to $A^a$), X and Y are =N—, Z is =CH— and $A^a$ for a compound in each case corresponds to one group of Table A.

Table 282

Compounds of the formula I.A where $R^1$ and $R^2$ are methyl, $R^3$ is hydrogen, U is oxygen and V is amino (—NH—), $W^a$ is —CH$_2$O—N=C(CH$_3$)—* (*=bond to $A^a$), X and Y are =N—, Z is =CH— and $A^a$ for a compound in each case corresponds to one group of Table A.

Table 283

Compounds of the formula I.A where $R^1$ and $R^2$ are methyl, $R^3$ is hydrogen, U is oxygen and V is amino (—NH—), $W^a$ is —CH$_2$O—N=C(CH$_3$)—C(C$_6$H$_5$)=NO—* (*=bond to $A^a$), X and Y are =N—, Z is =CH— and $A^a$ for a compound in each case corresponds to one group of Table A.

Table 284

Compounds of the formula I.A where $R^1$ and $R^2$ are methyl, $R^3$ is hydrogen, U is oxygen and V is amino (—NH—), $W^a$ is —CH$_2$O—N=C(CH$_3$)—C(2-Cl—C$_6$H$_4$)=NO—* (*=bond to $A^a$), X and Y are =N—, Z is =CH— and $A^a$ for a compound in each case corresponds to one group of Table A.

Table 285

Compounds of the formula I.A where $R^1$ and $R^2$ are methyl, $R^3$ is hydrogen, U is oxygen and V is amino (—NH—), $W^a$ is —CH$_2$O—N=C(CH$_3$)—C(4-Cl—C$_6$H$_4$)=NO—* (*=bond to $A^a$), X and Y are =N—, Z is =CH— and $A^a$ for a compound in each case corresponds to one group of Table A.

Table 286

Compounds of the formula I.A where $R^1$ and $R^2$ are methyl, $R^3$ is hydrogen, U is oxygen and V is amino (—NH—), $W^a$ is a direct bond, X and Z are =N—, Y is =CH— and $A^a$ for a compound in each case corresponds to one group of Table A.

Table 287

Compounds of the formula I.A where $R^1$ and $R^2$ are methyl, $R^3$ is hydrogen, U is oxygen and V is amino (—NH—), $W^a$ is —CH=CH—, X and Z are =N—, Y is =CH— and $A^a$ for a compound in each case corresponds to one group of Table A.

Table 288

Compounds of the formula I.A where $R^1$ and $R^2$ are methyl, $R^3$ is hydrogen, U is oxygen and V is amino (—NH—), $W^a$ is —C≡C—, X and Z are =N—, Y is =CH— and $A^a$ for a compound in each case corresponds to one group of Table A.

Table 289
Compounds of the formula I.A where $R^1$ and $R^2$ are methyl, $R^3$ is hydrogen, U is oxygen and V is amino (—NH—), $W^a$ is oxygen (—O—), X and Z are =N—, Y is =CH— and $A^a$ for a compound in each case corresponds to one group of Table A.

Table 290
Compounds of the formula I.A where $R^1$ and $R^2$ are methyl, $R^3$ is hydrogen, U is oxygen and V is amino (—NH—), $W^a$ is —CH$_2$O—* (*=bond to $A^a$), X and Z are =N—, Y is =CH— and $A^a$ for a compound in each case corresponds to one group of Table A.

Table 291
Compounds of the formula I.A where $R^1$ and $R^2$ are methyl, $R^3$ is hydrogen, U is oxygen and V is amino (—NH—), $W^a$ is —OCH$_2$—* (*=bond to $A^a$), X and Z are =N—, Y is =CH— and $A^a$ for a compound in each case corresponds to one group of Table A.

Table 292
Compounds of the formula I.A where $R^1$ and $R^2$ are methyl, $R^3$ is hydrogen, U is oxygen and V is amino (—NH—), $W^a$ is —CO—O—* (*=bond to $A^a$), X and Z are =N—, Y is =CH— and $A^a$ for a compound in each case corresponds to one group of Table A.

Table 293
Compounds of the formula I.A where $R^1$ and $R^2$ are methyl, $R^3$ is hydrogen, U is oxygen and V is amino (—NH—), $W^a$ is —O—CO—* (*=bond to $A^a$), X and Z are =N—, Y is =CH— and $A^a$ for a compound in each case corresponds to one group of Table A.

Table 294
Compounds of the formula I.A where $R^1$ and $R^2$ are methyl, $R^3$ is hydrogen, U is oxygen and V is amino (—NH—), $W^a$ is —CO—NH—* (*=bond to $A^a$), X and Z are =N—, Y is =CH— and $A^a$ for a compound in each case corresponds to one group of Table A.

Table 295
Compounds of the formula I.A where $R^1$ and $R^2$ are methyl, $R^3$ is hydrogen, U is oxygen and V is amino (—NH—), $W^a$ is —NH—CO—* (*=bond to $A^a$), X and Z are =N—, Y is =CH— and $A^a$ for a compound in each case corresponds to one group of Table A.

Table 296
Compounds of the formula I.A where $R^1$ and $R^2$ are methyl, $R^3$ is hydrogen, U is oxygen and V is amino (—NH—), $W^a$ is —C(CH$_3$)=NO—* (*=bond to $A^a$), X and Z are =N—, Y is =CH— and $A^a$ for a compound in each case corresponds to one group of Table A.

Table 297
Compounds of the formula I.A where $R^1$ and $R^2$ are methyl, $R^3$ is hydrogen, U is oxygen and V is amino (—NH—), $W^a$ is —CH$_2$O—N=C(CH$_3$)—* (*=bond to $A^a$), X and Z are =N—, Y is =CH— and $A^a$ for a compound in each case corresponds to one group of Table A.

Table 298
Compounds of the formula I.A where $R^1$ and $R^2$ are methyl, $R^3$ is hydrogen, U is oxygen and V is amino (—NH—), $W^a$ is —CH$_2$O—N=C(CH$_3$)—C(C$_6$H$_5$)=NO—* (*=bond to $A^a$), X and Z are =N—, Y is =CH— and $A^a$ for a compound in each case corresponds to one group of Table A.

Table 299
Compounds of the formula I.A where $R^1$ and $R^2$ are methyl, $R^3$ is hydrogen, U is oxygen and V is amino (—NH—), $W^a$ is —CH$_2$O—N=C(CH$_3$)—C(2-Cl—C$_6$H$_4$)=NO—* (*=bond to $A^a$), X and Z are =N—, Y is =CH— and $A^a$ for a compound in each case corresponds to one group of Table A.

Table 300
Compounds of the formula I.A where $R^1$ and $R^2$ are methyl, $R^3$ is hydrogen, U is oxygen and V is amino (—NH—), $W^a$ is —CH$_2$O—N=C(CH$_3$)—C(4-Cl—C$_6$H$_4$)=NO—* (*=bond to $A^a$), X and Z are =N—, Y is =CH— and $A^a$ for a compound in each case corresponds to one group of Table A.

Table 301
Compounds of the formula I.A where $R^1$ and $R^2$ are methyl, $R^3$ is hydrogen, U and V are amino (—NH—), $W^a$ is a direct bond, X, Y and Z are =CH— and $A^a$ for a compound in each case corresponds to one group of Table A.

Table 302
Compounds of the formula I.A where $R^1$ and $R^2$ are methyl, $R^3$ is hydrogen, U and V are amino (—NH—), $W^a$ is —CH=CH—, X, Y and Z are =CH— and $A^a$ for a compound in each case corresponds to one group of Table A.

Table 303
Compounds of the formula I.A where $R^1$ and $R^2$ are methyl, $R^3$ is hydrogen, U and V are amino (—NH—), $W^a$ is —C≡C—, X, Y and Z are =CH— and $A^a$ for a compound in each case corresponds to one group of Table A.

Table 304
Compounds of the formula I.A where $R^1$ and $R^2$ are methyl, $R^3$ is hydrogen, U and V are amino (—NH—), $W^a$ is oxygen (—O—), X, Y and Z are =CH— and $A^a$ for a compound in each case corresponds to one group of Table A.

Table 305
Compounds of the formula I.A where $R^1$ and $R^2$ are methyl, $R^3$ is hydrogen, U and V are amino (—NH—), $W^a$ is —CH$_2$O—* (*=bond to $A^a$), X, Y and Z are =CH— and $A^a$ for a compound in each case corresponds to one group of Table A.

Table 306
Compounds of the formula I.A where $R^1$ and $R^2$ are methyl, $R^3$ is hydrogen, U and V are amino (—NH—), $W^a$ is —OCH$_2$—* (*=bond to $A^a$), X, Y and Z are =CH— and $A^a$ for a compound in each case corresponds to one group of Table A.

Table 307
Compounds of the formula I.A where $R^1$ and $R^2$ are methyl, $R^3$ is hydrogen, U and V are amino (—NH—), $W^a$ is —CO—O—* (*=bond to $A^a$), X, Y and Z are =CH— and $A^a$ for a compound in each case corresponds to one group of Table A.

Table 308
Compounds of the formula I.A where $R^1$ and $R^2$ are methyl, $R^3$ is hydrogen, U and V are amino (—NH—), $W^a$ is —O—CO—* (*=bond to $A^a$), X, Y and Z are =CH— and $A^a$ for a compound in each case corresponds to one group of Table A.

Table 309
Compounds of the formula I.A where $R^1$ and $R^2$ are methyl, $R^3$ is hydrogen, U and V are amino (—NH—), $W^a$ is —CO—NH—* (*=bond to $A^a$), X, Y and Z are =CH— and $A^a$ for a compound in each case corresponds to one group of Table A.

Table 310
Compounds of the formula I.A where $R^1$ and $R^2$ are methyl, $R^3$ is hydrogen, U and V are amino (—NH—), $W^a$ is —NH—CO—* (*=bond to $A^a$), X, Y and Z are =CH— and $A^a$ for a compound in each case corresponds to one group of Table A.

Table 311
Compounds of the formula I.A where $R^1$ and $R^2$ are methyl, $R^3$ is hydrogen, U and V are amino (—NH—), $W^a$ is —C(CH$_3$)=NO—* (*=bond to $A^a$), X, Y and Z are Table 312
Compounds of the formula I.A where $R^1$ and $R^2$ are methyl, $R^3$ is hydrogen, U and V are amino (—NH—), $W^a$ is —CH$_2$O—N=C(CH$_3$)—* (*=bond to $A^a$), X, Y and Z are =CH— and $A^a$ for a compound in each case corresponds to one group of Table A.

Table 313
Compounds of the formula I.A where $R^1$ and $R^2$ are methyl, $R^3$ is hydrogen, U and V are amino (—NH—), $W^a$ is —CH$_2$O—N=C(CH$_3$)—C(C$_6$H$_5$)=NO—* (*=bond to $A^a$), X, Y and Z are =CH— and $A^a$ for a compound in each case corresponds to one group of Table A.

Table 314
Compounds of the formula I.A where $R^1$ and $R^2$ are methyl, $R^3$ is hydrogen, U and V are amino (—NH—), $W^a$ is —CH$_2$O—N=C(CH$_3$)—C(2-Cl—C$_6$H$_4$)=NO—* (*=bond to $A^a$), X, Y and Z are =CH— and $A^a$ for a compound in each case corresponds to one group of Table A.

Table 315
Compounds of the formula I.A where $R^1$ and $R^2$ are methyl, $R^3$ is hydrogen, U and V are amino (—NH—), $W^a$ is —CH$_2$O—N=C(CH$_3$)—C(4-Cl—C$_6$H$_4$)=NO—* (*=bond to $A^a$), X, Y and Z are =CH— and $A^a$ for a compound in each case corresponds to one group of Table A.

Table 316
Compounds of the formula I.A where $R^1$ and $R^2$ are methyl, $R^3$ is hydrogen, U and V are amino (—NH—), $W^a$ is a direct bond, X is =N—, Y and Z are =CH— and $A^a$ for a compound in each case corresponds to one group of Table A.

Table 317
Compounds of the formula I.A where $R^1$ and $R^2$ are methyl, $R^3$ is hydrogen, U and V are amino (—NH—), $W^a$ is —CH=CH—, X is =N—, Y and Z are =CH— and $A^a$ for a compound in each case corresponds to one group of Table A.

Table 318
Compounds of the formula I.A where $R^1$ and $R^2$ are methyl, $R^3$ is hydrogen, U and V are amino (—NH—), $W^a$ is —C≡C—, X is =N—, Y and Z are =CH— and $A^a$ for a compound in each case corresponds to one group of Table A.

Table 319
Compounds of the formula I.A where $R^1$ and $R^2$ are methyl, $R^3$ is hydrogen, U and V are amino (—NH—), $W^a$ is oxygen (—O—), X is =N—, Y and Z are =CH— and $A^a$ for a compound in each case corresponds to one group of Table A.

Table 320
Compounds of the formula I.A where $R^1$ and $R^2$ are methyl, $R^3$ is hydrogen, U and V are amino (—NH—), $W^a$ is —CH$_2$O—* (*=bond to $A^a$), X is =N—, Y and Z are =CH— and $A^a$ for a compound in each case corresponds to one group of Table A.

Table 321
Compounds of the formula I.A where $R^1$ and $R^2$ are methyl, $R^3$ is hydrogen, U and V are amino (—NH—), $W^a$ is —OCH$_2$—* (*=bond to $A^a$), X is =N—, Y and Z are =CH— and $A^a$ for a compound in each case corresponds to one group of Table A.

Table 322
Compounds of the formula I.A where $R^1$ and $R^2$ are methyl, $R^3$ is hydrogen, U and V are amino (—NH—), $W^a$ is —CO—O—* (*=bond to $A^a$), X is =N—, Y and Z are =CH— and $A^a$ for a compound in each case corresponds to one group of Table A.

Table 323
Compounds of the formula I.A where $R^1$ and $R^2$ are methyl, $R^3$ is hydrogen, U and V are amino (—NH—), $W^a$ is —O—CO—* (*=bond to $A^a$), X is =N—, Y and Z are =CH— and $A^a$ for a compound in each case corresponds to one group of Table A.

Table 324
Compounds of the formula I.A where $R^1$ and $R^2$ are methyl, $R^3$ is hydrogen, U and V are amino (—NH—), $W^a$ is —CO—NH—* (*=bond to $A^a$), X is =N—, Y and Z are =CH— and $A^a$ for a compound in each case corresponds to one group of Table A.

Table 325
Compounds of the formula I.A where $R^1$ and $R^2$ are methyl, $R^3$ is hydrogen, U and V are amino (—NH—), $W^a$ is —NH—CO—* (*=bond to $A^a$), X is =N—, Y and Z are =CH— and $A^a$ for a compound in each case corresponds to one group of Table A.

Table 326
Compounds of the formula I.A where $R^1$ and $R^2$ are methyl, $R^3$ is hydrogen, U and V are amino (—NH—), $W^a$ is —C(CH$_3$)=NO—* (*=bond to $A^a$), X is =N—, Y and Z are =CH— and $A^a$ for a compound in each case corresponds to one group of Table A.

Table 327
Compounds of the formula I.A where $R^1$ and $R^2$ are methyl, $R^3$ is hydrogen, U and V are amino (—NH—), $W^a$ is —CH$_2$O—N=C(CH$_3$)—* (*=bond to $A^a$), X is =N—, Y and Z are =CH— and $A^a$ for a compound in each case corresponds to one group of Table A.

Table 328
Compounds of the formula I.A where $R^1$ and $R^2$ are methyl, $R^3$ is hydrogen, U and V are amino (—NH—), $W^a$ is —CH$_2$O—N=C(CH$_3$)—C(C$_6$H$_5$)=NO—* (*=bond to $A^a$), X is =N—, Y and Z are =CH— and $A^a$ for a compound in each case corresponds to one group of Table A.

Table 329
Compounds of the formula I.A where $R^1$ and $R^2$ are methyl, $R^3$ is hydrogen, U and V are amino (—NH—), $W^a$ is —CH$_2$O—N=C(CH$_3$)—C(2-Cl—C$_6$H$_4$)=NO—* (*=bond to $A^a$), X is =N—, Y and Z are =CH— and $A^a$ for a compound in each case corresponds to one group of Table A.

Table 330
Compounds of the formula I.A where $R^1$ and $R^2$ are methyl, $R^3$ is hydrogen, U and V are amino (—NH—), $W^a$ is —CH$_2$O—N=C(CH$_3$)—C(4-Cl—C$_6$H$_4$)=NO—* (*=bond to $A^a$), X is =N—, Y and Z are =CH— and $A^a$ for a compound in each case corresponds to one group of Table A.

Table 331
Compounds of the formula I.A where $R^1$ and $R^2$ are methyl, $R^3$ is hydrogen, U and V are amino (—NH—), $W^a$ is a direct bond, X and Y are =N—, Z is =CH— and $A^a$ for a compound in each case corresponds to one group of Table A.

Table 332
Compounds of the formula I.A where $R^1$ and $R^2$ are methyl, $R^3$ is hydrogen, U and V are amino (—NH—), $W^a$ is —CH=CH—, X and Y are =N—, Z is =CH— and $A^a$ for a compound in each case corresponds to one group of Table A.

Table 333
Compounds of the formula I.A where $R^1$ and $R^2$ are methyl, $R^3$ is hydrogen, U and V are amino (—NH—), $W^a$ is —C≡C—, X and Y are =N—, Z is =CH— and $A^a$ for a compound in each case corresponds to one group of Table A.

Table 334
Compounds of the formula I.A where $R^1$ and $R^2$ are methyl, $R^3$ is hydrogen, U and V are amino (—NH—), $W^a$ is oxygen (—O—), X and Y are =N—, Z is =CH— and $A^a$ for a compound in each case corresponds to one group of Table A.

Table 335
Compounds of the formula I.A where $R^1$ and $R^2$ are methyl, $R^3$ is hydrogen, U and V are amino (—NH—), $W^a$ is —CH$_2$O—* (*=bond to $A^a$), X and Y are =N—, Z is =CH— and $A^a$ for a compound in each case corresponds to one group of Table A.

Table 336
Compounds of the formula I.A where $R^1$ and $R^2$ are methyl, $R^3$ is hydrogen, U and V are amino (—NH—), $W^a$ is —OCH$_2$—* (*=bond to $A^a$), X and Y are =N—, Z is =CH— and $A^a$ for a compound in each case corresponds to one group of Table A.

Table 337
Compounds of the formula I.A where $R^1$ and $R^2$ are methyl, $R^3$ is hydrogen, U and V are amino (—NH—), $W^a$ is —CO—O—* (*=bond to $A^a$), X and Y are =N—, Z is =CH— and $A^a$ for a compound in each case corresponds to one group of Table A.

Table 338
Compounds of the formula I.A where $R^1$ and $R^2$ are methyl, $R^3$ is hydrogen, U and V are amino (—NH—), $W^a$ is —O—CO—* (*=bond to $A^a$), X and Y are =N—, Z is =CH— and $A^a$ for a compound in each case corresponds to one group of Table A.

Table 339
Compounds of the formula I.A where $R^1$ and $R^2$ are methyl, $R^3$ is hydrogen, U and V are amino (—NH—), $W^a$ is —CO—NH—* (*=bond to $A^a$), X and Y are =N—, Z is =CH— and $A^a$ for a compound in each case corresponds to one group of Table A.

Table 340
Compounds of the formula I.A where $R^1$ and $R^2$ are methyl, $R^3$ is hydrogen, U and V are amino (—NH—), $W^a$ is —NH—CO—* (*=bond to $A^a$), X and Y are =N—, Z is =CH— and $A^a$ for a compound in each case corresponds to one group of Table A.

Table 341
Compounds of the formula I.A where $R^1$ and $R^2$ are methyl, $R^3$ is hydrogen, U and V are amino (—NH—), $W^a$ is —C(CH$_3$)=NO—* (*=bond to $A^a$), X and Y are =N—, Z is =CH— and $A^a$ for a compound in each case corresponds to one group of Table A.

Table 342
Compounds of the formula I.A where $R^1$ and $R^2$ are methyl, $R^3$ is hydrogen, U and V are amino (—NH—), $W^a$ is —CH$_2$O—N=C(CH$_3$)—* (*=bond to $A^a$), X and Y are =N—, Z is =CH— and $A^a$ for a compound in each case corresponds to one group of Table A.

Table 343
Compounds of the formula I.A where $R^1$ and $R^2$ are methyl, $R^3$ is hydrogen, U and V are amino (—NH—), $W^a$ is —CH$_2$O—N=C(CH$_3$)—C(C$_6$H$_5$)=NO—* (*=bond to $A^a$), X and Y are =N—, Z is =CH— and $A^a$ for a compound in each case corresponds to one group of Table A.

Table 344
Compounds of the formula I.A where $R^1$ and $R^2$ are methyl, $R^3$ is hydrogen, U and V are amino (—NH—), $W^a$ is —CH$_2$O—N=C(CH$_3$)—C(2-Cl—C$_6$H$_4$)=NO—* (*=bond to $A^a$), X and Y are =N—, Z is =CH— and $A^a$ for a compound in each case corresponds to one group of Table A.

Table 345
Compounds of the formula I.A where $R^1$ and $R^2$ are methyl, $R^3$ is hydrogen, U and V are amino (—NH—), $W^a$ is —CH$_2$O—N=C(CH$_3$)—C(4-Cl—C$_6$H$_4$)=NO—* (*=bond to $A^a$), X and Y are =N—, Z is =CH— and $A^a$ for a compound in each case corresponds to one group of Table A.

Table 346
Compounds of the formula I.A where $R^1$ and $R^2$ are methyl, $R^3$ is hydrogen, U and V are amino (—NH—), $W^a$ is a direct bond, X and Z are =N—, Y is =CH— and $A^a$ for a compound in each case corresponds to one group of Table A.

Table 347
Compounds of the formula I.A where $R^1$ and $R^2$ are methyl, $R^3$ is hydrogen, U and V are amino (—NH—), $W^a$ is —CH=CH—, X and Z are =N—, Y is =CH— and $A^a$ for a compound in each case corresponds to one group of Table A.

Table 348
Compounds of the formula I.A where $R^1$ and $R^2$ are methyl, $R^3$ is hydrogen, U and V are amino (—NH—), $W^a$ is —C≡C—, X and Z are =N—, Y is =CH— and $A^a$ for a compound in each case corresponds to one group of Table A.

Table 349
Compounds of the formula I.A where $R^1$ and $R^2$ are methyl, $R^3$ is hydrogen, U and V are amino (—NH—), $W^a$ is oxygen (—O—), X and Z are =N—, Y is =CH— and $A^a$ for a compound in each case corresponds to one group of Table A.

Table 350
Compounds of the formula I.A where $R^1$ and $R^2$ are methyl, $R^3$ is hydrogen, U and V are amino (—NH—), $W^a$ is —CH$_2$O—* (*=bond to $A^a$), X and Z are =N—, Y is =CH— and $A^a$ for a compound in each case corresponds to one group of Table A.

Table 351
Compounds of the formula I.A where $R^1$ and $R^2$ are methyl, $R^3$ is hydrogen, U and V are amino (—NH—), $W^a$ is —OCH$_2$—* (*=bond to $A^a$), X and Z are =N—, Y is =CH— and $A^a$ for a compound in each case corresponds to one group of Table A.

Table 352
Compounds of the formula I.A where $R^1$ and $R^2$ are methyl, $R^3$ is hydrogen, U and V are amino (—NH—), $W^a$ is —CO—O—* (*=bond to $A^a$), X and Z are =N—, Y is =CH— and $A^a$ for a compound in each case corresponds to one group of Table A.

Table 353
Compounds of the formula I.A where $R^1$ and $R^2$ are methyl, $R^3$ is hydrogen, U and V are amino (—NH—), $W^a$ is —O—CO—* (*=bond to $A^a$), X and Z are =N—, Y is =CH— and $A^a$ for a compound in each case corresponds to one group of Table A.

Table 354
Compounds of the formula I.A where $R^1$ and $R^2$ are methyl, $R^3$ is hydrogen, U and V are amino (—NH—), $W^a$ is —CO—NH—* (*=bond to $A^a$), X and Z are =N—, Y is =CH— and $A^a$ for a compound in each case corresponds to one group of Table A.

Table 355
Compounds of the formula I.A where $R^1$ and $R^2$ are methyl, $R^3$ is hydrogen, U and V are amino (—NH—), $W^a$ is —NH—CO—* (*=bond to $A^a$), X and Z are =N—, Y is =CH— and $A^a$ for a compound in each case corresponds to one group of Table A.

Table 356
Compounds of the formula I.A where $R^1$ and $R^2$ are methyl, $R^3$ is hydrogen, U and V are amino (—NH—), $W^a$ is —C(CH$_3$)=NO—* (*=bond to $A^a$), X and Z are =N—, Y is =CH— and $A^a$ for a compound in each case corresponds to one group of Table A.

Table 357
Compounds of the formula I.A where $R^1$ and $R^2$ are methyl, $R^3$ is hydrogen, U and V are amino (—NH—), $W^a$ is —CH$_2$O—N=C(CH$_3$)—* (*=bond to $A^a$), X and Z are =N—, Y is =CH— and $A^a$ for a compound in each case corresponds to one group of Table A.

Table 358
Compounds of the formula I.A where $R^1$ and $R^2$ are methyl, $R^3$ is hydrogen, U and V are amino (—NH—), $W^a$ is —CH$_2$O—N=C(CH$_3$)—C(C$_6$H$_5$)=NO—* (*=bond to $A^a$), X and Z are =N—, Y is =CH— and $A^a$ for a compound in each case corresponds to one group of Table A.

Table 359
Compounds of the formula I.A where $R^1$ and $R^2$ are methyl, $R^3$ is hydrogen, U and V are amino (—NH—), $W^a$ is —CH$_2$O—N=C(CH$_3$)—C(2-Cl—C$_6$H$_4$)=NO—* (*=bond to $A^a$), X and Z are =N—, Y is =CH— and $A^a$ for a compound in each case corresponds to one group of Table A.

Table 360
Compounds of the formula I.A where $R^1$ and $R^2$ are methyl, $R^3$ is hydrogen, U and V are amino (—NH—), $W^a$ is —CH$_2$O—N=C(CH$_3$)—C(4-Cl—C$_6$H$_4$)=NO—* (*=bond to $A^a$), X and Z are =N—, Y is =CH— and $A^a$ for a compound in each case corresponds to one group of Table A.

Table 361
Compounds of the formula I.A where $R^1$ and $R^2$ are methyl, $R^3$ is hydrogen, U and V are oxygen, $W^a$ is a direct bond, X, Y and Z are =CH— and $A^a$ for a compound in each case corresponds to one group of Table B.

Table 362
Compounds of the formula I.A where $R^1$ and $R^2$ are methyl, $R^3$ is hydrogen, U and V are oxygen, $W^a$ is —C(CH$_3$)=NO—* (*=bond to $A^a$), X, Y and Z are =CH— and $A^a$ for a compound in each case corresponds to one group of Table B.

Table 363
Compounds of the formula I.A where $R^1$ and $R^2$ are methyl, $R^3$ is hydrogen, U and V are oxygen, $W^a$ is —CH$_2$O—N=C(CH$_3$)—* (*=bond to $A^a$), X, Y and Z are =CH— and $A^a$ for a compound in each case corresponds to one group of Table B.

Table 364
Compounds of the formula I.A where $R^1$ and $R^2$ are methyl, $R^3$ is hydrogen, U and V are oxygen, $W^a$ is —CH$_2$O—N=C(CH$_3$)—C(C$_6$H$_5$)=NO—* (*=bond to $A^a$), X, Y and Z are =CH— and $A^a$ for a compound in each case corresponds to one group of Table B.

Table 365
Compounds of the formula I.A where $R^1$ and $R^2$ are methyl, $R^3$ is hydrogen, U and V are oxygen, $W^a$ is —CH$_2$O—N=C(CH$_3$)—C(2-Cl—C$_6$H$_4$)=NO—* (*=bond to $A^a$), X, Y and Z are =CH— and $A^a$ for a compound in each case corresponds to one group of Table B.

Table 366
Compounds of the formula I.A where $R^1$ and $R^2$ are methyl, $R^3$ is hydrogen, U and V are oxygen, $W^a$ is —CH$_2$O—N=C(CH$_3$)—C(4-Cl—C$_6$H$_4$)=NO—* (*=bond to $A^a$), X, Y and Z are =CH— and $A^a$ for a compound in each case corresponds to one group of Table B.

Table 367
Compounds of the formula I.A where $R^1$ and $R^2$ are methyl, $R^3$ is hydrogen, U and V are oxygen, $W^a$ is a direct bond, X is =N—, Y and Z are =CH— and $A^a$ for a compound in each case corresponds to one group of Table B.

Table 368
Compounds of the formula I.A where $R^1$ and $R^2$ are methyl, $R^3$ is hydrogen, U and V are oxygen, $W^a$ is —C(CH$_3$)=NO—* (*=bond to $A^a$), X is =N—, Y and Z are =CH— and $A^a$ for a compound in each case corresponds to one group of Table B.

Table 369
Compounds of the formula I.A where $R^1$ and $R^2$ are methyl, $R^3$ is hydrogen, U and V are oxygen, $W^a$ is —CH$_2$O—N=C(CH$_3$)—* (*=bond to $A^a$), X is =N—, Y and Z are =CH— and $A^a$ for a compound in each case corresponds to one group of Table B.

Table 370
Compounds of the formula I.A where $R^1$ and $R^2$ are methyl, $R^3$ is hydrogen, U and V are oxygen, $W^a$ is —CH$_2$O—N=C(CH$_3$)—C(C$_6$H$_5$)=NO—* (*=bond to $A^a$), X is =N—, Y and Z are =CH— and $A^a$ for a compound in each case corresponds to one group of Table B.

Table 371
Compounds of the formula I.A where $R^1$ and $R^2$ are methyl, $R^3$ is hydrogen, U and V are oxygen, $W^a$ is —CH$_2$O—N=C(CH$_3$)—C(2-Cl—C$_6$H$_4$)=NO—* (*=bond to $A^a$), X is =N—, Y and Z are =CH— and $A^a$ for a compound in each case corresponds to one group of Table B.

Table 372
Compounds of the formula I.A where $R^1$ and $R^2$ are methyl, $R^3$ is hydrogen, U and V are oxygen, $W^a$ is —CH$_2$O—N=C(CH$_3$)—C(4-Cl—C$_6$H$_4$)=NO—* (*=bond to $A^a$), X is =N—, Y and Z are =CH— and $A^a$ for a compound in each case corresponds to one group of Table B.

Table 373
Compounds of the formula I.A where $R^1$ and $R^2$ are methyl, $R^3$ is hydrogen, U and V are oxygen, $W^a$ is a direct bond, X and Y are =N—, Z is =CH— and $A^a$ for a compound in each case corresponds to one group of Table B.

Table 374
Compounds of the formula I.A where $R^1$ and $R^2$ are methyl, $R^3$ is hydrogen, U and V are oxygen, $W^a$ is —C(CH$_3$)=NO—* (*=bond to $A^a$), X and Y are =N—, Z is =CH— and $A^a$ for a compound in each case corresponds to one group of Table B.

Table 375
Compounds of the formula I.A where $R^1$ and $R^2$ are methyl, $R^3$ is hydrogen, U and V are oxygen, $W^a$ is —CH$_2$O—N=C(CH$_3$)—* (*=bond to $A^a$), X and Y are =N—, Z is =CH— and $A^a$ for a compound in each case corresponds to one group of Table B.

Table 376
Compounds of the formula I.A where $R^1$ and $R^2$ are methyl, $R^3$ is hydrogen, U and V are oxygen, $W^a$ is —CH$_2$O—N=C(CH$_3$)—C(C$_6$H$_5$)=NO—* (*=bond to $A^a$), X and Y are =N—, Z is =CH— and $A^a$ for a compound in each case corresponds to one group of Table B.

Table 377
Compounds of the formula I.A where $R^1$ and $R^2$ are methyl, $R^3$ is hydrogen, U and V are oxygen, $W^a$ is —CH$_2$O—N=C(CH$_3$)—C(2-Cl—C$_6$H$_4$)=NO—* (*=bond to $A^a$), X and Y are =N—, Z is =CH— and $A^a$ for a compound in each case corresponds to one group of Table B.

Table 378
Compounds of the formula I.A where $R^1$ and $R^2$ are methyl, $R^3$ is hydrogen, U and V are oxygen, $W^a$ is —CH$_2$O—N=C(CH$_3$)—C(4-Cl—C$_6$H$_4$)=NO—* (*=bond to $A^a$), X and Y are =N—, Z is =CH— and $A^a$ for a compound in each case corresponds to one group of Table B.

Table 379
Compounds of the formula I.A where $R^1$ and $R^2$ are methyl, $R^3$ is hydrogen, U and V are oxygen, $W^a$ is a direct bond, X and Z are =N—, Y is =CH— and $A^a$ for a compound in each case corresponds to one group of Table B.

Table 380
Compounds of the formula I.A where $R^1$ and $R^2$ are methyl, $R^3$ is hydrogen, U and V are oxygen, $W^a$ is —C(CH$_3$)=NO—* (*=bond to $A^a$), X and Z are =N—, Y is =CH— and $A^a$ for a compound in each case corresponds to one group of Table B.

Table 381
Compounds of the formula I.A where $R^1$ and $R^2$ are methyl, $R^3$ is hydrogen, U and V are oxygen, $W^a$ is —CH$_2$O—N=C(CH$_3$)—* (*=bond to $A^a$), X and Z are =N—, Y is =CH— and $A^a$ for a compound in each case corresponds to one group of Table B.

Table 382
Compounds of the formula I.A where $R^1$ and $R^2$ are methyl, $R^3$ is hydrogen, U and V are oxygen, $W^a$ is —CH$_2$O—N=C(CH$_3$)—C(C$_6$H$_5$)=NO—* (*=bond to $A^a$), X and Z are =N—, Y is =CH— and $A^a$ for a compound in each case corresponds to one group of Table B.

Table 383
Compounds of the formula I.A where $R^1$ and $R^2$ are methyl, $R^3$ is hydrogen, U and V are oxygen, $W^a$ is —CH$_2$O—N=C(CH$_3$)—C(2-Cl—C$_6$H$_4$)=NO—* (*=bond to $A^a$), X and Z are =N—, Y is =CH— and $A^a$ for a compound in each case corresponds to one group of Table B.

Table 384
Compounds of the formula I.A where $R^1$ and $R^2$ are methyl, $R^3$ is hydrogen, U and V are oxygen, $W^a$ is —CH$_2$O—N=C(CH$_3$)—C(4-Cl—C$_6$H$_4$)=NO—* (*=bond to $A^a$), X and Z are =N—, Y is =CH— and $A^a$ for a compound in each case corresponds to one group of Table B.

Table 385
Compounds of the formula I.A where $R^1$ and $R^2$ are methyl, $R^3$ is hydrogen, U is amino (—NH—) and V is oxygen, $W^a$ is a direct bond, X, Y and Z are =CH— and $A^a$ for a compound in each case corresponds to one group of Table B.

Table 386
Compounds of the formula I.A where $R^1$ and $R^2$ are methyl, $R^3$ is hydrogen, U is amino (—NH—) and V is oxygen, $W^a$ is —C(CH$_3$)=NO—* (*=bond to $A^a$), X, Y and Z are =CH— and $A^a$ for a compound in each case corresponds to one group of Table B.

Table 387
Compounds of the formula I.A where $R^1$ and $R^2$ are methyl, $R^3$ is hydrogen, U is amino (—NH—) and V is oxygen, $W^a$ is —CH$_2$O—N=C(CH$_3$)—* (*=bond to $A^a$), X, Y and Z are =CH— and $A^a$ for a compound in each case corresponds to one group of Table B.

Table 388
Compounds of the formula I.A where $R^1$ and $R^2$ are methyl, $R^3$ is hydrogen, U is amino (—NH—) and V is oxygen, $W^a$ is —CH$_2$O—N=C(CH$_3$)—C(C$_6$H$_5$)=NO—* (*=bond to $A^a$), X, Y and Z are =CH— and $A^a$ for a compound in each case corresponds to one group of Table B.

Table 389
Compounds of the formula I.A where $R^1$ and $R^2$ are methyl, $R^3$ is hydrogen, U is amino (—NH—) and V is oxygen, $W^a$ is —CH$_2$O—N=C(CH$_3$)—C(2-Cl—C$_6$H$_4$)=NO—* (*=bond to $A^a$), X, Y and Z are =CH— and $A^a$ for a compound in each case corresponds to one group of Table B.

Table 390
Compounds of the formula I.A where $R^1$ and $R^2$ are methyl, $R^3$ is hydrogen, U is amino (—NH—) and V is oxygen, $W^a$ is —CH$_2$O—N=C(CH$_3$)—C(4-Cl—C$_6$H$_4$)=NO—* (*=bond to $A^a$), X, Y and Z are =CH— and $A^a$ for a compound in each case corresponds to one group of Table B.

Table 391
Compounds of the formula I.A where $R^1$ and $R^2$ are methyl, $R^3$ is hydrogen, U is amino (—NH—) and V is oxygen, $W^a$ is a direct bond, X is =N—, Y and Z are =CH— and $A^a$ for a compound in each case corresponds to one group of Table B.

Table 392
Compounds of the formula I.A where $R^1$ and $R^2$ are methyl, $R^3$ is hydrogen, U is amino (—NH—) and V is oxygen, $W^a$ is —C(CH$_3$)=NO—* (*=bond to $A^a$), X is =N—, Y and Z are =CH— and $A^a$ for a compound in each case corresponds to one group of Table B.

Table 393
Compounds of the formula I.A where $R^1$ and $R^2$ are methyl, $R^3$ is hydrogen, U is amino (—NH—) and V is oxygen, $W^a$ is —CH$_2$O—N=C(CH$_3$)—* (*=bond to $A^a$), X is =N—, Y and Z are =CH— and $A^a$ for a compound in each case corresponds to one group of Table B.

Table 394
Compounds of the formula I.A where $R^1$ and $R^2$ are methyl, $R^3$ is hydrogen, U is amino (—NH—) and V is oxygen, $W^a$ is —CH$_2$O—N=C(CH$_3$)—C(C$_6$H$_5$)=NO—* (*=bond to $A^a$), X is =N—, Y and Z are =CH— and $A^a$ for a compound in each case corresponds to one group of Table B.

Table 395
Compounds of the formula I.A where $R^1$ and $R^2$ are methyl, $R^3$ is hydrogen, U is amino (—NH—) and V is oxygen, $W^a$ is —CH$_2$O—N=C(CH$_3$)—C(2-Cl—C$_6$H$_4$)=NO—* bond to $A^a$), X is =N—, Y and Z are =CH— and $A^a$ for a compound in each case corresponds to one group of Table B.

Table 396
Compounds of the formula I.A where $R^1$ and $R^2$ are methyl, $R^3$ is hydrogen, U is amino (—NH—) and V is oxygen, $W^a$ is —CH$_2$O—N=C(CH$_3$)—C(4-Cl—C$_6$H$_4$)=NO—* (*=bond to $A^a$), X is =N—, Y and Z are =CH— and $A^a$ for a compound in each case corresponds to one group of Table B.

Table 397
Compounds of the formula I.A where $R^1$ and $R^2$ are methyl, $R^3$ is hydrogen, U is amino (—NH—) and V is oxygen, $W^a$ is a direct bond, X and Y are =N—, Z is =CH— and $A^a$ for a compound in each case corresponds to one group of Table B.

Table 398
Compounds of the formula I.A where $R^1$ and $R^2$ are methyl, $R^3$ is hydrogen, U is amino (—NH—) and V is oxygen, $W^a$ is —C(CH$_3$)=NO—* (*=bond to $A^a$), X and Y are =N—, Z is =CH— and $A^a$ for a compound in each case corresponds to one group of Table B.

Table 399
Compounds of the formula I.A where $R^1$ and $R^2$ are methyl, $R^3$ is hydrogen, U is amino (—NH—) and V is oxygen, $W^a$ is —$CH_2O$—N=C($CH_3$)—* (*=bond to $A^a$), X and Y are =N—, Z is =CH— and $A^a$ for a compound in each case corresponds to one group of Table B.

Table 400
Compounds of the formula I.A where $R^1$ and $R^2$ are methyl, $R^3$ is hydrogen, U is amino (—NH—) and V is oxygen, $W^a$ is —$CH_2O$—N=C($CH_3$)—C($C_6H_5$)=NO—* (*=bond to $A^a$), X and Y are =N—, Z is =CH— and $A^a$ for a compound in each case corresponds to one group of Table B.

Table 401
Compounds of the formula I.A where $R^1$ and $R^2$ are methyl, $R^3$ is hydrogen, U is amino (—NH—) and V is oxygen, $W^a$ is —$CH_2O$—N=C($CH_3$)—C(2-Cl—$C_6H_4$)=NO—* (*=bond to $A^a$), X and Y are =N—, Z is =CH— and $A^a$ for a compound in each case corresponds to one group of Table B.

Table 402
Compounds of the formula I.A where $R^1$ and $R^2$ are methyl, $R^3$ is hydrogen, U is amino (—NH—) and V is oxygen, $W^a$ is —$CH_2O$—N=C($CH_3$)—C(4-Cl—$C_6H_4$)=NO—* (*=bond to $A^a$), X and Y are =N—, Z is =CH— and $A^a$ for a compound in each case corresponds to one group of Table B.

Table 403
Compounds of the formula I.A where $R^1$ and $R^2$ are methyl, $R^3$ is hydrogen, U is amino (—NH—) and v is oxygen, $W^a$ is a direct bond, X and Z are =N—, Y is =CH— and $A^a$ for a compound in each case corresponds to one group of Table B.

Table 404
Compounds of the formula I.A where $R^1$ and $R^2$ are methyl, $R^3$ is hydrogen, U is amino (—NH—) and V is oxygen, $W^a$ is —C($CH_3$)=NO—* (*=bond to $A^a$), X and Z are =N—, Y is =CH— and $A^a$ for a compound in each case corresponds to one group of Table B.

Table 405
Compounds of the formula I.A where $R^1$ and $R^2$ are methyl, $R^3$ is hydrogen, U is amino (—NH—) and V is oxygen, $W^a$ is —$CH_2O$—N=C($CH_3$)—* (*=bond to $A^a$), X and Z are =N—, Y is =CH— and $A^a$ for a compound in each case corresponds to one group of Table B.

Table 406
Compounds of the formula I.A where $R^1$ and $R^2$ are methyl, $R^3$ is hydrogen, U is amino (—NH—) and V is oxygen, $W^a$ is —$CH_2O$—N=C($CH_3$)—C($C_6H_5$)=NO—* (*=bond to $A^a$), X and Z are =N—, Y is =CH— and $A^a$ for a compound in each case corresponds to one group of Table B.

Table 407
Compounds of the formula I.A where $R^1$ and $R^2$ are methyl, $R^3$ is hydrogen, U is amino (—NH—) and V is oxygen, $W^a$ is —$CH_2O$—N=C($CH_3$)—C(2-Cl—$C_6H_4$)=NO—* (*=bond to $A^a$), X and Z are =N—, Y is =CH— and $A^a$ for a compound in each case corresponds to one group of Table B.

Table 408
Compounds of the formula I.A where $R^1$ and $R^2$ are methyl, $R^3$ is hydrogen, U is amino (—NH—) and V is oxygen, $W^a$ is —$CH_2O$—N=C($CH_3$)—C(4-Cl—$C_6H_4$)=NO—* (*=bond to $A^a$), X and Z are =N—, Y is =CH— and $A^a$ for a compound in each case corresponds to one group of Table B.

Table 409
Compounds of the formula I.A where $R^1$ and $R^2$ are methyl, $R^3$ is hydrogen, U is oxygen and V is sulfur, $W^a$ is a direct bond, X, Y and Z are =CH— and $A^a$ for a compound in each case corresponds to one group of Table B.

Table 410
Compounds of the formula I.A where $R^1$ and $R^2$ are methyl, $R^3$ is hydrogen, U is oxygen and V is sulfur, $W^a$ is —C($CH_3$)=NO—* (*=bond to $A^a$), X, Y and Z are =CH— and $A^a$ for a compound in each case corresponds to one group of Table B.

Table 411
Compounds of the formula I.A where $R^1$ and $R^2$ are methyl, $R^3$ is hydrogen, U is oxygen and V is sulfur, $W^a$ is —$CH_2O$—N=C($CH_3$)—* (*=bond to $A^a$), X, Y and Z are =CH— and $A^a$ for a compound in each case corresponds to one group of Table B.

Table 412
Compounds of the formula I.A where $R^1$ and $R^2$ are methyl, $R^3$ is hydrogen, U is oxygen and V is sulfur, $W^a$ is —$CH_2O$—N=C($CH_3$)—C($C_6H_5$)=NO—* (*=bond to $A^a$), X, Y and Z are =CH— and $A^a$ for a compound in each case corresponds to one group of Table B.

Table 413
Compounds of the formula I.A where $R^1$ and $R^2$ are methyl, $R^3$ is hydrogen, U is oxygen and V is sulfur, $W^a$ is —$CH_2O$—N=C($CH_3$)—C(2-Cl—$C_6H_4$)=NO—* (*=bond to $A^a$), X, Y and Z are =CH— and $A^a$ for a compound in each case corresponds to one group of Table B.

Table 414
Compounds of the formula I.A where $R^1$ and $R^2$ are methyl, $R^3$ is hydrogen, U is oxygen and V is sulfur, $W^a$ is —$CH_2O$—N=C($CH_3$)—C(4-Cl—$C_6H_4$)=NO—* (*=bond to $A^a$), X, Y and Z are =CH— and $A^a$ for a compound in each case corresponds to one group of Table B.

Table 415
Compounds of the formula I.A where $R^1$ and $R^2$ are methyl, $R^3$ is hydrogen, U is oxygen and V is sulfur, $W^a$ is a direct bond, X is =N—, Y and Z are =CH— and $A^a$ for a compound in each case corresponds to one group of Table B.

Table 416
Compounds of the formula I.A where $R^1$ and $R^2$ are methyl, $R^3$ is hydrogen, U is oxygen and V is sulfur, $W^a$ is —C($CH_3$)=NO—* (*=bond to $A^a$), X is =N—, Y and Z are =CH— and $A^a$ for a compound in each case corresponds to one group of Table B.

Table 417
Compounds of the formula I.A where $R^1$ and $R^2$ are methyl, $R^3$ is hydrogen, U is oxygen and V is sulfur, $W^a$ is —$CH_2O$—N=C($CH_3$)—* (*=bond to $A^a$), X is =N—, Y and Z are =CH— and $A^a$ for a compound in each case corresponds to one group of Table B.

Table 418
Compounds of the formula I.A where $R^1$ and $R^2$ are methyl, $R^3$ is hydrogen, U is oxygen and V is sulfur, $W^a$ is —$CH_2O$—N=C($CH_3$)—C($C_6H_5$)=NO—* (*=bond to $A^a$), X is =N—, Y and Z are =CH— and $A^a$ for a compound in each case corresponds to one group of Table B.

Table 419
Compounds of the formula I.A where $R^1$ and $R^2$ are methyl, $R^3$ is hydrogen, U is oxygen and V is sulfur, $W^a$ is —$CH_2O$—N=C($CH_3$)—C(2-Cl—$C_6H_4$)=NO—* (*=bond to $A^a$), X is =N—, Y and Z are =CH— and $A^a$ for a compound in each case corresponds to one group of Table B.

Table 420
Compounds of the formula I.A where $R^1$ and $R^2$ are methyl, $R^3$ is hydrogen, U is oxygen and V is sulfur, $W^a$ is —$CH_2O$—N=C($CH_3$)—C(4-Cl—$C_6H_4$)=NO—* (*=bond to $A^a$), X is =N—, Y and Z are =CH— and $A^a$ for a compound in each case corresponds to one group of Table B.

Table 421
Compounds of the formula I.A where $R^1$ and $R^2$ are methyl, $R^3$ is hydrogen, U is oxygen and V is sulfur, $W^a$ is a direct bond, X and Y are =N—, Z is =CH— and $A^a$ for a compound in each case corresponds to one group of Table B.

Table 422
Compounds of the formula I.A where $R^1$ and $R^2$ are methyl, $R^3$ is hydrogen, U is oxygen and V is sulfur, $W^a$ is —C(CH$_3$)=NO—* (*=bond to $A^a$), X and Y are =N—, Z is =CH— and $A^a$ for a compound in each case corresponds to one group of Table B.

Table 423
Compounds of the formula I.A where $R^1$ and $R^2$ are methyl, $R^3$ is hydrogen, U is oxygen and V is sulfur, $W^a$ is —CH$_2$O—N=C(CH$_3$)—* (*=bond to $A^a$), X and Y are =N—, Z is =CH— and $A^a$ for a compound in each case corresponds to one group of Table B.

Table 424
Compounds of the formula I.A where $R^1$ and $R^2$ are methyl, $R^3$ is hydrogen, U is oxygen and V is sulfur, $W^a$ is —CH$_2$O—N=C(CH$_3$)—C(C$_6$H$_5$)=NO—* (*=bond to $A^a$), X and Y are =N—, Z is =CH— and $A^a$ for a compound in each case corresponds to one group of Table B.

Table 425
Compounds of the formula I.A where $R^1$ and $R^2$ are methyl, $R^3$ is hydrogen, U is oxygen and V is sulfur, $W^a$ is —CH$_2$O—N=C(CH$_3$)—C(2-Cl—C$_6$H$_4$)=NO—* (*=bond to $A^a$), X and Y are =N—, Z is =CH— and $A^a$ for a compound in each case corresponds to one group of Table B.

Table 426
Compounds of the formula I.A where $R^1$ and $R^2$ are methyl, $R^3$ is hydrogen, U is oxygen and V is sulfur, $W^a$ is —CH$_2$O—N=C(CH$_3$)—C(4-Cl—C$_6$H$_4$)=NO—* (*=bond to $A^a$), X and Y are =N—, Z is =CH— and $A^a$ for a compound in each case corresponds to one group of Table B.

Table 427
Compounds of the formula I.A where $R^1$ and $R^2$ are methyl, $R^3$ is hydrogen, U is oxygen and V is sulfur, $W^a$ is a direct bond, X and Z are =N—, Y is =CH— and $A^a$ for a compound in each case corresponds to one group of Table B.

Table 428
Compounds of the formula I.A where $R^1$ and $R^2$ are methyl, $R^3$ is hydrogen, U is oxygen and V is sulfur, $W^a$ is —C(CH$_3$)=NO—* (*=bond to $A^a$), X and Z are =N—, Y is =CH— and $A^a$ for a compound in each case corresponds to one group of Table B.

Table 429
Compounds of the formula I.A where $R^1$ and $R^2$ are methyl, $R^3$ is hydrogen, U is oxygen and V is sulfur, $W^a$ is —CH$_2$O—N=C(CH$_3$)—* (*=bond to $A^a$), X and Z are =N—, Y is =CH— and $A^a$ for a compound in each case corresponds to one group of Table B.

Table 430
Compounds of the formula I.A where $R^1$ and $R^2$ are methyl, $R^3$ is hydrogen, U is oxygen and V is sulfur, $W^a$ is —CH$_2$O—N=C(CH$_3$)—C(C$_6$H$_5$)=NO—* (*=bond to $A^a$), X and Z are =N—, Y is =CH— and $A^a$ for a compound in each case corresponds to one group of Table B.

Table 431
Compounds of the formula I.A where $R^1$ and $R^2$ are methyl, $R^3$ is hydrogen, U is oxygen and V is sulfur, $W^a$ is —CH$_2$O—N=C(CH$_3$)—C(2-Cl—C$_6$H$_4$)=NO—* (*=bond to $A^a$), X and Z are =N—, Y is =CH— and $A^a$ for a compound in each case corresponds to one group of Table B.

Table 432
Compounds of the formula I.A where $R^1$ and $R^2$ are methyl, $R^3$ is hydrogen, U is oxygen and V is sulfur, $W^a$ is —CH$_2$O—N=C(CH$_3$)—C(4-Cl—C$_6$H$_4$)=NO—* (*=bond to $A^a$), X and Z are =N—, Y is =CH— and $A^a$ for a compound in each case corresponds to one group of Table B.

Table 433
Compounds of the formula I.A where $R^1$ and $R^2$ are methyl, $R^3$ is hydrogen, U is amino (—NH—) and V is sulfur, $W^a$ is a direct bond, X, Y and Z are =CH— and $A^a$ for a compound in each case corresponds to one group of Table B.

Table 434
Compounds of the formula I.A where $R^1$ and $R^2$ are methyl, $R^3$ is hydrogen, U is amino (—NH—) and V is sulfur, $W^a$ is —C(CH$_3$)=NO—* (*=bond to $A^a$), X, Y and Z are =CH— and $A^a$ for a compound in each case corresponds to one group of Table B.

Table 435
Compounds of the formula I.A where $R^1$ and $R^2$ are methyl, $R^3$ is hydrogen, U is amino (—NH—) and V is sulfur, $W^a$ is —CH$_2$O—N=C(CH$_3$)—* (*=bond to $A^a$), X, Y and Z are =CH— and $A^a$ for a compound in each case corresponds to one group of Table B.

Table 436
Compounds of the formula I.A where $R^1$ and $R^2$ are methyl, $R^3$ is hydrogen, U is amino (—NH—) and V is sulfur, $W^a$ is —CH$_2$O—N=C(CH$_3$)—C(C$_6$H$_5$)=NO—* (*=bond to $A^a$), X, Y and Z are =CH— and $A^a$ for a compound in each case corresponds to one group of Table B.

Table 437
Compounds of the formula I.A where $R^1$ and $R^2$ are methyl, $R^3$ is hydrogen, U is amino (—NH—) and V is sulfur, $W^a$ is —CH$_2$O—N=C(CH$_3$)—C(2-Cl—C$_6$H$_4$)=NO—* (*=bond to $A^a$), X, Y and Z are =CH— and $A^a$ for a compound in each case corresponds to one group of Table B.

Table 438
Compounds of the formula I.A where $R^1$ and $R^2$ are methyl, $R^3$ is hydrogen, U is amino (—NH—) and V is sulfur, $W^a$ is —CH$_2$O—N=C(CH$_3$)—C(4-Cl—C$_6$H$_4$)=NO—* (*=bond to $A^a$), X, Y and Z are =CH— and $A^a$ for a compound in each case corresponds to one group of Table B.

Table 439
Compounds of the formula I.A where $R^1$ and $R^2$ are methyl, $R^3$ is hydrogen, U is amino (—NH—) and V is sulfur, $W^a$ is a direct bond, X is =N—, Y and Z are =CH— and $A^a$ for a compound in each case corresponds to one group of Table B.

Table 440
Compounds of the formula I.A where $R^1$ and $R^2$ are methyl, $R^3$ is hydrogen, U is amino (—NH—) and V is sulfur, $W^a$ is —C(CH$_3$)=NO—* (*=bond to $A^a$), X is =N—, Y and Z are =CH— and $A^a$ for a compound in each case corresponds to one group of Table B.

Table 441
Compounds of the formula I.A where $R^1$ and $R^2$ are methyl, $R^3$ is hydrogen, U is amino (—NH—) and V is sulfur, $W^a$ is —CH$_2$O—N=C(CH$_3$)—* (*=bond to $A^a$), X is =N—, Y and Z are =CH— and $A^a$ for a compound in each case corresponds to one group of Table B.

Table 442
Compounds of the formula I.A where $R^1$ and $R^2$ are methyl, $R^3$ is hydrogen, U is amino (—NH—) and V is sulfur, $W^a$ is —CH$_2$O—N=C(CH$_3$)—C(C$_6$H$_5$)=NO—*

(*=bond to $A^a$), X is =N—, Y and Z are =CH— and $A^a$ for a compound in each case corresponds to one group of Table B.

Table 443
Compounds of the formula I.A where $R^1$ and $R^2$ are methyl, $R^3$ is hydrogen, U is amino (—NH—) and V is sulfur, $W^a$ is —CH$_2$O—N=C(CH$_3$)—C(2-Cl—C$_6$H$_4$)=NO—* (*=bond to $A^a$), X is =N—, Y and Z are =CH— and $A^a$ for a compound in each case corresponds to one group of Table B.

Table 444
Compounds of the formula I.A where $R^1$ and $R^2$ are methyl, $R^3$ is hydrogen, U is amino (—NH—) and V is sulfur, $W^a$ is —CH$_2$O—N=C(CH$_3$)—C(4-Cl—C$_6$H$_4$)=NO—* (*=bond to $A^a$), X is =N—, Y and Z are =CH— and $A^a$ for a compound in each case corresponds to one group of Table B.

Table 445
Compounds of the formula I.A where $R^1$ and $R^2$ are methyl, $R^3$ is hydrogen, U is amino (—NH—) and V is sulfur, $W^a$ is a direct bond, X and Y are =N—, Z is =CH— and $A^a$ for a compound in each case corresponds to one group of Table B.

Table 446
Compounds of the formula I.A where $R^1$ and $R^2$ are methyl, $R^3$ is hydrogen, U is amino (—NH—) and V is sulfur, $W^a$ is —C(CH$_3$)=NO—* (*=bond to $A^a$), X and Y are =N—, Z is =CH— and $A^a$ for a compound in each case corresponds to one group of Table B.

Table 447
Compounds of the formula I.A where $R^1$ and $R^2$ are methyl, $R^3$ is hydrogen, U is amino (—NH—) and V is sulfur, $W^a$ is —CH$_2$O—N=C(CH$_3$)—* (*=bond to $A^a$), X and Y are =N—, Z is =CH— and $A^a$ for a compound in each case corresponds to one group of Table B.

Table 448
Compounds of the formula I.A where $R^1$ and $R^2$ are methyl, $R^3$ is hydrogen, U is amino (—NH—) and V is sulfur, $W^a$ is —CH$_2$O—N=C(CH$_3$)—C(C$_6$H$_5$)=NO—* (*=bond to $A^a$), X and Y are =N—, Z is =CH— and $A^a$ for a compound in each case corresponds to one group of Table B.

Table 449
Compounds of the formula I.A where $R^1$ and $R^2$ are methyl, $R^3$ is hydrogen, U is amino (—NH—) and V is sulfur, $W^a$ is —CH$_2$O—N=C(CH$_3$)—C(2-Cl—C$_6$H$_4$)=NO—* (*=bond to $A^a$), X and Y are =N—, Z is =CH— and $A^a$ for a compound in each case corresponds to one group of Table B.

Table 450
Compounds of the formula I.A where $R^1$ and $R^2$ are methyl, $R^3$ is hydrogen, U is amino (—NH—) and V is sulfur, $W^a$ is —CH$_2$O—N=C(CH$_3$)—C(4-Cl—C$_6$H$_4$)=NO—* (*=bond to $A^a$), X and Y are =N—, Z is =CH— and $A^a$ for a compound in each case corresponds to one group of Table B.

Table 451
Compounds of the formula I.A where $R^1$ and $R^2$ are methyl, $R^3$ is hydrogen, U is amino (—NH—) and V is sulfur, $W^a$ is a direct bond, X and Z are =N—, Y is =CH— and $A^a$ for a compound in each case corresponds to one group of Table B.

Table 452
Compounds of the formula I.A where $R^1$ and $R^2$ are methyl, $R^3$ is hydrogen, U is amino (—NH—) and V is sulfur, $W^a$ is —C(CH$_3$)=NO—* (*=bond to $A^a$), X and Z are =N—, Y is =CH— and $A^a$ for a compound in each case corresponds to one group of Table B.

Table 453
Compounds of the formula I.A where $R^1$ and $R^2$ are methyl, $R^3$ is hydrogen, U is amino (—NH—) and V is sulfur, $W^a$ is —CH$_2$O—N=C(CH$_3$)—* (*=bond to $A^a$), X and Z are =N—, Y is =CH— and $A^a$ for a compound in each case corresponds to one group of Table B.

Table 454
Compounds of the formula I.A where $R^1$ and $R^2$ are methyl, $R^3$ is hydrogen, U is amino (—NH—) and V is sulfur, $W^a$ is —CH$_2$O—N=C(CH$_3$)—C(C$_6$H$_5$)=NO—* (*=bond to $A^a$), X and Z are =N—, Y is =CH— and $A^a$ for a compound in each case corresponds to one group of Table B.

Table 455
Compounds of the formula I.A where $R^1$ and $R^2$ are methyl, $R^3$ is hydrogen, U is amino (—NH—) and V is sulfur, $W^a$ is —CH$_2$O—N=C(CH$_3$)—C(2-Cl—C$_6$H$_4$)=NO—* (*=bond to $A^a$), X and Z are =N—, Y is =CH— and $A^a$ for a compound in each case corresponds to one group of Table B.

Table 456
Compounds of the formula I.A where $R^1$ and $R^2$ are methyl, $R^3$ is hydrogen, U is amino (—NH—) and V is sulfur, $W^a$ is —CH$_2$O—N=C(CH$_3$)—C(4-Cl—C$_6$H$_4$)=NO—* (*=bond to $A^a$), X and Z are =N—, Y is =CH— and $A^a$ for a compound in each case corresponds to one group of Table B.

Table 457
Compounds of the formula I.A where $R^1$ and $R^2$ are methyl, $R^3$ is hydrogen, U is oxygen and V is amino (—NH—), $W^a$ is a direct bond, X, Y and Z are =CH— and $A^a$ for a compound in each case corresponds to one group of Table B.

Table 458
Compounds of the formula I.A where $R^1$ and $R^2$ are methyl, $R^3$ is hydrogen, U is oxygen and V is amino (—NH—), $W^a$ is —C(CH$_3$)=NO—* (*=bond to $A^a$), X, Y and Z are =CH— and $A^a$ for a compound in each case corresponds to one group of Table B.

Table 459
Compounds of the formula I.A where $R^1$ and $R^2$ are methyl, $R^3$ is hydrogen, U is oxygen and V is amino (—NH—), $W^a$ is —CH$_2$O—N=C(CH$_3$)—* (*=bond to $A^a$), X, Y and Z are =CH— and $A^a$ for a compound in each case corresponds to one group of Table B.

Table 460
Compounds of the formula I.A where $R^1$ and $R^2$ are methyl, $R^3$ is hydrogen, U is oxygen and V is amino (—NH—), $W^a$ is —CH$_2$O—N=C(CH$_3$)—C(C$_6$H$_5$)=NO—* (*=bond to $A^a$), X, Y and Z are =CH— and $A^a$ for a compound in each case corresponds to one group of Table B.

Table 461
Compounds of the formula I.A where $R^1$ and $R^2$ are methyl, $R^3$ is hydrogen, U is oxygen and V is amino (—NH—), $W^a$ is —CH$_2$O—N=C(CH$_3$)—C(2-Cl—C$_6$H$_4$)=NO—* (*=bond to $A^a$), X, Y and Z are =CH— and $A^a$ for a compound in each case corresponds to one group of Table B.

Table 462
Compounds of the formula I.A where $R^1$ and $R^2$ are methyl, $R^3$ is hydrogen, U is oxygen and V is amino (—NH—), $W^a$ is —CH$_2$O—N=C(CH$_3$)—C(4-Cl—C$_6$H$_4$)=NO—* (*=bond to $A^a$), X, Y and Z are =CH— and $A^a$ for a compound in each case corresponds to one group of Table B.

Table 463
Compounds of the formula I.A where $R^1$ and $R^2$ are methyl, $R^3$ is hydrogen, U is oxygen and V is amino (—NH—), $W^a$ is a direct bond, X is =N—, Y and Z are =CH— and $A^a$ for a compound in each case corresponds to one group of Table B.

Table 464
Compounds of the formula I.A where $R^1$ and $R^2$ are methyl, $R^3$ is hydrogen, U is oxygen and V is amino (—NH—), $W^a$ is —C(CH$_3$)=NO—* (*=bond to $A^a$), X is =N—, Y and Z are =CH— and $A^a$ for a compound in each case corresponds to one group of Table B.

Table 465
Compounds of the formula I.A where $R^1$ and $R^2$ are methyl, $R^3$ is hydrogen, U is oxygen and V is amino (—NH—), $W^a$ is —CH$_2$O—N=C(CH$_3$)—* (*=bond to $A^a$), X is =N—, Y and Z are =CH— and $A^a$ for a compound in each case corresponds to one group of Table B.

Table 466
Compounds of the formula I.A where $R^1$ and $R^2$ are methyl, $R^3$ is hydrogen, U is oxygen and V is amino (—NH—), $W^a$ is —CH$_2$O—N=C(CH$_3$)—C(C$_6$H$_5$)=NO—* (*=bond to $A^a$), X is =N—, Y and Z are =CH— and $A^a$ for a compound in each case corresponds to one group of Table B.

Table 467
Compounds of the formula I.A where $R^1$ and $R^2$ are methyl, $R^3$ is hydrogen, U is oxygen and V is amino (—NH—), $W^a$ is —CH$_2$O—N=C(CH$_3$)—C(2-Cl—C$_6$H$_4$)=NO—* (*=bond to $A^a$), X is =N—, Y and Z are =CH— and $A^a$ for a compound in each case corresponds to one group of Table B.

Table 468
Compounds of the formula I.A where $R^1$ and $R^2$ are methyl, $R^3$ is hydrogen, U is oxygen and V is amino (—NH—), $W^a$ is —CH$_2$O—N=C(CH$_3$)—C(4-Cl—C$_6$H$_4$)=NO—* (*=bond to $A^a$), X is =N—, Y and Z are =CH— and $A^a$ for a compound in each case corresponds to one group of Table B.

Table 469
Compounds of the formula I.A where $R^1$ and $R^2$ are methyl, $R^3$ is hydrogen, U is oxygen and V is amino (—NH—), $W^a$ is a direct bond, X and Y are =N—, Z is =CH— and $A^a$ for a compound in each case corresponds to one group of Table B.

Table 470
Compounds of the formula I.A where $R^1$ and $R^2$ are methyl, $R^3$ is hydrogen, U is oxygen and V is amino (—NH—), $W^a$ is —C(CH$_3$)=NO—* (*=bond to $A^a$), X and Y are =N—, Z is =CH— and $A^a$ for a compound in each case corresponds to one group of Table B.

Table 471
Compounds of the formula I.A where $R^1$ and $R^2$ are methyl, $R^3$ is hydrogen, U is oxygen and V is amino (—NH—), $W^a$ is —CH$_2$O—N=C(CH$_3$)—* (*=bond to $A^a$), X and Y are =N—, Z is =CH— and $A^a$ for a compound in each case corresponds to one group of Table B.

Table 472
Compounds of the formula I.A where $R^1$ and $R^2$ are methyl, $R^3$ is hydrogen, U is oxygen and V is amino (—NH—), $W^a$ is —CH$_2$O—N=C(CH$_3$)—C(C$_6$H$_5$)=NO—* (*=bond to $A^a$), X and Y are =N—, Z is =CH— and $A^a$ for a compound in each case corresponds to one group of Table B.

Table 473
Compounds of the formula I.A where $R^1$ and $R^2$ are methyl, $R^3$ is hydrogen, U is oxygen and V is amino (—NH—), $W^a$ is —CH$_2$O—N=C(CH$_3$)—C(2-Cl—C$_6$H$_4$)=NO—* (*=bond to $A^a$), X and Y are =N—, Z is =CH— and $A^a$ for a compound in each case corresponds to one group of Table B.

Table 474
Compounds of the formula I.A where $R^1$ and $R^2$ are methyl, $R^3$ is hydrogen, U is oxygen and V is amino (—NH—), $W^a$ is —CH$_2$O—N=C(CH$_3$)—C(4-Cl—C$_6$H$_4$)=NO—* (*=bond to $A^a$), X and Y are =N—, Z is =CH— and $A^a$ for a compound in each case corresponds to one group of Table B.

Table 475
Compounds of the formula I.A where $R^1$ and $R^2$ are methyl, $R^3$ is hydrogen, U is oxygen and V is amino (—NH—), $W^a$ is a direct bond, X and Z are =N—, Y is =CH— and $A^a$ for a compound in each case corresponds to one group of Table B.

Table 476
Compounds of the formula I.A where $R^1$ and $R^2$ are methyl, $R^3$ is hydrogen, U is oxygen and V is amino (—NH—), $W^a$ is —C(CH$_3$)=NO—* (*=bond to $A^a$), X and Z are =N—, Y is =CH— and $A^a$ for a compound in each case corresponds to one group of Table B.

Table 477
Compounds of the formula I.A where $R^1$ and $R^2$ are methyl, $R^3$ is hydrogen, U is oxygen and V is amino (—NH—), $W^a$ is —CH$_2$O—N=C(CH$_3$)—* (*=bond to $A^a$), X and Z are =N—, Y is =CH— and $A^a$ for a compound in each case corresponds to one group of Table B.

Table 478
Compounds of the formula I.A where $R^1$ and $R^2$ are methyl, $R^3$ is hydrogen, U is oxygen and V is amino (—NH—), $W^a$ is —CH$_2$O—N=C(CH$_3$)—C(C$_6$H$_5$)=NO—* (*=bond to $A^a$), X and Z are =N—, Y is =CH— and $A^a$ for a compound in each case corresponds to one group of Table B.

Table 479
Compounds of the formula I.A where $R^1$ and $R^2$ are methyl, $R^3$ is hydrogen, U is oxygen and V is amino (—NH—), $W^a$ is —CH$_2$O—N=C(CH$_3$)—C(2-Cl—C$_6$H$_4$)=NO—* (*=bond to $A^a$), X and Z are =N—, Y is =CH— and $A^a$ for a compound in each case corresponds to one group of Table B.

Table 480
Compounds of the formula I.A where $R^1$ and $R^2$ are methyl, $R^3$ is hydrogen, U is oxygen and V is amino (—NH—), $W^a$ is —CH$_2$O—N=C(CH$_3$)—C(4-Cl—C$_6$H$_4$)=NO—* (*=bond to $A^a$), X and Z are =N—, Y is =CH— and $A^a$ for a compound in each case corresponds to one group of Table B.

Table 481
Compounds of the formula I.A where $R^1$ and $R^2$ are methyl, $R^3$ is hydrogen, U and V are amino (—NH—), $W^a$ is a direct bond, X, Y and Z are =CH— and $A^a$ for a compound in each case corresponds to one group of Table B.

Table 482
Compounds of the formula I.A where $R^1$ and $R^2$ are methyl, $R^3$ is hydrogen, U and V are amino (—NH—), $W^a$ is —C(CH$_3$)=NO—* (*=bond to $A^a$), X, Y and Z are =CH— and $A^a$ for a compound in each case corresponds to one group of Table B.

Table 483
Compounds of the formula I.A where $R^1$ and $R^2$ are methyl, $R^3$ is hydrogen, U and V are amino (—NH—), $W^a$ is —CH$_2$O—N=C(CH$_3$)—* (*=bond to $A^a$), X, Y and Z are =CH— and $A^a$ for a compound in each case corresponds to one group of Table B.

Table 484
Compounds of the formula I.A where $R^1$ and $R^2$ are methyl, $R^3$ is hydrogen, U and V are amino (—NH—), $W^a$ is —CH$_2$O—N═C(CH$_3$)—C(C$_6$H$_5$)═NO—* (*=bond to A$^a$), X, Y and Z are ═CH— and A$^a$ for a compound in each case corresponds to one group of Table B.

Table 485
Compounds of the formula I.A where $R^1$ and $R^2$ are methyl, $R^3$ is hydrogen, U and V are amino (—NH—), $W^a$ is —CH$_2$O—N═C(CH$_3$)—C(2-Cl—C$_6$H$_4$)═NO—* (*=bond to A$^a$), X, Y and Z are ═CH— and A$^a$ for a compound in each case corresponds to one group of Table B.

Table 486
Compounds of the formula I.A where $R^1$ and $R^2$ are methyl, $R^3$ is hydrogen, U and V are amino (—NH—), $W^a$ is —CH$_2$O—N═C(CH$_3$)—C(4-Cl—C$_6$H$_4$)═NO—* (*=bond to A$^a$), X, Y and Z are ═CH— and A$^a$ for a compound in each case corresponds to one group of Table B.

Table 487
Compounds of the formula I.A where $R^1$ and $R^2$ are methyl, $R^3$ is hydrogen, U and V are amino (—NH—), $W^a$ is a direct bond, X is ═N—, Y and Z are ═CH— and A$^a$ for a compound in each case corresponds to one group of Table B.

Table 488
Compounds of the formula I.A where $R^1$ and $R^2$ are methyl, $R^3$ is hydrogen, U and V are amino (—NH—), $W^a$ is —C(CH$_3$)═NO—* (*=bond to A$^a$), X is ═N—, Y and Z are ═CH— and A$^a$ for a compound in each case corresponds to one group of Table B.

Table 489
Compounds of the formula I.A where $R^1$ and $R^2$ are methyl, $R^3$ is hydrogen, U and V are amino (—NH—), $W^a$ is —CH$_2$O—N═C(CH$_3$)—* (*=bond to A$^a$), X is ═N—, Y and Z are ═CH— and A$^a$ for a compound in each case corresponds to one group of Table B.

Table 490
Compounds of the formula I.A where $R^1$ and $R^2$ are methyl, $R^3$ is hydrogen, U and V are amino (—NH—), $W^a$ is —CH$_2$O—N═C(CH$_3$)—C(C$_6$H$_5$)═NO—* (*=bond to A$^a$), X is ═N—, Y and Z are ═CH— and A$^a$ for a compound in each case corresponds to one group of Table B.

Table 491
Compounds of the formula I.A where $R^1$ and $R^2$ are methyl, $R^3$ is hydrogen, U and V are amino (—NH—), $W^a$ is —CH$_2$O—N═C(CH$_3$)—C(2-Cl—C$_6$H$_4$)═NO—* (*=bond to A$^a$), X is ═N—, Y and Z are ═CH— and A$^a$ for a compound in each case corresponds to one group of Table B.

Table 492
Compounds of the formula I.A where $R^1$ and $R^2$ are methyl, $R^3$ is hydrogen, U and V are amino (—NH—), $W^a$ is —CH$_2$O—N═C(CH$_3$)—C(4-Cl—C$_6$H$_4$)═NO—* (*=bond to A$^a$), X is ═N—, Y and Z are ═CH— and A$^a$ for a compound in each case corresponds to one group of Table B.

Table 493
Compounds of the formula I.A where $R^1$ and $R^2$ are methyl, $R^3$ is hydrogen, U and V are amino (—NH—), $W^a$ is a direct bond, X and Y are ═N—, Z is ═CH— and A$^a$ for a compound in each case corresponds to one group of Table B.

Table 494
Compounds of the formula I.A where $R^1$ and $R^2$ are methyl, $R^3$ is hydrogen, U and V are amino (—NH—), $W^a$ is —C(CH$_3$)═NO—* (*=bond to A$^a$), X and Y are ═N—, Z is ═CH— and A$^a$ for a compound in each case corresponds to one group of Table B.

Table 495
Compounds of the formula I.A where $R^1$ and $R^2$ are methyl, $R^3$ is hydrogen, U and V are amino (—NH—), $W^a$ is —CH$_2$O—N═C(CH$_3$)—* (*=bond to A$^a$), X and Y are ═N—, Z is ═CH— and A$^a$ for a compound in each case corresponds to one group of Table B.

Table 496
Compounds of the formula I.A where $R^1$ and $R^2$ are methyl, $R^3$ is hydrogen, U and V are amino (—NH—), $W^a$ is —CH$_2$O—N═C(CH$_3$)—C(C$_6$H$_5$)═NO—* (*=bond to A$^a$), X and Y are ═N—, Z is ═CH— and A$^a$ for a compound in each case corresponds to one group of Table B.

Table 497
Compounds of the formula I.A where $R^1$ and $R^2$ are methyl, $R^3$ is hydrogen, U and V are amino (—NH—), $W^a$ is —CH$_2$O—N═C(CH$_3$)—C(2-Cl—C$_6$H$_4$)═NO—* (*=bond to A$^a$), X and Y are ═N—, Z is ═CH— and A$^a$ for a compound in each case corresponds to one group of Table B.

Table 498
Compounds of the formula I.A where $R^1$ and $R^2$ are methyl, $R^3$ is hydrogen, U and V are amino (—NH—), $W^a$ is —CH$_2$O—N═C(CH$_3$)—C(4-Cl—C$_6$H$_4$)═NO—* (*=bond to A$^a$), X and Y are ═N—, Z is ═CH— and A$^a$ for a compound in each case corresponds to one group of Table B.

Table 499
Compounds of the formula I.A where $R^1$ and $R^2$ are methyl, $R^3$ is hydrogen, U and V are amino (—NH—), $W^a$ is a direct bond, X and Z are ═N—, Y is ═CH— and A$^a$ for a compound in each case corresponds to one group of Table B.

Table 500
Compounds of the formula I.A where $R^1$ and $R^2$ are methyl, $R^3$ is hydrogen, U and V are amino (—NH—), $W^a$ is —C(CH$_3$)═NO—* (*=bond to A$^a$), X and Z are ═N—, Y is ═CH— and A$^a$ for a compound in each case corresponds to one group of Table B.

Table 501
Compounds of the formula I.A where $R^1$ and $R^2$ are methyl, $R^3$ is hydrogen, U and V are amino (—NH—), $W^a$ is —CH$_2$O—N═C(CH$_3$)—* (*=bond to A$^a$), X and Z are ═N—, Y is ═CH— and A$^a$ for a compound in each case corresponds to one group of Table B.

Table 502
Compounds of the formula I.A where $R^1$ and $R^2$ are methyl, $R^3$ is hydrogen, U and V are amino (—NH—), $W^a$ is —CH$_2$O—N═C(CH$_3$)—C(C$_6$H$_5$)═NO—* (*=bond to A$^a$), X and Z are ═N—, Y is ═CH— and A$^a$ for a compound in each case corresponds to one group of Table B.

Table 503
Compounds of the formula I.A where $R^1$ and $R^2$ are methyl, $R^3$ is hydrogen, U and V are amino (—NH—), $W^a$ is —CH$_2$O—N═C(CH$_3$)—C(2-Cl—C$_6$H$_4$)═NO—* (*=bond to A$^a$), X and Z are ═N—, Y is ═CH— and A$^a$ for a compound in each case corresponds to one group of Table B.

Table 504
Compounds of the formula I.A where $R^1$ and $R^2$ are methyl, $R^3$ is hydrogen, U and V are amino (—NH—), $W^a$ is —CH$_2$O—N═C(CH$_3$)—C(4-Cl—C$_6$H$_4$)═NO—* (*=bond to A$^a$), X and Z are ═N—, Y is ═CH— and A$^a$ for a compound in each case corresponds to one group of Table B.

Table 505
Compounds of the formula I.A where $R^1$ and $R^2$ are methyl, $R^3$ is hydrogen, U and V are oxygen, $W^a$ is —CH$_2$O—N=C(CH$_3$)—C(C$_6$H$_5$)=NO—* (*=bond to A$^a$), X, Y and Z are =CH— and A$^a$ for a compound in each case corresponds to one group of Table B.

Table 506
Compounds of the formula I.A where R$^1$ and R$^2$ are methyl, R$^3$ is hydrogen, U and V are oxygen, W$^a$ is —CH$_2$O—N=C(CH$_3$)—C(2-Cl—C$_6$H$_4$)=N—* (*=bond to A$^a$), X, Y and Z are =CH— and A$^a$ for a compound in each case corresponds to one group of Table B.

Table 507
Compounds of the formula I.A where R$^1$ and R$^2$ are methyl, R$^3$ is hydrogen, U and V are oxygen, W$^a$ is —CH$_2$O—N=C(CH$_3$)—C(4-Cl—C$_6$H$_4$)=N—* (*=bond to A$^a$), X, Y and Z are =CH— and A$^a$ for a compound in each case corresponds to one group of Table B.

Table 508
Compounds of the formula I.A where R$^1$ and R$^2$ are methyl, R$^3$ is hydrogen, U and V are oxygen, W$^a$ is —CH$_2$O—N=C(CH$_3$)—C(C$_6$H$_5$)=NO—* (*=bond to A$^a$), X is =N—, Y and Z are =CH— and A$^a$ for a compound in each case corresponds to one group of Table B.

Table 509
Compounds of the formula I.A where R$^1$ and R$^2$ are methyl, R$^3$ is hydrogen, U and V are oxygen, W$^a$ is —CH$_2$O—N=C(CH$_3$)—C(2-Cl—C$_6$H$_4$)=N—* (*=bond to A$^a$), X is =N—, Y and Z are =CH— and A$^a$ for a compound in each case corresponds to one group of Table B.

Table 510
Compounds of the formula I.A where R$^1$ and R$^2$ are methyl, R$^3$ is hydrogen, U and V are oxygen, W$^a$ is —CH$_2$O—N=C(CH$_3$)—C(4-Cl—C$_6$H$_4$)=N—* (*=bond to A$^a$), X is =N—, Y and Z are =CH— and A$^a$ for a compound in each case corresponds to one group of Table B.

Table 511
Compounds of the formula I.A where R$^1$ and R$^2$ are methyl, R$^3$ is hydrogen, U and V are oxygen, W$^a$ is —CH$_2$O—N=C(CH$_3$)—C(C$_6$H$_5$)=N—* (*=bond to A$^a$), X and Y are =N—, Z is =CH— and A$^a$ for a compound in each case corresponds to one group of Table B.

Table 512
Compounds of the formula I.A where R$^1$ and R$^2$ are methyl, R$^3$ is hydrogen, U and V are oxygen, W$^a$ is —CH$_2$O—N=C(CH$_3$)—C(2-Cl—C$_6$H$_4$)=N—* (*=bond to A$^a$), X and Y are =N—, Z is =CH— and A$^a$ for a compound in each case corresponds to one group of Table B.

Table 513
Compounds of the formula I.A where R$^1$ and R$^2$ are methyl, R$^3$ is hydrogen, U and V are oxygen, W$^a$ is —CH$_2$O—N=C(CH$_3$)—C(4-Cl—C$_6$H$_4$)=N—* (*=bond to A$^a$), X and Y are =N—, Z is =CH— and A$^a$ for a compound in each case corresponds to one group of Table B.

Table 514
Compounds of the formula I.A where R$^1$ and R$^2$ are methyl, R$^3$ is hydrogen, U and V are oxygen, W$^a$ is —CH$_2$O—N=C(CH$_3$)—C(C$_6$H$_5$)=N—* (*=bond to A$^a$), X and Z are =N—, Y is =CH— and A$^a$ for a compound in each case corresponds to one group of Table B.

Table 515
Compounds of the formula I.A where R$^1$ and R$^2$ are methyl, R$^3$ is hydrogen, U and V are oxygen, W$^a$ is —CH$_2$O—N=C(CH$_3$)—C(2-Cl—C$_6$H$_4$)=N—* (*=bond to A$^a$), X and Z are =N—, Y is =CH— and A$^a$ for a compound in each case corresponds to one group of Table B.

Table 516
Compounds of the formula I.A where R$^1$ and R$^2$ are methyl, R$^3$ is hydrogen, U and V are oxygen, W$^a$ is —CH$_2$O—N=C(CH$_3$)—C(4-Cl—C$_6$H$_4$)=N—* (*=bond to A$^a$), X and Z are =N—, Y is =CH— and A$^a$ for a compound in each case corresponds to one group of Table B.

Table 517
Compounds of the formula I.A where R$^1$ and R$^2$ are methyl, R$^3$ is hydrogen, U is amino (—NH—) and V is oxygen, W$^a$ is —CH$_2$O—N=C(CH$_3$)—C(C$_6$H$_5$)=N—* (*=bond to A$^a$), X, Y and Z are =CH— and A$^a$ for a compound in each case corresponds to one group of Table B.

Table 518
Compounds of the formula I.A where R$^1$ and R$^2$ are methyl, R$^3$ is hydrogen, U is amino (—NH—) and V is oxygen, W$^a$ is —CH$_2$O—N=C(CH$_3$)—C(2-Cl—C$_6$H$_4$)=N—* (*=bond to A$^a$), X, Y and Z are =CH— and A$^a$ for a compound in each case corresponds to one group of Table B.

Table 519
Compounds of the formula I.A where R$^1$ and R$^2$ are methyl, R$^3$ is hydrogen, U is amino (—NH—) and V is oxygen, W$^a$ is —CH$_2$O—N=C(CH$_3$)—C(4-Cl—C$_6$H$_4$)=N—* (*=bond to A$^a$), X, Y and Z are =CH— and A$^a$ for a compound in each case corresponds to one group of Table B.

Table 520
Compounds of the formula I.A where R$^1$ and R$^2$ are methyl, R$^3$ is hydrogen, U is amino (—NH—) and V is oxygen, W$^a$ is —CH$_2$O—N=C(CH$_3$)—C(C$_6$H$_5$)=N—* (*=bond to A$^a$), X is =N—, Y and Z are =CH— and A$^a$ for a compound in each case corresponds to one group of Table B.

Table 521
Compounds of the formula I.A where R$^1$ and R$^2$ are methyl, R$^3$ is hydrogen, U is amino (—NH—) and V is oxygen, W$^a$ is —CH$_2$O—N=C(CH$_3$)—C(2-Cl—C$_6$H$_4$)=N—* (*=bond to A$^a$), X is =N—, Y and Z are =CH— and A$^a$ for a compound in each case corresponds to one group of Table B.

Table 522
Compounds of the formula I.A where R$^1$ and R$^2$ are methyl, R$^3$ is hydrogen, U is amino (—NH—) and V is oxygen, W$^a$ is —CH$_2$O—N=C(CH$_3$)—C(4-Cl—C$_6$H$_4$)=N—* (*=bond to A$^a$), X is =N—, Y and Z are =CH— and A$^a$ for a compound in each case corresponds to one group of Table B.

Table 523
Compounds of the formula I.A where R$^1$ and R$^2$ are methyl, R$^3$ is hydrogen, U is amino (—NH—) and V is oxygen, W$^a$ is —CH$_2$O—N=C(CH$_3$)—C(C$_6$H$_5$)=N—* (*=bond to A$^a$), X and Y are =N—, Z is =CH— and A$^a$ for a compound in each case corresponds to one group of Table B.

Table 524
Compounds of the formula I.A where R$^1$ and R$^2$ are methyl, R$^3$ is hydrogen, U is amino (—NH—) and V is oxygen, W$^a$ is —CH$_2$O—N=C(CH$_3$)—C(2-Cl—C$_6$H$_4$)=N—* (*=bond to A$^a$), X and Y are =N—, Z is =CH— and A$^a$ for a compound in each case corresponds to one group of Table B.

Table 525
Compounds of the formula I.A where R$^1$ and R$^2$ are methyl, R$^3$ is hydrogen, U is amino (—NH—) and V is oxygen, W$^a$ is —CH$_2$O—N=C(CH$_3$)—C(4-Cl—C$_6$H$_4$)=N—* (*=bond to A$^a$), X and Y are =N—, Z is =CH— and A$^a$ for a compound in each case corresponds to one group of Table B.

Table 526
Compounds of the formula I.A where R$^1$ and R$^2$ are methyl, R$^3$ is hydrogen, U is amino (—NH—) and V is

Table 527
Compounds of the formula I.A where $R^1$ and $R^2$ are methyl, $R^3$ is hydrogen, U is amino (—NH—) and V is oxygen, $W^a$ is —CH$_2$O—N=C(CH$_3$)—C(2-Cl—C$_6$H$_4$)=N—* (*=bond to $A^a$), X and Z are =N—, Y is =CH— and $A^a$ for a compound in each case corresponds to one group of Table B.

Table 528
Compounds of the formula I.A where $R^1$ and $R^2$ are methyl, $R^3$ is hydrogen, U is amino (—NH—) and V is oxygen, $W^a$ is —CH$_2$O—N=C(CH$_3$)—C(4-Cl—C$_6$H$_4$)=N—* (*=bond to $A^a$), X and Z are =N—, Y is =CH— and $A^a$ for a compound in each case corresponds to one group of Table B.

Table 529
Compounds of the formula I.A where $R^1$ and $R^2$ are methyl, $R^3$ is hydrogen, U is oxygen and V is sulfur, $W^a$ is —CH$_2$O—N=C(CH$_3$)—C(C$_6$H$_5$)=N—* (*=bond to $A^a$), X, Y and Z are =CH— and $A^a$ for a compound in each case corresponds to one group of Table B.

Table 530
Compounds of the formula I.A where $R^1$ and $R^2$ are methyl, $R^3$ is hydrogen, U is oxygen and V is sulfur, $W^a$ is —CH$_2$O—N=C(CH$_3$)—C(2-Cl—C$_6$H$_4$)=N—* (*=bond to $A^a$), X, Y and Z are =CH— and $A^a$ for a compound in each case corresponds to one group of Table B.

Table 531
Compounds of the formula I.A where $R^1$ and $R^2$ are methyl, $R^3$ is hydrogen, U is oxygen and V is sulfur, $W^a$ is —CH$_2$O—N=C(CH$_3$)—C(4-Cl—C$_6$H$_4$)=N—* (*=bond to $A^a$), X, Y and Z are =CH— and $A^a$ for a compound in each case corresponds to one group of Table B.

Table 532
Compounds of the formula I.A where $R^1$ and $R^2$ are methyl, $R^3$ is hydrogen, U is oxygen and V is sulfur, $W^a$ is —CH$_2$O—N=C(CH$_3$)—C(C$_6$H$_5$)=N—* (*=bond to $A^a$), X is =N—, Y and Z are =CH— and $A^a$ for a compound in each case corresponds to one group of Table B.

Table 533
Compounds of the formula I.A where $R^1$ and $R^2$ are methyl, $R^3$ is hydrogen, U is oxygen and V is sulfur, $W^a$ is —CH$_2$O—N=C(CH$_3$)—C(2-Cl—C$_6$H$_4$)=N—* (*=bond to $A^a$), X is =N—, Y and Z are =CH— and $A^a$ for a compound in each case corresponds to one group of Table B.

Table 534
Compounds of the formula I.A where $R^1$ and $R^2$ are methyl, $R^3$ is hydrogen, U is oxygen and V is sulfur, $W^a$ is —CH$_2$O—N=C(CH$_3$)—C(4-Cl—C$_6$H$_4$)=N—* (*=bond to $A^a$), X is =N—, Y and Z are =CH— and $A^a$ for a compound in each case corresponds to one group of Table B.

Table 535
Compounds of the formula I.A where $R^1$ and $R^2$ are methyl, $R^3$ is hydrogen, U is oxygen and V is sulfur, $W^a$ is —CH$_2$O—N=C(CH$_3$)—C(C$_6$H$_5$)=N—* (*=bond to $A^a$), X and Y are =N—, Z is =CH— and $A^a$ for a compound in each case corresponds to one group of Table B.

Table 536
Compounds of the formula I.A where $R^1$ and $R^2$ are methyl, $R^3$ is hydrogen, U is oxygen and V is sulfur, $W^a$ is —CH$_2$O—N=C(CH$_3$)—C(2-Cl—C$_6$H$_4$)=N—* (*=bond to $A^a$), X and Y are =N—, Z is =CH— and $A^a$ for a compound in each case corresponds to one group of Table B.

Table 537
Compounds of the formula I.A where $R^1$ and $R^2$ are methyl, $R^3$ is hydrogen, U is oxygen and V is sulfur, $W^a$ is —CH$_2$O—N=C(CH$_3$)—C(4-Cl—C$_6$H$_4$)=N—* (*=bond to $A^a$), X and Y are =N—, Z is =CH— and $A^a$ for a compound in each case corresponds to one group of Table B.

Table 538
Compounds of the formula I.A where $R^1$ and $R^2$ are methyl, $R^3$ is hydrogen, U is oxygen and V is sulfur, $W^a$ is —CH$_2$O—N=C(CH$_3$)—C(C$_6$H$_5$)=N—* (*=bond to $A^a$), X and Z are =N—, Y is =CH— and $A^a$ for a compound in each case corresponds to one group of Table B.

Table 539
Compounds of the formula I.A where $R^1$ and $R^2$ are methyl, $R^3$ is hydrogen, U is oxygen and V is sulfur, $W^a$ is —CH$_2$O—N=C(CH$_3$)—C(2-Cl—C$_6$H$_4$)=N—* (*=bond to $A^a$), X and Z are =N—, Y is =CH— and $A^a$ for a compound in each case corresponds to one group of Table B.

Table 540
Compounds of the formula I.A where $R^1$ and $R^2$ are methyl, $R^3$ is hydrogen, U is oxygen and V is sulfur, $W^a$ is —CH$_2$O—N=C(CH$_3$)—C(4-Cl—C$_6$H$_4$)=N—* (*=bond to $A^a$), X and Z are =N—, Y is =CH— and $A^a$ for a compound in each case corresponds to one group of Table B.

Table 541
Compounds of the formula I.A where $R^1$ and $R^2$ are methyl, $R^3$ is hydrogen, U is amino (—NH—) and V is sulfur, $W^a$ is —CH$_2$O—N=C(CH$_3$)—C(C$_6$H$_5$)=N—* (*=bond to $A^a$), X, Y and Z are =CH— and $A^a$ for a compound in each case corresponds to one group of Table B.

Table 542
Compounds of the formula I.A where $R^1$ and $R^2$ are methyl, $R^3$ is hydrogen, U is amino (—NH—) and V is sulfur, $W^a$ is —CH$_2$O—N=C(CH$_3$)—C(2-Cl—C$_6$H$_4$)=N—* (*=bond to $A^a$), X, Y and Z are =CH— and $A^a$ for a compound in each case corresponds to one group of Table B.

Table 543
Compounds of the formula I.A where $R^1$ and $R^2$ are methyl, $R^3$ is hydrogen, U is amino (—NH—) and V is sulfur, $W^a$ is —CH$_2$O—N=C(CH$_3$)—C(4-Cl—C$_6$H$_4$)=N—* (*=bond to $A^a$), X, Y and Z are =CH— and $A^a$ for a compound in each case corresponds to one group of Table B.

Table 544
Compounds of the formula I.A where $R^1$ and $R^2$ are methyl, $R^3$ is hydrogen, U is amino (—NH—) and V is sulfur, $W^a$ is —CH$_2$O—N=C(CH$_3$)—C(C$_6$H$_5$)=N—* (*=bond to $A^a$), X is =N—, Y and Z are =CH— and $A^a$ for a compound in each case corresponds to one group of Table B.

Table 545
Compounds of the formula I.A where $R^1$ and $R^2$ are methyl, $R^3$ is hydrogen, U is amino (—NH—) and V is sulfur, $W^a$ is —CH$_2$O—N=C(CH$_3$)—C(2-Cl—C$_6$H$_4$)=N—* (*=bond to $A^a$), X is =N—, Y and Z are =CH— and $A^a$ for a compound in each case corresponds to one group of Table B.

Table 546
Compounds of the formula I.A where $R^1$ and $R^2$ are methyl, $R^3$ is hydrogen, U is amino (—NH—) and V is sulfur, $W^a$ is —CH$_2$O—N=C(CH$_3$)—C(4-Cl—C$_6$H$_4$)=N—* (*=bond to $A^a$), X is =N—, Y and Z are =CH— and $A^a$ for a compound in each case corresponds to one group of Table B.

Table 547
Compounds of the formula I.A where $R^1$ and $R^2$ are methyl, $R^3$ is hydrogen, U is amino (—NH—) and V is sulfur, $W^a$ is —$CH_2$O—N=C($CH_3$)—C($C_6H_5$)=N—* (*=bond to $A^a$), X and Y are =N—, Z is =CH— and $A^a$ for a compound in each case corresponds to one group of Table B.

Table 548

Compounds of the formula I.A where $R^1$ and $R^2$ are methyl, $R^3$ is hydrogen, U is amino (—NH—) and V is sulfur, $W^a$ is —$CH_2$O—N=C($CH_3$)—C(2-Cl—$C_6H_4$)=N—* (*=bond to $A^a$), X and Y are =N—, Z is =CH— and $A^a$ for a compound in each case corresponds to one group of Table B.

Table 549

Compounds of the formula I.A where $R^1$ and $R^2$ are methyl, $R^3$ is hydrogen, U is amino (—NH—) and V is sulfur, $W^a$ is —$CH_2$O—N=C($CH_3$)—C(4-Cl—$C_6H_4$)=N—* (*=bond to $A^a$), X and Y are =N—, Z is =CH— and $A^a$ for a compound in each case corresponds to one group of Table B.

Table 550

Compounds of the formula I.A where $R^1$ and $R^2$ are methyl, $R^3$ is hydrogen, U is amino (—NH—) and V is sulfur, $W^a$ is —$CH_2$O—N=C($CH_3$)—C($C_6H_5$)=N—* (*=bond to $A^a$), X and Z are =N—, Y is =CH— and $A^a$ for a compound in each case corresponds to one group of Table B.

Table 551

Compounds of the formula I.A where $R^1$ and $R^2$ are methyl, $R^3$ is hydrogen, U is amino (—NH—) and V is sulfur, $W^a$ is —$CH_2$O—N=C($CH_3$)—C(2-Cl—$C_6H_4$)=N—* (*=bond to $A^a$), X and Z are =N—, Y is =CH— and $A^a$ for a compound in each case corresponds to one group of Table B.

Table 552

Compounds of the formula I.A where $R^1$ and $R^2$ are methyl, $R^3$ is hydrogen, U is amino (—NH—) and V is sulfur, $W^a$ is —$CH_2$O—N=C($CH_3$)—C(4-Cl—$C_6H_4$)=N—* (*=bond to $A^a$), X and Z are =N—, Y is =CH— and $A^a$ for a compound in each case corresponds to one group of Table B.

Table 553

Compounds of the formula I.A where $R^1$ and $R^2$ are methyl, $R^3$ is hydrogen, U is oxygen and V is amino (—NH—), $W^a$ is —$CH_2$O—N=C($CH_3$)—C($C_6H_5$)=N—* (*=bond to $A^a$), X, Y and Z are =CH— and $A^a$ for a compound in each case corresponds to one group of Table B.

Table 554

Compounds of the formula I.A where $R^1$ and $R^2$ are methyl, $R^3$ is hydrogen, U is oxygen and V is amino (—NH—), $W^a$ is —$CH_2$O—N=C($CH_3$)—C(2-Cl—$C_6H_4$)=N—* (*=bond to $A^a$), X, Y and Z are =CH— and $A^a$ for a compound in each case corresponds to one group of Table B.

Table 555

Compounds of the formula I.A where $R^1$ and $R^2$ are methyl, $R^3$ is hydrogen, U is oxygen and V is amino (—NH—), $W^a$ is —$CH_2$O—N=C($CH_3$)—C(4-Cl—$C_6H_4$)=N—* (*=bond to $A^a$), X, Y and Z are =CH— and $A^a$ for a compound in each case corresponds to one group of Table B.

Table 556

Compounds of the formula I.A where $R^1$ and $R^2$ are methyl, $R^3$ is hydrogen, U is oxygen and V is amino (—NH—), $W^a$ is —$CH_2$O—N=C($CH_3$)—C($C_6H_5$)=N—* (*=bond to $A^a$), X is =N—, Y and Z are =CH— and $A^a$ for a compound in each case corresponds to one group of Table B.

Table 557

Compounds of the formula I.A where $R^1$ and $R^2$ are methyl, $R^3$ is hydrogen, U is oxygen and V is amino (—NH—), $W^a$ is —$CH_2$O—N=C($CH_3$)—C(2-Cl—$C_6H_4$)=N—* (*=bond to $A^a$), X is =N—, Y and Z are =CH— and $A^a$ for a compound in each case corresponds to one group of Table B.

Table 558

Compounds of the formula I.A where $R^1$ and $R^2$ are methyl, $R^3$ is hydrogen, U is oxygen and V is amino (—NH—), $W^a$ is —$CH_2$O—N=C($CH_3$)—C(4-Cl—$C_6H_4$)=N—* (*=bond to $A^a$), X is =N—, Y and Z are =CH— and $A^a$ for a compound in each case corresponds to one group of Table B.

Table 559

Compounds of the formula I.A where $R^1$ and $R^2$ are methyl, $R^3$ is hydrogen, U is oxygen and V is amino (—NH—), $W^a$ is —$CH_2$O—N=C($CH_3$)—C($C_6H_5$)=N—* (*=bond to $A^a$), X and Y are =N—, Z is =CH— and $A^a$ for a compound in each case corresponds to one group of Table B.

Table 560

Compounds of the formula I.A where $R^1$ and $R^2$ are methyl, $R^3$ is hydrogen, U is oxygen and V is amino (—NH—), $W^a$ is —$CH_2$O—N=C($CH_3$)—C(2-Cl—$C_6H_4$)=N—* (*=bond to $A^a$), X and Y are =N—, Z is =CH— and $A^a$ for a compound in each case corresponds to one group of Table B.

Table 561

Compounds of the formula I.A where $R^1$ and $R^2$ are methyl, $R^3$ is hydrogen, U is oxygen and V is amino (—NH—), $W^a$ is —$CH_2$O—N=C($CH_3$)—C(4-Cl—$C_6H_4$)=N—* (*=bond to $A^a$), X and Y are =N—, Z is =CH— and $A^a$ for a compound in each case corresponds to one group of Table B.

Table 562

Compounds of the formula I.A where $R^1$ and $R^2$ are methyl, $R^3$ is hydrogen, U is oxygen and V is amino (—NH—), $W^a$ is —$CH_2$O—N=C($CH_3$)—C($C_6H_5$)=N—* (*=bond to $A^a$), X and Z are =N—, Y is =CH— and $A^a$ for a compound in each case corresponds to one group of Table B.

Table 563

Compounds of the formula I.A where $R^1$ and $R^2$ are methyl, $R^3$ is hydrogen, U is oxygen and V is amino (—NH—), $W^a$ is —$CH_2$O—N=C($CH_3$)—C(2-Cl—$C_6H_4$)=N—* (*=bond to $A^a$), X and Z are =N—, Y is =CH— and $A^a$ for a compound in each case corresponds to one group of Table B.

Table 564

Compounds of the formula I.A where $R^1$ and $R^2$ are methyl, $R^3$ is hydrogen, U is oxygen and V is amino (—NH—), $W^a$ is —$CH_2$O—N=C($CH_3$)—C(4-Cl—$C_6H_4$)=N—* (*=bond to $A^a$), X and Z are =N—, Y is =CH— and $A^a$ for a compound in each case corresponds to one group of Table B.

Table 565

Compounds of the formula I.A where $R^1$ and $R^2$ are methyl, $R^3$ is hydrogen, U and V are amino (—NH—), $W^a$ is —$CH_2$O—N=C($CH_3$)—C($C_6H_5$)=N—* (*=bond to $A^a$), X, Y and Z are =CH— and $A^a$ for a compound in each case corresponds to one group of Table B.

Table 566

Compounds of the formula I.A where $R^1$ and $R^2$ are methyl, $R^3$ is hydrogen, U and V are amino (—NH—), $W^a$ is —$CH_2$O—N=C($CH_3$)—C(2-Cl—$C_6H_4$)=N—* (*=bond to $A^a$), X, Y and Z are =CH— and $A^a$ for a compound in each case corresponds to one group of Table B.

Table 567

Compounds of the formula I.A where $R^1$ and $R^2$ are methyl, $R^3$ is hydrogen, U and V are amino (—NH—), $W^a$ is —CH$_2$O—N═C(CH$_3$)—C(4-Cl—C$_6$H$_4$)═N—* (*=bond to $A^a$), X, Y and Z are ═CH— and $A^a$ for a compound in each case corresponds to one group of Table B.

Table 568

Compounds of the formula I.A where $R^1$ and $R^2$ are methyl, $R^3$ is hydrogen, U and V are amino (—NH—), $W^a$ is —CH$_2$O—N═C(CH$_3$)—C(C$_6$H$_5$)═N—* (*=bond to $A^a$), X is ═N—, Y and Z are ═CH— and $A^a$ for a compound in each case corresponds to one group of Table B.

Table 569

Compounds of the formula I.A where $R^1$ and $R^2$ are methyl, $R^3$ is hydrogen, U and V are amino (—NH—), $W^a$ is —CH$_2$O—N═C(CH$_3$)—C(2-Cl—C$_6$H$_4$)═N—* (*=bond to $A^a$), X is ═N—, Y and Z are ═CH— and $A^a$ for a compound in each case corresponds to one group of Table B.

Table 570

Compounds of the formula I.A where $R^1$ and $R^2$ are methyl, $R^3$ is hydrogen, U and V are amino (—NH—), $W^a$ is —CH$_2$O—N═C(CH$_3$)—C(4-Cl—C$_6$H$_4$)═N—* (*=bond to $A^a$), X is ═N—, Y and Z are ═CH— and $A^a$ for a compound in each case corresponds to one group of Table B.

Table 571

Compounds of the formula I.A where $R^1$ and $R^2$ are methyl, $R^3$ is hydrogen, U and V are amino (—NH—), $W^a$ is —CH$_2$O—N═C(CH$_3$)—C(C$_6$H$_5$)═N—* (*=bond to $A^a$), X and Y are ═N—, Z is ═CH— and $A^a$ for a compound in each case corresponds to one group of Table B.

Table 572

Compounds of the formula I.A where $R^1$ and $R^2$ are methyl, $R^3$ is hydrogen, U and V are amino (—NH—), $W^a$ is —CH$_2$O—N═C(CH$_3$)—C(2-Cl—C$_6$H$_4$)═N—* (*=bond to $A^a$), X and Y are ═N—, Z is ═CH— and $A^a$ for a compound in each case corresponds to one group of Table B.

Table 573

Compounds of the formula I.A where $R^1$ and $R^2$ are methyl, $R^3$ is hydrogen, U and V are amino (—NH—), $W^a$ is —CH$_2$O—N═C(CH$_3$)—C(4-Cl—C$_6$H$_4$)═N—* (*=bond to $A^a$), X and Y are ═N—, Z is ═CH— and $A^a$ for a compound in each case corresponds to one group of Table B.

Table 574

Compounds of the formula I.A where $R^1$ and $R^2$ are methyl, $R^3$ is hydrogen, U and V are amino (—NH—), $W^a$ is —CH$_2$O—N═C(CH$_3$)—C(C$_6$H$_5$)═N—* (*=bond to $A^a$), X and Z are ═N—, Y is ═CH— and $A^a$ for a compound in each case corresponds to one group of Table B.

Table 575

Compounds of the formula I.A where $R^1$ and $R^2$ are methyl, $R^3$ is hydrogen, U and V are amino (—NH—), $W^a$ is —CH$_2$O—N═C(CH$_3$)—C(2-Cl—C$_6$H$_4$)═N—* (*=bond to $A^a$), X and Z are ═N—, Y is ═CH— and $A^a$ for a compound in each case corresponds to one group of Table B.

Table 576

Compounds of the formula I.A where $R^1$ and $R^2$ are methyl, $R^3$ is hydrogen, U and V are amino (—NH—), $W^a$ is —CH$_2$O—N═C(CH$_3$)—C(4-Cl—C$_6$H$_4$)═N—* (*=bond to $A^a$), X and Z are ═N—, Y is ═CH— and $A^a$ for a compound in each case corresponds to one group of Table B.

TABLE A

| No. | $A^a$ | No. | $A^a$ | No. | $A^a$ |
|---|---|---|---|---|---|
| 1 | phenyl | 127 | 2,5-dichlorophenyl | 253 | 2-bromo-4-chlorophenyl |
| 2 | 2-fluorophenyl | 128 | 3,4-dichlorophenyl | 254 | 2-bromo-4-fluorophenyl |
| 3 | 3-fluorophenyl | 129 | 3,5-dichlorophenyl | 255 | 3-bromo-4-chlorophenyl |
| 4 | 4-fluorophenyl | 130 | 2,3,4-trichlorophenyl | 256 | 3-chloro-4-fluorophenyl |
| 5 | 2-chlorophenyl | 131 | 2,3,5-trichlorophenyl | 257 | 3-fluoro-4-chlorophenyl |
| 6 | 2-chloro-4-fluorophenyl | 132 | 2,3,6-trichlorophenyl | 258 | 2-cyanophenyl |
| 7 | 2-chloro-5-fluorophenyl | 133 | 3,4,5-trichlorophenyl | 259 | 4-cyanophenyl |
| 8 | 2-chloro-6-fluorophenyl | 134 | 2-bromophenyl | 260 | 2-nitrophenyl |
| 9 | 2-ethylphenyl | 135 | 3-bromophenyl | 261 | 2-methylphenyl |
| 10 | 3-ethylphenyl | 136 | 4-bromophenyl | 262 | 3-methylphenyl |
| 11 | 3,5-diethylphenyl | 137 | 2,4-dibromophenyl | 263 | 4-methylphenyl |
| 12 | 2-n-propylphenyl | 138 | 3-bromo-4-fluorophenyl | 264 | 2,4-dimethylphenyl |
| 13 | 3-chorophenyl | 139 | 3-bromo-4-methoxyphenyl | 265 | 2,6-dimethylphenyl |
| 14 | 4-chlorophenyl | 140 | 2-iodophenyl | 266 | 3,4-dimethylphenyl |
| 15 | 2,4-dichlorophenyl | 141 | 2-chloro-4-bromophenyl | 267 | 3,5-dimethylphenyl |
| 16 | 2,3,4-trimethylphenyl | 142 | 2-methyl-4-phenoxyphenyl | 268 | 3-n-hexoxyphenyl |
| 17 | 2,3,5-trimethylphenyl | 143 | 2-methyl-4-benzyloxyphenyl | 269 | 4-n-hexoxyphenyl |
| 18 | 2,3,6-trimethylphenyl | 144 | 2-methyl-3-chlorophenyl | 270 | 3-allyloxyphenyl |
| 19 | 2,4,5-trimethylphenyl | 145 | 2-methyl-4-chlorophenyl | 271 | 4-iso-propoxyphenyl |
| 20 | 2,4,6-trimethylphenyl | 146 | 2-methyl-5-chlorophenyl | 272 | 2-phenylphenyl |
| 21 | 3,4,5-trimethylphenyl | 147 | 2-methyl-6-chlorophenyl | 273 | 3-phenylphenyl |
| 22 | 3-n-propylphenyl | 148 | 2-methyl-4-fluorophenyl | 274 | 4-phenylphenyl |
| 23 | 4-n-propylphenyl | 149 | 2-methyl-3-bromophenyl | 275 | 2-phenoxyphenyl |
| 24 | 2-iso-propylphenyl | 150 | 2-methyl-4-methoxyphenyl | 276 | 4-phenoxyphenyl |
| 25 | 3-iso-propylphenyl | 151 | 2-methyl-5-methoxyphenyl | 277 | 1-naphthyl |
| 26 | 4-iso-propylphenyl | 152 | 2-methyl-6-methoxyphenyl | 278 | 2-naphthyl |
| 27 | 2,3-di-isopropylphenyl | 153 | 2-methyl-4-isopropoxyphenyl | 279 | 9-anthryl |
| 28 | 3,5-di-isopropylphenyl | 154 | 2-methyl-2,5-dimethoxyphenyl | 280 | 2-fluoro-4-phenoxyphenyl |
| 29 | 4-n-butylphenyl | 155 | 2-methoxyphenyl | 281 | 3-fluoro-4-phenoxyphenyl |
| 30 | 4-sec-butylphenyl | 156 | 3-methoxyphenyl | 282 | 4-fluoro-4-phenoxyphenyl |
| 31 | 4-iso-butylphenyl | 157 | 4-methoxyphenyl | 283 | 2-chloro-4-phenoxyphenyl |
| 32 | 2-methyl-4-tert-butylphenyl | 158 | 2-chloro-5-methylphenyl | 284 | 4-chloro-4-phenoxyphenyl |
| 33 | 2-methyl-6-tert-butylphenyl | 159 | 2-chloro-4-isopropylphenyl | 285 | 2-bromo-4-phenoxyphenyl |
| 34 | 2-methyl-4-isopropylphenyl | 160 | 3-n-propoxyphenyl | 286 | 3-bromo-4-phenoxyphenyl |
| 35 | 2-methyl-4-cyclohexylphenyl | 161 | 3-n-butoxyphenyl | 287 | 4-bromo-4-phenoxyphenyl |

TABLE A-continued

| No. | Aª | No. | Aª | No. | Aª |
|---|---|---|---|---|---|
| 36 | 2-methyl-4-phenylphenyl | 162 | 3-iso-butoxyphenyl | 288 | 3-methyl-4-phenoxyphenyl |
| 37 | 2-methyl-4-benzylphenyl | 163 | 3-n-pentoxyphenyl | 289 | 4-methyl-4-phenoxyphenyl |
| 38 | 3-tert-butyl-4-phenoxy-phenyl | 164 | 4-(imidazol-1'-yl)phenyl | 290 | 2,5-dimethylphenyl |
| 39 | 2-methoxy-4-phenoxyphenyl | 165 | 4-(piperazin-1'-yl)phenyl | 291 | 2-methyl-4-iodophenyl |
| 40 | 3-methoxy-4-phenoxyphenyl | 166 | 4-(morpholin-1'-yl)phenyl | 292 | 2-methyl-5-iodophenyl |
| 41 | 4-methoxy-4-phenoxyphenyl | 167 | 4-(piperidin-1'-yl)phenyl | 293 | 2,5-dimethyl-4-iodophenyl |
| 42 | 3-5-dichloro-4-phenoxyphenyl | 168 | 4-(pyridyl-2'-oxy)phenyl | 294 | 2-me-5-isopropylphenyl |
| 43 | 3-4-dichloro-4-phenoxyphenyl | 169 | 2-cyclopropylphenyl | 295 | 6-ethyl-2-pyridyl |
| 44 | 4-ethyl-4-phenoxyphenyl | 170 | 3-cyclopropylphenyl | 296 | 6-n-propyl-2-pyridyl |
| 45 | 4-iso-propyl-4-phenoxyphenyl | 171 | 3-cyclohexylphenyl | 297 | 6-iso-propyl-2-pyridyl |
| 46 | 2,4-dimethoxyphenyl | 172 | 4-cyclohexylphenyl | 298 | 6-n-butyl-2-pyridyl |
| 47 | 2,5-dimethoxyphenyl | 173 | 4-oxiranylphenyl | 299 | 6-tert-butyl-2-pyridyl |
| 48 | 3,6-dimethoxyphenyl | 174 | 4-(pyrid-2-yl)phenyl | 300 | 6-n-pnetyl-2-pyridyl |
| 49 | 2,3,4-trimethoxyphenyl | 175 | 3-(pyrid-2-yl)phenyl | 301 | 6-n-hexyl-2-pyridyl |
| 50 | 2-ethoxyphenyl | 176 | 4-(pyrid-3-yl)phenyl | 302 | 6-phenyl-2-pyridyl |
| 51 | 2-iso-propoxyphenyl | 177 | 3-(pyrid-3-yl)phenyl | 303 | 6-benzyl-2-pyridyl |
| 52 | 2-methyl-3-isopropylphenyl | 178 | 3-(pyrimid-2-yl)phenyl | 304 | 6-trifluoromethyl-2-pyridyl |
| 53 | 2-methyl-5-isopropylphenyl | 179 | 3-phenoxyphenyl | 305 | 6-methoxy-2-pyridyl |
| 54 | 2-benzyloxyphenyl | 180 | 2-fluoro-3-phenoxyphenyl | 306 | 6-chloro-2-pyridyl |
| 55 | 3-benzyloxyphenyl | 181 | 2-methyl-3-phenoxyphenyl | 307 | 3,6-dimethyl-2-pyridyl |
| 56 | 4-benzyloxyphenyl | 182 | 5,6-methyl-2-pyridyl | 308 | 3,6-diethyl-2-pyrdyl |
| 57 | 4,6-dimethyl-2-pyridyl | 183 | 5,6-dimethyl-2-pyridyl | 309 | 4-phenyl-6-methyl-2-pyridyl |
| 58 | 4,6-diphenyl-2-pyridyl | 184 | 3,4-dichloro-6-methyl-pyridyl | 310 | 3,4,5-trichloro-6-phenyl-2-pyridyl |
| 59 | 4-trifluoromethyl-6-methyl-6-2-pyridyl | 185 | 3-acetyl-4,6-dimethyl-2-pyridyl | 311 | 3-cyano-6-methyl-2-pyridyl |
| 60 | 3-cyano-6-ethyl-2-pyridyl | 186 | 3-cyano-6-n-propyl-2-pyridyl | 312 | 3-cyano-isopropyl-2-pyridyl |
| 61 | 3-cyano-6-cyclopropyl-2-pyridyl | 187 | 3-cyano-6-n-butyl-2-pyridyl | 313 | 3-cyano-6-tert-butyl-2-pyridyl |
| 62 | 3-cyano-6-cyclohexyl-2-pyridyl | 188 | 3-cyano-6-phenyl-2-pyridyl | 314 | 3-methyloxycarbonyl-6-isopropyl-2-pyridyl |
| 63 | 3-ethyloxycarbonyl-6-isopropyl-2-pyridyl | 189 | 3-cyano-4,6-dimethyl-2-pyridyl | 315 | 3,5,6-trichloro-2-pyridyl |
| 64 | 5-trifluoromethyl-2-pyridyl | 190 | 3-chloro-5-trifluoromethyl-2-pyridyl | 316 | 6-cyclopropyl-2-pyridyl |
| 65 | 6-bromo-2-pyridyl | 191 | 4-trifluoromethyl-5-chloro-2-pyridyl | 317 | 4-tert-butyl-2-pyridyl |
| 66 | 3,6-bis(trifluoromethyl)-2-pyridyl | 192 | 5-trifluoromethyl-2-pyridyl | 318 | 3-fluoro-2-pyridyl |
| 67 | 3-chloro-2-pyridyl | 193 | 4-bromo-2-pyridyl | 319 | 5-methyl-2-pyridyl |
| 68 | 3-fluoro-5-trifluoromethyl-2-pyridyl | 194 | 3,6-dichloro-5-trifluoro-methyl-2-pyridyl | 320 | 6-chloro-4-cyano-2-pyridyl |
| 69 | 4,6-difluoro-2-pyridyl | 195 | 3,5-dichloro-6-fluoro-2-pyridyl | 321 | 6-methoxy-3-nitro-2-pyridyl |
| 70 | 4-cyano-6-fluoro-2-pyridyl | 196 | 4-cyano-3,5,6-trifluoro-2-pyridyl | 322 | 6-chloro-5-nitro-2-pyridyl |
| 71 | 4,6-dicyano-2-pyridyl | 197 | 5-trichloromethyl-2-pyridyl | 323 | 5-cyano-2-pyridyl |
| 72 | 5-bromo-4-trifluoromethyl-2-pyridyl | 198 | 3-nitro-5-trifluoromethyl-2-pyridyl | 324 | 5-formamido-2-pyridyl |
| 73 | 5-amino-2-pyridyl | 199 | 5-nitro-2-pyridyl | 325 | 4-methyl-5-nitro-2-pyridyl |
| 74 | 5-difluoromethyl-2-pyridyl | 200 | 5-fluoromethyl-2-pyridyl | 326 | 5-methoxycarbonyl-2-pyridyl |
| 75 | 5-chloro-6-methoxy-2-pyridyl | 201 | 5,6-dichloro-2-pyridyl | 327 | 6-bromo-5-chloro-2-pyridyl |
| 76 | 5-chloro-6-acetoxy-2-pyridyl | 202 | 5-bromo-6-fluoro-2-pyridyl | 328 | 5-bromo-6-cyano-2-pyridyl |
| 77 | 5-bromo-6-hydroxy-2-pyridyl | 203 | 5-bromo-6-methoxy-2-pyridyl | 329 | 5,6-dibromo-2-pyridyl |
| 78 | 6-phenoxy-2-pyridyl | 204 | 4-phenyl-2-pyridyl | 330 | 4-phenoxy-2-pyridyl |
| 79 | 6-hydroxy-2-pyridyl | 205 | 6-hydroxy-2-pyridyl | 331 | 6-ethoxy-2-pyridyl |
| 80 | 6-benzyloxy-2-pyridyl | 206 | 4-benzyloxy-2-pyridyl | 332 | 4,6-bis(trifluoromethyl)-2-pyridyl |
| 81 | 6-formyl-2-pyridyl | 207 | 6-amino-2-pyridyl | 333 | 4-amino-2-pyridyl |
| 82 | 4-carboxy-2-pyridyl | 208 | 3-bromo-5-trifluoromethyl-2-pyridyl | 334 | 6-methyl-3-nitro-2-pyridyl |
| 83 | 3-nitro-2-pyridyl | 209 | 3-fluoro-5-trifluoromethyl-2-pyridyl | 335 | 3-pyridyl |
| 84 | 2-fluoro-3-pyridyl | 210 | 4-trifluoromethyl-3-pyridyl | 336 | 5-methyl-3-pyridyl |
| 85 | 6-methoxy-3-pyridyl | 211 | 4-cyano-2,5,6-trifluoro-3-pyridyl | 337 | 4-pyridyl |
| 86 | 2-chloro-4-pyridyl | 212 | 3-trifluoromethyl-4-pyridyl | 338 | 2-chloro-6-fluoro-4-pyridyl |
| 87 | 2,3,5,6-tetrafluoro-4-pyridyl | 213 | 2-pyrimidinyl | 339 | 4,6-dimethyl-2-pyrimidinyl |

TABLE A-continued

| No. | A$^a$ | No. | A$^a$ | No. | A$^a$ |
|---|---|---|---|---|---|
| 88 | 4-trifluoromethyl-2-pyrimidinyl | 214 | 4,5,6-trimethyl-2-pyrimidinyl | 340 | 4-benzyl-6-methyl-2-pyrimidinyl |
| 89 | 4-methyl-6-phenyl-2-pyrimidinyl | 215 | 4,6-dimethyl-5-chloro-2-pyrimidinyl | 341 | 4-fluoro-2-pyrimidinyl |
| 90 | 5-methyl-2-pyrimidinyl | 216 | 4,6-difluoro-2-pyrimidinyl | 342 | 4-pyrimidinyl |
| 91 | 2,6-dimethyl-4-pyrimidinyl | 217 | 2,6-bis-(trifluoromethyl)-4-pyrimidinyl | 343 | 2-chloromethyl-6-methyl-4-pyrimidinyl |
| 92 | 2-methyl-6-chloromethyl-4-pyrimidinyl | 218 | 2-isopropyl-6-methyl-4-pyrimidinyl | 344 | 2-isopropyl-6-chloro-methyl-4-pyrimidinyl |
| 93 | 2-cyclopropyl-6-chloro-methyl-4-pyrimidinyl | 219 | 2-cyclopropyl-6-methyl-4-pyrimidinyl | 345 | 2-methyl-6-methoxy-methyl-4-pyrimidinyl |
| 94 | 2-iso-propyl-6-methoxy-methyl-4-pyrimidinyl | 220 | 2-phenyl-4-pyrimidinyl | 346 | 2,5-dimethyl-4-pyrimidinyl |
| 95 | 2-methylthio-6-trifluoro-methyl-4-pyrimidinyl | 221 | 1,2-methylthio-5-chloro-6-trifluoromethyl-4-pyrimidinyl | 347 | 2-methylthio-5-n-octyl-6-methyl-4-pyrimidinyl |
| 96 | 2-methyl-6-trifluoromethyl-4-pyrimidinyl | 222 | 2-n-propyl-6-trifluoro-methyl-4-pyrimidinyl | 348 | 2-isopropyl-6-trifluoro-methyl-4-pyrimidinyl |
| 97 | 2-n-propyl-6-methyl-4-pyrimidinyl | 223 | 2-tert-butyl-6-trifluoro-methyl-4-pyrimidinyl | 349 | 2-methyl-5-chloro-6-tri-fluoromethyl-4-pyrimidinyl |
| 98 | 2-n-propyl-5-chloro-6-tri-fluoromethyl-4-pyrimidinyl | 224 | 2-isopropyl-5-chloro-6-trifluoromethyl 4-pyrimidinyl | 350 | 2-tert-butyl-5-chloro-6-trifluoromethyl-4-pyrimidinyl |
| 99 | 2-chloro-4-pyrimidinyl | 225 | 5-methoxy-4-pyrimidinyl | 351 | 6-trifluoromethyl-4-pyrimidinyl |
| 100 | 2-chloro-6-trichloromethyl-4-pyrimidinyl | 226 | 2,6-dichloro-4-pyrimidinyl | 352 | 2-phenyl-6-trifluoro-methyl-4-pyrimidinyl |
| 101 | 2-methylthio-6-difluoro-methoxy-4-pyrimidyl | 227 | 2-ethyl-6-trifluoromethyl-4-pyrimidinyl | 353 | 2-cyclopropyl-6-tri-fluoromethyl-4-pyrimidinyl |
| 102 | 2-phenyl-6-trifluoromethyl-4-pyrimidinyl | 228 | 2-methylthio-5-chloro-6-methoxy-4-pyrimidinyl | 354 | 2-dimethylamino-5-n-butyl-6-methyl-4-pyrimidinyl |
| 103 | 2-dimethylamino-5-nitro-6-methyl-4-pyrimidinyl | 229 | 2-quinolyl | 355 | 3-methyl-2-quinolyl |
| 104 | 4-methyl-2-quinolyl | 230 | 4-ethyl-2-quinolyl | 356 | 4-phenyl-2-quinolyl |
| 105 | 6-methyl-2-quinolyl | 231 | 6-chloro-2-quinolyl | 357 | 8-methyl-2-quinolyl |
| 106 | 8-chloro-2-quinolyl | 232 | 4-ethoxycarbonyl-2-quinolyl | 358 | 3,4-dimethyl-2-quinolyl |
| 107 | 4-methyl-8-methoxy-2-quinolyl | 233 | 4-phenyl-8-ethoxy-2-quinolyl | 359 | 4-methyl-8-chloro-2-quinolyl |
| 108 | 4-methyl-8-fluoro-2-quinolyl | 234 | 4-quinolyl | 360 | 2-methyl-4-quinolyl |
| 109 | 2-trichloromethyl-4-quinolyl | 235 | 2-trifluoromethyl-2-quinolyl | 361 | 2-isopropyl-4-quinolyl |
| 110 | 2-n-pentyl-4-quinolyl | 236 | 2-phenyl-4-quinolyl | 362 | 2-methoxycarbonyl-4-quinolyl |
| 111 | 2,6-dimethyl-4-quinolyl | 237 | 2-methyl-6-chloro-4-quinolyl [sic] | 363 | 2-methyl-6-fluoro-4-quinolyl |
| 112 | 8-quinolyl | 238 | 2-methyl-8-quinolyl | 364 | 5,7-dichloro-8-quinolyl |
| 113 | 2-pyrazinyl | 239 | 6-chloro-2-pyrazinyl | 365 | 5-methyl-2-pyrazinyl |
| 114 | 3-pyridazinyl | 240 | 5-chloro-3-pyridazinyl | 366 | 2-thienyl |
| 115 | 3-thienyl | 241 | 4-chloro-3-thienyl | 367 | 2-chloro-3-thienyl |
| 116 | 5-chloro-3-thienyl | 242 | 4-chloro-2-thienyl | 368 | 2-quinoxalinyl |
| 117 | 3-methyl-2-quinoxalinyl | 243 | 7,8-dimethyl-2-quinoxalinyl | 369 | 7,8-dichloro-2-quin-oxalinyl |
| 118 | 7-methyl-2-quinoxalinyl | 244 | 8-methyl-2-quinoxalinyl | 370 | 7-methoxy-2-quinoxalinyl |
| 119 | 3-phenyl-5-isoxazolyl | 245 | 2-benzoxazolyl | 371 | 2-benzothiazolyl |
| 120 | 1-phenyl-pyrazol-4-yl | 246 | 2-n-propyl-6-methyl-4-pyrimidinyl | 372 | 2-cyclopentyl-6-tri-fluoromethyl-4-pyrimidinyl |
| 121 | 2-cyclohexyl-6-trifluoro-methyl-4-pyrimidinyl | 247 | 2-cyclohexyl-5-chloro-6-methyl-4-pyrimidinyl | 373 | 2-n-propyl-5-chloro-6-methyl-4-pyrimidinyl |
| 122 | pyrazol-1-yl | 248 | 4-chloropyrazol-1-yl | 374 | 3,5-dimethylpyrazol-1-yl |
| 123 | 1,2-benzisoxazol-3-yl | 249 | 1-(4-chlorophenyl)-pyrazol-4-yl | 375 | 1-(4-methylphenyl)-pyrazo1-4-yl |
| 124 | 1-phenylpyrazol-4-yl | 250 | 1-methyl-3-trifluoromethyl-pyrazol-5-yl | 376 | 1-(4-fluorophenyl)-pyrazol-4-yl |
| 125 | 5-phenylisoxazol-3-yl | 251 | benzotriazol-1-yl | 377 | 3-cyano-5-nitro-2-pyridyl |

TABLE D.1

| No. | Aᵃ |
|---|---|
| 01 | 1-CH₃-pyrrol-3-yl |
| 02 | 1-CH(CH₃)₂-pyrrol-3-yl |
| 03 | 1-C(CH₃)₃-pyrrol-3-yl |
| 04 | 1-cyclopropylpyrrol-3-yl |
| 05 | 1-C₆H₅-pyrrol-3-yl |
| 06 | 1-(2-CH₃—C₆H₄)pyrrol-3-yl |
| 07 | 1-(3-CH₃—C₆H₄)pyrrol-3-yl |
| 08 | 1-(4-CH₃—C₆H₄)pyrrol-3-yl |
| 09 | 1-(3-OCH₃—C₆H₄)pyrrol-3-yl |
| 10 | 1-(4-OCH₃—C₆H₄)pyrrol-3-yl |
| 11 | 1-(4-NO₂—C₆H₄)pyrrol-3-yl |
| 12 | 1-(3-NO₂—C₆H₄)pyrrol-3-yl |
| 13 | 1-(4-CN—C₆H₄)pyrrol-3-yl |
| 14 | 1-(3-CN—C₆H₄)pyrrol-3-yl |
| 15 | 1-(3-CF₃—C₆H₄)pyrrol-3-yl |
| 16 | 1-(4-CF₃—C₆H₄)pyrrol-3-yl |
| 17 | 1-(4-C(CH₃)₃—C₆H₄)pyrrol-3-yl |
| 18 | 1-(4-C₆H₅—C₆H₄)pyrrol-3-yl |
| 19 | 1-(2-Cl—C₆H₄)pyrrol-3-yl |
| 20 | 1-(3-Cl—C₆H₄)pyrrol-3-yl |
| 21 | 1-(4-Cl—C₆H₄)pyrrol-3-yl |
| 22 | 1-(2-Br—C₆H₄)pyrrol-3-yl |
| 23 | 1-(3-Br—C₆H₄)pyrrol-3-yl |
| 24 | 1-(4-Br—C₆H₄)pyrrol-3-yl |
| 25 | 1-(2-F—C₆H₄)pyrrol-3-yl |
| 26 | 1-(3-F—C₆H₄)pyrrol-3-yl |
| 27 | 1-(4-F—C₆H₄)pyrrol-3-yl |
| 28 | 1-(2,4-Cl₂—C₆H₃)pyrrol-3-yl |
| 29 | 1-(2,5-Cl₂—C₆H₃)pyrrol-3-yl |
| 30 | 1-(2,6-Cl₂—C₆H₃)pyrrol-3-yl |
| 31 | 1-(3,4-Cl₂—C₆H₃)pyrrol-3-yl |
| 32 | 1-(2,4-F₂—C₆H₃)pyrrol-3-yl |
| 33 | 1-(2,5-F₂—C₆H₃)pyrrol-3-yl |
| 34 | 1-(2,6-F₂—C₆H₃)pyrrol-3-yl |
| 35 | 1-(3,4-F₂—C₆H₃)pyrrol-3-yl |
| 36 | 1-(2-Cl, 5-OCH₃—C₆H₃)pyrrol-3-yl |
| 37 | 1-(2-Cl, 5-CH₃—C₆H₃)pyrrol-3-yl |
| 38 | 1-(5-Cl, 2-OCH₃—C₆H₃)pyrrol-3-yl |
| 39 | 1-(5-Cl, 2-CH₃—C₆H₃)pyrrol-3-yl |
| 40 | 1-[2,5-(CH₃)₂—C₆H₃]pyrrol-3-yl |
| 41 | 1-CH₃-pyrrol-2-yl |
| 42 | 1-CH(CH₃)₂-pyrrol-2-yl |
| 43 | 1-C(CH₃)₃-pyrrol-2-yl |
| 44 | 1-cyclopropylpyrrol-2-yl |
| 45 | 1-C₆H₅-pyrrol-2-yl |
| 46 | 1-(2-CH₃—C₆H₄)pyrrol-2-yl |
| 47 | 1-(3-CH₃—C₆H₄)pyrrol-2-yl |
| 48 | 1-(4-CH₃—C₆H₄)pyrrol-2-yl |
| 49 | 1-(3-OCH₃—C₆H₄)pyrrol-2-yl |
| 50 | 1-(4-OCH₃—C₆H₄)pyrrol-2-yl |
| 51 | 1-(4-NO₂—C₆H₄)pyrrol-2-yl |
| 52 | 1-(3-NO₂—C₆H₄)pyrrol-2-yl |
| 53 | 1-(4-CN—C₆H₄)pyrrol-2-yl |
| 54 | 1-(3-CN—C₆H₄)pyrrol-2-yl |
| 55 | 1-(3-CF₃—C₆H₄)pyrrol-2-yl |
| 56 | 1-(4-CF₃—C₆H₄)pyrrol-2-yl |
| 57 | 1-(4-C(CH₃)₃—C₆H₄)pyrrol-2-yl |
| 58 | 1-(4-C₆H₅—C₆H₄)pyrrol-2-yl |
| 59 | 1-(2-Cl—C₆H₄)pyrrol-2-yl |
| 60 | 1-(3-Cl—C₆H₄)pyrrol-2-yl |
| 61 | 1-(4-Cl—C₆H₄)pyrrol-2-yl |
| 62 | 1-(2-Br—C₆H₄)pyrrol-2-yl |
| 63 | 1-(3-Br—C₆H₄)pyrrol-2-yl |
| 64 | 1-(4-Br—C₆H₄)pyrrol-2-yl |
| 65 | 1-(2-F—C₆H₄)pyrrol-2-yl |
| 66 | 1-(3-F—C₆H₄)pyrrol-2-yl |
| 67 | 1-(4-F—C₆H₄)pyrrol-2-yl |
| 68 | 1-(2,4-Cl₂—C₆H₃)pyrrol-2-yl |
| 69 | 1-(2,5-Cl₂—C₆H₃)pyrrol-2-yl |
| 70 | 1-(2,6-Cl₂—C₆H₃)pyrrol-2-yl |
| 71 | 1-(3,4-Cl₂—C₆H₃)pyrrol-2-yl |
| 72 | 1-(2,4-F₂—C₆H₃)pyrrol-2-yl |
| 73 | 1-(2,5-F₂—C₆H₃)pyrrol-2-yl |
| 74 | 1-(2,6-F₂—C₆H₃)pyrrol-2-yl |
| 75 | 1-(3,4-F₂—C₆H₃)pyrrol-2-yl |
| 76 | 1-(2-Cl, 5-OCH₃—C₆H₃)pyrrol-2-yl |
| 77 | 1-(2-Cl, 5-CH₃—C₆H₃)pyrrol-2-yl |
| 78 | 1-(5-Cl, 2-OCH₃—C₆H₃)pyrrol-2-yl |
| 79 | 1-(5-Cl, 2-CH₃—C₆H₃)pyrrol-2-yl |
| 80 | 1-[2,5-(CH₃)₂—C₆H₃]pyrrol-2-yl |
| 81 | 5-CH₃-furan-2-yl |
| 82 | 5-CH(CH₃)₂-furan-2-yl |
| 83 | 5-C(CH₃)₃-furan-2-yl |
| 84 | 5-cyclopropylfuran-2-yl |
| 85 | 5-C₆H₅-furan-2-yl |
| 86 | 5-(2-CH₃—C₆H₄)furan-2-yl |
| 87 | 5-(3-CH₃—C₆H₄)furan-2-yl |
| 88 | 5-(4-CH₃—C₆H₄)furan-2-yl |
| 89 | 5-(3-OCH₃—C₆H₄)furan-2-yl |
| 90 | 5-(4-OCH₃—C₆H₄)furan-2-yl |
| 91 | 5-(4-NO₂—C₆H₄)furan-2-yl |
| 92 | 5-(3-NO₂—C₆H₄)furan-2-yl |
| 93 | 5-(4-CN—C₆H₄)furan-2-yl |
| 94 | 5-(3-CN—C₆H₄)furan-2-yl |
| 95 | 5-(3-CF₃—C₆H₄)furan-2-yl |
| 96 | 5-(4-CF₃—C₆H₄)furan-2-yl |
| 97 | 5-(4-C(CH₃)₃—C₆H₄)furan-2-yl |
| 98 | 5-(4-C₆H₅—C₆H₄)furan-2-yl |
| 99 | 5-(2-Cl—C₆H₄)furan-2-yl |
| 100 | 5-(3-Cl—C₆H₄)furan-2-yl |
| 101 | 5-(4-Cl—C₆H₄)furan-2-yl |
| 102 | 5-(2-Br—C₆H₄)furan-2-yl |
| 103 | 5-(3-Br—C₆H₄)furan-2-yl |
| 104 | 5-(4-Br—C₆H₄)furan-2-yl |
| 105 | 5-(2-F—C₆H₄)furan-2-yl |
| 106 | 5-(3-F—C₆H₄)furan-2-yl |
| 107 | 5-(4-F—C₆H₄)furan-2-yl |
| 108 | 5-(2,4-Cl₂—C₆H₃)furan-2-yl |
| 109 | 5-(2,5-Cl₂—C₆H₃)furan-2-yl |
| 110 | 5-(2,6-Cl₂—C₆H₃)furan-2-yl |
| 111 | 5-(3,4-Cl₂—C₆H₃)furan-2-yl |
| 112 | 5-(2,4-F₂—C₆H₃)furan-2-yl |
| 113 | 5-(2,5-F₂—C₆H₃)furan-2-yl |
| 114 | 5-(2,6-F₂—C₆H₃)furan-2-yl |
| 115 | 5-(3,4-F₂—C₆H₃)furan-2-yl |
| 116 | 5-(2-Cl, 5-OCH₃—C₆H₃)furan-2-yl |
| 117 | 5-(2-Cl, 5-CH₃—C₆H₃)furan-2-yl |
| 118 | 5-(5-Cl, 2-OCH₃—C₆H₃)furan-2-yl |
| 119 | 5-(5-Cl, 2-CH₃—C₆H₃)furan-2-yl |
| 120 | 5-[2,5-(CH₃)₂—C₆H₃]furan-2-yl |
| 121 | 4-CH₃-furan-2-yl |
| 122 | 4-CH(CH₃)₂-furan-2-yl |
| 123 | 4-C(CH₃)₃-furan-2-yl |
| 124 | 4-cyclopropylfuran-2-yl |
| 125 | 4-C₆H₅-furan-2-yl |
| 126 | 4-(2-CH₃—C₆H₄)furan-2-yl |
| 127 | 4-(3-CH₃—C₆H₄)furan-2-yl |
| 128 | 4-(4-CH₃—C₆H₄)furan-2-yl |
| 129 | 4-(3-OCH₃—C₆H₄)furan-2-yl |
| 130 | 4-(4-OCH₃—C₆H₄)furan-2-yl |
| 131 | 4-(4-NO₂—C₆H₄)furan-2-yl |
| 132 | 4-(3-NO₂—C₆H₄)furan-2-yl |
| 133 | 4-(4-CN—C₆H₄)furan-2-yl |
| 134 | 4-(3-CN—C₆H₄)furan-2-yl |
| 135 | 4-(3-CF₃—C₆H₄)furan-2-yl |
| 136 | 4-(4-CF₃—C₆H₄)furan-2-yl |
| 137 | 4-(4-C(CH₃)₃—C₆H₄)furan-2-yl |
| 138 | 4-(4-C₆H₅—C₆H₄)furan-2-yl |
| 139 | 4-(2-Cl—C₆H₄)furan-2-yl |
| 140 | 4-(3-Cl—C₆H₄)furan-2-yl |
| 141 | 4-(4-Cl—C₆H₄)furan-2-yl |
| 142 | 4-(2-Br—C₆H₄)furan-2-yl |
| 143 | 4-(3-Br—C₆H₄)furan-2-yl |
| 144 | 4-(4-Br—C₆H₄)furan-2-yl |
| 145 | 4-(2-F—C₆H₄)furan-2-yl |
| 146 | 4-(3-F—C₆H₄)furan-2-yl |
| 147 | 4-(4-F—C₆H₄)furan-2-yl |
| 148 | 4-(2,4-Cl₂—C₆H₃)furan-2-yl |
| 149 | 4-(2,5-Cl₂—C₆H₃)furan-2-yl |
| 150 | 4-(2,6-Cl₂—C₆H₃)furan-2-yl |
| 151 | 4-(3,4-Cl₂—C₆H₃)furan-2-yl |
| 152 | 4-(2,4-F₂—C₆H₃)furan-2-yl |
| 153 | 4-(2,5-F₂—C₆H₃)furan-2-yl |
| 154 | 4-(2,6-F₂—C₆H₃)furan-2-yl |

TABLE D.1-continued

| No. | A$^a$ |
|---|---|
| 155 | 4-(3,4-F$_2$—C$_6$H$_3$)furan-2-yl |
| 156 | 4-(2-Cl, 5-OCH$_3$—C$_6$H$_3$)furan-2-yl |
| 157 | 4-(2-Cl, 5-CH$_3$—C$_6$H$_3$)furan-2-yl |
| 158 | 4-(5-Cl, 2-OCH$_3$—C$_6$H$_3$)furan-2-yl |
| 159 | 4-(5-Cl, 2-CH$_3$—C$_6$H$_3$)furan-2-yl |
| 160 | 4-[2,5-(CH$_3$)$_2$—C$_6$H$_3$]furan-2-yl |
| 161 | 5-CH$_3$-thien-2-yl |
| 162 | 5-CH(CH$_3$)$_2$-thien-2-yl |
| 163 | 5-C(CH$_3$)$_3$-thien-2-yl |
| 164 | 5-cyclopropylthien-2-yl |
| 165 | 5-C$_6$H$_5$-thien-2-yl |
| 166 | 5-(2-CH$_3$—C$_6$H$_4$)thien-2-yl |
| 167 | 5-(3-CH$_3$—C$_6$H$_4$)thien-2-yl |
| 168 | 5-(4-CH$_3$—C$_6$H$_4$)thien-2-yl |
| 169 | 5-(3-OCH$_3$—C$_6$H$_4$)thien-2-yl |
| 170 | 5-(4-OCH$_3$—C$_6$H$_4$)thien-2-yl |
| 171 | 5-(4-NO$_2$—C$_6$H$_4$)thien-2-yl |
| 172 | 5-(3-NO$_2$—C$_6$H$_4$)thien-2-yl |
| 173 | 5-(4-CN—C$_6$H$_4$)thien-2-yl |
| 174 | 5-(3-CN—C$_6$H$_4$)thien-2-yl |
| 175 | 5-(3-CF$_3$—C$_6$H$_4$)thien-2-yl |
| 176 | 5-(4-CF$_3$—C$_6$H$_4$)thien-2-yl |
| 177 | 5-(4-C(CH$_3$)$_3$—C$_6$H$_4$)thien-2-yl |
| 178 | 5-(4-C$_6$H$_5$—C$_6$H$_4$)thien-2-yl |
| 179 | 5-(2-Cl—C$_6$H$_4$)thien-2-yl |
| 180 | 5-(3-Cl—C$_6$H$_4$)thien-2-yl |
| 181 | 5-(4-Cl—C$_6$H$_4$)thien-2-yl |
| 182 | 5-(2-Br—C$_6$H$_4$)thien-2-yl |
| 183 | 5-(3-Br—C$_6$H$_4$)thien-2-yl |
| 184 | 5-(4-Br—C$_6$H$_4$)thien-2-yl |
| 185 | 5-(2-F—C$_6$H$_4$)thien-2-yl |
| 186 | 5-(3-F—C$_6$H$_4$)thien-2-yl |
| 187 | 5-(4-F—C$_6$H$_4$)thien-2-yl |
| 188 | 5-(2,4-Cl$_2$—C$_6$H$_3$)thien-2-yl |
| 189 | 5-(2,5-Cl$_2$—C$_6$H$_3$)thien-2-yl |
| 190 | 5-(2,6-Cl$_2$—C$_6$H$_3$)thien-2-yl |
| 191 | 5-(3,4-Cl$_2$—C$_6$H$_3$)thien-2-yl |
| 192 | 5-(2,4-F$_2$—C$_6$H$_3$)thien-2-yl |
| 193 | 5-(2,5-F$_2$—C$_6$H$_3$)thien-2-yl |
| 194 | 5-(2,6-F$_2$—C$_6$H$_3$)thien-2-yl |
| 195 | 5-(3,4-F$_2$—C$_6$H$_3$)thien-2-yl |
| 196 | 5-(2-Cl, 5-OCH$_3$—C$_6$H$_3$)thien-2-yl |
| 197 | 5-(2-Cl, 5-CH$_3$—C$_6$H$_3$)thien-2-yl |
| 198 | 5-(5-Cl, 2-OCH$_3$—C$_6$H$_3$)thien-2-yl |
| 199 | 5-(5-Cl, 2-CH$_3$—C$_6$H$_3$)thien-2-yl |
| 200 | 5-[2,5-(CH$_3$)$_2$—C$_6$H$_3$]thien-2-yl |
| 201 | 4-CH$_3$-thien-2-yl |
| 202 | 4-CH(CH$_3$)$_2$-thien-2-yl |
| 203 | 4-C(CH$_3$)$_3$-thien-2-yl |
| 204 | 4-cyclopropylthien-2-yl |
| 205 | 4-C$_6$H$_5$-thien-2-yl |
| 206 | 4-(2-CH$_3$—C$_6$H$_4$)thien-2-yl |
| 207 | 4-(3-CH$_3$—C$_6$H$_4$)thien-2-yl |
| 208 | 4-(4-CH$_3$—C$_6$H$_4$)thien-2-yl |
| 209 | 4-(3-OCH$_3$—C$_6$H$_4$)thien-2-yl |
| 210 | 4-(4-OCH$_3$—C$_6$H$_4$)thien-2-yl |
| 211 | 4-(4-NO$_2$—C$_6$H$_4$)thien-2-yl |
| 212 | 4-(3-NO$_2$—C$_6$H$_4$)thien-2-yl |
| 213 | 4-(4-CN—C$_6$H$_4$)thien-2-yl |
| 214 | 4-(3-CN—C$_6$H$_4$)thien-2-yl |
| 215 | 4-(3-CF$_3$—C$_6$H$_4$)thien-2-yl |
| 216 | 4-(4-CF$_3$—C$_6$H$_4$)thien-2-yl |
| 217 | 4-(4-C(CH$_3$)$_3$—C$_6$H$_4$)thien-2-yl |
| 218 | 4-(4-C$_6$H$_5$—C$_6$H$_4$)thien-2-yl |
| 219 | 4-(2-Cl—C$_6$H$_4$)thien-2-yl |
| 220 | 4-(3-Cl—C$_6$H$_4$)thien-2-yl |
| 221 | 4-(4-Cl-C$_6$H$_4$)thien-2-yl |
| 222 | 4-(2-Br—C$_6$H$_4$)thien-2-yl |
| 223 | 4-(3-Br—C$_6$H$_4$)thien-2-yl |
| 224 | 4-(4-Br—C$_6$H$_4$)thien-2-yl |
| 225 | 4-(2-F—C$_6$H$_4$)thien-2-yl |
| 226 | 4-(3-F—C$_6$H$_4$)thien-2-yl |
| 227 | 4-(4-F—C$_6$H$_4$)thien-2-yl |
| 228 | 4-(2,4-Cl$_2$—C$_6$H$_3$)thien-2-yl |
| 229 | 4-(2,5-Cl$_2$—C$_6$H$_3$)thien-2-yl |
| 230 | 4-(2,6-Cl$_2$—C$_6$H$_3$)thien-2-yl |
| 231 | 4-(3,4-Cl$_2$—C$_6$H$_3$)thien-2-yl |
| 232 | 4-(2,4-F$_2$—C$_6$H$_3$)thien-2-yl |
| 233 | 4-(2,5-F$_2$—C$_6$H$_3$)thien-2-yl |
| 234 | 4-(2,6-F$_2$—C$_6$H$_3$)thien-2-yl |
| 235 | 4-(3,4-F$_2$—C$_6$H$_3$)thien-2-yl |
| 236 | 4-(2-Cl, 5-OCH$_3$—C$_6$H$_3$)thien-2-yl |
| 237 | 4-(2-Cl, 5-CH$_3$—C$_6$H$_3$)thien-2-yl |
| 238 | 4-(5-Cl, 2-OCH$_3$—C$_6$H$_3$)thien-2-yl |
| 239 | 4-(5-Cl, 2-CH$_3$—C$_6$H$_3$)thien-2-yl |
| 240 | 4-[2,5-(CH$_3$)$_2$—C$_6$H$_3$]thien-2-yl |
| 241 | 2-CH$_3$-thien-4-yl |
| 242 | 2-CH(CH$_3$)$_2$-thien-4-yl |
| 243 | 2-C(CH$_3$)$_3$-thien-4-yl |
| 244 | 2-cyclopropylthien-4-yl |
| 245 | 2-C$_6$H$_5$-thien-4-yl |
| 246 | 2-(2-CH$_3$—C$_6$H$_4$)thien-4-yl |
| 247 | 2-(3-CH$_3$—C$_6$H$_4$)thien-4-yl |
| 248 | 2-(4-CH$_3$—C$_6$H$_4$)thien-4-yl |
| 249 | 2-(3-OCH$_3$—C$_6$H$_4$)thien-4-yl |
| 250 | 2-(4-OCH$_3$—C$_6$H$_4$)thien-4-yl |
| 251 | 2-(4-NO$_2$—C$_6$H$_4$)thien-4-yl |
| 252 | 2-(3-NO$_2$—C$_6$H$_4$)thien-4-yl |
| 253 | 2-(4-CN—C$_6$H$_4$)thien-4-yl |
| 254 | 2-(3-CN—C$_6$H$_4$)thien-4-yl |
| 255 | 2-(3-CF$_3$—C$_6$H$_4$)thien-4-yl |
| 256 | 2-(4-CF$_3$—C$_6$H$_4$)thien-4-yl |
| 257 | 2-(4-C(CH$_3$)$_3$—C$_6$H$_4$)thien-4-yl |
| 258 | 2-(4-C$_6$H$_5$—C$_6$H$_4$)thien-4-yl |
| 259 | 2-(2-Cl—C$_6$H$_4$)thien-4-yl |
| 260 | 2-(3-Cl—C$_6$H$_4$)thien-4-yl |
| 261 | 2-(4-Cl—C$_6$H$_4$)thien-4-yl |
| 262 | 2-(2-Br—C$_6$H$_4$)thien-4-yl |
| 263 | 2-(3-Br—C$_6$H$_4$)thien-4-yl |
| 264 | 2-(4-Br—C$_6$H$_4$)thien-4-yl |
| 265 | 2-(2-F—C$_6$H$_4$)thien-4-yl |
| 266 | 2-(3-F—C$_6$H$_4$)thien-4-yl |
| 267 | 2-(4-F—C$_6$H$_4$)thien-4-yl |
| 268 | 2-(2,4-Cl$_2$—C$_6$H$_3$)thien-4-yl |
| 269 | 2-(2,5-Cl$_2$—C$_6$H$_3$)thien-4-yl |
| 270 | 2-(2,6-Cl$_2$—C$_6$H$_3$)thien-4-yl |
| 271 | 2-(3,4-Cl$_2$—C$_6$H$_3$)thien-4-yl |
| 272 | 2-(2,4-F$_2$—C$_6$H$_3$)thien-4-yl |
| 273 | 2-2,5-F$_2$—C$_6$H$_3$)thien-4-yl |
| 274 | 2-(2,6-F$_2$—C$_6$H$_3$)thien-4-yl |
| 275 | 2-(3,4-F$_2$—C$_6$H$_3$)thien-4-yl |
| 276 | 2-(2-Cl, 5-OCH$_3$—C$_6$H$_3$)thien-4-yl |
| 277 | 2-(2-Cl, 5-CH$_3$—C$_6$H$_3$)thien-4-yl |
| 278 | 2-(5-Cl, 2-OCH$_3$—C$_6$H$_3$)thien-4-yl |
| 279 | 2-(5-Cl, 2-CH$_3$—C$_6$H$_3$)thien-4-yl |
| 280 | 2-[2,5-(CH$_3$)$_2$—C$_6$H$_3$]thien-4-yl |
| 281 | 1-CH$_3$-pyrazol-4-yl |
| 282 | 1-CH(CH$_3$)$_2$-pyrazol-4-yl |
| 283 | 1-C(CH$_3$)$_3$-pyrazol-4-yl |
| 284 | 1-cyclopropylpyrazol-4-yl |
| 285 | 1-C$_6$H$_5$-pyrazol-4-yl |
| 286 | 1-(2-CH$_3$—C$_6$H$_4$)pyrazol-4-yl |
| 287 | 1-(3-CH$_3$—C$_6$H$_4$)pyrazol-4-yl |
| 288 | 1-(4-CH$_3$—C$_6$H$_4$)pyrazol-4-yl |
| 289 | 1-(3-OCH$_3$—C$_6$H$_4$)pyrazol-4-yl |
| 290 | 1-(4-OCH$_3$—C$_6$H$_4$)pyrazol-4-yl |
| 291 | 1-(4-NO$_2$—C$_6$H$_4$)pyrazol-4-yl |
| 292 | 1-(3-NO$_2$—C$_6$H$_4$)pyrazol-4-yl |
| 293 | 1-(4-CN—C$_6$H$_4$)pyrazol-4-yl |
| 294 | 1-(3-CN—C$_6$H$_4$)pyrazol-4-yl |
| 295 | 1-(3-CF$_3$—C$_6$H$_4$)pyrazol-4-yl |
| 296 | 1-(4-CF$_3$—C$_6$H$_4$)pyrazol-4-yl |
| 297 | 1-(4-C(CH$_3$)$_3$—C$_6$H$_4$)pyrazol-4-yl |
| 298 | 1-(4-C$_6$H$_5$—C$_6$H$_4$)pyrazol-4-yl |
| 299 | 1-(2-Cl—C$_6$H$_4$)pyrazol-4-yl |
| 300 | 1-(3-Cl—C$_6$H$_4$)pyrazol-4-yl |
| 301 | 1-(4-Cl—C$_6$H$_4$)pyrazol-4-yl |
| 302 | 1-(2-Br—C$_6$H$_4$)pyrazol-4-yl |
| 303 | 1-(3-Br—C$_6$H$_4$)pyrazol-4-yl |
| 304 | 1-(4-Br—C$_6$H$_4$)pyrazol-4-yl |
| 305 | 1-(2-F—C$_6$H$_4$)pyrazol-4-yl |
| 306 | 1-(3-F—C$_6$H$_4$)pyrazol-4-yl |
| 307 | 1-(4-F—C$_6$H$_4$)pyrazol-4-yl |
| 308 | 1-(2,4-Cl$_2$—C$_6$H$_3$)pyrazol-4-yl |

TABLE D.1-continued

| No. | A^a |
|---|---|
| 309 | 1-(2,5-Cl$_2$—C$_6$H$_3$)pyrazol-4-yl |
| 230 | 1-(2,6-Cl$_2$—C$_6$H$_3$)pyrazol-4-yl |
| 311 | 1-(3,4-Cl$_2$—C$_6$H$_3$)pyrazol-4-yl |
| 312 | 1-(2,4-F$_2$—C$_6$H$_3$)pyrazol-4-yl |
| 313 | 1-(2,5-F$_2$—C$_6$H$_3$)pyrazol-4-yl |
| 314 | 1-(2,6-F$_2$—C$_6$H$_3$)pyrazol-4-yl |
| 315 | 1-(3,4-F$_2$—C$_6$H$_3$)pyrazol-4-yl |
| 316 | 1-(2-Cl, 5-OCH$_3$—C$_6$H$_3$)pyrazol-4-yl |
| 317 | 1-(2-Cl, 5-CH$_3$—C$_6$H$_3$)pyrazol-4-yl |
| 318 | 1-(5-Cl, 2-OCH$_3$—C$_6$H$_3$)pyrazol-4-yl |
| 319 | 1-(5-Cl, 2-CH$_3$—C$_6$H$_3$)pyrazol-4-yl |
| 320 | 1-[2,5-(CH$_3$)$_2$—C$_6$H$_3$]pyrazol-4-yl |
| 321 | 1,5-(CH$_3$)$_2$-pyrazol-3-yl |
| 322 | 1-CH$_3$, 5-CH(CH$_3$)$_2$-pyrazol-3-yl |
| 323 | 1-CH$_3$, 5-C(CH$_3$)$_3$-pyrazol-3-yl |
| 324 | 1-CH$_3$, 5-cyclopropylpyrazol-3-yl |
| 325 | 1-CH$_3$, 5-C$_6$H$_5$-pyrazol-3-yl |
| 326 | 1-CH$_3$, 5-(2-CH$_3$—C$_6$H$_4$)pyrazol-3-yl |
| 327 | 1-CH$_3$, 5-(3-CH$_3$—C$_6$H$_4$)pyrazol-3-yl |
| 328 | 1-CH$_3$, 5-(4-CH$_3$—C$_6$H$_4$)pyrazol-3-yl |
| 329 | 1-CH$_3$, 5-(3-OCH$_3$—C$_6$H$_4$)pyrazol-3-yl |
| 330 | 1-CH$_3$, 5-(4-OCH$_3$—C$_6$H$_4$)pyrazol-3-yl |
| 331 | 1-CH$_3$, 5-(4-NO$_2$—C$_6$H$_4$)pyrazol-3-yl |
| 332 | 1-CH$_3$, 5-(3-NO$_2$—C$_6$H$_4$)pyrazol-3-yl |
| 333 | 1-CH$_3$, 5-(4-CN—C$_6$H$_4$)pyrazol-3-yl |
| 334 | 1-CH$_3$, 5-(3-CN—C$_6$H$_4$)pyrazol-3-yl |
| 335 | 1-CH$_3$, 5-(3-CF$_3$—C$_6$H$_4$)pyrazol-3-yl |
| 336 | 1-CH$_3$, 5-(4-CF$_3$—C$_6$H$_4$)pyrazol-3-yl |
| 337 | 1-CH$_3$, 5-(4-C(CH$_3$)$_3$—C$_6$H$_4$)pyrazol-3-yl |
| 338 | 1-CH$_3$, 5-(4-C$_6$H$_5$—C$_6$H$_4$)pyrazol-3-yl |
| 339 | 1-CH$_3$, 5-(2-Cl—C$_6$H$_4$)pyrazol-3-yl |
| 340 | 1-CH$_3$, 5-(3-Cl—C$_6$H$_4$)pyrazol-3-yl |
| 341 | 1-CH$_3$, 5-(4-Cl—C$_6$H$_4$)pyrazol-3-yl |
| 342 | 1-CH$_3$, 5-(2-Br—C$_6$H$_4$)pyrazol-3-yl |
| 343 | 1-CH$_3$, 5-(3-Br—C$_6$H$_4$)pyrazol-3-yl |
| 344 | 1-CH$_3$, 5-(4-Br—C$_6$H$_4$)pyrazol-3-yl |
| 345 | 1-CH$_3$, 5-(2-F—C$_6$H$_4$)pyrazol-3-yl |
| 346 | 1-CH$_3$, 5-(3-F—C$_6$H$_4$)pyrazol-3-yl |
| 347 | 1-CH$_3$, 5-(4-F—C$_6$H$_4$)pyrazol-3-yl |
| 348 | 1-CH$_3$, 5-(2,4-Cl$_2$—C$_6$H$_3$)pyrazol-3-yl |
| 349 | 1-CH$_3$, 5-(2,5-Cl$_2$—C$_6$H$_3$)pyrazol-3-yl |
| 350 | 1-CH$_3$, 5-(2,6-Cl$_2$—C$_6$H$_3$)pyrazol-3-yl |
| 351 | 1-CH$_3$, 5-(3,4-Cl$_2$—C$_6$H$_3$)pyrazol-3-yl |
| 352 | 1-CH$_3$, 5-(2,4-F$_2$—C$_6$H$_3$)pyrazol-3-yl |
| 353 | 1-CH$_3$, 5-(2,5-F$_2$—C$_6$H$_3$)pyrazol-3-yl |
| 354 | 1-CH$_3$, 5-(2,6-F$_2$—C$_6$H$_3$)pyrazol-3-yl |
| 355 | 1-CH$_3$, 5-(3,4-F$_2$—C$_6$H$_3$)pyrazol-3-yl |
| 356 | 1-CH$_3$, 5-(2-Cl, 5-OCH$_3$—C$_6$H$_3$)pyrazol-3-yl |
| 357 | 1-CH$_3$, 5-(2-Cl, 5-CH$_3$—C$_6$H$_3$)pyrazol-3-yl |
| 358 | 1-CH$_3$, 5-(5-Cl, 2-OCH$_3$—C$_6$H$_3$)pyrazol-3-yl |
| 359 | 1-CH$_3$, 5-(5-Cl, 2-CH$_3$—C$_6$H$_3$)pyrazol-3-yl |
| 360 | 1-CH$_3$, 5-[2,5-(CH$_3$)$_2$—C$_6$H$_3$]pyrazol-3-yl |
| 361 | 3-CH$_3$-isoxazol-5-yl |
| 362 | 3-CH(CH$_3$)$_2$-isoxazol-5-yl |
| 363 | 3-C(CH$_3$)$_3$-isoxazol-5-yl |
| 364 | 3-cyclopropylisoxazol-5-yl |
| 365 | 3-C$_6$H$_5$-isoxazol-5-yl |
| 366 | 3-(2-CH$_3$—C$_6$H$_4$)isoxazol-5-yl |
| 367 | 3-(3-CH$_3$—C$_6$H$_4$)isoxazol-5-yl |
| 368 | 3-(4-CH$_3$—C$_6$H$_4$)isoxazol-5-yl |
| 369 | 3-(3-OCH$_3$—C$_6$H$_4$)isoxazol-5-yl |
| 370 | 3-(4-OCH$_3$—C$_6$H$_4$)isoxazol-5-yl |
| 371 | 3-(4-NO$_2$—C$_6$H$_4$)isoxazol-5-yl |
| 372 | 3-(3-NO$_2$—C$_6$H$_4$)isoxazol-5-yl |
| 373 | 3-(4-CN—C$_6$H$_4$)isoxazol-5-yl |
| 374 | 3-(3-CN—C$_6$H$_4$)isoxazol-5-yl |
| 375 | 3-(3-CF$_3$—C$_6$H$_4$)isoxazol-5-yl |
| 376 | 3-(4-CF$_3$—C$_6$H$_4$)isoxazol-5-yl |
| 377 | 3-(4-C(CH$_3$)$_3$—C$_6$H$_4$)isoxazol-5-yl |
| 378 | 3-(4-C$_6$H$_5$—C$_6$H$_4$)isoxazol-5-yl |
| 379 | 3-(2-Cl—C$_6$H$_4$)isoxazol-5-yl |
| 380 | 3-(3-Cl—C$_6$H$_4$)isoxazol-5-yl |
| 381 | 3-(4-Cl—C$_6$H$_4$)isoxazol-5-yl |
| 382 | 3-(2-Br—C$_6$H$_4$)isoxazol-5-yl |
| 383 | 3-(3-Br—C$_6$H$_4$)isoxazol-5-yl |
| 384 | 3-(4-Br—C$_6$H$_4$)isoxazol-5-yl |
| 385 | 3-(2-F—C$_6$H$_4$)isoxazol-5-yl |
| 386 | 3-(3-F—C$_6$H$_4$)isoxazol-5-yl |
| 387 | 3-(4-F—C$_6$H$_4$)isoxazol-5-yl |
| 388 | 3-(2,4-Cl$_2$—C$_6$H$_3$)isoxazol-5-yl |
| 389 | 3-(2,5-Cl$_2$—C$_6$H$_3$)isoxazol-5-yl |
| 390 | 3-(2,6-Cl$_2$—C$_6$H$_3$)isoxazol-5-yl |
| 391 | 3-(3,4-Cl$_2$—C$_6$H$_3$)isoxazol-5-yl |
| 392 | 3-(2,4-F$_2$—C$_6$H$_3$)isoxazol-5-yl |
| 393 | 3-(2,5-F$_2$—C$_6$H$_3$)isoxazol-5-yl |
| 394 | 3-(2,6-F$_2$—C$_6$H$_3$)isoxazol-5-yl |
| 395 | 3-(3,4-F$_2$—C$_6$H$_3$)isoxazol-5-yl |
| 396 | 3-(2-Cl, 5-OCH$_3$—C$_6$H$_3$)isoxazol-5-yl |
| 397 | 3-(2-Cl, 5-CH$_3$—C$_6$H$_3$)isoxazol-5-yl |
| 398 | 3-(5-Cl, 2-OCH$_3$—C$_6$H$_3$)isoxazol-5-yl |
| 399 | 3-(5-Cl, 2-CH$_3$—C$_6$H$_3$)isoxazol-5-yl |
| 400 | 3-[2,5-(CH$_3$)$_2$—C$_6$H$_3$]isoxazol-5-yl |
| 401 | 3-CH$_3$-4-Cl-isoxazol-5-yl |
| 402 | 3-CH(CH$_3$)$_2$-4-Cl-isoxazol-5-yl |
| 403 | 3-C(CH$_3$)$_3$-4-Cl-isoxazol-5-yl |
| 404 | 3-cyclopropyl-4-Cl-isoxazol-5-yl |
| 405 | 3-C$_6$H$_5$-4-Cl-isoxazol-5-yl |
| 406 | 3-(2-CH$_3$—C$_6$H$_4$)-4-Cl-isoxazol-5-yl |
| 407 | 3-(3-CH$_3$—C$_6$H$_4$)-4-Cl-isoxazol-5-yl |
| 408 | 3-(4-CH$_3$—C$_6$H$_4$)-4-Cl-isoxazol-5-yl |
| 409 | 3-(3-OCH$_3$—C$_6$H$_4$)-4-Cl-isoxazoi-5-yl |
| 410 | 3-(4-OCH$_3$—C$_6$H$_4$)-4-Cl-isoxazol-5-yl |
| 411 | 3-(4-NO$_2$—C$_6$H$_4$)-4-Cl-isoxazol-5-yl |
| 412 | 3-(3-NO$_2$—C$_6$H$_4$)-4-Cl-isoxazol-5-yl |
| 413 | 3-(4-CN—C$_6$H$_4$)-4-Cl-isoxazol-5-yl |
| 414 | 3-(3-CN—C$_6$H$_4$)-4-Cl-isoxazol-5-yl |
| 415 | 3-(3-CF$_3$—C$_6$H$_4$)-4-Cl-isoxazol-5-yl |
| 416 | 3-(4-CF$_3$—C$_6$H$_4$)-4-Cl-isoxazol-5-yl |
| 417 | 3-(4-C(CH$_3$)$_3$—C$_6$H$_4$)-4-Cl-isoxazol-5-yl |
| 418 | 3-(4-C$_6$H$_5$—C$_6$H$_4$)-4-Cl-isoxazol-5-yl |
| 419 | 3-(2-Cl—C$_6$H$_4$)-4-Cl-isoxazol-5-yl |
| 420 | 3-(3-Cl—C$_6$H$_4$)-4-Cl-isoxazol-5-yl |
| 421 | 3-(4-Cl—C$_6$H$_4$)-4-Cl-isoxazol-5-yl |
| 422 | 3-(2-Br—C$_6$H$_4$)-4-Cl-isoxazol-5-yl |
| 423 | 3-(3-Br—C$_6$H$_4$)-4-Cl-isoxazol-5-yl |
| 424 | 3-(4-Br—C$_6$H$_4$)-4-Cl-isoxazol-5-yl |
| 425 | 3-(2-F—C$_6$H$_4$)-4-Cl-isoxazol-5-yl |
| 426 | 3-(3-F—C$_6$H$_4$)-4-Cl-isoxazol-5-yl |
| 427 | 3-(4-F—C$_6$H$_4$)-4-Cl-isoxazol-5-yl |
| 428 | 3-(2,4-Cl$_2$—C$_6$H$_3$)-4-Cl-isoxazol-5-yl |
| 429 | 3-(2,5-Cl$_2$—C$_6$H$_3$)-4-Cl-isoxazol-5-yl |
| 430 | 3-(2,6-Cl$_2$—C$_6$H$_3$)-4-Cl-isoxazol-5-yl |
| 431 | 3-(3,4-Cl$_2$—C$_6$H$_3$)-4-Cl-isoxazol-5-yl |
| 432 | 3-(2,4-F$_2$—C$_6$H$_3$)-4-Cl-isoxazol-5-yl |
| 433 | 3-(2,5-F$_2$—C$_6$H$_3$)-4-Cl-isoxazol-5-yl |
| 434 | 3-(2,6-F$_2$—C$_6$H$_3$)-4-Cl-isoxazol-5-yl |
| 435 | 3-(3,4-F$_2$—C$_6$H$_3$)-4-Cl-isoxazol-5-yl |
| 436 | 3-(2-Cl, 5-OCH$_3$—C$_6$H$_3$)-4-Cl-isoxazol-5-yl |
| 437 | 3-(2-Cl, 5-CH$_3$—C$_6$H$_3$)-4-Cl-isoxazol-5-yl |
| 438 | 3-(5-Cl, 2-OCH$_3$—C$_6$H$_3$)-4-Cl-isoxazol-5-yl |
| 439 | 3-(5-Cl, 2-CH$_3$—C$_6$H$_3$)-4-Cl-isoxazol-5-yl |
| 440 | 3-[2,5-(CH$_3$)$_2$—C$_6$H$_3$]-4-Cl-isoxazol-5-yl |
| 441 | 5-CH$_3$-isoxazol-3-yl |
| 442 | 5-CH(CH$_3$)$_2$-isoxazol-3-yl |
| 443 | 5-C(CH$_3$)$_3$-isoxazol-3-yl |
| 444 | 5-cyclopropylisoxazol-3-yl |
| 445 | 5-C$_6$H$_5$-isoxazol-3-yl |
| 446 | 5-(2-CH$_3$—C$_6$H$_4$)isoxazol-3-yl |
| 447 | 5-(3-CH$_3$—C$_6$H$_4$)isoxazol-3-yl |
| 448 | 5-(4-CH$_3$—C$_6$H$_4$)isoxazol-3-yl |
| 449 | 5-(3-OCH$_3$—C$_6$H$_4$)isoxazol-3-yl |
| 450 | 5-(4-OCH$_3$—C$_6$H$_4$)isoxazol-3-yl |
| 451 | 5-(4-NO$_2$—C$_6$H$_4$)isoxazol-3-yl |
| 452 | 5-(3-NO$_2$—C$_6$H$_4$)isoxazol-3-yl |
| 453 | 5-(4-CN—C$_6$H$_4$)isoxazol-3-yl |
| 454 | 5-(3-CN—C$_6$H$_4$)isoxazol-3-yl |
| 455 | 5-(3-CF$_3$—C$_6$H$_4$)isoxazol-3-yl |
| 456 | 5-(4-CF$_3$—C$_6$H$_4$)isoxazol-3-yl |
| 457 | 5-(4-C(CH$_3$)$_3$—C$_6$H$_4$)isoxazol-3-yl |
| 458 | 5-(4-C$_6$H$_5$—C$_6$H$_4$)isoxazol-3-yl |
| 459 | 5-(2-Cl—C$_6$H$_4$)isoxazol-3-yl |
| 460 | 5-(3-Cl—C$_6$H$_4$)isoxazol-3-yl |
| 461 | 5-(4-Cl—C$_6$H$_4$)isoxazol-3-yl |
| 462 | 5-(2-Br—C$_6$H$_4$)isoxazol-3-yl |

TABLE D.1-continued

| No. | A[a] |
|---|---|
| 463 | 5-(3-Br—C$_6$H$_4$)isoxazol-3-yl |
| 464 | 5-(4-Br—C$_6$H$_4$)isoxazol-3-yl |
| 465 | 5-(2-F—C$_6$H$_4$)isoxazol-3-yl |
| 466 | 5-(3-F—C$_6$H$_4$)isoxazol-3-yl |
| 467 | 5-(4-F—C$_6$H$_4$)isoxazol-3-yl |
| 468 | 5-(2,4-Cl$_2$—C$_6$H$_3$)isoxazol-3-yl |
| 469 | 5-(2,5-Cl$_2$—C$_6$H$_3$)isoxazol-3-yl |
| 470 | 5-(2,6-Cl$_2$—C$_6$H$_3$)isoxazol-3-yl |
| 471 | 5-(3,4-Cl$_2$—C$_6$H$_3$)isoxazol-3-yl |
| 472 | 5-(2,4-F$_2$—C$_6$H$_3$)isoxazol-3-yl |
| 473 | 5-(2,5-F$_2$—C$_6$H$_3$)isoxazol-3-yl |
| 474 | 5-(2,6-F$_2$—C$_6$H$_3$)isoxazol-3-yl |
| 475 | 5-(3,4-F$_2$—C$_6$H$_3$)isoxazol-3-yl |
| 476 | 5-(2-Cl, 5-OCH$_3$—C$_6$H$_3$)isoxazol-3-yl |
| 477 | 5-(2-Cl, 5-CH$_3$—C$_6$H$_3$)isoxazol-3-yl |
| 478 | 5-(5-Cl, 2-OCH$_3$—C$_6$H$_3$)isoxazol-3-yl |
| 479 | 5-(5-Cl, 2-CH$_3$—C$_6$H$_3$)isoxazol-3-yl |
| 480 | 5-[2,5-(CH$_3$)$_2$—C$_6$H$_3$]isoxazol-3-yl |
| 481 | 3-CH$_3$-isothiazol-5-yl |
| 482 | 3-CH(CH$_3$)$_2$-isothiazol-5-yl |
| 483 | 3-C(CH$_3$)$_3$-isothiazol-5-yl |
| 484 | 3-cyclopropylisothiazol-5-yl |
| 485 | 3-C$_6$H$_5$-isothiazol-5-yl |
| 486 | 3-(2-CH$_3$—C$_6$H$_4$)isothiazol-5-yl |
| 487 | 3-(3-CH$_3$—C$_6$H$_4$)isothiazol-5-yl |
| 488 | 3-(4-CH$_3$—C$_6$H$_4$)isothiazol-5-yl |
| 489 | 3-(3-OCH$_3$—C$_6$H$_4$)isothiazol-5-yl |
| 490 | 3-(4-OCH$_3$—C$_6$H$_4$)isothiazol-5-yl |
| 491 | 3-(4-NO$_2$—C$_6$H$_4$)isothiazol-5-yl |
| 492 | 3-(3-NO$_2$—C$_6$H$_4$)isothiazol-5-yl |
| 493 | 3-(4-CN—C$_6$H$_4$)isothiazol-5-yl |
| 494 | 3-(3-CN—C$_6$H$_4$)isothiazol-5-yl |
| 495 | 3-(3-CF$_3$—C$_6$H$_4$)isothiazol-5-yl |
| 496 | 3-(4-CF$_3$—C$_6$H$_4$)isothiazol-5-yl |
| 497 | 3-(4-C(CH$_3$)$_3$—C$_6$H$_4$)isothiazol-5-yl |
| 498 | 3-(4-C$_6$H$_5$—C$_6$H$_4$)isothiazol-5-yl |
| 499 | 3-(2-Cl—C$_6$H$_4$)isothiazol-5-yl |
| 500 | 3-(3-Cl—C$_6$H$_4$)isothiazol-5-yl |
| 501 | 3-(4-Cl—C$_6$H$_4$)isothiazol-5-yl |
| 502 | 3-(2-Br—C$_6$H$_4$)isothiazol-5-yl |
| 503 | 3-(3-Br—C$_6$H$_4$)isothiazol-5-yl |
| 504 | 3-(4-Br—C$_6$H$_4$)isothiazol-5-yl |
| 505 | 3-(2-F—C$_6$H$_4$)isothiazol-5-yl |
| 506 | 3-(3-F—C$_6$H$_4$)isothiazol-5-yl |
| 507 | 3-(4-F—C$_6$H$_4$)isothiazol-5-yl |
| 508 | 3-(2,4-Cl$_2$—C$_6$H$_3$)isothiazol-5-yl |
| 509 | 3-(2,5-Cl$_2$—C$_6$H$_3$)isothiazol-5-yl |
| 510 | 3-(2,6-Cl$_2$—C$_6$H$_3$)isothiazol-5-yl |
| 511 | 3-(3,4-Cl$_2$—C$_6$H$_3$)isothiazol-5-yl |
| 512 | 3-(2,4-F$_2$—C$_6$H$_3$)isothiazol-5-yl |
| 513 | 3-(2,5-F$_2$—C$_6$H$_3$)isothiazol-5-yl |
| 514 | 3-(2,6-F$_2$—C$_6$H$_3$)isothiazol-5-yl |
| 515 | 3-(3,4-F$_2$—C$_6$H$_3$)isothiazol-5-yl |
| 516 | 3-(2-Cl, 5-OCH$_3$—C$_6$H$_3$)isothiazol-5-yl |
| 517 | 3-(2-Cl, 5-CH$_3$—C$_6$H$_3$)isothiazol-5-yl |
| 518 | 3-(5-Cl, 2-OCH$_3$—C$_6$H$_3$)isothiazol-5-yl |
| 519 | 3-(5-Cl, 2-CH$_3$—C$_6$H$_3$)isothiazol-5-yl |
| 520 | 3-[2,5-(CH$_3$)$_2$—C$_6$H$_3$]isothiazol-5-yl |
| 521 | 2-CH$_3$-oxazol-4-yl |
| 522 | 2-CH(CH$_3$)$_2$-oxazol-4-yl |
| 523 | 2-C(CH$_3$)$_3$-oxazol-4-yl |
| 524 | 2-cyclopropyloxazol-4-yl |
| 525 | 2-C$_6$H$_5$-oxazol-4-yl |
| 526 | 2-(2-CH$_3$—C$_6$H$_4$)oxazol-4-yl |
| 527 | 2-(3-CH$_3$—C$_6$H$_4$)oxazol-4-yl |
| 528 | 2-(4-CH$_3$—C$_6$H$_4$)oxazol-4-yl |
| 529 | 2-(3-OCH$_3$—C$_6$H$_4$)oxazol-4-yl |
| 530 | 2-(4-OCH$_3$—C$_6$H$_4$)oxazol-4-yl |
| 531 | 2-(4-NO$_2$—C$_6$H$_4$)oxazol-4-yl |
| 532 | 2-(3-NO$_2$—C$_6$H$_4$)oxazol-4-yl |
| 533 | 2-(4-CN—C$_6$H$_4$)oxazol-4-yl |
| 534 | 2-(3-CN—C$_6$H$_4$)oxazol-4-yl |
| 535 | 2-(3-CF$_3$—C$_6$H$_4$)oxazol-4-yl |
| 536 | 2-(4-CF$_3$—C$_6$H$_4$)oxazol-4-yl |
| 537 | 2-(4-C(CH$_3$)$_3$—C$_6$H$_4$)oxazol-4-yl |
| 538 | 2-(4-C$_6$H$_5$—C$_6$H$_4$)oxazol-4-yl |
| 539 | 2-(2-Cl—C$_6$H$_4$)oxazol-4-yl |
| 540 | 2-(3-Cl—C$_6$H$_4$)oxazol-4-yl |
| 541 | 2-(4-Cl—C$_6$H$_4$)oxazol-4-yl |
| 542 | 2-(2-Br—C$_6$H$_4$)oxazol-4-yl |
| 543 | 2-(3-Br—C$_6$H$_4$)oxazol-4-yl |
| 544 | 2-(4-Br—C$_6$H$_4$)oxazol-4-yl |
| 545 | 2-(2-F—C$_6$H$_4$)oxazol-4-yl |
| 546 | 2-(3-F—C$_6$H$_4$)oxazol-4-yl |
| 547 | 2-(4-F—C$_6$H$_4$)oxazol-4-yl |
| 548 | 2-(2,4-Cl$_2$—C$_6$H$_3$)oxazol-4-yl |
| 549 | 2-(2,5-Cl$_2$—C$_6$H$_3$)oxazol-4-yl |
| 550 | 2-(2,6-Cl$_2$—C$_6$H$_3$)oxazol-4-yl |
| 551 | 2-(3,4-Cl$_2$—C$_6$H$_3$)oxazol-4-yl |
| 552 | 2-(2,4-F$_2$—C$_6$H$_3$)oxazol-4-yl |
| 553 | 2-(2,5-F$_2$—C$_6$H$_3$)oxazol-4-yl |
| 554 | 2-(2,6-F$_2$—C$_6$H$_3$)oxazol-4-yl |
| 555 | 2-(3,4-F$_2$—C$_6$H$_3$)oxazol-4-yl |
| 556 | 2-(2-Cl, 5-OCH$_3$—C$_6$H$_3$)oxazol-4-yl |
| 557 | 2-(2-Cl, 5-CH$_3$—C$_6$H$_3$)oxazol-4-yl |
| 558 | 2-(5-Cl, 2-OCH$_3$—C$_6$H$_3$)oxazol-4-yl |
| 559 | 2-(5-Cl, 2-CH$_3$—C$_6$H$_3$)oxazol-4-yl |
| 560 | 2-[2,5-(CH$_3$)$_2$—C$_6$H$_3$]oxazol-4-yl |
| 561 | 2-CH$_3$-thiazol-4-yl |
| 562 | 2-CH(CH$_3$)$_2$-thiazol-4-yl |
| 563 | 2-C(CH$_3$)$_3$-thiazol-4-yl |
| 564 | 2-cyclopropylthiazol-4-yl |
| 565 | 2-C$_6$H$_5$-thiazol-4-yl |
| 566 | 2-(2-CH$_3$—C$_6$H$_4$)thiazol-4-yl |
| 567 | 2-(3-CH$_3$—C$_6$H$_4$)thiazol-4-yl |
| 568 | 2-(4-CH$_3$—C$_6$H$_4$)thiazol-4-yl |
| 569 | 2-(3-OCH$_3$—C$_6$H$_4$)thiazol-4-yl |
| 570 | 2-(4-OCH$_3$—C$_6$H$_4$)thiazol-4-yl |
| 571 | 2-(4-NO$_2$—C$_6$H$_4$)thiazol-4-yl |
| 572 | 2-(3-NO$_2$—C$_6$H$_4$)thiazol-4-yl |
| 573 | 2-(4-CN—C$_6$H$_4$)thiazol-4-yl |
| 574 | 2-(3-CN—C$_6$H$_4$)thiazol-4-yl |
| 575 | 2-(3-CF$_3$—C$_6$H$_4$)thiazol-4-yl |
| 576 | 2-(4-CF$_3$—C$_6$H$_4$)thiazol-4-yl |
| 577 | 2-(4-C(CH$_3$)$_3$—C$_6$H$_4$)thiazol-4-yl |
| 578 | 2-(4-C$_6$H$_5$—C$_6$H$_4$)thiazol-4-yl |
| 579 | 2-(2-Cl—C$_6$H$_4$)thiazol-4-yl |
| 580 | 2-(3-Cl—C$_6$H$_4$)thiazol-4-yl |
| 581 | 2-(4-Cl—C$_6$H$_4$)thiazol-4-yl |
| 582 | 2-(2-Br—C$_6$H$_4$)thiazol-4-yl |
| 583 | 2-(3-Br—C$_6$H$_4$)thiazol-4-yl |
| 584 | 2-(4-Br—C$_6$H$_4$)thiazol-4-yl |
| 585 | 2-(2-F—C$_6$H$_4$)thiazol-4-yl |
| 586 | 2-(3-F—C$_6$H$_4$)thiazol-4-yl |
| 587 | 2-(4-F—C$_6$H$_4$)thiazol-4-yl |
| 588 | 2-(2,4-Cl$_2$—C$_6$H$_3$)thiazol-4-yl |
| 589 | 2-(2,5-Cl$_2$—C$_6$H$_3$)thiazol-4-yl |
| 590 | 2-(2,6-Cl$_2$—C$_6$H$_3$)thiazol-4-yl |
| 591 | 2-(3,4-Cl$_2$—C$_6$H$_3$)thiazol-4-yl |
| 592 | 2-(2,4-F$_2$—C$_6$H$_3$)thiazol-4-yl |
| 593 | 2-(2,5-F$_2$—C$_6$H$_3$)thiazol-4-yl |
| 594 | 2-(2,6-F$_2$—C$_6$H$_3$)thiazol-4-yl |
| 595 | 2-(3,4-F$_2$—C$_6$H$_3$)thiazol-4-yl |
| 596 | 2-(2-Cl, 5-OCH$_3$—C$_6$H$_3$)thiazol-4-yl |
| 597 | 2-(2-Cl, 5-CH$_3$—C$_6$H$_3$)thiazol-4-yl |
| 598 | 2-(5-Cl, 2-OCH$_3$—C$_6$H$_3$)thiazol-4-yl |
| 599 | 2-(5-Cl, 2-CH$_3$—C$_6$H$_3$)thiazol-4-yl |
| 600 | 2-[2,5-(CH$_3$)$_2$—C$_6$H$_3$]thiazol-4-yl |
| 601 | 1,3-(CH$_3$)$_2$-1,2,4-triazol-5-yl |
| 602 | 1-CH$_3$, 3-CH(CH$_3$)$_2$-1,2,4-triazol-5-yl |
| 603 | 1-CH$_3$, 3-C(CH$_3$)$_3$-1,2,4-triazol-5-yl |
| 604 | 1-CH$_3$, 3-cyclopropyl-1,2,4-triazol-5-yl |
| 605 | 1-CH$_3$, 3-C$_6$H$_5$-1,2,4-triazol-5-yl |
| 606 | 1-CH$_3$, 3-(2-CH$_3$—C$_6$H$_4$)-1,2,4-triazol-5-yl |
| 607 | 1-CH$_3$, 3-(3-CH$_3$—C$_6$H$_4$)-1,2,4-triazol-5-yl |
| 608 | 1-CH$_3$, 3-(4-CH$_3$—C$_6$H$_4$)-1,2,4-triazol-5-yl |
| 609 | 1-CH$_3$, 3-(3-OCH$_3$—C$_6$H$_4$)-1,2,4-triazol-5-yl |
| 610 | 1-CH$_3$, 3-(4-OCH$_3$—C$_6$H$_4$)-1,2,4-triazol-5-yl |
| 611 | 1-CH$_3$, 3-(4-NO$_2$—C$_6$H$_4$)-1,2,4-triazol-5-yl |
| 612 | 1-CH$_3$, 3-(3-NO$_2$—C$_6$H$_4$)-1,2,4-triazol-5-yl |
| 613 | 1-CH$_3$, 3-(4-CN—C$_6$H$_4$)-1,2,4-triazol-5-yl |
| 614 | 1-CH$_3$, 3-(3-CN—C$_6$H$_4$)-1,2,4-triazol-5-yl |
| 615 | 1-CH$_3$, 3-(3-CF$_3$—C$_6$H$_4$)-1,2,4-triazol-5-yl |
| 616 | 1-CH$_3$, 3-(4-CF$_3$—C$_6$H$_4$)-1,2,4-triazol-5-yl |

TABLE D.1-continued

| No. | A[a] |
|---|---|
| 617 | 1-CH$_3$, 3-(4-C(CH$_3$)$_3$—C$_6$H$_4$)-1,2,4-triazol-5-yl |
| 618 | 1-CH$_3$, 3-(4-C$_6$H$_5$—C$_6$H$_4$)-1,2,4-triazol-5-yl |
| 619 | 1-CH$_3$, 3-(2-Cl—C$_6$H$_4$)-1,2,4-triazol-5-yl |
| 620 | 1-CH$_3$, 3-(3-Cl—C$_6$H$_4$)-1,2,4-triazol-5-yl |
| 621 | 1-CH$_3$, 3-(4-Cl—C$_6$H$_4$)-1,2,4-triazol-5-yl |
| 622 | 1-CH$_3$, 3-(2-Br—C$_6$H$_4$)-1,2,4-triazol-5-yl |
| 623 | 1-CH$_3$, 3-(3-Br—C$_6$H$_4$)-1,2,4-triazol-5-yl |
| 624 | 1-CH$_3$, 3-(4-Br—C$_6$H$_4$)-1,2,4-triazol-5-yl |
| 625 | 1-CH$_3$, 3-(2-F—C$_6$H$_4$)-1,2,4-triazol-5-yl |
| 626 | 1-CH$_3$, 3-(3-F—C$_6$H$_4$)-1,2,4-triazol-5-yl |
| 627 | 1-CH$_3$, 3-(4-F—C$_6$H$_4$)-1,2,4-triazol-5-yl |
| 628 | 1-CH$_3$, 3-(2,4-Cl$_2$—C$_6$H$_3$)-1,2,4-triazol-5-yl |
| 629 | 1-CH$_3$, 3-(2,5-Cl$_2$—C$_6$H$_3$)-1,2,4-triazol-5-yl |
| 630 | 1-CH$_3$, 3-(2,6-Cl$_2$—C$_6$H$_3$)-1,2,4-triazol-5-yl |
| 631 | 1-CH$_3$, 3-(3,4-Cl$_2$—C$_6$H$_3$)-1,2,4-triazol-5-yl |
| 632 | 1-CH$_3$, 3-(2,4-F$_2$—C$_6$H$_3$)-1,2,4-triazol-5-yl |
| 633 | 1-CH$_3$, 3-(2,5-F$_2$—C$_6$H$_3$)-1,2,4-triazol-5-yl |
| 634 | 1-CH$_3$, 3-(2,6-F$_2$—C$_6$H$_3$)-1,2,4-triazol-5-yl |
| 635 | 1-CH$_3$, 3-(3,4-F$_2$—C$_6$H$_3$)-1,2,4-triazol-5-yl |
| 636 | 1-CH$_3$, 3-(2-Cl, 5-OCH$_3$—C$_6$H$_3$)-1,2,4-triazol-5-yl |
| 637 | 1-CH$_3$, 3-(2-Cl, 5-CH$_3$—C$_6$H$_3$)-1,2,4-triazol-5-yl |
| 638 | 1-CH$_3$, 3-(5-Cl, 2-OCH$_3$—C$_6$H$_3$)-1,2,4-triazol-5-yl |
| 639 | 1-CH$_3$, 3-(5-Cl, 2-CH$_3$—C$_6$H$_3$)-1,214-triazol-5-yl |
| 640 | 1-CH$_3$, 3-[2,5-(CH$_3$)$_2$—C$_6$H$_3$]-1,2,4-triazol-5-yl |
| 641 | 5-CH$_3$-1,3,4-oxadiazol-2-yl |
| 642 | 5-CH(CH$_3$)$_2$-1,3,4-oxadiazol-2-yl |
| 643 | 5-C(CH$_3$)$_3$-1,3,4-oxadiazol-2-yl |
| 644 | 5-cyclopropyl-1,3,4-oxadiazol-2-yl |
| 645 | 5-C$_6$H$_5$-1,3,4-oxadiazol-2-yl |
| 646 | 5-(2-CH$_3$—C$_6$H$_4$)-1,3,4-oxadiazol-2-yl |
| 647 | 5-(3-CH$_3$—C$_6$H$_4$)-1,3,4-oxadiazol-2-yl |
| 648 | 5-(4-CH$_3$—C$_6$H$_4$)-1,3,4-oxadiazol-2-yl |
| 649 | 5-(3-OCH$_3$—C$_6$H$_4$)-1,3,4-oxadiazol-2-yl |
| 650 | 5-(4-OCH$_3$—C$_6$H$_4$)-1,3,4-oxadiazol-2-yl |
| 651 | 5-(4-NO$_2$—C$_6$H$_4$)-1,3,4-oxadiazol-2-yl |
| 652 | 5-(3-NO$_2$—C$_6$H$_4$)-1,3,4-oxadiazol-2-yl |
| 653 | 5-(4-CN—C$_6$H$_4$)-1,3,4-oxadiazol-2-yl |
| 654 | 5-(3-CN—C$_6$H$_4$)-11#l 4-oxadiazol-2-yl |
| 655 | 5-(3-CF$_3$—C$_6$H$_4$)-1,3,4-oxadiazol-2-yl |
| 656 | 5-(4-CF$_3$—C$_6$H$_4$)-1,3,4-oxadiazol-2-yl |
| 657 | 5-(4-C(CH$_3$)$_3$—C$_6$H$_4$)-1,3,4-oxadiazol-2-yl |
| 658 | 5-(4-C$_6$H$_5$—C$_6$H$_4$)-1,3,4-oxadiazol-2-yl |
| 659 | 5-(2-Cl—C$_6$H$_4$)-1,3,4-oxadiazol-2-yl |
| 660 | 5-(3-Cl—C$_6$H$_4$)-1,3,4-oxadiazol-2-yl |
| 661 | 5-(4-Cl—C$_6$H$_4$)-1,3,4-oxadiazol-2-yl |
| 662 | 5-(2-Br—C$_6$H$_4$)-1,3,4-oxadiazol-2-yl |
| 663 | 5-(3-Br—C$_6$H$_4$)-1,3,4-oxadiazol-2-yl |
| 664 | 5-(4-Br—C$_6$H$_4$)-1,3,4-oxadiazol-2-yl |
| 665 | 5-(2-F—C$_6$H$_4$)-1,3,4-oxadiazol-2-yl |
| 666 | 5-(3-F—C$_6$H$_4$)-1,3,4-oxadiazol-2-yl |
| 667 | 5-(4-F—C$_6$H$_4$)-1,3,4-oxadiazol-2-yl |
| 668 | 5-(2,4-Cl$_2$—C$_6$H$_3$)-1,3,4-oxadiazol-2-yl |
| 669 | 5-(2,5-Cl$_2$—C$_6$H$_3$)-1,3,4-oxadiazol-2-yl |
| 670 | 5-(2,6-Cl$_2$—C$_6$H$_3$)-1,3,4-oxadiazol-2-yl |
| 671 | 5-(3,4-Cl$_2$—C$_6$H$_3$)-1,3,4-oxadiazol-2-yl |
| 672 | 5-(2,4-F$_2$—C$_6$H$_3$)-1,3,4-oxadiazol-2-yl |
| 673 | 5-(2,5-F$_2$—C$_6$H$_3$)-1,3,4-oxadiazol-2-yl |
| 674 | 5-(2,6-F$_2$—C$_6$H$_3$)-1,3,4-oxadiazol-2-yl |
| 675 | 5-(3,4-F$_2$—C$_6$H$_3$)-1,3,4-oxadiazol-2-yl |
| 676 | 5-(2-Cl, 5-OCH$_3$—C$_6$H$_3$)-1,3,4-oxadiazol-2-yl |
| 677 | 5-(2-Cl, 5-CH$_3$—C$_6$H$_3$)-1,3,4-oxadiazol-2-yl |
| 678 | 5-(5-Cl, 2-OCH$_3$—C$_6$H$_3$)-1,3,4-oxadiazol-2-yl |
| 679 | 5-(5-Cl, 2-CH$_3$—C$_6$H$_3$)-1,3,4-oxadiazol-2-yl |
| 680 | 5-[2,5-(CH$_3$)$_2$—C$_6$H$_3$]-1,3,4-oxadiazol-2-yl |
| 681 | 5-CH$_3$-1,2,4-oxadiazol-3-yl |
| 682 | 5-CH(CH$_3$)$_2$-1,2,4-oxadiazol-3-yl |
| 683 | 5-C(CH$_3$)$_3$-1,2,4-oxadiazol-3-yl |
| 684 | 5-cyclopropyl-1,2,4-oxadiazol-3-yl |
| 685 | 5-C$_6$H$_5$-1,2,4-oxadiazol-3-yl |
| 686 | 5-(2-CH$_3$—C$_6$H$_4$)-1,2,4-oxadiazol-3-yl |
| 687 | 5-(3-CH$_3$—C$_6$H$_4$)-1,2,4-oxadiazol-3-yl |
| 688 | 5-(4-CH$_3$—C$_6$H$_4$)-1,2,4-oxadiazol-3-yl |
| 689 | 5-(3-OCH$_3$—C$_6$H$_4$)-1,2,4-oxadiazol-3-yl |
| 690 | 5-(4-OCH$_3$—C$_6$H$_4$)-1,2,4-oxadiazol-3-yl |
| 691 | 5-(4-NO$_2$—C$_6$H$_4$)-1,2,4-oxadiazol-3-yl |
| 692 | 5-(3-NO$_2$—C$_6$H$_4$)-1,2,4-oxadiazol-3-yl |
| 693 | 5-(4-CN—C$_6$H$_4$)-1,2,4-oxadiazol-3-yl |
| 694 | 5-(3-CN—C$_6$H$_4$)-1,2,4-oxadiazol-3-yl |
| 695 | 5-(3-CF$_3$—C$_6$H$_4$)-1,2,4-oxadiazol-3-yl |
| 696 | 5-(4-CF$_3$—C$_6$H$_4$)-1,2,4-oxadiazol-3-yl |
| 697 | 5-(4-C(CH$_3$)$_3$—C$_6$H$_4$)-1,2,4-oxadiazol-3-yl |
| 698 | 5-(4-C$_6$H$_5$—C$_6$H$_4$)-1,2,4-oxadiazol-3-yl |
| 699 | 5-(2-Cl—C$_6$H$_4$)-1,2,4-oxadiazol-3-yl |
| 700 | 5-(3-Cl—C$_6$H$_4$)-1,2,4-oxadiazol-3-yl |
| 701 | 5-(4-Cl—C$_6$H$_4$)-1,2,4-oxadiazol-3-yl |
| 702 | 5-(2-Br—C$_6$H$_4$)-1,2,4-oxadiazol-3-yl |
| 703 | 5-(3-Br—C$_6$H$_4$)-1,2,4-oxadiazol-3-yl |
| 704 | 5-(4-Br—C$_6$H$_4$)-1,2,4-oxadiazol-3-yl |
| 705 | 5-(2-F—C$_6$H$_4$)-1,2,4-oxadiazol-3-yl |
| 706 | 5-(3-F—C$_6$H$_4$)-1,2,4-oxadiazol-3-yl |
| 707 | 5-(4-F—C$_6$H$_4$)-1,2,4-oxadiazol-3-yl |
| 708 | 5-(2,4-Cl$_2$—C$_6$H$_3$)-1,2,4-oxadiazol-3-yl |
| 709 | 5-(2,5-Cl$_2$—C$_6$H$_3$)-1,2,4-oxadiazol-3-yl |
| 710 | 5-(2,6-Cl$_2$—C$_6$H$_3$)-1,2,4-oxadiazol-3-yl |
| 711 | 5-(3,4-Cl$_2$—C$_6$H$_3$)-1,2,4-oxadiazol-3-yl |
| 712 | 5-(2,4-F$_2$—C$_6$H$_3$)-1,2,4-oxadiazol-3-yl |
| 713 | 5-(2,5-F$_2$—C$_6$H$_3$)-1,2,4-oxadiazol-3-yl |
| 714 | 5-(2,6-F$_2$—C$_6$H$_3$)-1,2,4-oxadiazol-3-yl |
| 715 | 5-(3,4-F$_2$—C$_6$H$_3$)-1,2,4-oxadiazol-3-yl |
| 716 | 5-(2-Cl, 5-OCH$_3$—C$_6$H$_3$)-1,2,4-oxadiazol-3-yl |
| 717 | 5-(2-Cl, 5-CH$_3$—C$_6$H$_3$)-1,2,4-oxadiazol-3-yl |
| 718 | 5-(5-Cl, 2-OCH$_3$—C$_6$H$_3$)-1,2,4-oxadiazol-3-yl |
| 719 | 5-(5-Cl, 2-CH$_3$—C$_6$H$_3$)-1,2,4-oxadiazol-3-yl |
| 720 | 5-[2,5-(CH$_3$)$_2$—C$_6$H$_3$]-1,2,4-oxadiazol-3-yl |
| 721 | 3-CH$_3$-1,2,4-oxadiazol-5-yl |
| 722 | 3-CH(CH$_3$)$_2$-1,2,4-oxadiazol-5-yl |
| 723 | 3-C(CH$_3$)$_3$-1,2,4-oxadiazol-5-yl |
| 724 | 3-cyclopropyl-1,2,4-oxadiazol-5-yl |
| 725 | 3-C$_6$H$_5$-1,2,4-oxadiazol-5-yl |
| 726 | 3-(2-CH$_3$—C$_6$H$_4$)-1,2,4-oxadiazol-5-yl |
| 727 | 3-(3-CH$_3$—C$_6$H$_4$)-1,2,4-oxadiazol-5-yl |
| 728 | 3-(4-CH$_3$—C$_6$H$_4$)-1,2,4-oxadiazol-5-yl |
| 729 | 3-(3-OCH$_3$—C$_6$H$_4$)-1,2,4-oxadiazol-5-yl |
| 730 | 3-4-OCH$_3$—C$_6$H$_4$)-1,2,4-oxadiazol-5-yl |
| 731 | 3-(4-NO$_2$—C$_6$H$_4$)-1,2,4-oxadiazol-5-yl |
| 732 | 3-(3-NO$_2$—C$_6$H$_4$)-1,2,4-oxadiazol-5-yl |
| 733 | 3-(4-CN—C$_6$H$_4$)-1,2,4-oxadiazol-5-yl |
| 734 | 3-(3-CN—C$_6$H$_4$)-1,2,4-oxadiazol-5-yl |
| 735 | 3-(3-CF$_3$—C$_6$H$_4$)-1,2,4-oxadiazol-5-yl |
| 736 | 3-(4-CF$_3$—C$_6$H$_4$)-1,2,4-oxadiazol-5-yl |
| 737 | 3-(4-C(CH$_3$)$_3$—C$_6$H$_4$)-1,2,4-oxadiazol-5-yl |
| 738 | 3-(4-C$_6$H$_5$—C$_6$H$_4$)-112,4-oxadiazol-5-yl |
| 739 | 3-(2-Cl—C$_6$H$_4$)-1,2,4-oxadiazol-5-yl |
| 740 | 3-(3-Cl—C$_6$H$_4$)-1,2,4-oxadiazol-5-yl |
| 741 | 3-(4-Cl—C$_6$H$_4$)-1,2,4-oxadiazol-5-yl |
| 742 | 3-(2-Br—C$_6$H$_4$)-1,2,4-oxadiazol-5-yl |
| 743 | 3-(3-Br—C$_6$H$_4$)-1,2,4-oxadiazol-5-yl |
| 744 | 3-(4-Br—C$_6$H$_4$)-1,2,4-oxadiazol-5-yl |
| 745 | 3-(2-F—C$_6$H$_4$)-1,2,4-oxadiazol-5-yl |
| 746 | 3-(3-F—C$_6$H$_4$)-1,2,4-oxadiazol-5-yl |
| 747 | 3-(4-F—C$_6$H$_4$)-1,2,4-oxadiazol-5-yl |
| 748 | 3-(2,4-Cl$_2$—C$_6$H$_3$)-1,2,4-oxadiazol-5-yl |
| 749 | 3-(2,5-Cl$_2$—C$_6$H$_3$)-1,2,4-oxadiazol-5-yl |
| 750 | 3-(2,6-Cl$_2$—C$_6$H$_3$)-1,2,4-oxadiazol-5-yl |
| 751 | 3-(3,4-Cl$_2$—C$_6$H$_3$)-1,2,4-oxadiazol-5-yl |
| 752 | 3-(2,4-F$_2$—C$_6$H$_3$)-1,2,4-oxadiazol-5-yl |
| 753 | 3-(2,5-F$_2$—C$_6$H$_3$)-1,2,4-oxadiazol-5-yl |
| 754 | 3-(2,6-F$_2$—C$_6$H$_3$)-1,2,4-oxadiazQl-5-yl |
| 755 | 3-(3,4-F$_2$—C$_6$H$_3$)-1,2,4-oxadiazol-5-yl |
| 756 | 3-(2-Cl, 5-OCH$_3$—C$_6$H$_3$)-1,2,4-oxadiazol-5-yl |
| 757 | 3-(2-Cl, 5-CH$_3$—C$_6$H$_3$)-1,2,4-oxadiazol-5-yl |
| 758 | 3-(5-Cl, 2-OCH$_3$—C$_6$H$_3$)-1,2,4-oxadiazol-5-yl |
| 759 | 3-(5-Cl, 2-CH$_3$—C$_6$H$_3$)-1,2,4-oxadiazol-5-yl |
| 760 | 3-[2,5-(CH$_3$)$_2$—C$_6$H$_3$]-1,2,4-oxadiazol-5-yl |
| 761 | 5-CH$_3$-1,2,4-thiadiazol-3-yl |
| 762 | 5-CH(CH$_3$)$_2$-1,2,4-thiadiazol-3-yl |
| 763 | 5-C(CH$_3$)$_3$-1,2,4-thiadiazol-3-yl |
| 764 | 5-cyclopropyl-1,2,4-thiadiazol-3-yl |
| 765 | 5-C$_6$H$_5$-1,2,4-thiadiazol-3-yl |
| 766 | 5-(2-CH$_3$—C$_6$H$_4$)-1,2,4-thiadiazol-3-yl |
| 767 | 5-(3-CH$_3$—C$_6$H$_4$)-1,2,4-thiadiazol-3-yl |
| 768 | 5-(4-CH$_3$—C$_6$H$_4$)-1,2,4-thiadiazol-3-yl |
| 777 | 5-(3-OCH$_3$—C$_6$H$_4$)-1,2,4-thiadiazol-3-yl |
| 770 | 5-(4-OCH$_3$—C$_6$H$_4$)-1,2,4-thiadiazol-3-yl |

TABLE D.1-continued

| No. | A$^a$ |
|---|---|
| 771 | 5-(4-NO$_2$—C$_6$H$_4$)-1,2,4-thiadiazol-3-yl |
| 772 | 5-(3-NO$_2$—C$_6$H$_4$)-1,2,4-thiadiazol-3-yl |
| 773 | 5-(4-CN—C$_6$H$_4$)-1,2,4-thiadiazol-3-yl |
| 774 | 5-(3-CN—C$_6$H$_4$)-1,2,4-thiadiazol-3-yl |
| 775 | 5-(3-CF$_3$—C$_6$H$_4$)-1,2,4-thiadiazol-3-yl |
| 776 | 5-(4-CF$_3$—C$_6$H$_4$)-1,2,4-thiadiazol-3-yl |
| 777 | 5-(4-C(CH$_3$)$_3$—C$_6$H$_4$)-1,2,4-thiadiazol-3-yl |
| 778 | 5-(4-C$_6$H$_5$—C$_6$H$_4$)-1,2,4-thiadiazol-3-yl |
| 779 | 5-(2-Cl—C$_6$H$_4$)-1,2,4-thiadiazol-3-yl |
| 780 | 5-(3-Cl—C$_6$H$_4$)-1,2,4-thiadiazol-3-yl |
| 781 | 5-(4-Cl—C$_6$H$_4$)-1,2,4-thiadiazol-3-yl |
| 782 | 5-(2-Br—C$_6$H$_4$)-1,2,4-thiadiazol-3-yl |
| 783 | 5-(3-Br—C$_6$H$_4$)-1,2,4-thiadiazol-3-yl |
| 784 | 5-(4-Br—C$_6$H$_4$)-1,2,4-thiadiazol-3-yl |
| 785 | 5-(2-F—C$_6$H$_4$)-1,2,4-thiadiazol-3-yl |
| 786 | 5-(3-F—C$_6$H$_4$)-1,2,4-thiadiazol-3-yl |
| 787 | 5-(4-F—C$_6$H$_4$)-1,2,4-thiadiazol-3-yl |
| 788 | 5-(2,4-Cl$_2$—C$_6$H$_3$)-1,2,4-thiadiazol-3-yl |
| 789 | 5-(2,5-Cl$_2$—C$_6$H$_3$)-1,2,4-thiadiazol-3-yl |
| 790 | 5-(2,6-Cl$_2$—C$_6$H$_3$)-1,2,4-thiadiazol-3-yl |
| 791 | 5-(3,4-Cl$_2$—C$_6$H$_3$)-1,2,4-thiadiazol-3-yl |
| 792 | 5-(2,4-F$_2$—C$_6$H$_3$)-1,2,4-thiadiazol-3-yl |
| 793 | 5-(2,-5-F$_2$—C$_6$H$_3$)-1,2,4-thiadiazol-3-yl |
| 794 | 5-(2,6-F$_2$—C$_6$H$_3$)-1,2,4-thiadiazol-3-yl |
| 795 | 5-(3,4-F$_2$—C$_6$H$_3$)-1,2,4-thiadiazol-3-yl |
| 796 | 5-(2-Cl, 5-OCH$_3$—C$_6$H$_3$)-1,2,4-thiadiazol-3-yl |
| 797 | 5-(2-Cl, 5-CH$_3$—C$_6$H$_3$)-1,2,4-thiadiazol-3-yl |
| 798 | 5-(5-Cl, 2-OCH$_3$—C$_6$H$_3$)-1,2,4-thiadiazol-3-yl |
| 799 | 5-(5-Cl, 2-CH$_3$—C$_6$H$_3$)-1,2,4-thiadiazol-3-yl |
| 800 | 5-[2,5-(CH$_3$)$_2$—C$_6$H$_3$]-1,2,4-thiadiazol-3-yl |
| 801 | 5-CH$_3$-1,3,4-thiadiazol-2-yl |
| 802 | 5-CH(CH$_3$)$_2$-1,3,4-thiadiazol-2-yl |
| 803 | 5-C(CH$_3$)$_3$-1,3,4-thiadiazol-2-yl |
| 804 | 5-cyclopropyl-1,3,4-thiadiazol-2-yl |
| 805 | 5-C$_6$H$_5$-1,3,4-thiadiazol-2-yl |
| 806 | 5-(2-CH$_3$—C$_6$H$_4$)-1,3,4-thiadiazol-2-yl |
| 807 | 5-(3-CH$_3$—C$_6$H$_4$)-1,3,4-thiadiazol-2-yl |
| 808 | 5-(4-CH$_3$—C$_6$H$_4$)-1,3,4-thiadiazol-2-yl |
| 809 | 5-(3-OCH$_3$—C$_6$H$_4$)-1,3,4-thiadiazol-2-yl |
| 810 | 5-(4-OCH$_3$—C$_6$H$_4$)-1,3,4-thiadiazol-2-yl |
| 811 | 5-(4-NO$_2$—C$_6$H$_4$)-1,3,4-thiadiazol-2-yl |
| 812 | 5-(3-NO$_2$—C$_6$H$_4$)-1,3,4-thiadiazol-2-yl |
| 813 | 5-(4-CN—C$_6$H$_4$)-1,3,4-thiadiazol-2-yl |
| 814 | 5-(3-CN—C$_6$H$_4$)-1,3,4-thiadiazol-2-yl |
| 815 | 5-(3-CF$_3$—C$_6$H$_4$)-1,3,4-thiadiazol-2-yl |
| 816 | 5-(4-CF$_3$—C$_6$H$_4$)-1,3,4-thiadiazol-2-yl |
| 817 | 5-(4-C(CH$_3$)$_3$—C$_6$H$_4$)-1,3,4-thiadiazol-2-yl |
| 818 | 5-(4-C$_6$H$_5$—C$_6$H$_4$)-1,3,4-thiadiazol-2-yl |
| 819 | 5-(2-Cl—C$_6$H$_4$)-1,3,4-thiadiazol-2-yl |
| 820 | 5-(3-Cl—C$_6$H$_4$)-1,3,4-thiadiazol-2-yl |
| 821 | 5-(4-Cl—C$_6$H$_4$)-1,3,4-thiadiazol-2-yl |
| 822 | 5-(2-Br—C$_6$H$_4$)-1,3,4-thiadiazol-2-yl |
| 823 | 5-(3-Br—C$_6$H$_4$)-1,3,4-thiadiazol-2-yl |
| 824 | 5-(4-Br—C$_6$H$_4$)-1,3,4-thiadiazol-2-yl |
| 825 | 5-(2-F—C$_6$H$_4$)-1,3,4-thiadiazol-2-yl |
| 826 | 5-(3-F—C$_6$H$_4$)-1,3,4-thiadiazol-2-yl |
| 827 | 5-(4-F—C$_6$H$_4$)-1,3,4-thiadiazol-2-yl |
| 828 | 5-(2,4-Cl$_2$—C$_6$H$_3$)-1,3,4-thiadiazol-2-yl |
| 829 | 5-(2,5-Cl$_2$—C$_6$H$_3$)-1,3,4-thiadiazol-2-yl |
| 830 | 5-(2,6-Cl$_2$—C$_6$H$_3$)-1,3,4-thiadiazol-2-yl |
| 831 | 5-(3,4-Cl$_2$—C$_6$H$_3$)-1,3,4-thiadiazol-2-yl |
| 832 | 5-(2,4-F$_2$—C$_6$H$_3$)-1,3,4-thiadiazol-2-yl |
| 833 | 5-(2,5-F$_2$—C$_6$H$_3$)-1,3,4-thiadiazol-2-yl |
| 834 | 5-(2,6-F$_2$—C$_6$H$_3$)-1,3,4-thiadiazol-2-yl |
| 835 | 5-(3,4-F$_2$—C$_6$H$_3$)-1,3,4-thiadiazol-2-yl |
| 836 | 5-(2-Cl, 5-OCH$_3$—C$_6$H$_3$)-1,3,4-thiadiazol-2-yl |
| 837 | 5-(2-Cl, 5-CH$_3$—C$_6$H$_3$)-1,3,4-thiadiazol-2-yl |
| 838 | 5-(5-Cl, 2-OCH$_3$—C$_6$H$_3$)-1,3,4-thiadiazol-2-yl |
| 839 | 5-(5-Cl, 2-CH$_3$—C$_6$H$_3$)-1,3,4-thiadiazol-2-yl |
| 840 | 5-[2,5-(CH$_3$)$_2$—C$_6$H$_3$]-1,3,4-thiadiazol-2-yl |
| 841 | 1,3-(CH$_3$)$_2$-pyrazol-4-yl |
| 842 | 3-CH$_3$, 1-CH(CH$_3$)$_2$-pyrazol-4-yl |
| 843 | 3-CH$_3$, 1-C(CH$_3$)$_3$-pyrazol-4-yl |
| 844 | 3-CH$_3$, 1-cyclopropyl-pyrazol-4-yl |
| 845 | 3-CH$_3$, 1-C$_6$H$_5$-pyrazol-4-yl |
| 846 | 3-CH$_3$, 1-(2-CH$_3$—C$_6$H$_4$)pyrazol-4-yl |
| 847 | 3-CH$_3$, 1-(3-CH$_3$—C$_6$H$_4$)pyrazol-4-yl |
| 848 | 3-CH$_3$, 1-(4-CH$_3$—C$_6$H$_4$)pyrazol-4-yl |
| 849 | 3-CH$_3$, 1-(3-OCH$_3$—C$_6$H$_4$)pyrazol-4-yl |
| 850 | 3-CH$_3$, 1-(4-OCH$_3$—C$_6$H$_4$)pyrazol-4-yl |
| 851 | 3-CH$_3$, 1-(4-NO$_2$—C$_6$H$_4$)pyrazol-4-yl |
| 852 | 3-CH$_3$, 1-(3-NO$_2$—C$_6$H$_4$)pyrazol-4-yl |
| 853 | 3-CH$_3$, 1-(4-CN—C$_6$H$_4$)pyrazol-4-yl |
| 854 | 3-CH$_3$, 1-(3-CN—C$_6$H$_4$)pyrazol-4-yl |
| 855 | 3-CH$_3$, 1-(3-CF$_3$—C$_6$H$_4$)pyrazol-4-yl |
| 856 | 3-CH$_3$, 1-(4-CF$_3$—C$_6$H$_4$)pyrazol-4-yl |
| 857 | 3-CH$_3$, 1-(4-C(CH$_3$)$_3$—C$_6$H$_4$)pyrazol-4-yl |
| 858 | 3-CH$_3$, 1-(4-C$_6$H$_5$—C$_6$H$_4$)pyrazol-4-yl |
| 859 | 3-CH$_3$, 1-(2-Cl—C$_6$H$_4$)pyrazol-4-yl |
| 860 | 3-CH$_3$, 1-(3-Cl—C$_6$H$_4$)pyrazol-4-yl |
| 861 | 3-CH$_3$, 1-(4-Cl—C$_6$H$_4$)pyrazol-4-yl |
| 862 | 3-CH$_3$, 1-(2-Br—C$_6$H$_4$)pyrazol-4-yl |
| 863 | 3-CH$_3$, 1-(3-Br—C$_6$H$_4$)pyrazol-4-yl |
| 864 | 3-CH$_3$, 1-(4-Br—C$_6$H$_4$)pyrazol-4-yl |
| 865 | 3-CH$_3$, 1-(2-F—C$_6$H$_4$)pyrazol-4-yl |
| 866 | 3-CH$_3$, 1-(3-F—C$_6$H$_4$)pyrazol-4-yl |
| 867 | 3-CH$_3$, 1-(4-F—C$_6$H$_4$)pyrazol-4-yl |
| 868 | 3-CH$_3$, 1-(2,4-Cl$_2$—C$_6$H$_3$)pyrazol-4-yl |
| 869 | 3-CH$_3$, 1-(2,5-Cl$_2$—C$_6$H$_3$)pyrazol-4-yl |
| 870 | 3-CH$_3$, 1-(2,6-Cl$_2$—C$_6$H$_3$)pyrazol-4-yl |
| 871 | 3-CH$_3$, 1-(3,4-Cl$_2$—C$_6$H$_3$)pyrazol-4-yl |
| 872 | 3-CH$_3$, 1-(2,4-F$_2$—C$_6$H$_3$)pyrazol-4-yl |
| 873 | 3-CH$_3$, 1-(2,5-F$_2$—C$_6$H$_3$)pyrazol-4-yl |
| 874 | 3-CH$_3$, 1-(2,6-F$_2$—C$_6$H$_3$)pyrazol-4-yl |
| 875 | 3-CH$_3$, 1-(3,4-F$_2$—C$_6$H$_3$)pyrazol-4-yl |
| 876 | 3-CH$_3$, 1-(2-Cl, 5-OCH$_3$—C$_6$H$_3$)pyrazol-4-yl |
| 877 | 3-CH$_3$, 1-(2-Cl, 5-CH$_3$—C$_6$H$_3$)pyrazol-4-yl |
| 878 | 3-CH$_3$, 1-(5-Cl, 2-OCH$_3$—C$_6$H$_3$)pyrazol-4-yl |
| 879 | 3-CH$_3$, 1-(5-Cl, 2-CH$_3$—C$_6$H$_3$)pyrazol-4-yl |
| 880 | 3-CH$_3$, 1-[2,5-(CH$_3$)$_2$—C$_6$H$_3$]pyrazol-4-yl |
| 881 | 3,5-(CH$_3$)$_2$, 1-C$_6$H$_5$-pyrazol-4-yl |
| 882 | 3,5-(CH$_3$)$_2$, 1-(2-CH$_3$—C$_6$H$_4$)pyrazol-4-yl |
| 883 | 3,5-(CH$_3$)$_2$, 1-(3-CH$_3$—C$_6$H$_4$)pyrazol-4-yl |
| 884 | 3,5-(CH$_3$)$_2$, 1-(4-CH$_3$—C$_6$H$_4$)pyrazol-4-yl |
| 885 | 3,5-(CH$_3$)$_2$, 1-(3-OCH$_3$—C$_6$H$_4$)pyrazol-4-yl |
| 886 | 3,5-(CH$_3$)$_2$, 1-(4-OCH$_3$—C$_6$H$_4$)pyrazol-4-yl |
| 887 | 3,5-(CH$_3$)$_2$, 1-(4-NO$_2$—C$_6$H$_4$)pyrazol-4-yl |
| 888 | 3,5-(CH$_3$)$_2$, 1-(3-NO$_2$—C$_6$H$_4$)pyrazol-4-yl |
| 889 | 3,5-(CH$_3$)$_2$, 1-(4-CN—C$_6$H$_4$)pyrazol-4-yl |
| 890 | 3,5-(CH$_3$)$_2$, 1-(3-CN—C$_6$H$_4$)pyrazol-4-yl |
| 891 | 3,5-(CH$_3$)$_2$, 1-(3-CF$_3$—C$_6$H$_4$)pyrazol-4-yl |
| 892 | 3,5-(CH$_3$)$_2$, 1-(4-CF$_3$—C$_6$H$_4$)pyrazol-4-yl |
| 893 | 3,5-(CH$_3$)$_2$, 1-(4-C(CH$_3$)$_3$—C$_6$H$_4$)pyrazol-4-yl |
| 894 | 3,5-(CH$_3$)$_2$, 1-(4-C$_6$H$_5$—C$_6$H$_4$)pyrazol-4-yl |
| 895 | 3,5-(CH$_3$)$_2$, 1-(2-Cl—C$_6$H$_4$)pyrazol-4-yl |
| 896 | 3,5-(CH$_3$)$_2$, 1-(3-Cl—C$_6$H$_4$)pyrazol-4-yl |
| 897 | 3,5-(CH$_3$)$_2$, 1-(4-Cl—C$_6$H$_4$)pyrazol-4-yl |
| 898 | 3,5-(CH$_3$)$_2$, 1-(2-Br—C$_6$H$_4$)pyrazol-4-yl |
| 899 | 3,5-(CH$_3$)$_2$, 1-(3-Br—C$_6$H$_4$)pyrazol-4-yl |
| 900 | 3,5-(CH$_3$)$_2$, 1-(4-Br—C$_6$H$_4$)pyrazol-4-yl |
| 901 | 3,5-(CH$_3$)$_2$, 1-(2-F—C$_6$H$_4$)pyrazol-4-yl |
| 902 | 3,5-(CH$_3$)$_2$, 1-(3-F—C$_6$H$_4$)pyrazol-4-yl |
| 903 | 3,5-(CH$_3$)$_2$, 1-(4-F—C$_6$H$_4$)pyrazol-4-yl |
| 904 | 3,5-(CH$_3$)$_2$, 1-(2,4-Cl$_2$—C$_6$H$_3$)pyrazol-4-yl |
| 905 | 3,5-(CH$_3$)$_2$, 1-(2,5-Cl$_2$—C$_6$H$_3$)pyrazol-4-yl |
| 906 | 3,5-(CH$_3$)$_2$, 1-(2,6-Cl$_2$—C$_6$H$_3$)pyrazol-4-yl |
| 907 | 3,5-(CH$_3$)$_2$, 1-(3,4-Cl$_2$—C$_6$H$_3$)pyrazol-4-yl |
| 908 | 3,5-(CH$_3$)$_2$, 1-(2,4-F$_2$—C$_6$H$_3$)pyrazol-4-yl |
| 909 | 3,5-(CH$_3$)$_2$, 1-(2,5-F$_2$—C$_6$H$_3$)pyrazol-4-yl |
| 910 | 3,5-(CH$_3$)$_2$, 1-(2,6-F$_2$—C$_6$H$_3$)pyrazol-4-yl |
| 911 | 3,5-(CH$_3$)$_2$, 1-(3,4-F$_2$—C$_6$H$_3$)pyrazol-4-yl |
| 912 | 3,5-(CH$_3$)$_2$, 1-(2-Cl, 5-OCH$_3$—C$_6$H$_3$)pyrazol-4-yl |
| 913 | 3,5-(CH$_3$)$_2$, 1-(2-Cl, 5-CH$_3$—C$_6$H$_3$)pyrazol-4-yl |
| 914 | 3,5-(CH$_3$)$_2$, 1-(5-Cl, 2-OCH$_3$—C$_6$H$_3$)pyrazol-4-yl |
| 915 | 3,5-(CH$_3$)$_2$, 1-(5-Cl, 2-CH$_3$—C$_6$H$_3$)pyrazol-4-yl |
| 916 | 3,5-(CH$_3$)$_2$, 1-[2,5-(CH$_3$)$_2$—C$_6$H$_3$]-pyrazol-4-yl |

TABLE B

| No. | $A^a$ | No. | $A^a$ |
|---|---|---|---|
| 1 | H | 30 | 2-Cl—$C_6H_4$—$CH_2$ |
| 2 | $CH_3$ | 31 | 3-Cl—$C_6H_4$—$CH_2$ |
| 3 | $CH_3CH_2$ | 32 | 4-Cl—$C_6H_4$—$CH_2$ |
| 4 | $CH_3CH_2CH_2$ | 33 | 2,5-$Cl_2$—$C_6H_3$—$CH_2$ |
| 5 | $CH_3CH(CH_3)$ | 34 | 2-$CH_3$—$C_6H_4$—$CH_2$ |
| 6 | $(CH_3)_3C$ | 35 | 3-$CH_3$—$C_6H_4$—$CH_2$ |
| 7 | $CH_2$=CH—$CH_2$ | 36 | 4-$CH_3$—$C_6H_4$—$CH_2$ |
| 8 | HC≡C—$CH_2$ | 37 | 2,3-$(CH_3)_2$—$C_6H_3$—$CH_2$ |
| 9 | $CH_3OCH_2CH_2$ | 38 | 2,4-$(CH_3)_2$—$C_6H_3$—$CH_2$ |
| 10 | Cyclopropyl-$CH_2$ | 39 | 2,4,6-$(CH_3)_3$—$C_6H_2$—$CH_2$ |
| 11 | $CH_2$=CH—$CH_2$—$CH_2$ | 40 | 2,4,6-$(CH_3)_3$—$C_6H_2$—$CH_2$ |
| 12 | $CH_3$—CH=CH—$CH_2$ | 41 | 2-$CF_3$—$C_6H_4$—$CH_2$ |
| 13 | $CH_3$—$(CH_2)_3$ | 42 | 3-$CF_3$—$C_6H_4$—$CH_2$ |
| 14 | $CH_3$—$(CH_2)_4$ | 43 | 4-$CF_3$—$C_6H_4$—$CH^2$ [sic] |
| 15 | $CH_3$—$(CH_2)_5$ | 44 | 2-$CF_3$-5-$CH_3$—$C_6H_5$—$CH_2$ |
| 16 | Cyclohexyl | 45 | 2-$CH_3$-5-$CF_3$—$C_6H_3$—$CH_2$ |
| 17 | 2-$CH_3$-cyclohexyl | 46 | 2-Br—$C_6H_4$—$CH_2$ |
| 18 | $CH_3$—$CH_2$—$C(CH_3)2$ | 47 | 2-(Isopropyl)-$C_6H_4$—$CH_2$ |
| 19 | $CH_3$—$CH(CH_3)$—$CH_2$ | 48 | 2-(Isopropyl)-3-Cl—$C_6H_3$—$CH_2$ |
| 20 | $CH_3$—$CH(CH_3)$—$CH_2$—$CH_2$ | 49 | 2-$CH_3$-5-t-$C_4$—$H_9$—$C_6H_3$—$CH_2$ |
| 21 | $CH_2$=$C(CH_3)$—$CH_2$ | 50 | 2-$CH_3$-5-t-$C_4H_9$—$C_6H_3$—$CH_2$ |
| 22 | HC≡C—$C(CH_3)$=CH—$CH_2$ | 51 | 3-$CH_3$-5-t-$C_4H_9$—$C_6H_3$—$CH_2$ |
| 23 | $Cl(CH_3)$—C≡CH | 52 | 2-Cl-5-t-$C_4H_9$—$C_6H_3$—$CH_2$ |
| 24 | $CH_2$=$C(Cl)$—$CH_2$— | 53 | 3-Cl-5-t-$C_4H_9$—$C_6H_3$—$CH_2$ |
| 25 | ClCH=CH—$CH_2$— | 54 | 2-$OCH_3$—$C_6H_4$—$CH_2$ |
| 26 | $C_6H_5$—$CH_2$ | 55 | 3-$OCH_3$—$C_6H_4$—$CH_2$ |
| 27 | 2-F—$C_6H_4$—$CH_2$ | 56 | 2-$CH_3$-5-$OCH_3$—$C_6H_3$—$CH_2$ |
| 28 | 3-F—$C_6H_4$—$CH_2$ | 57 | 3-$CH_3$-5-$OCH_3$—$C_6H_3$—$CH_2$ |
| 29 | 4-F—$C_6H_4$—$CH_2$ | 58 | 3-Cl—5-$OCH_3$—$C_6H_3$—$CH_2$ |

The compounds of the formula I according to the invention are suitable for controlling fungal pests and animal pests from the class of the insects, arachnids and nematodes. They can be applied as fungicides and pesticides in crop protection and in the hygiene, stock-protection and veterinary sectors.

The insect pests include:

from the order of the lepidopterans (Lepidoptera) for example *Adoxophyes orana, Agrotis ypsilon, Agrotis segetum, Alabama argillacea, Anticarsia gemmatalis, Argyresthia conjugella, Autographa gamma, Cacoecia murinana, Capua reticulana, Choristoneura fumiferana, Chilo partellus, Choristoneura occidentalis, Cirphis unipuncta, Cnaphalocrocis medinalis, Crocidolomia binotalis, Cydia pomonella, Dendrolimus pini, Diaphania nitidalis, Diatraea grandiosella, Earias insulana, Elasmopalpus lignosellus, Eupoecilia ambiguella, Feltia subterranea, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera scitella, Lithocolletis blancardella, Lobesia botrana, Loxostege sticticalis, Lymantria dispar, Lymantria monacha, Lyonetia clerkella, Manduca sexta, Malacosoma neustria, Mamestra brassicae, Mocis repanda, Operophthera brumata, Orgyia pseudotsugata, Ostrinia nubilalis, Pandemis heparana, Panolis flammea, Pectinophora gossypiella, Phthorimaea operculella, Phyllocnistis citrella, Pieris brassicae, Plathypena scabra, Platynota stultana, Plutella xylostella, Prays citri, Prays oleae, Prodenia sunia, Prodenia ornithogalli, Pseudoplusia includens, Rhyacionia frustrana, Scrobipalpula absoluta, Sesamia inferens, Sparganothis pilleriana, Spodoptera frugiperda, Spodoptera littoralis, Spodoptera litura, Syllepta derogata, Synanthedon myopaeformis, Thaumatopoea pityocampa, Tortrix viridana, Trichoplusia ni, Tryporyza incertulas, Zeiraphera canadensis,* furthermore *Galleria mellonella* and *Sitotroga cerealella, Ephestia cautella, Tineola bisselliella;* from the order of the beetles (Coleoptera), for example *Agriotes lineatus, Agriotes obscurus, Anthonomus grandis, Anthonomus pomorum, Apion vorax, Atomaria linearis, Blastophagus piniperda, Cassida nebulosa, Cerotoma trifurcata, Ceuthorhynchus assimilis, Ceuthorhynchus napi, Chaetocnema tibialis, Conoderus vespertinus, Crioceris asparagi, Dendroctonus refipennis, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllopertha horticola, Phyllophaga sp., Phyllotreta chrysocephala, Phyllotreta nemorum, Phyllotreta striolata, Popillia japonica, Psylliodes napi, Scolytus intricatus, Sitona lineatus,* furthermore *Bruchus rufimanus, Bruchus pisorum, Bruchus lentis, Sitophilus granaria, Lasioderma serricorne, Oryzaephilus surinamensis, Rhyzopertha dominica, Sitophilus oryzae, Tribolium castaneum, Trogoderma granarium, Zabrotes subfasciatus;* from the order of the dipterans (Diptera), for example *Anastrepha ludens, Ceratitis capitata, Contarinia sorghicola, Dacus cucurbitae, Dacus oleae, Dasineura brassicae, Delia coarctata, Delia radicum, Hydrellia griseola, Hylemyia platura, Liriomyza sativae, Liriomyza trifolii, Mayetiola destructor, Orseolia oryzae, Oscinella frit, Pegomya hyoscyami, Phorbia antiqua, Phorbia brassicae, Phorbia coarctata, Rhagoletis cerasi, Rhagoletis pomonella, Tipula oleracea, Tipula paludosa,* furthermore *Aedes aegypti, Aedes vexans, Anopheles maculipennis, Chrysomya bezziana, Chrysomya* hominivorax, Chrysomya macellaria, Cordylobia anthropophaga, Culex pipiens, Fannia canicularis, Gasterophilus intestinalis, Glossina morsitans, Haematobia irritans, Haplodiplosis equestris, Hypoderma lineata, Lucilia caprina, Lucilia cuprina, Lucilia sericata, Musca domestica, Muscina stabulans, Oestrus ovis, Tabanus bovinus, Simulium damnosum;

from the order of the thrips (Thysanoptera), for example Frankliniella fusca, Frankliniella occidentalis, Frankliniella tritici, Haplothrips tritici, Scirtothrips citri, Thrips oryzae, Thrips palmi, Thrips tabaci;

from the order of the hymenopterans (Hymenoptera), for example Athalia rosae, Atta cephalotes, Atta sexdens, Atta texana, Hoplocampa minuta, Hoplocampa testudinea, Iridomyrmes humilis, Iridomyrmex purpureus, Monomorium pharaonis, Solenopsis geminata, Solenopsis invicta, Solenopsis richteri;

from the order of the heteropterans (Heteroptera), for example Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus hesperus, Lygus lineolaris, Lygus pratensis, Nezara viridula, Piesma quadrata, Solubea insularis, Thyanta perditor;

from the order of the homopterans (Homoptera), for example Acyrthosiphon onobrychis, Acyrthosiphon pisum, Adelges laricis, Aonidiella aurantii, Aphidula nasturtii, Aphis fabae, Aphis gossypii, Aphis pomi, Aulacorthum solani, Bemisia tabaci, Brachycaudus cardui, Brevicoryne brassicae, Dalbulus maidis, Dreyfusia nordmannianae, Dreyfusia piceae, Dysaphis radicola, Empoasca fabae, Eriosoma lanigerum, Laodelphax striatella, Macrosiphum avenae, Macrosiphum euphorbiae, Macrosiphon rosae, Megoura viciae, Metopolophium dirhodum, Myzus persicae, Myzus cerasi, Nephotettix cincticeps, Nilaparvata lugens, Perkinsiella saccharicida, Phorodon humuli, Planococcus citri, Psylla mali, Psylla piri, Psylla pyricol, Quadraspidiotus perniciosus, Rhopalosiphum maidis, Saissetia oleae, Schizaphis graminum, Selenaspidus articulatus, Sitobion avenae, Sogatella furcifera, Toxoptera citricida, Trialeurodes abutilonea, Trialeurodes vaporariorum, Viteus vitifolii;

from the order of the termites (Isoptera), for example Calotermes flavicollis, Leucotermes flavipes, Macrotermes subhyalinus, Odontotermes formosanus, Reticulitermes lucifugus, Termes natalensis;

from the order of the orthopterans (Orthoptera), for example Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Schistocerca americana, Schistocerca peregrina, Stauronotus maroccanus, Schistocerca gregaria, furthermore Acheta domestica, Blatta orientalis, Blattella germanica, Periplaneta americana;

from the order of the Arachnoidea, for example phytophagous mites, such as Aculops lycopersicae, Aculops pelekassi, Aculus schlechtendali, Brevipalpus phoenicis, Bryobia praetiosa, Eotetranychus carpini, Eutetranychus banksii, Eriophyes sheldoni, Oligonychus pratensis, Panonychus ulmi, Panonychus citri, Phyllocoptruta oleivora, Polyphagotarsonemus latus, Tarsonemus pallidus, Tetranychus cinnabarinus, Tetranychus kanzawai, Tetranchus pacificus, Tetranychus urticae, ticks, such as Amblyomma americanum, Amblyomma variegatum, Argas persicus, Boophilus annulatus, Boophilus decoloratus, Boophilus microplus, Dermacentor silvarum, Hyalomma truncatum, Ixodes ricinus, Ixodes rubicundus, Ornithodorus moubata, Otobius megnini, Rhipicephalus appendiculatus and Rhipicephalus evertsi, and also animal-parasitic mites, such as Dermanyssus gallinae, Psoroptes ovis and Sarcoptes scabiei;

from the class of the nematodes, for example root knot nematodes, eg. Meloidogyne hapla, Meloidogyne incognita, Meloidogyne javanica, cyst-forming nematodes, eg. Globodera pallida, Globodera rostochiensis, Heterodera avenae, Heterodera glycines, Heterodera schachtii, migratory endoparasites and semi-endoparasitic nematodes, eg. Heliocotylenchus multicinctus, Hirschmanniella oryzae, Hoplolaimus spp, Pratylenchus brachyurus, Pratylenchus fallax, Pratylenchus penetrans, Pratylenchus vulnus, Radopholus similis, Rotylenchus reniformis, Scutellonema bradys, Tylenchulus semipenetrans, stem eel worms and foliar nematodes, eg. Anguina tritici, Aphelenchoides besseyi, Ditylenchus angustus, Ditylenchus dipsaci, and vectors of viruses, eg. Longidorus spp, Trichodorus christei, Trichodorus viruliferus, Xiphinema index, Xiphinema mediterraneum.

The active ingredients can be applied as such, in the form of their formulations or in the form of the use forms prepared therefrom, eg. in the form of ready-to-spray solutions, powders, suspensions or dispersions, emulsions, oil dispersions, pastes, dusts, materials for spreading, or granules, by means of spraying, atomizing, dusting, spreading or pouring. The use forms depend entirely on the intended uses; in any case, they should guarantee the finest possible distribution of the active ingredients according to the invention.

When used as fungicides, some of the compounds of the formula I have a systemic action. They can be employed against a broad spectrum of phytopathogenic fungi, in particular from the class of the Ascomycetes, Deuteromycetes Phycomycetes and Basidiomycetes in the form of foliar- and soil-acting fungicides.

They are particularly important for controlling a large number of fungi on a variety of crop plants such as wheat, rye, barley, oats, rice, maize, lawns, cotton, soya beans, coffee, sugar cane, grape vine, fruit species, ornamentals, vegetable species such as cucumbers, beans and cucurbits, and on the seeds of these plants.

The compounds I are especially suitable for controlling the following plant diseases:

Erysiphe graminis (powdery mildew) in cereals,
Erysiphe cichoracearum and Sphaerotheca fuliginea in cucurbits,
Podosphaera leucotricha in apples,
Uncinula necator in grape vines,
Puccinia species in cereals,
Rhizoctonia species in cotton and lawns,
Ustilago species in cereals and sugar cane,
Venturia inaequalis (scab) in apples,
Helminthosporium species in cereals,
Septoria nodorum in wheat,
Botrytis cinerea (gray mold) in strawberries, grape vines,
Cercospora arachidicola in groundnuts,
Pseudocercosporella herpotrichoides in wheat, barley,
Pyricularia oryzae in rice,
Phytophthora infestans in potatoes and tomatoes,
Fusarium and Verticillium species in a variety of plants,
Plasmopara viticola in grape vines,
Alternaria species in vegetables and fruit.

The novel compounds can also be employed in the protection of materials (protection of wood), for example against Paecilomyces variotii.

They can be converted into the customary formulations, such as solutions, emulsions, suspensions, dusts, powders, pastes or granules. The use forms depend on the application in question; in any case, they should guarantee the finest possible distribution of the active ingredients.

The formulations are prepared in a known manner, for example by extending the active ingredient with solvents and/or carriers, if desired using emulsifiers and dispersants, it also being possible to use other organic solvents as auxiliary solvents if water is used as the diluent.

Auxiliaries for this purpose are essentially:

Solvents, such as aromatics (eg. xylene), chlorinated aromatics (eg. chlorobenzenes), paraffins (eg. mineral oil fractions), alcohols (eg. methanol, butanol), ketones (eg. cyclohexanone), amines (eg. ethanolamine, dimethylformamide) and water;

carriers such as ground natural minerals (eg. kaolins, clays, talc, chalk) and ground synthetic minerals (eg. highly-disperse silica, silicates);

emulsifiers, such as non ion and anionic emulsifiers (eg. polyoxyethylene fatty alcohol ethers, alkylsulfonates and arylsulfonates) and dispersants such as lignosulfite waste liquors and methylcellulose.

Suitable surface-active substances are the alkali metal, alkaline earth metal and ammonium salts of aromatic sulfonic acids, for example lignosulfonic acid, phenolsulfonic acid, naphthalenesulfonic acid and dibutylnaphthalenesulfonic acid, and of fatty acids, alkyl- and alkylarylsulfonates, alkyl sulfates, lauryl ether sulfates and fatty alcohol sulfates, and also salts of sulfated hexa-, hepta- and octadecanols, and of fatty alcohol glycol ethers, condensation products of sulfonated naphthalene and its derivatives with formaldehyde, condensation products of naphthalene or of the naphthalenesulfonic acids with phenol and formaldehyde, polyoxyethylene octylphenol ether, ethoxylated isooctyl-, octyl- or nonylphenol, alkylphenol [sic] polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene [sic], lauryl alcohol polyglycol ether acetate, sorbitol esters, lignosulfite waste liquors or methylcellulose.

Aqueous use forms can be prepared from emulsion concentrates, dispersions, pastes, wettable powders or water dispersible granules by adding water. To prepare emulsions, pastes or oil dispersions, the substrates [sic], as such or dissolved in an oil or solvent, can be homogenized in water by means of wetting agents, tackifiers, dispersants or emulsifiers. Alternatively, it is possible to prepare concentrates composed of active ingredient, wetting agents, tackifiers, dispersants or emulsifiers and, if desired, solvents or oil, and these are suitable for dilution with water.

Powders, materials for spreading and dusts can be prepared by mixing or concomitantly grinding the active ingredients with a solid carrier.

Granules, for example coated granules, impregnated granules and homogeneous granules, can be prepared by binding the active ingredients to solid carriers.

Solid carriers are mineral earths such as silica gel, silicic acids, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate, ureas and products of vegetable origin, such as cereal meal, tree bark meal, wood meal and nutshell meal, cellulose powder, or other solid carriers.

The active ingredient concentrations in the ready-to-use preparations can be varied within relatively wide ranges.

Quite generally, the compositions comprise from 0.0001 to 95% by weight of active ingredient.

Formulations comprising more than 95% by weight of active ingredient can be applied successfully by the ultralow-volume method (ULV), it even being possible to use the active ingredient without additives.

For use as fungicides, concentrations of from 0.01 to 95% by eight, preferably from 0.5 to 90% by weight, of active ingredient are recommended. Formulations which are suitable for use as insecticides comprise 0.0001 to 10% by weight, preferably 0.01 to 1% by weight, of active ingredient.

The active ingredients are normally employed in a purity of 90% to 100%, preferably 95% to 100% (according to NMR spectrum).

Examples of such preparations are:

I. a solution of 90 parts by weight of a compound I according to the invention and 10 parts by weight of N-methyl-α-pyrrolidone, which is suitable for use in the form of microdrops;

II. a solution of 20 parts by weight of a compound I according to the invention in a mixture of 80 parts by weight of alkylated benzene, 10 parts by weight of the adduct of 8 to 10 mol of ethylene oxide to 1 mol of oleic acid N-monoethanolamide, 5 parts by weight of the calcium salt of dodecylbenzenesulfonic acid, 5 parts by weight of the adduct of 40 mol of ethylene oxide to 1 mol of castor oil; a dispersion is obtained by finely distributing the formulation in water.

III. a solution of 20 parts by weight of a compound I according to the invention in a mixture of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil; a dispersion is obtained by finely distributing the formulation in water.

IV. an aqueous dispersion of 20 parts by weight of a compound I according to the invention in a mixture of 25 parts by weight of cyclohexanone, 65 parts by weight of a mineral oil fraction of boiling point 210 to 280° C. and 10 parts by weight of the adduct of 40 mol of ethylene oxide to 1 mol of castor oil; a dispersion is obtained by finely distributing the formulation in water.

V. a mixture of 20 parts by weight of a compound I according to the invention, 3 parts by weight of sodium diisobutylnaphthalene-α-sulfonate, 17 parts by weight of sodium lignosulfonate from a sulfite waste liquor and 60 parts by weight of pulverulent silica gel, ground in a hammer mill; a spray mixture is obtained by finely distributing the mixture in water;

VI. an intimate mixture of 3 parts by weight of a compound I according to the invention and 97 parts by weight of finely particulate kaolin; this dust comprises 3% by weight of active ingredient;

VII. an intimate mixture of 30 parts by weight of a compound I according to the invention, 92 parts by weight of pulverulent silica gel and 8 parts by weight of liquid paraffin which was sprayed onto the surface of this silica gel; this formulation imparts good adhesion properties to the active ingredient;

VIII. a stable aqueous dispersion of 40 parts by weight of a compound I according to the invention, 10 parts by weight of the sodium salt of a phenosulfonic [sic] acid/urea/formaldehyde condensate, 2 parts by weight of silica gel and 48 parts by weight of water, which can be diluted further;

IX. a stable oily dispersion of 20 parts by weight of a compound I according to the invention, 2 parts by weight of calcium dodecylbenzenesulfonate, 8 parts by weight of fatty alcohol polyglycol ether, 2 parts by weight of the sodium salt of a phenolsulfonic acid/urea/formaldehyde condensate and 68 parts by weight of a paraffinic mineral oil;

X. a mixture of 10 parts by weight of a compound I according to the invention, 4 parts by weight of sodium diisobutylnaphthalene-α-sulfonate, 20 parts by weight of sodium lignosulfonate from a sulfite waste liquor, 38 parts by weight of silica gel and 38 parts by weight of kaolin, ground in a hammer mill. A spray mixture comprising 0.1% by weight of the active ingredient is obtained by finely distributing the mixture in 10 000 parts by weight of water.

The compounds I are applied by treating the fungi, or the seeds, plants, materials or the soil to be protected against fungal infection, with a fungicidally active amount of the active ingredients.

Application is effected before or after infection of the materials, plants or seeds with the fungi.

Depending on the nature of the desired effect, the rates are from 0.02 to 3 kg of active ingredient per ha, preferably 0.1 to 1 kg/ha.

In the treatment of seed, amounts of from 0.001 to 50 g, preferably 0.01 to 10 g, of active ingredient are generally required per kilogram of seed.

In the open, the rate required for controlling pests is from 0.02 to 10, preferably 0.1 to 2.0, kg of active ingredient per ha.

The compounds I, alone or in combination with herbicides or fungicides, can also be applied jointly in the form of a mixture with other crop protection products, for example growth regulators or pesticides or bactericides. Also of interest is the miscibility with fertilizers or with mineral salt solutions, which are employed for treating nutrient and trace element deficiencies.

The crop protection products and fertilizers can be added to the compositions according to the invention in a ratio by weight of 1:10 to 10:1, if appropriate also just before application (tank mix). In many cases, mixing them with fungicides or insecticides results in a widening of the fungicidal spectrum of action.

The following list of fungicides together with which the compounds according to the invention can be used is intended to illustrate possible combinations, but not to limit them:

sulfur, dithiocarbamates and their derivatives, such as iron (III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfides [sic], ammonia complex of zinc (N,N-ethylenebisdithiocarbamate), ammonia complex of zinc (N,N'-propylenebisdithiocarbamate), zink (N,N'-propylenebisdithiocarbamate), N,N'-polypropylenebis (thiocarbamoyl)disulfide; nitro derivatives, such as dinitro(1-methylheptyl)phenyl crotonate, 2-sec-butyl-4,6-dinitrophenyl 3,3-dimethylacrylate, 2-sec-butyl-4,6-dinitrophenyl isopropyl carbonate, di-isopropyl 5-nitroisophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-β-[bis-(dimethylamino)phosphinyl]-3-phenyl-1,2,4-triazole, 2,3-dicyano-1,4-dithioanthraquinone, 2-thio-1,3-dithiolo-β-[4,5-b]quinoxaline, methyl 1-(butylcarbamoyl)-2-benzimidazolecarbamate, 2-methoxycarbonylaminobenzimidazole, 2-(furyl-(2))-benzimidazole, 2-(thiazolyl-(4))-benzimidazole, N-(1,1,2,2-tetrachloroethylthio)-tetrahydrophthalimide, N-trichloromethylthio-tetrahydrophthalimide, N-trichloromethylthiophthalimide, N-dichlorofluoromethylthio-N',N'-dimethyl-N-phenylsulfuric diamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, 2-thiopyridine 1-oxide, 8-hydroxyquinoline or its copper salt, 2,3-dihydro-5-carboxanilido-6-methyl-1,4-oxathiin, 2,3-dihydro-5-carboxanilido-6-methyl-1,4-oxathiin 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, 2,5-dimethylfuran-3-carboxylic acid cyclohexylamide, N-cyclohexyl-N-methoxy-2,5-dimethylfuran-3-carboxamide, 2-methylbenzoanilide, 2-iodobenzoanilide, N-formyl-N-morpholine-2,2,2-trichloroethyl acetal, piperazine-1,4-diylbis(1-(2,2,2-trichloroethyl)formamide, 1-(3,4-dichloroanilino)-1-formylamino-2,2,2-trichloroethane, 2,6-dimethyl-N-tridecylmorpholine or its salts, 2,6-dimethyl-N-cyclodedecylmorpholine or its salts, N-[3-(p-tert-butylphenyl)-2-methylpropyl]-cis-2,6-dimethylmorpholine, N-[3-(p-tert-butylphenyl)-2-methylpropyl]-piperidine, 1-[2-(2,4-dichlorophenyl)-4-ethyl-1,3-dioxolan-2-ylethyl]-1H-1,2,4-triazole, 1-[2-(2,4-dichlorophenyl)-4-n-propyl-1,3-dioxolan-2-yl-ethyl]-1H-1,2,4-triazole, N-(n-propyl)-N-(2,4,6-trichlorophenoxyethyl)-N'-imidazolylurea, 1-(4-chlorophenoxy)-3,3-dimethyl- 1-(1H-1,2,4-triazol-1-yl)-2-butanone, 1-(4-chlorophenoxy)-3,3-dimethyl-1-(1H-1,2,4-triazol-1-yl)-2-butanol, α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene, and a variety of fungicides such as dodecylguanidine acetate, 3-[3-(3,5-dimethyl-2-oxycyclohexyl)-2-hydroxyethyl]-glutarimide, hexachlorobenzene, DL-methyl N-(2,6-dimethylphenyl)-N-furoyl(2)-alaninate, DL-methyl N-(2,6-dimethylphenyl)-N-(2'-methoxyacetyl)alaninate, N-(2,6-dimethylphenyl)-N-chloroacetyl-D,L-2-aminobutyrolactone, DL-methyl N-(2,6-dimethylphenyl)-N-(phenylacetyl)alaninate, 5-methyl-5-vinyl-3-(3,5-dichlorophenyl)-2,4-dioxo-1,3-oxazolidine, 3-[3,5-dichlorophenyl(5-methyl-5-methoxymethyl]-1,3-oxazolidine-2,4-dione [sic], 3-(3,5-dichlorophenyl)-1-isopropylcarbamoylhydantoin, N-(3,5-dichlorophenyl)-1,2-dimethylcyclopropane-1,2-dicarboximide, 2-cyano-[N-(ethylaminocarbonyl)-2-methoximino]-acetamide, 1-[2-(2,4-dichlorophenyl)-pentyl]-1H-1,2,4-triazole, 2,4-difluoro-α-(1H-1,2,4-triazolyl-1-methyl)-benzhydryl alcohol, N-(3-chloro-2,6-dinitro-4-trifluoromethylphenyl)-5-trifluoromethyl-3-chloro-2-aminopyridine and 1-((bis(4-fluorophenyl)-methylsilyl)-methyl)-1H-1,2,4-triazole.

SYNTHESIS EXAMPLES

The protocols described in the Synthesis Examples which follow were used for obtaining other compounds I by altering the starting compounds accordingly. The compounds thus obtained together with the physical data are listed in the Table which follows.

Example 1

Methyl α-(3-iodophenoxy)crotonate

A solution of 11 g (0.05 mol) of 3-iodophenol is added dropwise at 0 to 5° C. to a solution of 3 g (0.055 mol) of KOH in 30 ml of dimethylformamide. 9 g (0.05 mol) of methyl 3-bromocrotonate are added at this temperature, and stirring of the solution is continued for one hour at room temperature. The mixture is treated with ice-water and extracted using methyl tert-butyl ether, and the methyl tert-butyl ether phase is dried over $Na_2SO_4$ and concentrated in vacuo. The residue is purified by chromatography on silica gel (cyclohexane/ethyl acetate: 99/1). This gives 9.7 g (61% of theory) of the title compound as an oil.

$^1$H NMR ($COCl_3$, δ scale)=1.83 (d, 3H); 3.73 (s, 3H); 6.75 (q, 1H); 6.80–7.40 (m, 4H).

Example 2

Methyl 2-(4'-chlorobiphenyl-4'-yloxy)but-2-enoate

A mixture of 2.2 g (0.07 mol) of methyl α-(3-iodophenoxy)crotonate, 1.8 g (0.021 mol) of $NaHCO_3$, 1.1 g (0.007 mol) of 4-chlorophenylboronic acid and 20 mg of palladium tetrahistriphenylphosphine [sic] in 30 ml of water and 30 ml of dimethoxyethane is refluxed for 3 hours. Working-up is carried out by extraction using diethyl ether, drying the diethyl ether phase over $Na_2SO_4$ and evaporating the solvent in vacuo.

The residue is purified by chromatography on silica gel (cyclohexane/ethyl acetate: 98/2). This gives 2.2 g (90% of theory) of the title compound as an oil.

$^1$H NMR ($COCl_3$, δ scale)=1.82 (d, 3H); 3.8 (s, 3H); 6.73 (q, 1H); 6.82–7.55 (m, 8H).

Example 3

Methyl 2-[(3'-acetylphenyl)methylamino]but-2-enoate

A mixture of 4.7 g (0.032 mol) of 1-(3-methylaminophenyl)ethanone, 100 mg of p-toluenesulfonic acid and 3.7 g (0.07 mol) of methyl 2-oxobutyrate in 100 ml of toluene is heated for 4 hours on a water separator. The reaction mixture is evaporated in vacuo and the residue is purified by column chromatography over silica gel (cyclohexane/ethyl acetate: 95/5). This gives 3.4 g (69% of theory) of the title compound as a solid (m.p.=73°–76° C.).

$^1$H NMR: ($COCl_3$, δ scale)=1.81 (d, 3H), 2.61 (s, 3H); 3.09 (s, 3H); 3.79 (s, 3H); 6.76 (g, 1H); 7.10–7.60 (m, 4H).

Example 4

Methyl 2-{3-[1-(1-m-tolylethoxyimino)ethyl]phenyl-N-methylaminobutenoate

A mixture of 1.2 g of methyl 2-[(3'-acetylphenyl)methylamino]but-2-enoate, 0.72 g (0.005 mol) of 1-(4-methylphenyl)ethylhydroxylamine, 2 g of $MgSO_4$ [sic] and 100 mg of Dowex® in 100 ml of dry methanol is refluxed for 3 hours.

Working-up is carried out by evaporating the reaction solution in vacuo and subsequently chromatographing the residue on silica gel (cyclohexane/ethyl acetate: 97/3). This gives 1.2 g (63% of theory) of the title compound as an oil.

$^1$H NMR ($COCl_3$, δ scale) =1.62 (d, 3H); 1.82 (d, 3H); 2.21 (s, 3H); 2.29 (s, 3H); 3.05 (s, 3H); 3.75 (s, 3H); 5.24 (g, 1H); 6.60–7.25 (m, 8H).

TABLE

| No. | R$^1$U | R$^2$ | V | X | Y | Z | R$^3$ | R$^4$ | Physical data |
|---|---|---|---|---|---|---|---|---|---|
| 01 | OCH$_3$ | CH$_3$ | O | CH | CH | CH | H | C$_6$H$_5$ | $^1$H: 1.80(d, 3H); 3.74(s, 3H); 6.74(g, 1H) ; 6.75–7.40(m, 9H) |
| 02 | OCH$_3$ | CH$_3$ | O | CH | CH | CH | H | 2-Cl—C$_6$H$_4$ | $^1$H: 1.81(d, 3H); 6.77(g, 1H); 6.90–7.45(m, 8H) |
| 03 | OCH$_3$ | CH$_3$ | O | CH | CH | CH | H | 3-Cl—C$_6$H$_4$ | $^1$H: 1.80(d, 3H); 3.75(s, 3H); 6.71(g, 1H); 6.82–7.55(m, 8H) |
| 04 | OCH$_3$ | CH$_3$ | O | CH | CH | CH | H | 4-Cl—C$_6$H$_4$ | $^1$H: 1.82(d, 3H); 3.8(s, 3H); 6.73(g, 1H); 6.85–7.50(m, 8H) |
| 05 | OCH$_3$ | CH$_3$ | O | C—CH$_3$ | CH | CH | H | C$_6$H$_5$ | $^1$H: 1.81(d, 3H); 2.30(s, 3H); 6.60–7.40(m, 8H) |
| 06 | OCH$_3$ | CH$_3$ | O | CH | CH | CH | H | CH=NOCH$_2$-(4-Cl—C$_6$H$_4$) | m.p.: 66–68° C. |
| 07 | OCH$_3$ | CH$_3$ | O | CH | CH | CH | H | CH=CH-[4-Cl,3-(4-Cl—C$_6$H$_4$)-isoxazol-5-yl] | m.p.: 141–143° C. |
| 08 | OCH$_3$ | CH$_3$ | O | CH | CH | CH | W | CH=CH-(3-CH$_3$—C$_6$H$_4$) | $^1$H: 1.80(d, 3H); 2.38(s, 3H); 3.15(s, 3H); 6.76(g, 1H); 7.00–7.45(m, 8H) |
| 09 | OCH$_3$ | CH$_3$ | O | CH | CH | CH | H | 3,4-Cl$_2$—C$_6$H$_3$ | m.p.: 83–85° C. |
| 10 | OCH$_3$ | CH$_3$ | d | CH | CH | CH | H | 3,5-Cl$_2$—C$_6$H$_3$ | $^1$H: 1.80(d, 3H); 3.72(s, 3H); 6.75(g, 1H); 6.85–7.45(m, 7H) |
| 11 | OCH$_3$ | CH$_3$ | O | CH | CH | CH | H | 3-F—C$_6$H$_4$ | $^1$H: 1.78(d, 3H); 3.78(s, 3H); 6.78(s, 3H); 6.78(g, 1H); 6.90–7.40(m, 8H) |
| 12 | OCH$_3$ | CH$_3$ | O | CH | CH | CH | H | 3-CH$_3$—C$_6$H$_4$ | $^1$H: 1.80(d, 3H); 2.41(s, 3H; 6.78 (g, 1H); 6.90–7.40(m, 8H) |
| 13 | OCH$_3$ | CH$_3$ | O | CH | CH | CH | H | C$_6$H$_4$—C$_6$H$_5$ | m.p.: 109–110° C. |
| 14 | OCH$_3$ | CH$_3$ | O | CH | CH | CH | H | 4-C(CH$_3$)$_3$—C$_6$H$_4$ | $^1$H: 1.35(s, 9H); 1.82(d, 3H); 3.70(s, 3H); 6.74(g, 1H); 6.90–7.45(m, 8H) |
| 15 | OCH$_3$ | CH$_3$ | O | CH | CH | CH | H | 4-OCH$_3$—C$_6$H$_4$ | $^1$H: 1.80(d, 3H); 3.72(s, 3H); 3.82(s, 3H); 6.75(g, 1H); 6.90–7.50(m, 8H) |

TABLE-continued

| No. | R¹U | R² | V | X | Y | Z | R³ | R⁴ | Physical data |
|---|---|---|---|---|---|---|---|---|---|
| 16 | OCH$_3$ | CH$_3$ | O | CH | CH | CH | H | 3-OCH$_3$—C$_6$H$_4$ | $^1$H: 1.82(d, 3H); 3.73(s, 3H); 3.84(s, 3H); 6.72(g, 1H); 6.85–7.35(m, 8H) |
| 17 | OCH$_3$ | CH$_3$ | O | CH | CH | CH | H | 2,3-[OCH$_2$CH$_2$O]—C$_6$H$_3$ | $^1$H: 1.83(d, 3H); 3.70(s, 3H); 4.30(s, 4H); 6.73(g, 1H); 6.80–7.35(m, 7H) |
| 18 | OCH$_3$ | CH$_3$ | O | CH | CH | CH | H | 3,5-(CF$_3$)$_2$—C$_6$H$_3$ | $^1$H: 1.82(d, 3H); 3.74(s, 3H); 6.72(g, 1H); 6.90–7.30(m, 4H); 7.90(s, 1H); 8.00(s, 1H) |
| 19 | OCH$_3$ | CH$_3$ | O | CH | CH | CH | H | 6-OCH$_3$-naphthalen-2-yl | m.p.: 101–103° C. |
| 20 | OCH$_3$ | CH$_3$ | O | CH | CH | CH | H | 4-CH$_3$—C$_6$H$_4$ | $^1$H: 1.80(d, 3H); 2.38(s, 3H); 3.80(s, 3H); 6.72(g, 1H); 6.80–7.50(m, 8H) |
| 21 | OCH$_3$ | CH$_3$ | O | CH | CH | CH | H | 3-NH$_2$—C$_6$H$_4$ | $^1$H: 1.82(d, 3H); (s, 3H); 6.60–7.25(m, 8H) |
| 22 | OCH$_3$ | CH$_3$ | O | CH | CH | CH | H | Naphthalen-2-yl | $^1$H: 1.84(d, 3H); 3.72(s, 3H); 6.68(g, 1H); 7.00–8.00(m, 11H) |
| 23 | OCH$_3$ | CH$_3$ | O | N | CH | CH | H | 3,4-(CH$_3$)$_2$—C$_6$H$_3$ | m.p.: 85–87° C. |
| 24 | OCH$_3$ | CH$_3$ | O | CH | CH | CH | H | NH—C$_6$H$_5$ | $^1$H: 1.82(d, 3H); 3.72(s, 3H); 5.70(s, 1H); 6.40(dd, 1H); 6.90–7.3(m, 8H); 6.60–7.25(m, 9H) |
| 25 | OCH$_3$ | CH$_3$ | O | CH | CH | CH | H | C(CH3)=NO—CH$_2$-[4-Cl—C$_6$H$_4$] | $^1$H: 1.78(d, 3H); 2.25(s, 3H); 3.80(s, 3H); 5.15(s, 2H); 6.70(g, 1H) |
| 26 | OCH$_3$ | CH$_3$ | O | CH | CH | CH | H | CH=NO—CH(CH$_3$)-[4-Cl—C$_6$H$_4$] | $^1$H: 1.55(d, 3H); 1.77(d, 3H); 3.70(s, 3H); 5.30(g, 1H); 6.70 (g, 1H); 6.90–7.30(m, 8H); 8.05(s, 1H) |
| 27 | OCH$_3$ | CH$_3$ | O | CH | CH | CH | H | 1-CH=CH$_2$, 1-CO$_2$CH$_3$-oxiran-2-yl | $^1$H: 1.72(d, 3H); 3.75(s, 3H); 4.45(s, 1H); 5.25(d, 1H); 5.41 (d, 1H), 5.90(dd, 1H), 6.75–7.25(m, 5H) |
| 28 | OCH$_3$ | CH$_3$ | O | CH | CH | CH | H | CHO | $^1$H: 1.80(d, 3H); 3.70(s, 3H); 6.80(g, 1H); 7.3–7.6(m, 4H); 10.0(s, 1H) |
| 29 | OCH$_3$ | CH$_3$ | O | CH | CH | CH | H | COCH$_3$ | $^1$H: 1.81(d, 3H); 2.61(s, 3H); 3.75(s, 3H); 3.75(s, 3H); 6.75 (g, 1H); 7.10–7.60(, 4H) |
| 30 | OCH$_3$ | CH$_3$ | O | CH | CH | CH | H | I | $^1$H: 1.83(d, 3H); 3.73(s, 3H); 6.75(g, 1H); 6.8–7.4(m, 4H) |
| 31 | OCH$_3$ | CH$_3$ | O | N | CH | CH | H | 3-Cl—C$_6$H$_4$ | IR(cm$^{-1}$): 1731, 1593, 1567, 1439, 1315, 1278 |
| 32 | OCH$_3$ | CH$_3$ | O | N | CH | CH | H | 2-Cl—C$_6$H$_4$ | IR(cm$^{-1}$): 1732, 1589, 1577, 1442, 1319, 1238 |
| 33 | OCH$_3$ | CH$_3$ | O | N | CH | CH | H | 4-Cl—C$_6$H$_4$ | IR(cm$^{-1}$): 1732, 1594, 1580, 1444, 1241, 796 |
| 34 | OCH$_3$ | CH$_3$ | O | N | CH | CH | H | 3-CH$_3$—C$_6$H$_4$ | IR(cm$^{-1}$): 1733, 1575, 1440, 1317, 1244, 783 |
| 35 | OCH$_3$ | CH$_3$ | O | CH | CH | CH | H | C(CH$_3$)=NOCH$_3$ | $^1$H: 1.76(d, 3H); 2.20(s, 3H); 3.70(s, 3H); 4.00(s, 3H); 6.70 (g, 1H); 6.90–7.35(m, 4H) |
| 36 | OCH$_3$ | CH$_3$ | O | CH | CH | CH | H | CH=NOCH$_3$ | $^1$H: 1.80(d, 3H); 3.72(s, 3H); 4.00(s, 3H); 4.00(s, 3H); 6.70 (g, 1H); 6.82–7.40(m, 4H); 8.05 (s, 1H) |
| 37 | OCH$_3$ | CH$_3$ | N(CH$_3$) | CH | CH | CH | H | C(CH$_3$)=NOCH$_3$ | $^1$H: 1.72(d, 3H); 2.20(s, 3H); 3.10(s, 3H); 3.70(s, 3H); 4.00 (s, 3H); 6.82–7.40(m, 4H); 8.05 (s, 1H); 6.60(dd, 1H); 6.80–7.40(m, 4H) |
| 38 | OCH$_3$ | CH$_3$ | O | CH | CH | CH | H | C(CH$_3$)=NOCH$_2$CH$_3$ | $^1$H: 1.30(t, 3H); 1.80(d, 3H); 2.20(s, 3H); 3.65(s, 3H); 4.25 (g, 2H); 6.80(g, 1H); 6.90–7.30(m, 4H) |
| 39 | OCH$_3$ | CH$_3$ | O | CH | cH | CH | H | CH=NOCH$_2$CH$_3$ | $^1$H: 1.30(t, 3H); 1.80(d, 3H); 3.68(s, 3H); 4.25(g, 2H); 6.80 (g, 1H); 6.85–7.30(m, 4H; 8.05 (s, 1H) |
| 40 | OCH$_3$ | CH$_3$ | N(CH$_3$) | CH | CH | CH | H | C(CH$_3$)=NOCH$_2$CH$_3$ | $^1$H: 1.31(t, 3H); 1.82(d, 3H); 2.25(s, 3H); 3.10(s, 3H); 3.70 (s, 3H); 4.25(g, 1H); 6.60(dd, 1H); 6.85–7.30(m, 4H) |
| 41 | OCH$_3$ | CH$_3$ | O | CH | CH | CH | H | C(CH$_3$)=NOCH(CH$_3$)$_2$ | $^1$H: 1.26(d, 6H); 1.79(d, 3H); 2.10(s, 3H); 3.70(s, 3H; 4.45 (m, 1H); 6.70(g, 1H); 6.90–7.30 (m, 4H) |

TABLE-continued

| No. | R¹U | R² | V | X | Y | Z | R³ | R⁴ | Physical data |
|---|---|---|---|---|---|---|---|---|---|
| 42 | OCH₃ | CH₃ | O | CH | CH | CH | H | CH=NOCH(CH₃)₂ | ¹H: 1.25(d, 6H); 1.80(d, 3H); 3.72(s, 3H); 4.45(m, 1H); 6.72 (g, 1H); 6.70(g, 1H); 6.90–7.30 (m, 4H) |
| 43 | OCH₃ | CH₃ | N(CH₃) | CH | CH | CH | H | C(CH₃)=NOCH(CH₃)₂ | ¹H: 1.25(d, 6H); 1.78(d, 3H); 2.05(s, 3H); 3.10(s, 3H); 3.70 (s, 3H); 4.40(m, 1H); 6.60 (g, 1H); 6.90–7.25(m, 4H) |
| 44 | OCH₃ | CH₃ | O | CH | CH | CH | H | C(CH₃)=NOCH(CH₃)—[C₆H₅] | ¹H: 1.55(d, 3H); 1.77(d, 3H); 2.25(s, 3H); 3.71(s, 3H); 5.20 (g, 1H); 6.80(g, 1H); 7.05–7.40 (m, 9H) |
| 45 | OCH₃ | CH₃ | O | CH | CH | CH | H | CH=NOCH(CH₃)—[C₆H₅] | ¹H: 1.60(d, 3H); 1.80(d, 3H); 3.72(s, 3H); 5.40(g, 1H); 6.72 (g, 1H); 6.90–7.40(m, 9H); 8.05 (s, 1H) |
| 46 | OCH₃ | CH₃ | N(CH₃) | CH | CH | CH | H | C(CH₃)=NOCH(CH₃)—[C₆H₅] | ¹H: 1.61(d, 3H); 3.09(s, 3H); 3.72(s, 3H); 5.40(g, 1H); 6.60 (g, 1H); 6.80–7.35(m, 9H) |
| 47 | OCH₃ | CH₃ | O | CH | CH | CH | H | C(CH₃)=NOCH(CH₃)-[4-CH₃—C₆H₄] | ¹H: 1.60(d, 3H); 1.80(d, 3H); 2.25(s, 3H); 2.35(s, 3H); 3.70 (s, 3H); 5.35(g, 1H); 6.80 (g, 1H); 6.90–7.30(m, 8H) |
| 48 | OCH₃ | CH₃ | O | CH | CH | CH | H | CH=NOCH(CH₃)-(4-CH₃—C₆H₄] | ¹H: 1.61(d, 3H); 1.78(d, 3H); 2.35(g, 3H); 3.68(s, 3H); 5.35 (g, 1H); 6.90–7.25(m, 8H); 8.06 (s, 1H) |
| 49 | OCH₃ | CH₃ | N(CH₃) | CH | CH | CH | H | C(CH₃)=NOCH(CH₃)-[4-CH₃—C₆H₄] | ¹H: 1.62(d, 3H); 1.82(d, 3H); 2.21(g, 3H); 2.29(g, 3H); 3.05 (g, 1H); 6.60–7.25(m, 8H) |
| 50 | OCH₃ | CH₃ | N(CH₃) | CH | CH | CH | H | C(CH₃)=NOCH(CH₃)-[4-Cl—C₆H₄] | ¹H: 1.58(d, 3H); 1.84(d, 3H); 2.25(s, 3H); 3.75(s, 3H); 5.26 (g, 1H); 6.70(g, 1H); 6.92–7.35 (m, 9H) |
| 51 | OCH₃ | CH₃ | O | CH | CH | CH | H | C(CH₃)=NOCH(CH₃)-[4-Cl—C₆H₄] | ¹H: 1.68(d, 3H); 1.78(d, 3H); 2.30(s, 3H); 3.05(s, 3H); 3.78 (s, 3H); 5.25(g, 1H); 6.45 (dd, 1H); 6.90–7.30(m, 8H) |
| 52 | OCH₃ | CH₃ | N(CH₃) | CH | CH | CH | H | C(CH₃)=NOCH₂-[4-Cl—C₆H₄] | ¹H: 1.78(d, 3H); 2.10(s, 3H); 3.75(s, 3H); 3.90(s, 2H); 5.20 (s, 2H); 6.60(dd, 1H); 6.80–7.40(m, 8H) |
| 53 | OCH₃ | CH₃ | O | CH | CH | CH | H | C(CH₃)=NOCH(CH₃)-[4-C(CH₃)₃—C₆H₄] | ¹H: 1.19(s, 9H); 1.60(d, 3H); 1.80(d, 3H); 2.25(g, 3H); 3.72 (s, 3H); 5.30(g, 1H); 6.70 (g, 1H); 7.10–7.40(m, 8H) |
| 54 | OCH₃ | CH₃ | O | CH | CH | CH | H | CH=NOCH(CH₃)-[4-C(CH₃)₃—C₆H₄] | ¹H: 1.18(s, 9H); 1.62(d, 3H); 1.82(d, 3H); 3.72(s, 3H); 5.31 (g, 1H); 7.05–7.40(m, 8H); 8.05 (s, 1H) |
| 55 | OCH₃ | CH₃ | N(CH₃) | CH | CH | CH | H | C(CH₃)=NOCH(CH₃)-[4-C(CH₃)₃—C₆H₄] | ¹H: 1.16(s, 9H); 1.64(d, 3H); 1.78(d, 3H); 3.74(s, 3H); 5.30 (q, 1H); 6.62(g, 1H); 6.90–7.40 (m, 8H) |
| 56 | OCH₃ | CH₃ | O | CH | CH | CH | H | C(CH₃)=NOCH(CH₃)-[4-OCH₃—C₆H₄] | ¹H: 1.60(d, 3H); 2.25(s, 3H); 3.75(s, 3H); 3.85(s, 3H); 5.25 (g, 1H); 6.80–7.30(m, 9H) |
| 57 | OCH₃ | CH₃ | O | CH | CH | CH | H | CH=NOCH(CH₃)-[4-OCH₃—C₆H₄] | ¹H: 1.61(d, 3H); 1.82(d, 3H); 3.75(s, 3H); 3.84(s, 3H); 5.25 (g, 1H); 6.70(g, 1H); 7.05–7.40 (m, 8H); 8.05(s, 1H) |
| 58 | OCH₃ | CH₃ | N(CH₃) | CH | CH | CH | H | C(CH₃)=NOCH(CH₃)-[4-OCH₃—C₆H₄] | ¹H: 1.62(d, 3H); 2.25(s, 3H); 3.65(s, 3H); 3.80(s, 3H); 5.25 (g, 1H); 6.60(dd, 1H); 6.80–7.40(m, 8H) |
| 59 | OCH₃ | CH₃ | O | CH | CH | CH | H | C(CH₃)=NOCH(CH₃)-[3-CF₃—C₆H₄] | ¹H: 1.65(d, 3H); 1.79(d, 3H); 2.30(s, 3H); 3.82(s, 3H); 5.28 (g, 1H); 6.70–7.30(g, 1H); 6.80–7.60(m, 8H) |
| 60 | OCH₃ | CH₃ | O | CH | CH | CH | H | CH=NOCH(CH₃)-[3-CF₃—C₆H₄] | ¹H: 1.64(d, 3H); 1.82(d, 3H); 3.70(s, 3H); 5.40(g, 1H); 6.72 (g, 1H); 6.80–7.62(m, 8H); 8.05 (s, 1H) |
| 61 | OCH₃ | CH₃ | N(CH₃) | CH | CH | CH | H | C(CH₃)=NOCH(CH₃)-[3-CF₃—C₆H₄] | ¹H: 1.65(d, 3H); 2.30(s, 3H); 3.80(s, 3H); 5.30(g, 1H); 6.75 (g, 1H); 6.82–7.60(m, 9H) |

TABLE-continued

| No. | R¹U | R² | V | X | Y | Z | R³ | R⁴ | Physical data |
|---|---|---|---|---|---|---|---|---|---|
| 62 | OCH₃ | CH₃ | O | CH | CH | CH | H | C(CH₃)=NOCH(CH₃)-[3,4-Cl₂—C₆H₃] | $^1$H: 1.68(d, 3H); 1.75(d, 3H); 2.28(s, 3H); 3.70(s, 3H); 5.25 (g, 1H); 6.70(g, 1H); 6.80–7.40 (m, 7H) |
| 63 | OCH₃ | CH₃ | O | CH | CH | CH | H | CH=NOCH(CH₃)-[3,4-Cl₂—C₆H₃] | $^1$H: 1.58(d, 3H); 1.78(d, 3H); 3.72(s, 3H); 5.22(g, 1H); 6.72 (g, 1H); 6.85–7.45(m, 7H) |
| 64 | OCH₃ | CH₃ | N(CH₃) | CH | CH | CH | H | C(CH₃)=NOCH(CH₃)-[3,4-Cl₂—C₆H₃] | $^1$H: 1.62(d, 3H); 1.76(d, 3H); 2.25(s, 3H); 3.05(s, 3H); 3.72 (s, 3H); 5.25(g, 1H); 6.60 (g, 1H); 6.80–7.40(m, 7H) |
| 65 | OCH₃ | CH₃ | N(CH₃) | CH | CH | CH | H | C₆H₅ | $^1$H: 1.75(d, 3H); 3.10(s, 3H); 6.60(g, 1H); 6.85–7.60(m, 9H) |
| 66 | OCH₃ | CH₃ | N(CH₃) | CH | CH | CH | H | 4-CH₃—C₆H₄ | m.p. = 116–117° C. |
| 67 | OCH₃ | CH₃ | N(CH₃) | CH | CH | CH | H | 4-C₆H₅—C₆H₄ | $^1$H: 1.80(d, 3H); 3.10(s, 3H); 3.72 (s, 3H); 6.60(dd, 1H); 6.80–7.80(m, 13H) |
| 68 | OCH₃ | CH₃ | O | CH | CH | CH | H | 4-{CH=NOCH(CH₃)-[4-CH₃—C₆H₅]-C₆H₄ | $^1$H: 1.60(d, 3H); 1.77(d, 3H); 2.40(s, 3H); 3.71(s, 3H); 5.35 (g, 1H); 6.72(g, 1H); 6.80–7.60 (m, 12H); 8.05(s, 1H) |
| 69 | OCH₃ | CH₃ | O | CH | CH | CH | H | 4-{CH=NOCH(CH₃)-[4-Cl—C₆H₅]-C₆H₄ | $^1$H: 1.54(d, 3H); 1.82(d, 3H); 3.72(s, 3H); 5.32(g, 1H); 6.70 (g, 1H); 6.90–7.50(m, 12H); 8.05(s, 1H) |
| 70 | OCH₃ | CH₃ | O | CH | CH | CH | H | 3-{CH=NOCH(CH₃)-[4-Cl—C₆H₅]-C₆H₄ | $^1$H: 1.55(d, 3H); 1.80(d, 3H); 3.70(s, 3H); 5.40(g, 1H); 6.80 (g, 1H); 6.90–7.70(m, 12H); 8.20(s, 1H) |
| 71 | NHCH₃ | CH₃ | O | CH | CH | CH | H | 3-{CH=NOCH(CH₃)-[4-Cl—C₆H₅]-C₆H₄ | m.p.: 110° C. |
| 72 | NHCH₃ | CH₃ | O | CH | CH | CH | H | 4-CHO—C₆H₄ | $^1$H: 1.82(d, 3H); 3.70(s, 3H); 6.78(g, 1H); 6.90–7.40(m, 4H); 7.70; 7.95(2d, 4H); 10.05 (s, 1H) |
| 73 | NHCH₃ | CH₃ | O | CH | CH | CH | H | 3-CHO—C₆H₄ | $^1$H: 1.84(d, 3H); 3.72(s, 3H); 6.70(g, 1H); 6.90–8.05(m, 8H); 10.06(s, 1H) |
| 74 | NHCH₃ | CH₃ | O | CH | CH | CH | H | COCH₃ | m.p.: 73–76° C. |
| 75 | NHCH₃ | CH₃ | O | CH | CH | CH | H | 3,4-(CH₃)₂—C₆H₃ | IR(cm$^{-1}$): 1735, 1607, 1479, 1436, 1325, 1199 |
| 76 | NHCH₃ | CH₃ | O | N | CH | CH | H | 4-CH₃—C₆H₄ | IR(cm$^{-1}$): 1732, 1595, 1571, 1445, 1239 |
| 77 | OCH₃ | CH₃ | O | N | CH | CH | H | CF₃ | $^1$H: 1.82(d, 3H); 3.70(s, 3H); 6.64(g, 1H); 7.05–7.95(m, 3H) |
| 78 | OCH₃ | CH₃ | O | N | CH | CH | H | CH(CH₃)₂ | $^1$H: 1.22(d, 6H); 1.81(d, 3H); 2.88 (sep, 1H); 3.72(s, 3H); 6.68(g, 1H); 6.75–7.60(m, 3H) |
| 79 | NHCH₃ | CH₃ | O | N | CH | CH | H | 3,4-(CH₃)₂—C₆H₃ | m.p.: 130° C. |
| 80 | OCH₃ | CH₃ | O | N | N | CH | H | 3-F—C₆H₄ | IR(cm$^{-1}$): 1735, 1566, 1431, 1270, 1133 |
| 81 | OCH₃ | CH₃ | O | N | N | CH | H | 4-Cl—C₆H₄ | m.p.: 82–83° C. |
| 82 | OCH₃ | CH₃ | O | N | N | CCH₃ | H | 3-CF₃—C₆H₄ | $^1$H: 1.83(d, 3H); 2.42(s, 3H; 2.58(s, 3H); 3.72(s, 3H); 6.75 (g, 1H); 7.20–7.40; 8.20–8.30 (m, 5H) |
| 83 | OCH₃ | CH₃ | O | N | N | CCH₃ | H | C₆H₅ | IR(cm$^{-1}$): 1734, 1561, 1433, 1390, 1264 |
| 84 | OCH₃ | CH₃ | O | N | N | CCH₃ | H | 3-Cl—C₆H₄ | $^1$H: 1.82(d, 3H); 3.78(s, 3H); 6.70(g, 1H); 6.95(d, 1H); 7.25–7.40; 8.20–8.30(2m, 4H); 8.60(d, 1H) |
| 85 | OCH₃ | CH₃ | O | N | N | CCH₃ | H | 4-F—C₆H₄ | m.p.: 73–75° C. |
| 86 | OCH₃ | CH₃ | O | N | N | CCH₃ | H | 3,4-(CH₃)₂—C₆H₃ | $^1$H: 1.8(d, 3H); 2.30, 2.35, 3.7 (in each case s, 3H); 6.7(g, 1H); 6.8, 7.2, 8.05, 8.1, 8.65(in each case d, 1H) |
| 87 | OCH₃ | CH₃ | 6 | CH | CH | CH | H | 2,4-Cl₂—C₆H₃ | $^1$H: 1.8(d, 3H); 3.80(s, 3H); 6.70 (g, 1H); 6.90–7.50(m, 7H) |
| 88 | OCH₃ | CH₃ | N(CH₃) | CH | CH | CH | H | 2,4-Cl₂—C₆H₃ | $^1$H: 1.8(d, 3H); 3.15(s, 3H); 3.7(s, 3H); 7.05(g, 1H), 6.6–7.65 (m, 7H) |

TABLE-continued

| No. | R¹U | R² | V | X | Y | Z | R³ | R⁴ | Physical data |
|---|---|---|---|---|---|---|---|---|---|
| 89 | OCH$_3$ | CH$_3$ | O | CH | CH | CH | H | 3-{C(CH$_3$)=NOCH3}-C$_6$H$_4$ | ¹H: 1.8(d, 3H); 2.15, 3.7m, 4.0 (in each case s, 3H); 6.75(g, 1H), 7.1–7.9(m, 8H) |
| 90 | OCH$_3$ | CH$_3$ | O | CH | CH | CH | H | 3-{C(CH$_3$)=NOCH(CH$_3$)$_2$}—C$_6$H$_4$ | ¹H: 1.35(d, 6H); 1.86d, 3H); 2+3+3, 85(in each case s, 3H); 4.5(hep, 1H)6.75(g, 1H); 6.85–7.9(m, 8H) |
| 91 | OCH$_3$ | CH$_3$ | N(CH$_3$) | CH | CH | CH | H | C(CH$_3$)=NOCH$_2$-[3,4-Cl$_2$—C$_6$H$_3$] | ¹H: 1.75(d, 3H); 3.05–3.76 (in each case s, 3H); 6.98(g, 1H); 6.55–7.5(m, 7H) |
| 92 | OCH$_3$ | CH$_3$ | N(CH$_3$) | CH | CH | CH | H | C(CH$_3$)=NOCH$_2$-[3-CF$_3$—C$_6$H$_4$] | ¹H: 1.75(d, 3H); 2.3, 3.1, 3.7 (in each case s, 3H); 5.15(s, 2H), 6.6–7.7(m, 9H) |
| 93 | OCH$_3$ | CH$_3$ | N(CH$_3$) | CH | CH | CH | H | C(CH$_3$)=NOCH$_2$-(3-CH$_3$—C$_6$H$_4$] | ¹H: 1.75(d, 3H); 2.1, 2.15, 3.05, 3.6(in each case s, 3H); 5.26 (s, 2H), 6.55–7.3(m, 9H) |
| 94 | OCH$_3$ | CH$_3$ | O | CH | CH | CH | H | C(CH$_3$)=NOCH$_2$-(3,4-Cl$_2$—C$_6$H$_3$) | ¹H: 1.8(d, 3H); 2.25, 3.75(in each case s, 3H); 5.15(s, 2H); 6.75 (g, 1H); 6.9–7.5(m, 7H) |
| 95 | OCH$_3$ | CH$_3$ | O | CH | CH | CH | H | C(CH$_3$)=NOCH$_2$-(3-CF$_3$—C$_6$H$_4$) | ¹H: 1.75(d, 3H); 2.3, 4.5(in each case s, 3H); 5.25(s, 2H); 6.75 (g, 1H); 6.8–7.7(m, 8H) |
| 96 | OCH$_3$ | CH$_3$ | O | CH | CH | CH | H | C(CH$_3$)=NOCH$_2$-[3-CH$_3$—C$_6$H$_4$] | ¹H: 1.86(d, 3H); 2.3, 2.4, 3.75 (in each case s, 3H); 5.2(s, 2H); 6.75 (g, 1H); 6.8–7.3(m, 8H) |
| 97 | OCH$_3$ | CH$_3$ | O | CH | CH | CH | H | CH=NOCH$_2$-[3,4-Cl$_2$—C$_6$H$_3$] | ¹H: 1.8(d, 1H); 3.85(s, 3H); 5.15(s, 2H), 6.9(g, 1H); 6.9–7.5(m, 7H) |
| 98 | OCH$_3$ | CH$_3$ | O | CH | CH | CH | H | CH=NOCH$_2$-(3-CF$_3$—C$_6$H$_4$) | ¹H: 1.78(d, 3H); 3.7(s, 3H); 5.15(s, 2H), 6.75(g, 1H); 6.8–7.75(m, 8H); 8.1(s, 1H) |
| 99 | OCH$_3$ | CH$_3$ | O | CH | CH | CH | H | CH=NOCH$_2$-(3-CH$_3$—C$_6$H$_4$) | ¹H: 1.86(d, 3H); 2.4, 3.7(in each case s, 3H); 5.2(s, 2H), 6.75(g, 1H); 7.05–7.3(m, 8H); 8.1(s, 1H) |
| 100 | OCH$_3$ | CH$_3$ | O | CH | CH | CH | H | CH$_2$O—C$_6$H$_5$ | ¹H: 1.75(d, 3H); 3.7(s, 3H); 5.05(s, 2H), 6.7(g, 1H); 6.8–7.35(m, 9H) |
| 101 | OCH$_3$ | CH$_3$ | O | CH | CH | CH | H | CH$_2$O-(2-CH3, 4-C(CH$_3$)=NOCH$_3$—C$_6$H$_3$] | ¹H: 1.8(d, 3H); 2.2, 2.3, 3.7, 3.95(in each case s, 3H); 6.75(g, 1H); 6.95–7.56(m, 7H) |
| 102 | OCH$_3$ | CH$_3$ | O | CH | CH | CH | H | C≡C—C$_6$H$_5$ | ¹H: 1.8(d, 3H); 3.70(s, 3H); 6.65(g, 1H); 6.80–7.60(m, 9H) |
| 103 | OCH$_3$ | CH$_3$ | N(CH$_3$) | CH | CH | CH | H | C≡C—C$_6$H$_5$ | ¹H: 1.78(d, 4H); 3.16(s, 3H); 7.0(g, 1H), 6.65–7.6(m, 9H) |
| 104 | OCH$_3$ | CH$_3$ | O | CH | CH | CH | H | O—C(CO$_2$CH$_3$)=CH—CH$_3$ | IR(cm⁻¹): 1731, 16.02 [sic], 1486, 1436, 1271, 1141 |
| 105 | OCH$_3$ | CH$_3$ | O | CH | CH | CH | H | CH$_2$o-[2-CH$_3$—C$_6$H$_4$] | ¹H: 1.75(d, 3H); 2.3u.3.7(in each case s, 3H); 5.1(s, 2H); 6.75(g, 1H); 6.8–7.35(m, 8H) |
| 106 | OCH$_3$ | CH$_3$ | O | CH | CH | CH | H | CH$_2$O-[2,5-(CH$_3$)$_2$—C$_6$H$_3$] | ¹H: 1.75(d, 3H); 2.25, 2.35, 3.7(in each case s, 3H); 5.1(s, 2H); 6.7–7.4(m, 7H) |
| 107 | OCH$_3$ | CH$_3$ | O | CH | CH | CH | H | CH$_2$O-[3,4-(CH$_3$)$_2$—C$_6$H$_3$] | ¹H: 1.75(d, 3H), 2.1, 2.15, 3.7(in each case s, 3H); 5.0(s, 2H); 6.65–7.3(m, 8H) |
| 108 | OCH$_3$ | CH$_3$ | O | CH | CH | CH | H | CH$_2$O-{2,5-(CH$_3$)$_2$, 4-[C(CH$_3$)=NOCH$_3$]—C$_6$H$_3$} | ¹H: 1.75(d, 3H), 2.15, 2.25, 2.3, 3.95(in each case s, 3H); 6.7–7.3(7H) |
| 109 | OCH$_3$ | CH$_3$ | O | CH | CH | CH | H | CH$_2$ON=C(CH$_3$)-[3,5-Cl$_2$—C$_6$H$_3$] | ¹H: 1.8(d, 3H), 2.2, 3.7, (in each case s, 3H); 5.2(s, 2H); 6.75(g, 1H); 6.8–7.6(m, 7H) |

TABLE-continued

| No. | $R^1U$ | $R^2$ | V | X | Y | Z | $R^3$ | $R^4$ | Physical data |
|---|---|---|---|---|---|---|---|---|---|
| 110 | $OCH_3$ | $CH_3$ | O | CH | CH | CH | H | $CH_2ON=C(CH_3)-C(CH_3)=NOCH_3$ | $^1H$: 1.75(d, 3H), 2.0, 2.05, 3.7, 3.95(in each case s, 3H); 5.15 (s, 2H); 6.75(g, 1H); 6.8–7.3 (m, 4H) |
| 111 | $OCH_3$ | $CH_3$ | O | CH | CH | CH | H | $CH_2ON=C(CH_3)-C(C_6H_5)=NOCH_3$ | $^1H$: 1.75(d, 3H), 2.2, 3.75, 3.9, 3.95(in each case s, 3H); 5.0 (s, 2H); 6.75(g, 1H); 6.8–7.2 (m, 9H) |
| 112 | $OCH_3$ | $CH_3$ | $N(CH_3)$ | CH | CH | CH | H | $CH_2O-[2-CH_3-C_6H_4]$ | $^1H$: 1.75(d, 3H), 2.3, 3.1, 3.7; (in each case s, 3H); 5.05 (s, 2H); 6.55–7.36(m, 9H) |
| 113 | $OCH_3$ | $CH_3$ | $N(CH_3)$ | CH | CH | CH | H | $CH_2O-\{2,5-(CH_3)_2, 4-[C(CH_3)=NOCH_3]-C_6H_2\}$ | $^1H$: 1.86(d, 3H), 2.2, 2.25, 2.35, 3.05, 3.7, 4.0 (in each case s, 3H); 5.0(s, 2H); 6.75–7.3(m, 6H) |
| 114 | $OCH_3$ | $CH_3$ | $N(CH_3)$ | CH | CH | CH | H | $CH_2ON=C(CH_3)-[3,5-Cl_2-C_6H_3]$ | m.p.: 75–76° C. |
| 115 | $OCH_3$ | $CH_3$ | $N(CH_3)$ | CH | CH | CH | H | $CH_2ON=C(CH_3)-C(CH_3)=NOCH_3$ | $^1H$: 4.75(d, 3H); 1.95, 2.0, 2.1, 3.95, 3.98(in each case s, 3H); 5.15 (s, 2H), 6.95(g, 1H); 6.75–7.3 (m, 4H) |
| 116 | $OCH_3$ | $CH_3$ | O | CH | CH | CH | H | 4-$CH_3$-oxazol-2-yl | $^1H$: 1.8(d, 3H); 2.25, 3.75(in each case s, 3H); 6.75; (g, 1H); 6.95–7.75(m, 4H) |
| 117 | $OCH_3$ | $CH_3$ | O | CH | CH | CH | H | pyridin-3-yl | $^1H$: 1.85(d, 3H); 3.75(s, 3H); 6.75; (g, 1H); 6.95–8.9(m, 8H) |
| 118 | $OCH_3$ | $CH_3$ | O | CH | CH | CH | H | 6-$CH_3$-pyridin-2-yl | $^1H$: 1.8(d, 3H); 2.65, 3.75 (in each case s, 3H); 6.75(g, 1H); 6.9–7.76(m, 7H) |
| 119 | $OCH_3$ | $CH_3$ | O | CH | CH | CH | H | pyrimidin-5-yl | $^1H$: 1.8(d, 3H); 3.75(s, 3H); 6.8(g, 1H); 6.95–7.3(m, 4H); 8.95(s, 2H); 9.2(s, 1H) |
| 120 | $OCH_3$ | $CH_3$ | O | CH | CH | CH | H | 3-$CF_3$-$C_6H_4$ | $^1H$: 1.85(d, 3H); 3.75(s, 3H); 6.75(g, 1H); 6.85–7.9(m, 8H) |
| 121 | $OCH_3$ | $CH_3$ | O | CH | CH | CH | H | furan-3-yl | $^1H$: 1.8(d, 3H); 3.75(s, 3H); 6.7–7.75(m, 8H) |
| 122 | $OCH_3$ | $CH_3$ | O | CH | CH | CH | H | thien-3-yl | $^1H$: 1.8(d, 3H); 3.75(s, 3H); 6.7–7.45(m, 8H) |
| 123 | $OCH_3$ | $CH_3$ | O | CH | CH | CH | $CH_3$ | 3-$CH_3$-$C_6H_4$ | m.p.: 76–78° C. |
| 124 | $OCH_3$ | $CH_3$ | O | CH | CH | CH | $CH_3$ | 4-$CH_3$-$C_6H_4$ | m.p.: 98–100° C. |
| 125 | $OCH_3$ | $CH_3$ | O | CH | CH | CH | $CH_3$ | 3-Cl-$C_6H_4$ | $^1H$: 1.8(d, 3H); 2.2, 3.75(in each case s, 3H); 6.7–7.5(m, 7H) |
| 126 | $OCH_3$ | $CH_3$ | O | CH | CH | CH | $CH_3$ | 3-$OCH_3$-$C_6H_4$ | $^1H$: 1.8(d, 3H); 2.4, 3.75, 3.9 (in each case s, 3H); 6.75–7.5(g, 1H); 6.9–7.4(m, 7H) |
| 127 | $OCH_3$ | $CH_3$ | O | CH | CH | CH | $CH_3$ | 3-F-$C_6H_4$ | $^1H$: 1.8(d, 3H); 2.4 + 3.7 (in each case s, 3H); 6.7–7.5(m, 8H) |
| 128 | $OCH_3$ | $CH_3$ | O | CH | CH | CH | $CH_3$ | 4-Cl-$C_6H_4$ | m.p.: 105° |
| 129 | $OCH_3$ | $CH_3$ | O | CH | CH | CH | $CH_3$ | 3,4-$Cl_2$-$C_6H_3$ | m.p.: 84–86° C. |
| 130 | $OCH_3$ | $CH_3$ | O | CH | CH | CH | Br | 4-Cl-$C_6H_4$ | m.p.: 129° C. |
| 131 | $NHCH_3$ | $CH_3$ | O | CH | CH | CH | Br | 4-Cl-$C_6H_4$ | m.p.: 126–128° C. |

Examples for the fungicidal action.

The fungicidal action of the compounds of the general formula I was demonstrated by the following experiments:

The active ingredients were formulated as a 20% strength emulsion in a mixture of 70% by weight of cyclohexanone, 20% by weight of Nekanil® LN (Lutensol® AP6, wetting agent having emulsifying and dispersing action based on ethoxylated alkylphenols) and 10% by weight of Emulphor® EL (Emulan® EL, emulsifier based on ethoxylated fatty alcohols) and diluted with water to give the desired concentration.

The compounds a (Example 1 in EP-A 383 117) and B (Example 50 in EP-A 471 261) were used as comparison compounds.

Action Against *Erysiphe graminis* var. *tritici* (Powdery Mildew of Wheat)

Leaves of wheat seedlings (cultiva "Frühgold") were first treated with the aqueous preparation of the active ingredients (rate of application: 16 ppm). After approximately 24 hours, the plants were dusted with spores of powdery mildew of wheat (*Erysiphe graminis* var. *tritici*). The plants which had been thus treated were subsequently incubated for 7 days at 20–22° C. and a relative atmospheric humidity of 75–80%. The extent of fungal development was then determined.

In this test, the plants which had been treated with compounds 4, 9, 13, 23, 25, 33, 59, 66, 86, 89, 90, 95, 96, 107, 109, 110, 118 and 123 to 130 according to the invention showed a disease level of 15% and less, while the disease level of the plants which had been treated with comparison compound A was 50%. The plants which had been treated with comparison compound B and the untreated (control) plants showed a disease level of 70%.

Action Against *Pyricularia oryzae* (Rice Blast Disease)

Rice seedlings (cultiva: "Tai Nong 67") were sprayed to drip point with the preparation of the active ingredient. After 24 hours, the plants were sprayed with an aqueous spore suspension of the fungus *Pyricularia oryzae* and kept for 6 days at 22–24° C. at a relative atmospheric humidity of 95–99%. The plants were scored visually.

In this test, the plants which had been treated with compounds 9, 23, 33, 40, 43, 44, 46, 47, 49, 51, 52, 56, 58, 59, 60 to 62, 64 to 67, 75, 90 to 96, 110, 115, 118 and 123 to 129 according to the invention showed a disease level of 25% or less, while the disease level of the plants which had been treated with comparison compounds A and B and the untreated (control) plants was 80%.

Examples for the action against animal pests.

The action of the compounds of the general formula I against animal pests was demonstrated by the following experiments:

The active ingredients were formulated
a. as a 0.1% strength solution in acetone or
b. as a 10% strength emulsion in a mixture of 70% by weight of cyclohexanone, 20% by weight of Nekanil® LN (Lutensol® AP6, wetting agent having emulsifying and dispersing action based on ethoxylated alkylphenols) and 10% by weight of Emulphor® EL (Emulan® EL, emulsifier based on ethoxylated fatty alcohols)
and diluted with acetone in the case of a. or with water in the cae of b. to give the desired concentration.

After conclusion of the experiments, the lowest concentration at which the compounds still caused an 80 to 100% inhibition or mortality in comparison with untreated controls (action threshold or minimum concentration) was determined in each case.

We claim:

1. An aryloxy-, -thio- and -aminocrotonate compound of the formula I

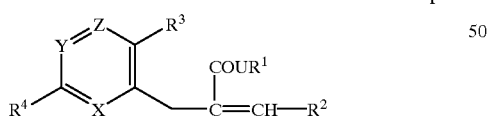

where the substituents have the following meanings:
U is oxygen (—O—), sulfur (—S—) or amino (—NH—);
V is oxygen (—O—), sulfur (—S—), amino (—NH—) or $C_1$–$C_{10}$-alkylamino (—N($C_1$–$C_{10}$-alkyl)-);
X, Y and Z independently of one another are =$CR^3$—;
$R^1$ and $R^2$ independently of one another are $C_1$–$C_4$-alkyl;
$R^3$ is hydrogen, cyano, nitro, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio and $C_1$–$C_4$-haloalkylthio;
$R^4$ is unsubstituted or substituted $C_2$–$C_{10}$-alkenyl, $C_2$–$C_{10}$-alkynyl or hetaryl which is bonded to the skeleton directly or via an oxy, mercapto, amino, carboxyl or carbonylamino group, is unsubstituted or substituted aryl which is bonded to the skeleton directly or via a mercapto, amino, carboxyl or carbonylamino group,
is a substituted alkyl group of the formula $CH_2OA^1$, wherein
$A^1$ is unsubstituted or substituted $C_3$–$C_{12}$-cycloalkyl;
is unsubstituted or substituted 5- or 6-membered heterocyclyl containing from one to three nitrogen atoms and/or one oxygen or sulfur atom, or one or two oxygen and/or sulfur atoms, as well as carbon ring members; or
is unsubstituted or substituted aryl or hetaryl;
is a substituted $C_1$–$C_{10}$-alkyl group of the formula $CR^a$=N—$W^a$—$A^2$, wherein
$R^a$ is hydrogen, $C_1$–$C_9$-alkyl or $C_1$–$C_9$-haloalkyl;
$W^a$ is oxygen, amino or $C_1$–$C_{10}$-alkylamino;
$A^2$ is hydrogen, unsubstituted or substituted $C_1$–$C_{10}$-alkyl, $C_2$–$C_{10}$-alkenyl or $C_2$–$C_{10}$-alkynyl, is unsubstituted or substituted $C_3$–$C_{12}$-cycloalkyl;
is unsubstituted or substituted 5- or 6-membered heterocyclyl containing from one to three nitrogen atoms and/or one oxygen or sulfur atom, or one or two oxygen and/or sulfur atoms, as well as carbon ring members; or
is unsubstituted or substituted aryl or hetaryl;
is a substituted $C_1$–$C_{10}$-alkyl group of the formula $CHR^c$—O—N=$CR^b$—$A^3$, wherein
$R^b$ is hydrogen, cyano, nitro, halogen, $C_1$–$C_{10}$-alkyl, $C_1$–$C_{10}$-haloalkyl, $C_3$–$C_{12}$-cycloalkyl, $C_1$–$C_{10}$-alkoxy, $C_1$–$C_{10}$-haloalkoxy, or unsubstituted or substituted aryl;
$R^c$ is hydrogen, $C_1$–$C_9$-alkyl or $C_3$–$C_{12}$-cycloalkyl;
$A^3$ is unsubstituted or substituted $C_1$–$C_{10}$-alkyl, $C_2$–$C_{10}$-alkenyl or $C_2$–$C_{10}$-alkynyl, is unsubstituted or substituted $C_3$–$C_{12}$-cycloalkyl;
is unsubstituted or substituted 5- or 6-membered heterocyclyl containing from one to three nitrogen atoms and/or one oxygen or sulfur atom, or one or two oxygen and/or sulfur atoms, as well as carbon ring members; or
is unsubstituted or substituted aryl or hetaryl;
or is a substituted $C_1$–$C_{10}$-alkyl group of the formula $CHR^f$—O—N=$CR^e$—$CR^d$=N—O—$A^4$, wherein
$R^d$ and $R^e$ are, independently of one another, hydrogen, cyano, nitro, halogen, $C_1$–$C_{10}$-alkyl, $C_1$–$C_{10}$-haloalkyl, $C_3$–$C_{12}$-cycloalkyl, $C_1$–$C_{10}$-alkoxy, $C_1$–$C_{10}$-haloalkoxy, or unsubstituted or substituted aryl;
$R^f$ is hydrogen, $C_1$–$C_9$-alkyl or $C_3$–$C_{12}$-cycloalkyl;
$A^4$ is unsubstituted or substituted $C_1$–$C_{10}$-alkyl, $C_2$–$C_{10}$-alkenyl or $C_2$–$C_{10}$-alkynyl, is unsubstituted or substituted $C_3$–$C_{12}$-cycloalkyl;
is unsubstituted or substituted 5- or 6-membered heterocyclyl containing from one to three nitrogen atoms and/or one oxygen or sulfur atom, or one or two oxygen and/or sulfur atoms, as well as carbon ring members; or
is unsubstituted or substituted aryl or hetaryl.

2. The compound of the formula I as defined in claim 1 wherein $R^4$ is unsubstituted or substituted $C_2$–$C_{10}$-alkenyl, $C_2$–$C_{10}$-alkynyl or hetaryl which is bonded to the skeleton directly or via an oxy, mercapto, amino, carboxyl or carbonylamino group.

3. The compound of the formula I as defined in claim 1 wherein $R^4$ is unsubstituted or substituted aryl which is bonded to the skeleton directly or via a mercapto, amino, carboxyl or carbonylamino group.

4. The compound of the formula I as defined in claim 1 wherein $R^4$ is unsubstituted or substituted aryl or hetaryl.

5. The compound of the formula I as defined in claim 1 wherein $R^4$ is of the formula $CH_2OA^1$, wherein $A^1$ is unsubstituted or substituted $C_3$–$C_{12}$-cycloalkyl;
is unsubstituted or substituted 5- or 6-membered heterocyclyl containing from one to three nitrogen atoms and/or one oxygen or sulfur atom, or one or two oxygen and/or sulfur atoms, as well as carbon ring members; or
is unsubstituted or substituted aryl or hetaryl.

6. The compound of the formula I as defined in claim 1 wherein $R^4$ is of the formula $CR^a$=N—$W^a$—$A^2$, wherein $R^a$ is hydrogen, $C_1$–$C_9$-alkyl or $C_1$–$C_9$-haloalkyl;
$W^a$ is oxygen, amino or $C_1$–$C_{10}$-alkylamino;
$A^2$ is hydrogen;
unsubstituted or substituted $C_1$–$C_{10}$-alkyl, $C_2$–$C_{10}$-alkenyl or $C_2$–$C_{10}$-alkynyl;
is unsubstituted or substituted $C_3$–$C_{12}$-cycloalkyl;
is unsubstituted or substituted 5- or 6-membered heterocyclyl containing from one to three nitrogen atoms and/or one oxygen or sulfur atom, or one or two oxygen and/or sulfur atoms, as well as carbon ring members; or
is unsubstituted or substituted aryl or hetaryl.

7. The compound of the formula I as defined in claim 1 wherein $R^4$ is of the formula $CHR^c$—O—N=$CR^b$—$A^3$, wherein $R^b$ is hydrogen, cyano, nitro, halogen, $C_1$–$C_{10}$-alkyl, $C_1$–$C_{10}$-haloalkyl, $C_3$–$C_{12}$-cycloalkyl, $C_1$–$C_{10}$-alkoxy, $C_1$–$C_{10}$-haloalkoxy, or unsubstituted or substituted aryl;

$R^c$ is hydrogen, $C_1$–$C_9$-alkyl or $C_3$–$C_{12}$-cycloalkyl;

$A^3$ is unsubstituted or substituted $C_1$–$C_{10}$-alkyl, $C_2$–$C_{10}$-alkenyl or $C_2$–$C_{10}$-alkynyl, is unsubstituted or substituted $C_3$–$C_{12}$-cycloalkyl;
is unsubstituted or substituted 5- or 6-membered heterocyclyl containing from one to three nitrogen atoms and/or one oxygen or sulfur atom, or one or two oxygen and/or sulfur atoms, as well as carbon ring members; or
is unsubstituted or substituted aryl or hetaryl.

8. The compound of the formula I as defined in claim 1 wherein $R^4$ is of the formula $CHR^f$—O—N=$CR^e$—$CR^d$=N—O—$A^4$, wherein $R^d$ and $R^e$ are, independently of one another, hydrogen, cyano, nitro, halogen, $C_1$–$C_{10}$-alkyl, $C_1$–$C_{10}$-haloalkyl, $C_3$–$C_{12}$-cycloalkyl, $C_1$–$C_{10}$-alkoxy, $C_1$–$C_{10}$-haloalkoxy, or unsubstituted or substituted aryl;

$R^f$ is hydrogen, $C_1$–$C_9$-alkyl or $C_3$–$C_{12}$-cycloalkyl;

$A^4$ is unsubstituted or substituted $C_1$–$C_{10}$-alkyl, $C_2$–$C_{10}$-alkenyl or $C_2$–$C_{10}$-alkynyl;
is unsubstituted or substituted $C_3$–$C_{12}$-cycloalkyl;
is unsubstituted or substituted 5- or 6-membered heterocyclyl containing from one to three nitrogen atoms and/or one oxygen or sulfur atom, or one or two oxygen and/or sulfur atoms, as well as carbon ring members; or
is unsubstituted or substituted aryl or hetaryl.

9. The compound of the formula I as defined in claim 1 where U is oxygen and V is oxygen or amino.

10. The compound of the formula I as defined in claim 1 where $R^1$ is methyl.

11. The compound of the formula I as defined in claim 1 where $R^2$ is methyl.

12. A process for the preparation of a compound of the formula I as defined in claim 1 where V is oxygen or sulfur, which comprises reacting a corresponding alcohol or a corresponding thiol of the formula IIa

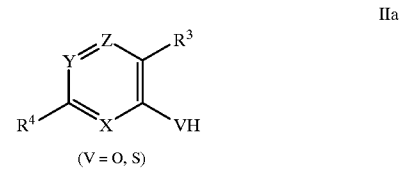

(V = O, S)

in the presence of a base with a crotonate of the formula III

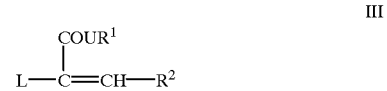

where L is a nucleophilically replaceable leaving group.

13. A process for the preparation of a compound of the formula I as defined in claim 1 where V is amino or alkylamino, which comprises reacting a corresponding amine of the formula IIb

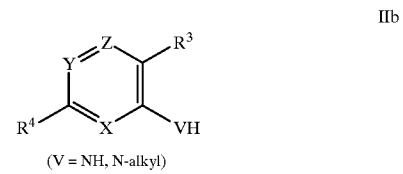

(V = NH, N-alkyl)

with an α-ketocarbonyl compound of the formula IV

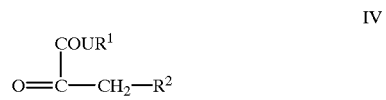

in the presence of a protic acid.

14. A composition which is suitable for controlling animal pests or fungal pests, comprising a solid or liquid carrier and a compound of the formula I as defined in claim 1.

15. A method for controlling fungal pests, which comprises treating the fungi, or the materials, plants, soil or seed to be protected against fungal attack, with an effective amount of a compound of the formula I as defined in claim 1.

16. A method for controlling animal pests, which comprises treating the pests, or the materials, plants, soil or seed to be protected against them, with an effective amount of a compound of the formula I as defined in claim 1.

* * * * *